United States Patent
Canale et al.

(10) Patent No.: US 12,419,501 B2
(45) Date of Patent: Sep. 23, 2025

(54) SYSTEMS, APPARATUS AND METHODS FOR ROBOTIC INTERVENTIONAL PROCEDURES USING A PLURALITY OF ELONGATED MEDICAL DEVICES

(71) Applicant: Corindus, Inc., Waltham, MA (US)

(72) Inventors: Cameron Canale, Groton, MA (US); Eric Klem, Lexington, MA (US); Omid Saber, Waltham, MA (US); Saeed Sokhanvar, Medfield, MA (US); Andrew Clark, Waltham, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 528 days.

(21) Appl. No.: 17/597,041

(22) PCT Filed: Jul. 14, 2020

(86) PCT No.: PCT/US2020/041964
§ 371 (c)(1),
(2) Date: Dec. 23, 2021

(87) PCT Pub. No.: WO2021/011554
PCT Pub. Date: Jan. 21, 2021

(65) Prior Publication Data
US 2022/0233263 A1 Jul. 28, 2022

Related U.S. Application Data

(60) Provisional application No. 62/874,247, filed on Jul. 15, 2019.

(51) Int. Cl.
*A61B 1/00* (2006.01)
*A61B 34/35* (2016.01)
(Continued)

(52) U.S. Cl.
CPC .......... *A61B 1/00147* (2013.01); *A61B 34/35* (2016.02); *A61M 25/0113* (2013.01); *A61B 2034/301* (2016.02); *A61B 2034/715* (2016.02)

(58) Field of Classification Search
CPC ................ A61B 1/00147; A61B 34/35; A61B 2034/301; A61B 2034/715; A61B 34/30; A61M 25/0113
See application file for complete search history.

(56) References Cited

U.S. PATENT DOCUMENTS

| | | | |
|---|---|---|---|
| 3,821,525 A | 6/1974 | Eaton et al. | |
| 5,312,338 A | 5/1994 | Nelson et al. | |

(Continued)

FOREIGN PATENT DOCUMENTS

| | | |
|---|---|---|
| CN | 101918073 | 12/2010 |
| CN | 106535808 | 3/2017 |

(Continued)

OTHER PUBLICATIONS

Extended European Search Report for Corresponding EP Application No. 20840837.7, dated Jun. 22, 2023.
(Continued)

*Primary Examiner* — Richard G Louis

(57) ABSTRACT

A robotic drive system for driving one or more elongated medical devices, the robotic drive can include a linear member and at least four device modules coupled to the linear member. Each device module may be independently controllable. The plurality of device modules may be switched between a first configuration where each device module is populated with an elongated medical device and a second configuration where a subset of the at least four device modules is populated with an elongated medical device.

55 Claims, 82 Drawing Sheets

(51) Int. Cl.
*A61M 25/01* (2006.01)
*A61B 34/00* (2016.01)
*A61B 34/30* (2016.01)

(56) References Cited

U.S. PATENT DOCUMENTS

| | | | |
|---|---|---|---|
| 5,350,101 A | 9/1994 | Godlewski | |
| 7,331,967 B2 | 2/2008 | Lee et al. | |
| 7,766,856 B2 | 8/2010 | Ferry et al. | |
| 7,766,894 B2 | 8/2010 | Weitzner et al. | |
| 7,972,298 B2 | 7/2011 | Wallace et al. | |
| 8,052,636 B2 | 11/2011 | Moll et al. | |
| 8,092,397 B2 | 1/2012 | Wallace et al. | |
| 8,343,096 B2 | 1/2013 | Kirschenman et al. | |
| 8,617,102 B2 | 12/2013 | Moll et al. | |
| 8,684,952 B2 | 4/2014 | Weitzner et al. | |
| 8,736,212 B2 | 5/2014 | Sandhu et al. | |
| 8,801,661 B2 | 8/2014 | Moll et al. | |
| 9,283,046 B2 | 3/2016 | Walker et al. | |
| 9,326,822 B2 | 5/2016 | Lewis et al. | |
| 9,408,669 B2 | 8/2016 | Kokish et al. | |
| 9,782,564 B2 | 10/2017 | Zirps et al. | |
| 9,814,864 B2 | 11/2017 | Scarpine et al. | |
| 9,825,455 B2 | 11/2017 | Sandhu et al. | |
| 10,213,264 B2 | 2/2019 | Tanner et al. | |
| 10,307,214 B2 | 6/2019 | Lathrop et al. | |
| 10,449,007 B2 | 10/2019 | Deboeuf et al. | |
| 2002/0177789 A1* | 11/2002 | Ferry | A61B 34/71 600/585 |
| 2004/0254566 A1 | 12/2004 | Plicchi et al. | |
| 2006/0041245 A1 | 2/2006 | Ferry et al. | |
| 2007/0060879 A1 | 3/2007 | Weitzner et al. | |
| 2008/0243064 A1 | 10/2008 | Stahler et al. | |
| 2008/0262513 A1 | 10/2008 | Stahler et al. | |
| 2009/0082722 A1 | 3/2009 | Munger et al. | |
| 2009/0247943 A1 | 10/2009 | Kirschenman et al. | |
| 2011/0040150 A1 | 2/2011 | Govari et al. | |
| 2011/0130718 A1* | 6/2011 | Kidd | A61B 34/30 604/95.01 |
| 2012/0071752 A1 | 3/2012 | Sewell et al. | |
| 2014/0066900 A1 | 3/2014 | Blacker | |
| 2014/0276389 A1 | 9/2014 | Walker | |
| 2014/0276391 A1 | 9/2014 | Yu | |
| 2015/0142013 A1 | 5/2015 | Tanner et al. | |
| 2017/0007343 A1 | 1/2017 | Yu | |
| 2017/0049995 A1* | 2/2017 | Blacker | A61M 25/09 |
| 2017/0348060 A1 | 12/2017 | Blacker | |
| 2018/0132950 A1 | 5/2018 | Kirschenman et al. | |
| 2019/0175887 A1 | 6/2019 | Shameli | |

FOREIGN PATENT DOCUMENTS

| | | |
|---|---|---|
| CN | 107307909 | 11/2017 |
| CN | 108309370 | 7/2018 |
| CN | 109069212 | 12/2018 |
| EP | 2124800 | 11/2010 |
| JP | 2014113181 | 6/2014 |
| JP | 2016537056 | 12/2016 |
| JP | 2018519087 | 7/2018 |

OTHER PUBLICATIONS

International Search Report for Corresponding PCT Application No. PCT/US2020/041964, received Dec. 8, 2020.

* cited by examiner

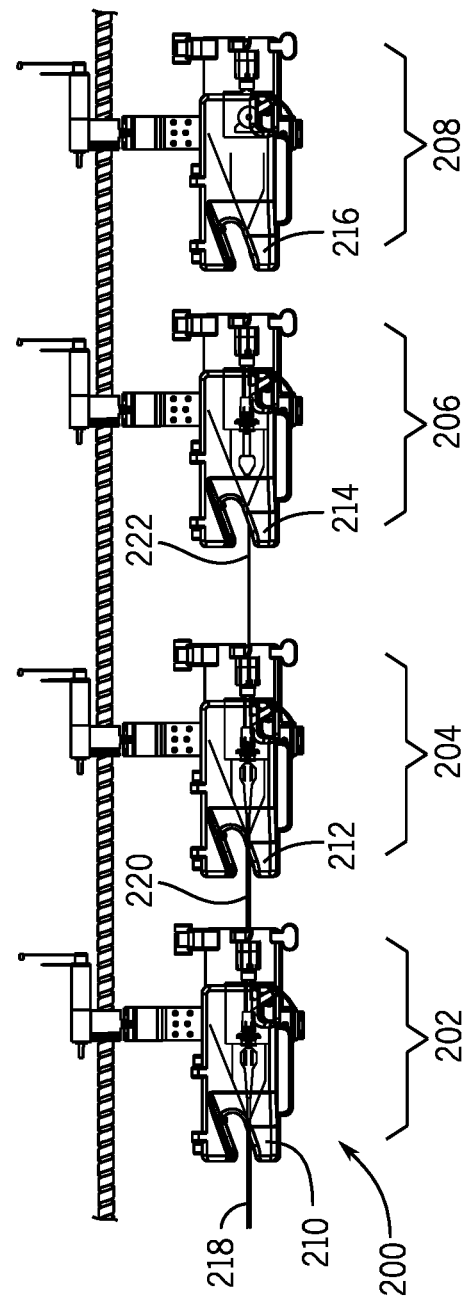

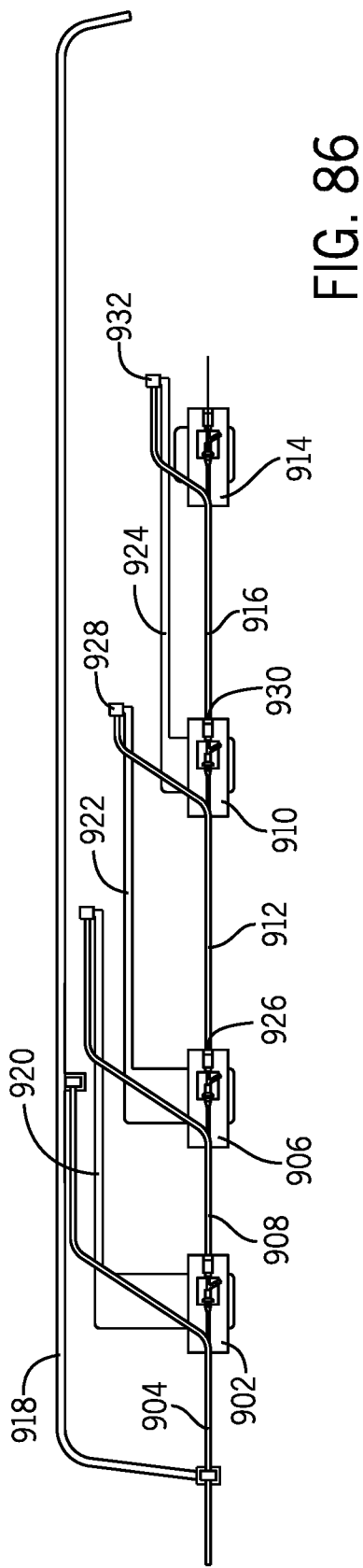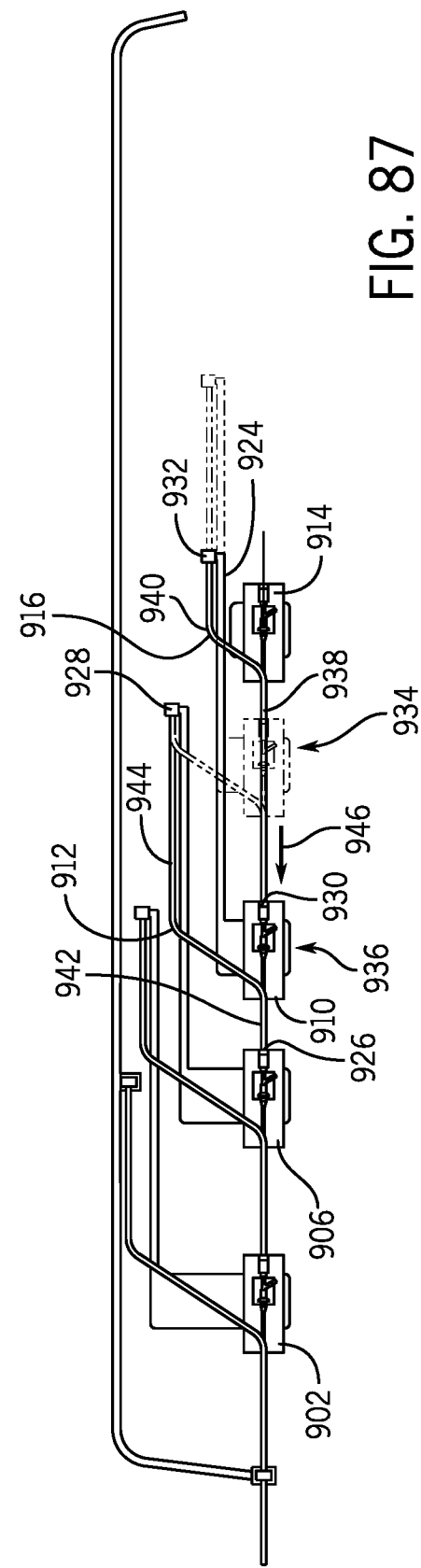

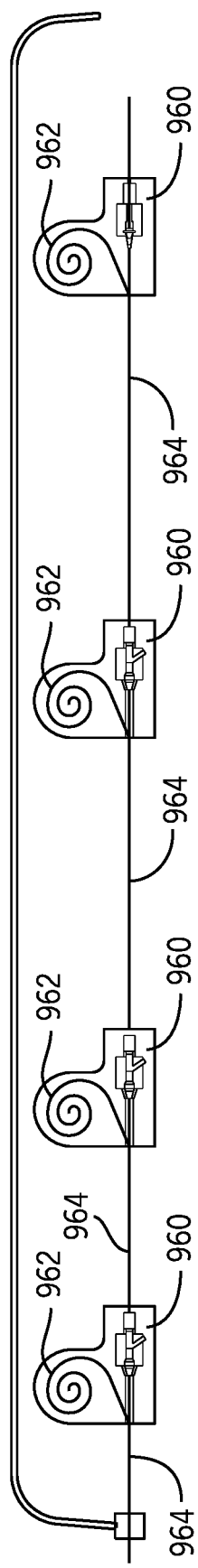
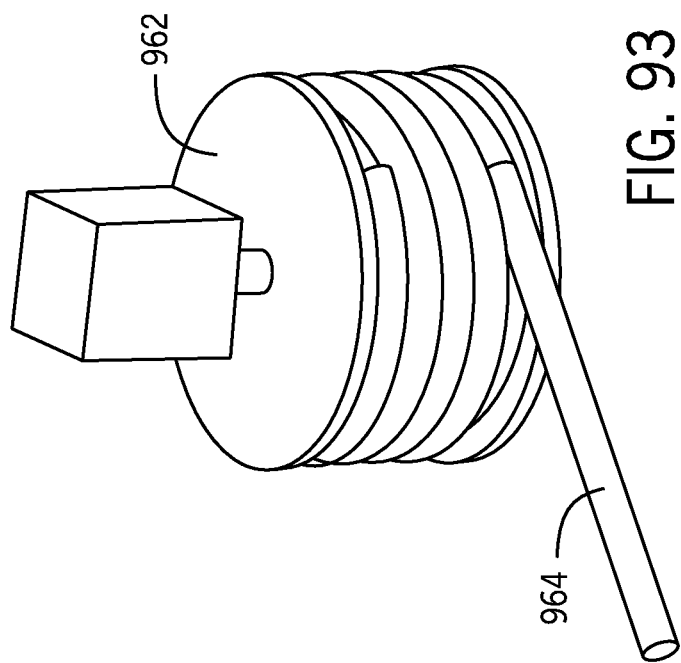
FIG. 92
FIG. 93

SYSTEMS, APPARATUS AND METHODS FOR ROBOTIC INTERVENTIONAL PROCEDURES USING A PLURALITY OF ELONGATED MEDICAL DEVICES

CROSS-REFERENCE TO RELATED APPLICATIONS

This application is based on, claims priority to, and incorporates herein by reference in its entirety U.S. Ser. No. 62/874,247, filed Jul. 15, 2019, and entitled "Systems, Apparatus and Methods for Robotic Interventional Procedures Using a Plurality of Elongated Medical Devices."

FIELD

The present invention relates generally to the field of robotic medical procedure systems and, in particular, to systems, apparatus and methods for robotically controlling the movement and operation of elongated medical devices in robotic interventional procedures.

BACKGROUND

Catheters and other elongated medical devices (EMDs) may be used for minimally invasive medical procedures for the diagnosis and treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature, and via the guidewire advancing a catheter to deliver therapy. The catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system is used. An OTW catheter has a lumen for the guidewire that extends the full length of the catheter. This provides a relatively stable system because the guidewire is supported along the whole length. This system, however, has some disadvantages, including higher friction, and longer overall length compared to rapid-exchange catheters (see below). Typically to remove or exchange an OTW catheter while maintaining the position of the indwelling guidewire, the exposed length (outside of the patient) of guidewire must be longer than the OTW catheter. A 300 cm long guidewire is typically sufficient for this purpose and is often referred to as an exchange length guidewire. Due to the length of the guidewire, two operators are needed to remove or exchange an OTW catheter. This becomes even more challenging if a triple coaxial, known in the art as a tri-axial system, is used (quadruple coaxial catheters have also been known to be used). However, due to its stability, an OTW system is often used in NVI and PVI procedures. On the other hand, PCI procedures often use rapid exchange (or monorail) catheters. The guidewire lumen in a rapid exchange catheter runs only through a distal section of the catheter, called the monorail or rapid exchange (RX) section. With a RX system, the operator manipulates the interventional devices parallel to each other (as opposed to with an OTW system, in which the devices are manipulated in a serial configuration), and the exposed length of guidewire only needs to be slightly longer than the RX section of the catheter. A rapid exchange length guidewire is typically 180-200 cm long. Given the shorter length guidewire and monorail, RX catheters can be exchanged by a single operator. However, RX catheters are often inadequate when more distal support is needed.

SUMMARY

In accordance with an embodiment, a robotic drive system for driving one or more elongated medical devices includes a linear member and at least four device modules coupled to the linear member. Each device module may be independently controllable. The plurality of device modules may be switched between a first configuration where each device module is populated with an elongated medical device and a second configuration where a subset of the at least four device modules is populated with an elongated medical device.

In accordance with another embodiment, a robotic drive system for driving one or more elongated medical devices includes a linear member and a plurality of device modules movably coupled to the linear member. Each drive module is configured to manipulate an elongated medical device and each device module may be independently controllable; The plurality of device modules may be switched between a first configuration including at least one device module configured to drive a proximal region of the corresponding elongated medical device along a first longitudinal axis and a second configuration including at least one device module configured to drive a proximal portion of the corresponding elongated medical device along a second longitudinal axis different from the first longitudinal axis.

In accordance with another embodiment, a robotic drive system for driving one or more elongated medical devices includes a linear member and at least four device modules coupled to the linear member. Each device module is configured to manipulate an elongated medical device and each device module may be independently controllable. The plurality of device modules may be switched between a triaxial configuration and a biaxial configuration. In the triaxial configuration, the elongated medical device manipulated by three of the at least four device modules is a catheter and the elongated medical device manipulated by a fourth device module of the at least four device modules is a wire-based device. In the biaxial configuration, the elongated medical device manipulated by two of the at least four device modules is a catheter, the elongated medical device manipulated by a third device module of the at least four device modules is a wire-based device and a fourth device module of the at least four device modules is unpopulated.

In accordance with another embodiment, a robotic drive system for driving one or more elongated medical devices includes a linear member, a first device module coupled to the linear member and a second device module coupled to the linear member at a position distal to the first device module. The first device module is configured to manipulate a first elongated medical device and may be independently controllable. The second device module is configured to manipulate a second elongated medical device and may be independently controllable. The robotic drive system further includes a device support having a section moveably positioned in the first device module and having a first end and a second end. The device support is configured to provide a channel to contain and support the first elongated medical device in a distance between the first device module and the second device module. The first end and the second end of the device support are coupled to the second device module.

In accordance with another embodiment, a robotic drive system for driving one or more elongated medical devices includes a linear member, a device module coupled to the linear member and a distal support arm having a device support connection located distal to the device module. The device module is configured to manipulate an elongated medical device and may be independently controllable. The robotic drive system further includes a device support moveably positioned in the device module and having a first end and a second end. The device support is configured to provide a channel to contain and support an elongated medical device in a distance between the device module and the device support connection. The first end and the second end of the device support are coupled to the distal support arm.

In accordance with another embodiment, a robotic drive system for driving one or more elongated medical devices includes a linear member; a first drive module coupled to the linear member, a cassette mounted to the first drive module and having a proximal end, and a second drive module coupled to the linear member at a position proximal to the first drive module. The second drive module is configured to be positioned in an area of overlap with the proximal end of the cassette mounted to the first drive module.

In accordance with an embodiment, a robotic drive system for driving one or more elongated medical devices includes a linear member, a first device module coupled to the linear member, a second device module coupled to the linear member, and a deployable elongated medical device having a first section and a second section. The first section is positioned on the first device module and the second section is positioned on the second device module. The first device module and the second device module may be independently controllable. An independent linear motion of the second device module along the rail may be used to actuate the second section of the deployable elongated medical device.

In accordance with another embodiment, a method for loading an elongated medical device to a device module in a robotic drive system having a plurality of device modules and configured for driving a plurality of elongated medical devices includes moving, using the robotic drive, a proximal device module to a position that is a predetermined distance from a distal device module that includes a distal elongated medical device having a hub, receiving a first end of a proximal elongated medical device in the hub of the distal elongated medical device and receiving the proximal elongated medical device in the proximal device module. The predetermined distance is determined based on a desired gap between a first end of the distal elongated medical device and the first end of the proximal elongated medical device when the proximal elongated medical device is being received in the proximal device module, a length of the distal elongated medical device and a length of the proximal elongated medical device.

In accordance with another embodiment, a robotic drive system for driving one or more elongated medical devices includes a linear member and a plurality of device modules coupled to the linear member. The plurality of device modules are configured to allow a prepared subassembly of a plurality of elongated medical devices to be side-loaded into the plurality of device modules. Each of the plurality of device modules receives one of the plurality of elongated medical devices.

In accordance with another embodiment a robotic drive system for driving one or more elongated medical devices includes a linear member having a length, a first device module configured to manipulate a first elongated medical device, a first stage coupled to the linear member and a first offset bracket connected between the first device module and the first stage to couple the first device module to the first stage. The first device module may be independently controllable and has a center point. The first stage has a center point. The first offset bracket defines a first offset distance between the center point of the first device module and the center point of the first stage. The system further includes a second device module configured to manipulate a second elongated medical device, a second stage coupled to the linear member, and a second offset bracket connected between the second device module and the second stage to couple the second device module to the second stage. The second device module may be independently controllable and has a center point. The second stage has a center point. The second offset bracket defines a second offset distance between the center point of the second device module and the center point of the second stage. A range of linear motion of the first device module along the linear member and a range of linear motion of the second device module along the linear member overlap. The range of linear motion of the first device module extends beyond the length of the linear member in a distal direction.

In accordance with another embodiment, a robotic drive system for driving one or more elongated medical devices includes a linear member having a length, a first device module configured to manipulate a first elongated medical device, a first stage coupled to the linear member and a first offset bracket connected between the first device module and the first stage to couple the first device module to the first stage. The first device module may be independently controllable and has a center point. The first stage has a center point. The first offset bracket defines a first offset distance between the center point of the first device module and the center point of the first stage. The system further includes a second device module configured to manipulate a second elongated medical device, a second stage coupled to the linear member, and a second offset bracket connected between the second device module and the second stage to couple the second device module to the second stage. The second device module may be independently controllable and has a center point. The second stage has a center point. The second offset bracket defines a second offset distance between the center point of the second device module and the center point of the second stage. The first offset distance and the second offset distance are configured to minimize the length of the linear member.

BRIEF DESCRIPTION OF THE DRAWINGS

The invention will become more fully understood from the following detailed description, taken in conjunction with the accompanying drawings, wherein the reference numerals refer to like parts in which:

FIG. 27 is a top view of a portion of a robotic drive configured to drive three elongated medical devices in accordance with an embodiment;

FIG. 86 shows a simplified top view of four device modules and four device supports for a robotic drive in accordance with an embodiment;

FIG. 87 shows a simplified top view illustrating movement of a device module relative to a device support in accordance with an embodiment;

FIG. 92 shows a simplified top view of device modules with device supports stored on a reel in accordance with an embodiment;

FIG. 93 shows an exemplary spooled tensioner in accordance with an embodiment;

Figure 40:
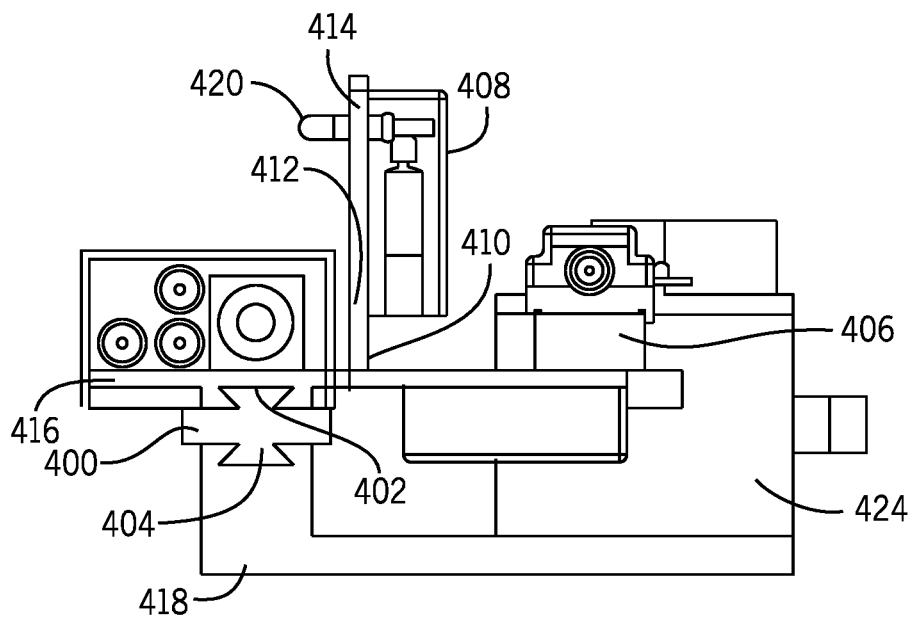
FIG. 40 is a front view of a robotic drive with a linear member having two slides in accordance with an embodiment.
Figure 115:
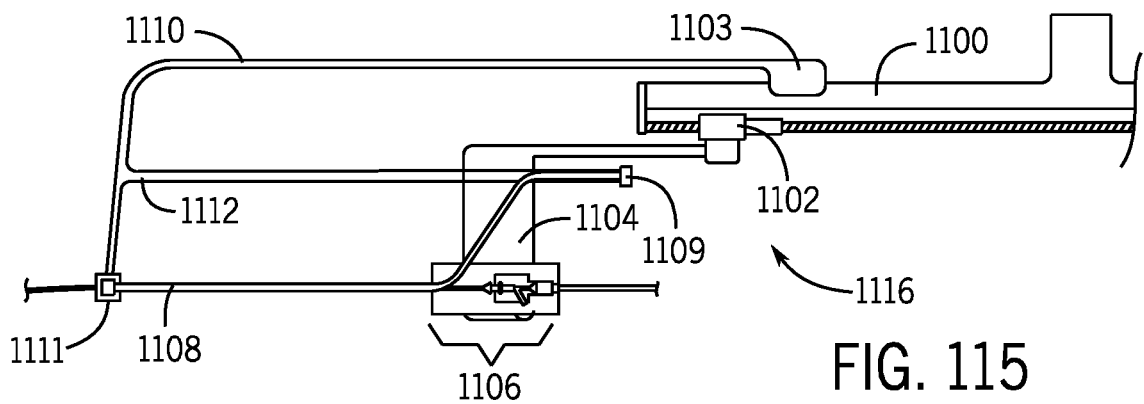
Figure 116:
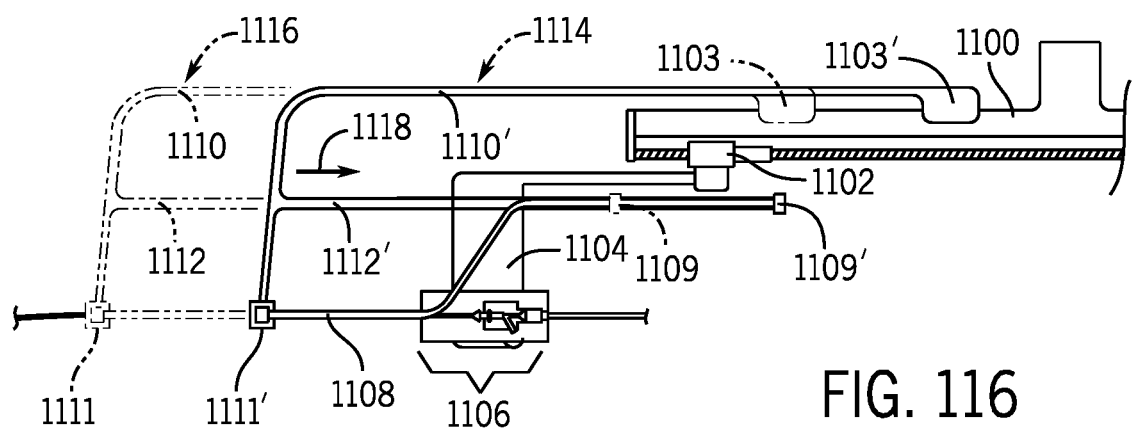
Figure 117:
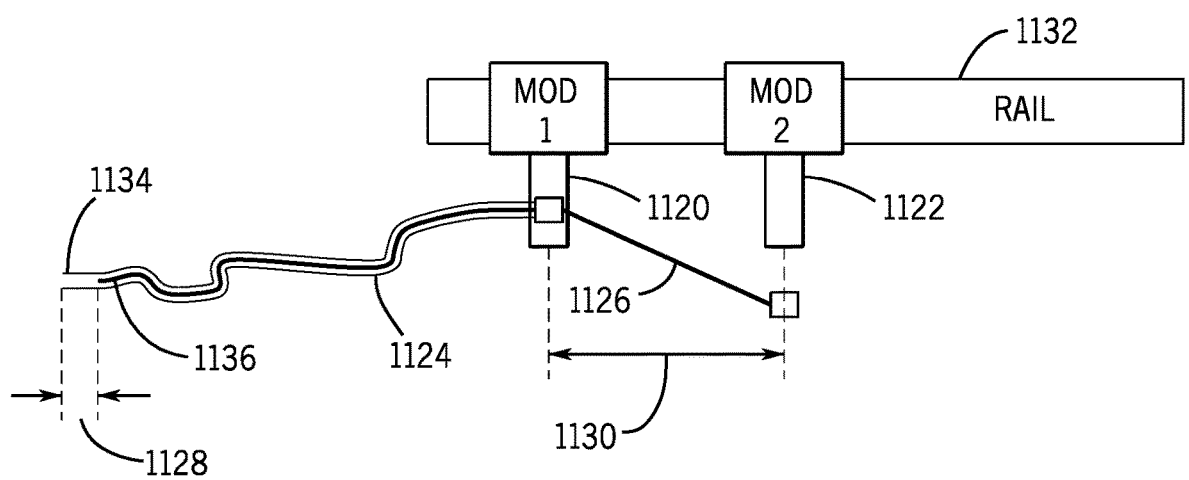
Figure 118:
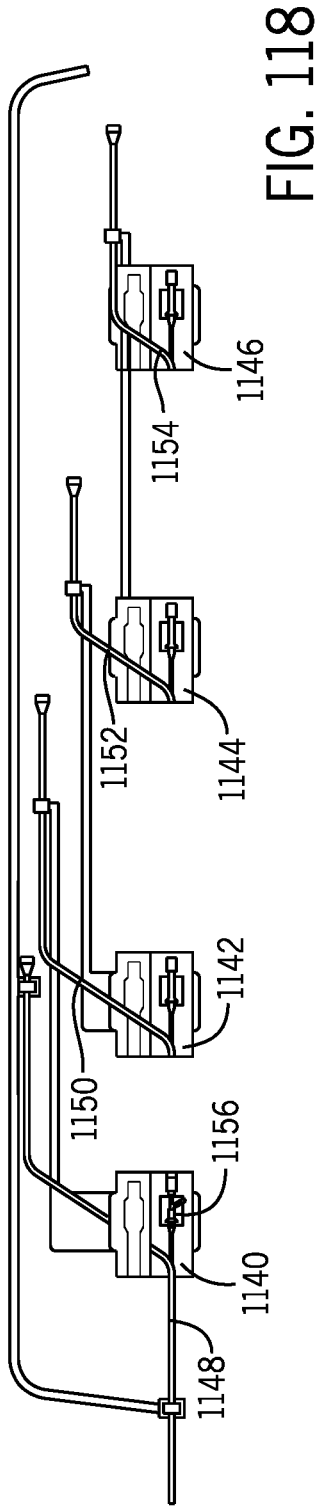
Figure 119:
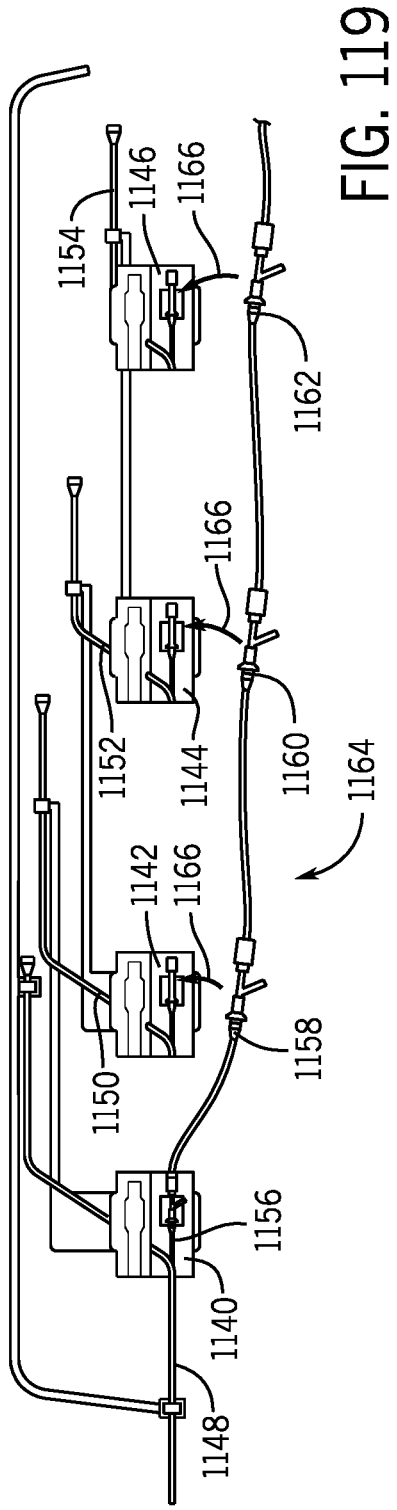
Figure 120:
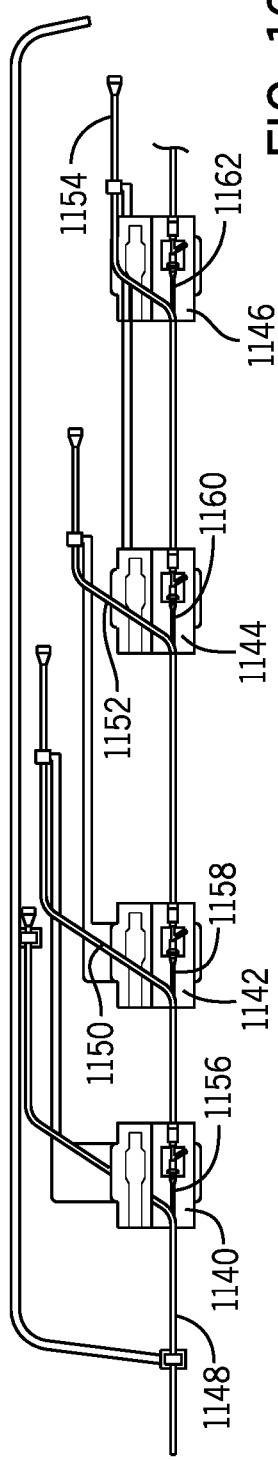
Figure 121:
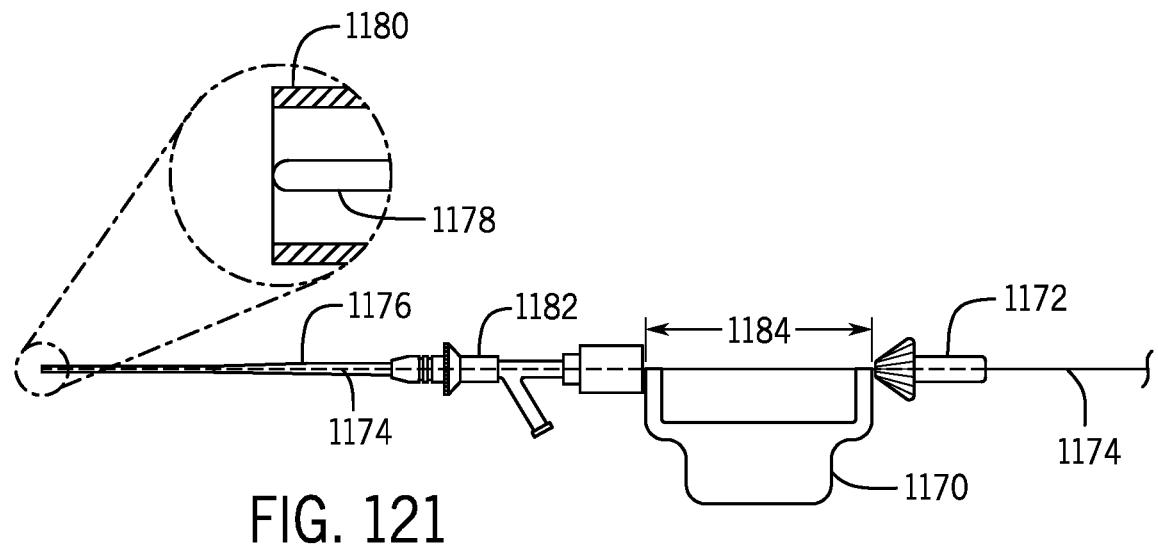
Figure 122:
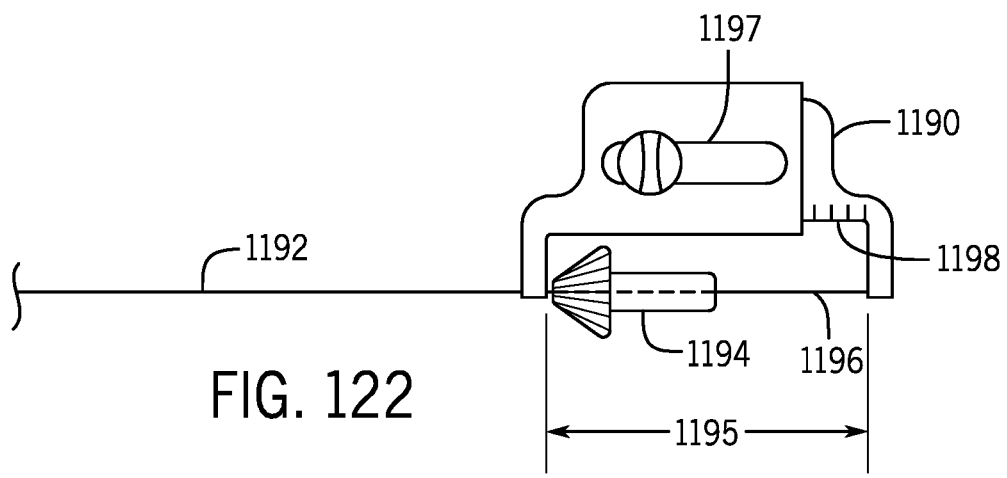
Figure 123:
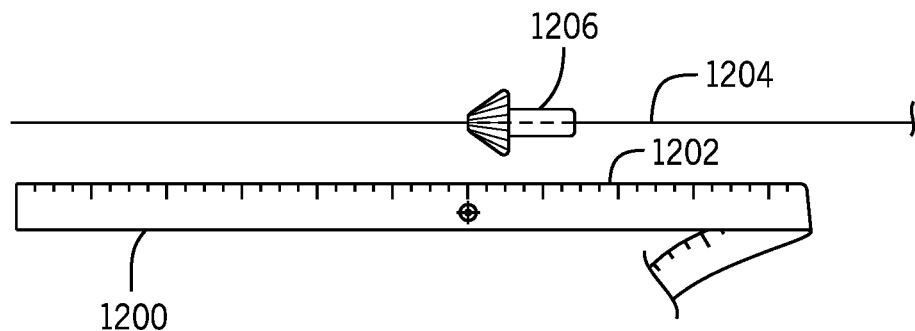
Figure 124:
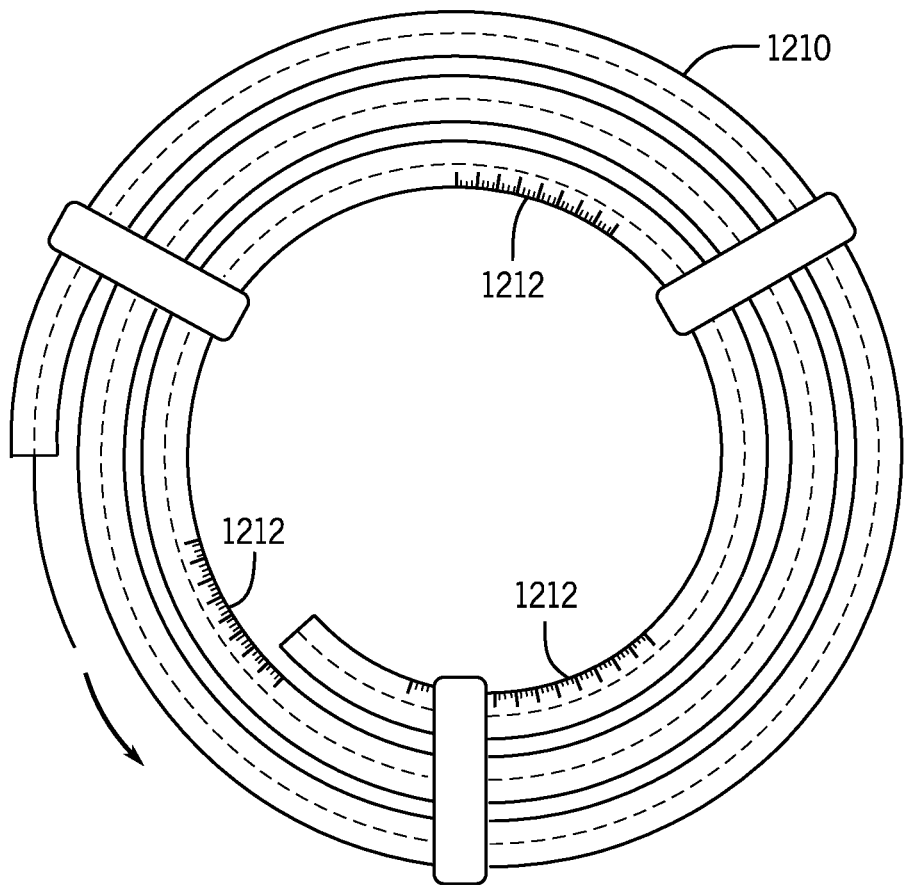

FIG. 115 40 is a top view of a moveable distal support arm and movable support arm in a second position in accordance with an embodiment;

FIG. 116 is a top view illustrating movement of a distal support arm and a support arm from the second position to the first position in accordance with an embodiment;

FIG. 117 is a block diagram illustrating a method for loading or unloading an EMD in a robotic drive with a safe loading distance in accordance with an embodiment;

FIG. 118 is a top view of device modules of a robotic drive in a loading position in accordance with an embodiment;

FIG. 119 is a top view of the device modules of FIG. 118 in a loading position and a set of prepared EMDs in accordance with an embodiment; and FIG. 120 is a top view of the set of prepared EMDs of FIG. 119 loaded into the appropriate device modules in accordance with an embodiment;

FIG. 121 is a schematic diagram of an elongated medical device, a gapping tool and an on-device adapter in accordance with an embodiment;

FIG. 122 is a schematic diagram of an elongated medical device, a gapping tool and an on-device adapter in accordance with an embodiment;

FIG. 123 is a diagram of an example gapping tool in accordance with an embodiment; and FIG. 124 is a diagram of an example gapping tool in accordance with an embodiment.

DETAILED DESCRIPTION

The following definitions will be used herein. The term elongated medical device (EMD) refers to, but is not limited to, catheters (e.g. guide catheters, microcatheters, balloon/stent catheters), wire-based devices (guidewires, embolization coils, stent retrievers, etc.), and devices that have a combination of these. Wire-based EMD includes, but is not limited to, guidewires, microwires, a proximal pusher for embolization coils, stent retrievers, self-expanding stents, and flow divertors. Typically wire-based EMD's do not have a hub or handle at its proximal terminal end. In one embodiment the EMD is a catheter having a hub at a proximal end of the catheter and a flexible shaft extending from the hub toward the distal end of the catheter, wherein the shaft is more flexible than the hub. In one embodiment the catheter includes an intermediary portion that transitions between the hub and the shaft that has an intermediate flexibility that is less rigid than the hub and more rigid than the shaft. In one embodiment the intermediary portion is a strain relief.

The terms distal and proximal define relative locations of two different features. With respect to a robotic drive the terms distal and proximal are defined by the position of the robotic drive in its intended use relative to a patient. When used to define a relative position, the distal feature is the feature of the robotic drive that is closer to the patient than a proximal feature when the robotic drive is in its intended in-use position. Within a patient, any vasculature landmark further away along the path from the access point is considered more distal than a landmark closer to the access point, where the access point is the point at which the EMD enters the patient. Similarly, the proximal feature is the feature that is farther from the patient than the distal feature when the robotic drive in its intended in-use position. When used to define direction, the distal direction refers to a path on which something is moving or is aimed to move or along which something is pointing or facing from a proximal feature toward a distal feature and/or patient when the robotic drive is in its intended in-use position. The proximal direction is the opposite direction of the distal direction.

The term longitudinal axis of a member (e.g., an EMD or other element in the catheter-based procedure system) is the direction of orientation going from a proximal portion of the member to a distal portion of the member. By way of example, the longitudinal axis of a guidewire is the direction of orientation from a proximal portion of the guide wire toward a distal portion of the guidewire even though the guidewire may be non-linear in the relevant portion. The term axial movement of a member refers to translation of the member along the longitudinal axis of the member. When a distal end of an EMD is axially moved in a distal direction along its longitudinal axis into or further into the patient, the EMD is being advanced. When the distal end of an EMD is axially moved in a proximal direction along its longitudinal axis out of or further out of the patient, the EMD is being withdrawn. The term rotational movement of a member refers to change in angular orientation of the member about the local longitudinal axis of the member. Rotational movement of an EMD corresponds to clockwise or counterclockwise rotation of the EMD about its longitudinal axis due to an applied torque.

The term axial insertion refers to inserting a first member into a second member along the longitudinal axes of the second member. The term lateral insertion refers to inserting a first member into a second member along a direction in a plane perpendicular to the longitudinal axis of the second member. This can also be referred to as radial loading or side loading. The term pinch refers to releasably fixing an EMD to a member such that the EMD and member move together when the member moves. The term unpinch refers to releasing the EMD from a member such that the EMD and member move independently when the member moves. The term clamp refers to releasably fixing an EMD to a member such that the EMD's movement is constrained with respect to the member. The member can be fixed with respect to a global coordinate system or with respect to a local coordinate system. The term unclamp refers to releasing the EMD from the member such that the EMD can move independently.

The term grip refers to the application of a force or torque to an EMD by a drive mechanism that causes motion of the EMD without slip in at least one degree of freedom. The term ungrip refers to the release of the application of force or torque to the EMD by a drive mechanism such that the position of the EMD is no longer constrained. In one example, an EMD gripped between two tires will rotate about its longitudinal axis when the tires move longitudinally relative to one another. The rotational movement of the EMD is different than the movement of the two tires. The position of an EMD that is gripped is constrained by the drive mechanism. The term buckling refers to the tendency of a flexible EMD when under axial compression to bend away from the longitudinal axis or intended path along which it is being advanced. In one embodiment axial compression occurs in response to resistance from being navigated in the vasculature. The distance an EMD may be driven along its longitudinal axis without support before the EMD buckles is referred to herein as the device buckling distance. The device buckling distance is a function of the device's stiffness, geometry (including but not limited to diameter), and force being applied to the EMD. Buckling may cause the EMD to form an arcuate portion different than the intended path. Kinking is a case of buckling in which deformation of the EMD is non-elastic resulting in a permanent set.

The terms top, up, and upper refer to the general direction away from the direction of gravity and the terms bottom, down, and lower refer to the general direction in the direction of gravity. The term inwardly refers to the inner portion of a feature. The term outwardly refers to the outer portion of a feature. The term sterile interface refers to an interface or boundary between a sterile and non-sterile unit. For example, a cassette may be a sterile interface between the robotic drive and at least one EMD. The term sterilizable unit refers to an apparatus that is capable of being sterilized (free from pathogenic microorganisms). This includes, but is not limited to, a cassette, consumable unit, drape, device adapter, and sterilizable drive modules/units (which may include electromechanical components). Sterilizable Units may come into contact with the patient, other sterile devices, or anything else placed within the sterile field of a medical procedure.

The term on-device adapter refers to sterile apparatus capable of releasably pinching an MED to provide a driving interface. For example, the on-device adapter is also known as an end-effector or EMD capturing device. In one non-limiting embodiment, the on-device adapter is a collet that is operatively controlled robotically to rotate the EMD about its longitudinal axis, to pinch and/or unpinch the EMD to the collet, and/or to translate the EMD along its longitudinal axis. In one embodiment the on-device adapter is a hub-drive mechanism such as a driven gear located on the hub of an EMD.

Figure 1:
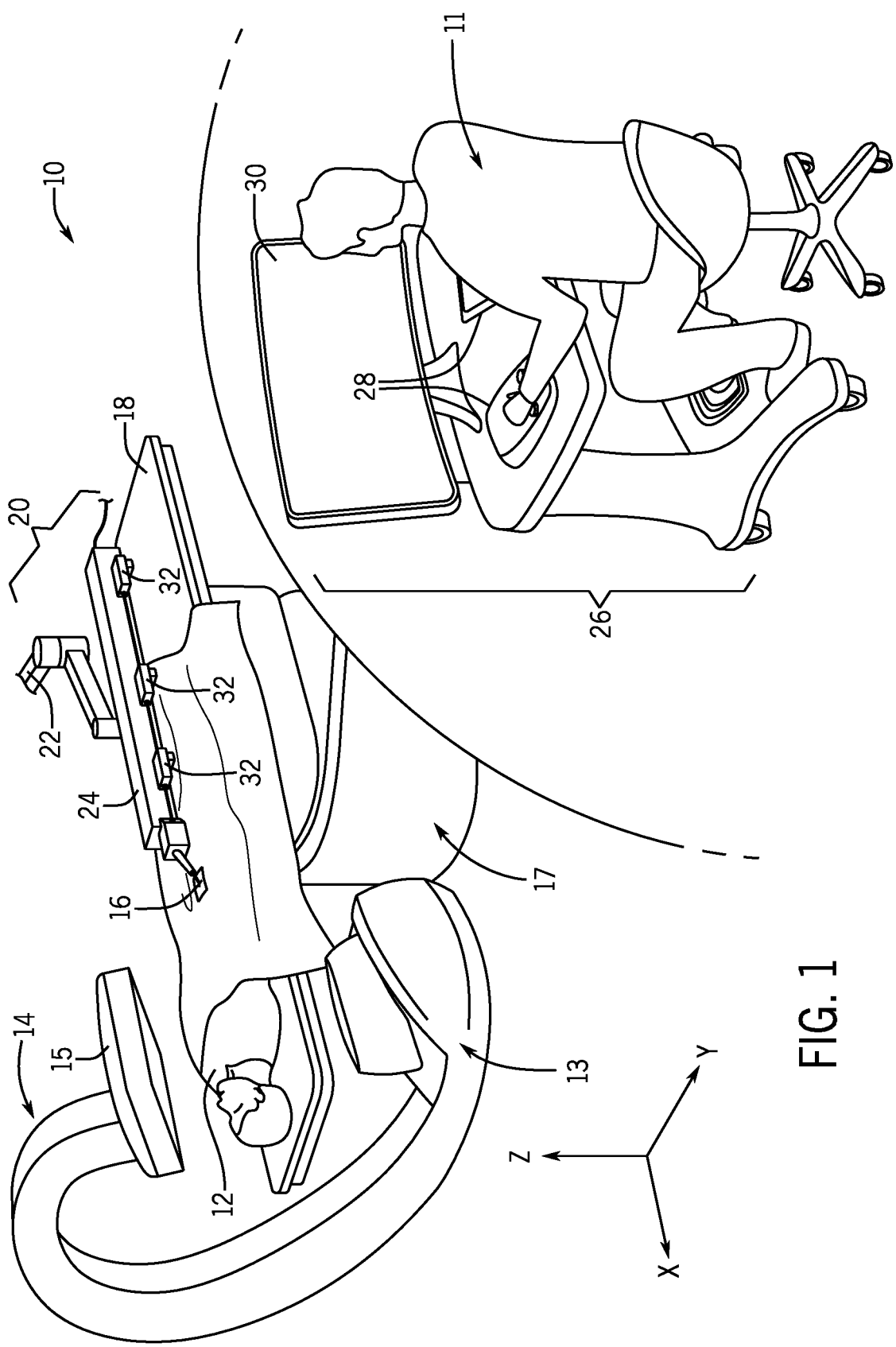
FIG. 1 is a perspective view of an exemplary catheter-based procedure system in accordance with an embodiment.

FIG. 1 is a perspective view of an exemplary catheter-based procedure system 10 in accordance with an embodiment. Catheter-based procedure system 10 may be used to perform catheter-based medical procedures, e.g., percutaneous intervention procedures such as a percutaneous coronary intervention (PCI) (e.g., to treat STEMI), a neurovascular interventional procedure (NVI) (e.g., to treat an emergent large vessel occlusion (ELVO)), peripheral vascular intervention procedures (PVI) (e.g., for critical limb ischemia (CLI), etc.). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedure.

Catheter-based procedure system 10 includes, among other elements, a bedside unit 20 and a control station 26. Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, a rail on the patient table 18, a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In an embodiment, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow the user or operator 11 to perform a catheter-based medical procedure via a robotic system by operating various controls such as the controls and inputs located at the control station 26. Bedside unit 20, and in particular robotic drive 24, may include any number and/or combination of components to provide bedside unit 20 with the functionality described herein. A user or operator 11 at control station 26 is referred to as the control station user or control station operator and referred to herein as user or operator. A user or operator at bedside unit 20 is referred to as bedside unit user or bedside unit operator. The robotic drive 24 includes a plurality of device modules 32a-d mounted to a rail or linear member 60 (shown in FIG. 3). The rail or linear member 60 guides and supports the device modules. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with control station 26, allowing signals generated by the user inputs of control station 26 to be transmitted wirelessly or via hardwire to bedside unit 20 to control various functions of bedside unit 20. As discussed below, control station 26 may include a control computing system 34 (shown in FIG. 2) or be coupled to the bedside unit 20 through a control computing system 34. Bedside unit 20 may also provide feedback signals (e.g., loads, speeds, operating conditions, warning signals, error codes, etc.) to control station 26, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components. Control station 26 or other similar control system may be located either at a local site (e.g., local control station 38 shown in FIG. 2) or at a remote site (e.g., remote control station and computer system 42 shown in FIG. 2). Catheter procedure system 10 may be operated by a control station at the local site, a control station at a remote site, or both the local control station and the remote control station at the same time. At a local site, user or operator 11 and control station 26 are located in the same room or an adjacent room to the patient 12 and bedside unit 20. As used herein, a local site is the location of the bedside unit 20 and a patient 12 or subject (e.g., animal or cadaver) and the remote site is the location of a user or operator 11 and a control station 26 used to control the bedside unit 20 remotely. A control station 26 (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, in different rooms in the same building, different buildings in the same city, different cities, or other different locations where the remote site does not have physical access to the bedside unit 20 and/or patient 12 at the local site.

Control station 26 generally includes one or more input modules 28 configured to receive user inputs to operate various components or systems of catheter-based procedure system 10. In the embodiment shown, control station 26 allows the user or operator 11 to control bedside unit 20 to perform a catheter-based medical procedure. For example, input modules 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input modules 28 may include one or more touch screens, joysticks, scroll wheels, and/or buttons. In addition to input modules 28, the control station 26 may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed, the power (e.g., electrical power) is shut off or removed to bedside unit 20. When in a speed control mode, a multiplier button acts to increase or decrease the speed at which the associated component is moved in response to a manipulation of input modules 28.

When in a position control mode, a multiplier button changes the mapping between input distance and the output commanded distance. Device selection buttons allow the user or operator 11 to select which of the percutaneous intervention devices loaded into the robotic drive 24 are controlled by input modules 28. Automated move buttons are used to enable algorithmic movements that the catheter-based procedure system 10 may perform on a percutaneous intervention device without direct command from the user or operator 11. In one embodiment, input modules 28 may include one or more controls or icons (not shown) displayed on a touch screen (that may or may not be part of a display 30), that, when activated, causes operation of a component of the catheter-based procedure system 10. Input modules 28 may also include a balloon or stent control that is configured to inflate or deflate a balloon and/or deploy a stent. Each of the input modules 28 may include one or more buttons, scroll wheels, joysticks, touch screen, etc. that may be used to control the particular component or components to which the control is dedicated. In addition, one or more touch screens may display one or more icons (not shown) related to various portions of input modules 28 or to various components of catheter-based procedure system 10.

Control station 26 may include a display 30. In other embodiments, the control station 26 may include two or more displays 30. Display 30 may be configured to display information or patient specific data to the user or operator 11 located at control station 26. For example, display 30 may be configured to display image data (e.g., X-ray images, MRI images, CT images, ultrasound images, etc.), hemodynamic data (e.g., blood pressure, heart rate, etc.), patient record information (e.g., medical history, age, weight, etc.), lesion or treatment assessment data (e.g., IVUS, OCT, FFR, etc.). In addition, display 30 may be configured to display procedure specific information (e.g., procedural checklist, recommendations, duration of procedure, catheter or guidewire position, volume of medicine or contrast agent delivered, etc.). Further, display 30 may be configured to display information to provide the functionalities associated with control computing system 34 (shown in FIG. 2). Display 30 may include touch screen capabilities to provide some of the user input capabilities of the system.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with control station 26. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment imaging system 14 is a fluoroscopy system including a C-arm having an X-ray source 13 and a detector 15, also known as an image intensifier.

Imaging system 14 may be configured to take X-ray images of the appropriate area of patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of control station 26 to properly position a guidewire, guide catheter, microcatheter, stent retriever, coil, stent, balloon, etc. during the procedure.

The image or images may be displayed on display 30. For example, images may be displayed on display 30 to allow the user or operator 11 to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
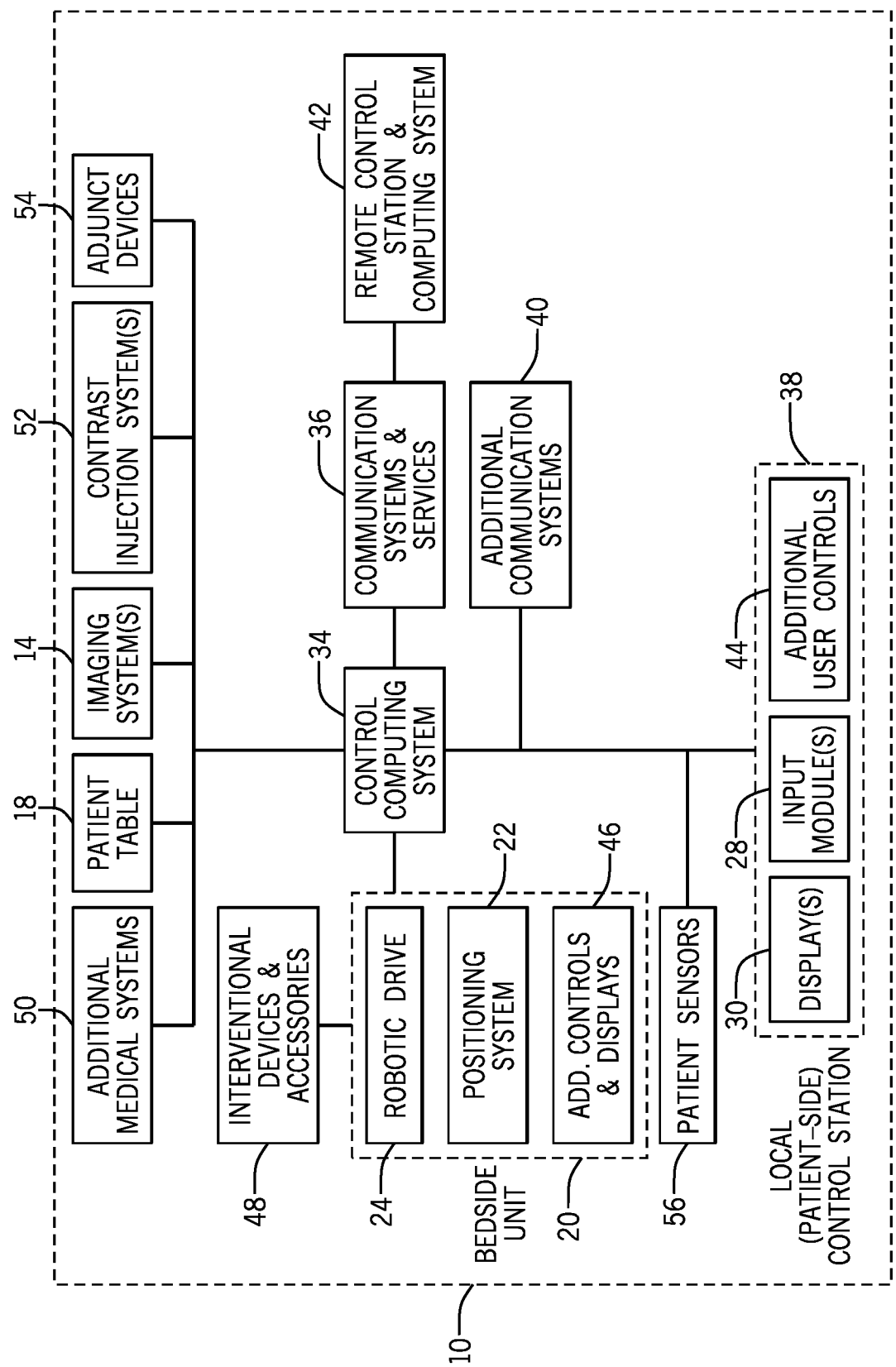
FIG. 2 is a schematic block diagram of an exemplary catheter-based procedure system in accordance with an embodiment.

FIG. 2 is a block diagram of catheter-based procedure system 10 in accordance with an exemplary embodiment. Catheter-procedure system 10 may include a control computing system 34. Control computing system 34 may physically be, for example, part of control station 26 (shown in FIG. 1). Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In an embodiment, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to generate control signals based on the user's interaction with input modules 28 (e.g., of a control station 26 (shown in FIG. 1) such as a local control station 38 or a remote control station 42) and/or based on information accessible to control computing system 34 such that a medical procedure may be performed using catheter-based procedure system 10. The local control station 38 includes one or more displays 30, one or more input modules 28, and additional user controls 44. The remote control station and computing system 42 may include similar components to the local control station 38. The remote 42 and local 38 control stations can be different and tailored based on their required functionalities. The additional user controls 44 may include, for example, one or more foot input controls. The foot input control may be configured to allow the user to select functions of the imaging system 14 such as turning on and off the X-ray and scrolling through different stored images.

In another embodiment, a foot input device may be configured to allow the user to select which devices are mapped to scroll wheels included in input modules 28. Additional communication systems 40 (e.g., audio conference, video conference, telepresence, etc.) may be employed to help the operator interact with the patient, medical staff (e.g., angiosuite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

Figure 3:
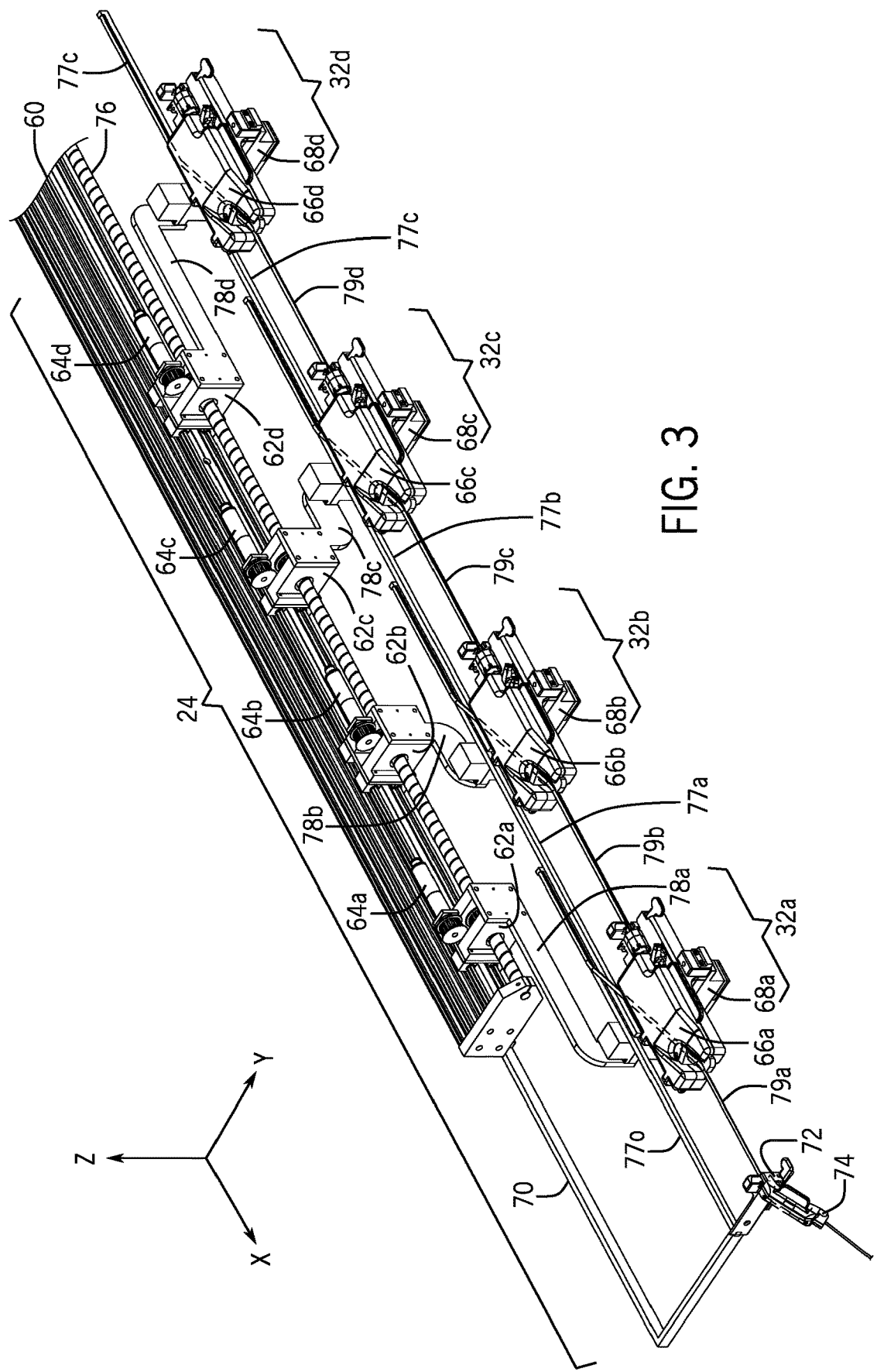
FIG. 3 is a perspective view of a robotic drive for a catheter-based procedure system in accordance with an embodiment.

As mentioned, control computing system 34 is in communication with bedside unit 20 which includes a robotic drive 24, a positioning system 22 and may include additional controls and displays 46, and may provide control signals to the bedside unit 20 to control the operation of the motors and drive mechanisms used to drive the percutaneous intervention devices (e.g., guidewire, catheter, etc.). The various drive mechanisms may be provided as part of a robotic drive 24. FIG. 3 is a perspective view of a robotic drive for a catheter-based procedure system 10 in accordance with an embodiment. In FIG. 3, a robotic drive 24 includes multiple device modules 32a-d coupled to a linear member 60. Each device module 32a-d is coupled to the linear member 60 via a stage 62a-d moveably mounted to the linear member 60. A device module 32a-d may be connected to a stage 62a-d using a connector such as an offset bracket 78a-d. In another embodiment, the device module 32a-d is directly mounted to the stage 62a-d. Each stage 62a-d may be independently actuated to move linearly along the linear member 60. Accordingly, each stage 62a-d (and the corresponding device module 32a-d coupled to the stage 62a-d) may independently move relative to each other and the linear member 60. A drive mechanism is used to actuate each stage 62a-d. In the embodiment shown in FIG. 3, the drive mechanism includes independent stage translation motors 64a-d coupled to each stage 62a-d and a stage drive mechanism 76, for example, a lead screw via a rotating nut, a rack via a pinion, a belt via a pinion or pulley, a chain via a sprocket, or the stage translation motors 64a-d may be linear motors themselves. In some embodiments, the stage drive mechanism 76 may be a combination of these mechanisms, for example, each stage 62a-d could employ a different type of stage drive mechanism. In an embodiment where the stage drive mechanism is a lead screw and rotating nut, the lead screw may be rotated and each stage 62a-d may engage and disengage from the lead screw to move, e.g., to advance or retract. In the embodiment shown in FIG. 3, the stages 62a-d and device modules 32a-d are in a serial drive configuration.

Each device module 32a-d includes a drive module 68a-d and a cassette 66a-d mounted on and coupled to the drive module 68a-d. In the embodiment shown in FIG. 3, each cassette 66a-d is mounted to the drive module 68a-d in a vertical orientation. In other embodiments, each cassette 66a-d may be mounted to the drive module 68a-d in other mounting orientations. Each cassette 66a-d is configured to interface with and support a proximal portion of an EMD (not shown). In addition, each cassette 66a-d may include elements to provide one or more degrees of freedom in addition to the linear motion provided by the actuation of the corresponding stage 62a-d to move linearly along the linear member 60. For example, the cassette 66a-d may include elements that may be used to rotate the EMD when the cassette is coupled to the drive module 68a-d. Each drive module 68a-d includes at least one coupler to provide a drive interface to the mechanisms in each cassette 66a-d to provide the additional degree of freedom. Each cassette 66a-d also includes a channel in which a device support 79a-d is positioned, and each device support 79a-d is used to prevent an EMD from buckling. A support arm 77a, 77b, and 77c is attached to each device module 32a, 32b, and 32c, respectively, to provide a fixed point for support of a proximal end of the device supports 79b, 79c, and 79d, respectively. The robotic drive 24 may also include a device support connection 72 connected to a device support 79, a distal support arm 70 and a support arm 77o. Support arm 77o is used to provide a fixed point for support of the proximal end of the distal most device support 79a housed in the distal most device module 32a. In addition, an introducer interface support (redirector) 74 may be connected to the device support connection 72 and an EMD (e.g., an introducer sheath). The configuration of robotic drive 24 has the benefit of reducing volume and weight of the drive robotic drive 24 by using actuators on a single linear member.

To prevent contaminating the patient with pathogens, healthcare staff use aseptic technique in a room housing the bedside unit 20 and the patient 12 or subject (shown in FIG. 1). A room housing the bedside unit 20 and patient 12 may be, for example, a cath lab or an angio suite. Aseptic technique consists of using sterile barriers, sterile equipment, proper patient preparation, environmental controls and contact guidelines. Accordingly, all EMDs and interventional accessories are sterilized and can only be in contact with either sterile barriers or sterile equipment. In an embodiment, a sterile drape (not shown) is placed over the non-sterile robotic drive 24. Each cassette 66a-d is sterilized and acts as a sterile interface between the draped robotic drive 24 and at least one EMD. Each cassette 66a-d can be designed to be sterile for single use or to be re-sterilized in whole or part so that the cassette 66a-d or its components can be used in multiple procedures.

As mentioned, the linear movement of each device module 32a-d along the rail or linear member 60 may be independently controlled. In an embodiment, the range of linear motion of each of the different device modules along the rail 60 can overlap. In other words, the range of positions where different device module can be located along the rail 60 can overlap such that different device modules can occupy the same space at different times, although not at the same time. In one embodiment, two successive device modules (e.g., 32a and 32b, 32b and 32c, 32c and 32d) can have overlapping ranges of linear motion. In another embodiment, non-successive modules (e.g., 32a and 32c or 32b and 32d) can have overlapping ranges of linear motion.

As mentioned, each cassette 66a-d of each device module 32a-d is configured to interface with and support a proximal portion of an EMD. In various embodiments, different numbers and types of EMDs may be utilized in the robotic drive 24 based on, for example, the type of procedure being performed using the robotic drive 24. For example, an EMD may be positioned in the first device module 32a, while the second 32b, third 32c, and fourth 32d device modules are unpopulated. In various other embodiments, any combination of populated device modules may be implemented using robotic drive 24 such as for example, populating the first 32a and second 32b device module with an EMD, populating the first 32a and fourth 32d device module with an EMD, populating the first 32a, second 32b and third 32c device module with an EMD, populating the first 32a, third 32c and fourth 32d device module with an EMD, populating the first 32a, second 32b and fourth 32d device module with an EMD, populating the first 32a, second 32b, and fourth 32d device module with an EMD, etc. In addition, each device module 32a-d may receive different types of EMDs, including but not limited to, a sheath (also referred to as a long sheath), a guide catheter, a balloon guide catheter, a guiding sheath, a diagnostic guidewire (also known as a angiographic guidewire), an intermediate catheter, a support catheter, a digital access catheter, an aspiration catheter, a microcatheter, a delivery catheter, a wire-based EMD (e.g., a guidewire, a microwire, a stent retriever, an embolization coil), etc. In some embodiments, the specific configuration of populated device modules and the specific types of EMDs, may be changed during a procedure, i.e., a procedure may utilize more than one configurations.

Hub driving or proximal driving refers to holding on to and manipulating an EMD from a proximal position (e.g., geared adapter on catheter hub). In one embodiment, hub driving refers to imparting a force or torque to the hub of a catheter to translate and/or rotate the catheter. In hub driving, often applying typical clinical loads would cause the EMD to buckle. Because of this, hub driving often requires additional anti-buckling features incorporated into the EMD or driving mechanism. For EMDs that do not have hubs or other interfaces (e.g., guidewire), device adapters may be added to the device to act as a temporary hub. Shaft driving refers to holding on to and manipulating an EMD along its shaft. For example, an on-device adapter may be placed just proximal of the hub or Y-connector the device is inserted into. If the location of the on-device adapter is at the proximity of an insertion point (to the body or another catheter, or valve), shaft driving does not typically require anti-buckling features (but may include anti-buckling features to improve drive capability). This type of shaft driving can be referred to as distal driving. In FIG. 3, each drive module 32a-d is configured to hub drive an EMD. However, in various embodiments described further below, the robotic drive 24 or one/or more device modules 32a-d may be configured to provide one or more EMDs that are shaft driven. As mentioned above, in FIG. 3 the drive modules 32a-d are in a serial drive configuration (e., over-the-wire (OTW). A serial drive configuration or layout uses actuators (or drives) to drive an EMD into a more distal EMD hub. EMDs may also be driven in a parallel configuration or layout. A parallel configuration or layout uses serial actuators (or drives) to drive two or more EMDs into a common EMD hub. Serial and parallel configurations can be added together in different combinations. In various embodiments described further below, the robotic drive 24 and/or one or more drive modules 32a-d may be configured to provide one or more drive modules 32a-d or EMDs in a parallel drive configuration (e.g., rapid exchange).

Figure 4:
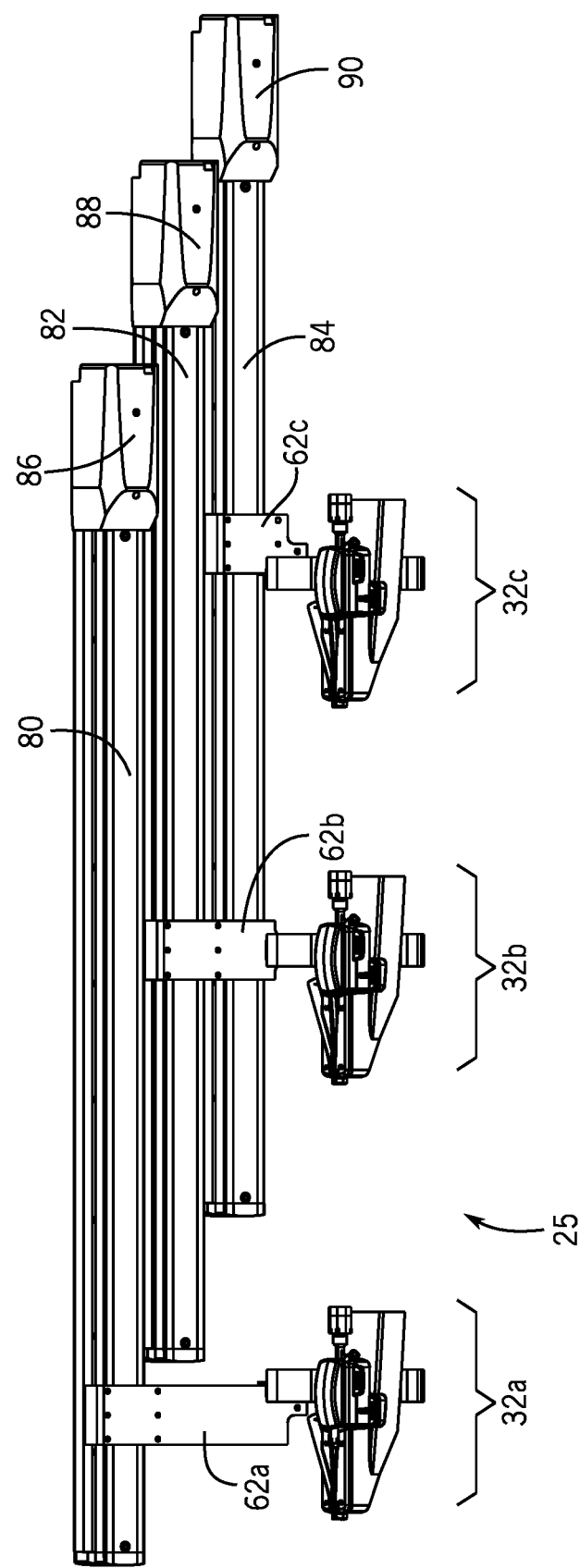
FIG. 4 is a perspective view of a portion of robotic drive for a catheter-based procedure system in accordance with an embodiment.

In an alternative embodiment, a separate rail or linear member may be used to support and translate each stage 62a-d and device module 32a-d. FIG. 4 is a perspective view of a portion of a robotic drive for a catheter procedure system in accordance with an embodiment. Robotic drive 25 includes a device module 32a coupled to a first rail or linear member 80 using a stage 62a, a device module 32b coupled to a second rail or linear member 82 using a stage 62b and a device module 32c coupled to a third rail or linear member 84 using a stage 62c. The first rail 60, second rail 82 and third rail 84 are parallel to one another. A first stage translation motor 86 is used to translate a stage 62a along the first rail 80, a second stage translation motor 88 is used to translate a stage 62b along the second rail 82 and a third stage translation motor 90 is used to translate a stage 62b along the third rail 84. One advantage of the configuration shown in FIG. 4 is that the stage translation motors used for linear translation are fixed. Accordingly, the mass of the moving device modules 32a-c and stages 62a-c is reduced and relocation to a more beneficial point (i.e., towards the back of the rail to help react moment loading). In various other embodiments described below with respect to FIGS. 71-77, a robotic drive with multiple parallel rails may be configured to allow device modules to pass each other.

Figure 5:
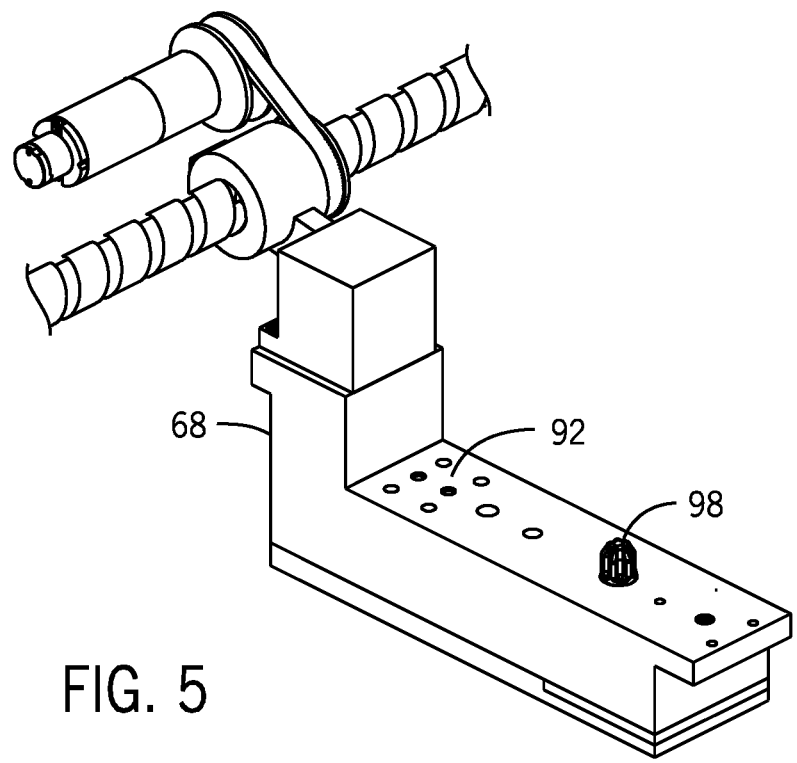
FIG. 5 is a perspective view of a drive module attached to a stage in accordance with an embodiment.
Figure 6:
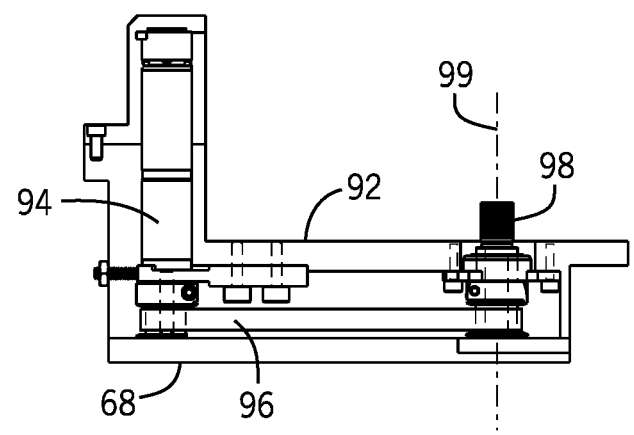
FIG. 6 is a side cross-sectional view of a drive module in accordance with an embodiment.

As mentioned above, each device module 32a-d includes a drive module 68a-d and a cassette 66a-d mounted on and coupled to the corresponding drive module 68a-d. Each cassette 66a-d is releasably coupled to a drive module 68a-d. FIG. 5 is a perspective view of a drive module attached to a stage in accordance with an embodiment and FIG. 6 is a side cross-sectional view of a drive module in accordance with an embodiment. Referring to FIGS. 5 and 6, the drive module includes a mounting surface 92 and a coupler 98. A motor 94 is connected to the coupler 98 via, for example, a belt 96. The motor 94 and belt 96 are used to change the rotational position of the coupler 98. In an embodiment, coupler 98 rotates about a coupler axis 99. Drive module 68 may include an encoder (not shown) for device position feedback. The drive module 68 shown in FIGS. 5 and 6 has one coupler 98, however, it should be understood that the drive module 68 may have more than one coupler 98 and more than one motor 94, as described further below. The rotation of the coupler 98 may be used to provide another degree of freedom to an elongated medical device positioned in a cassette mounted on the mounting surface 92 so as to interface with the coupler 98. For example, the coupler 98 may be used to rotate an elongated medical device in the cassette. Alternatively, the coupler 98 may be used to translate an elongated medical device. If the drive module 68 has two or more couplers 98, each coupler may be used to provide a different degree of freedom for one elongated medical device or multiple elongated medical devices coupled to the same drive module. As mentioned, a cassette 66 (shown in FIG. 3) may be positioned on the mounting surface 92 of the drive module 68 and used to interface with an elongated medical device positioned in the cassette. As described further below with respect to FIG. 100, in an embodiment the drive module 68 may also include one or more additional elements (not shown) on the mounting surface 92 such as, for example, positioning pins, alignment pins, locking pins, etc. to interact with elements on a cassette 66 mounted on the drive module 68 to enable a releasable attachment of the cassette 66 to the drive module 68.

Figure 7:
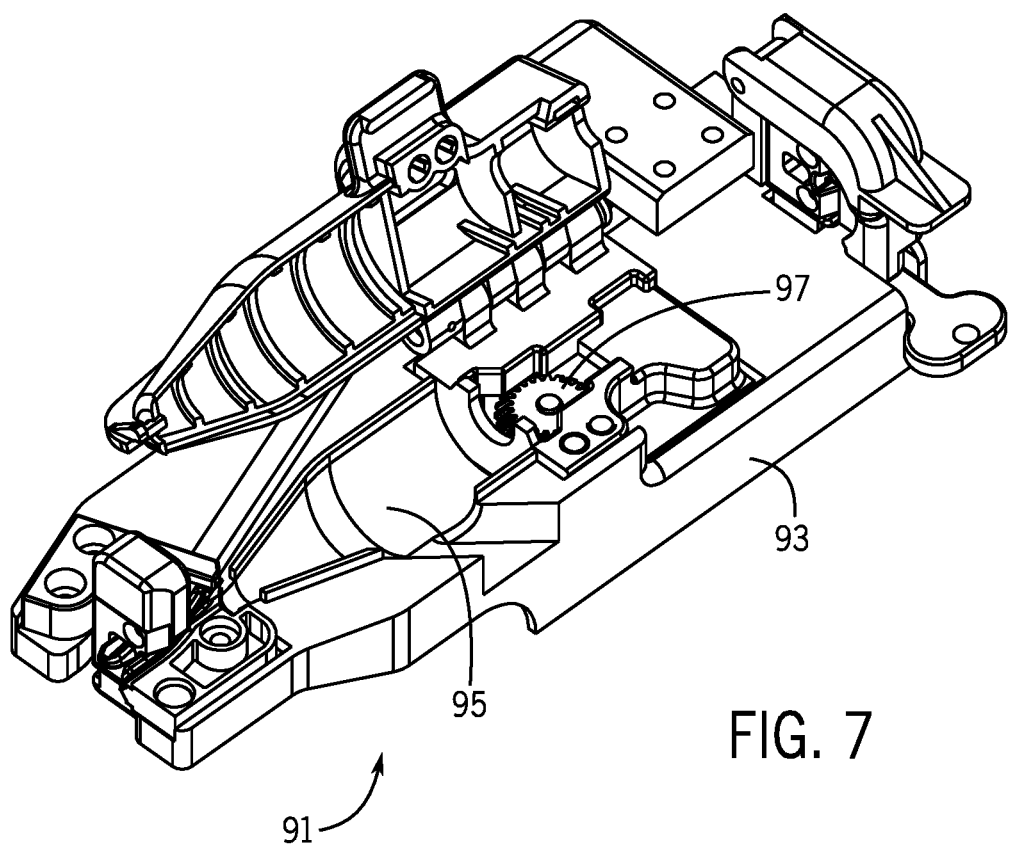
FIG. 7 is a perspective view of an exemplary cassette in accordance with an embodiment.
Figure 8:
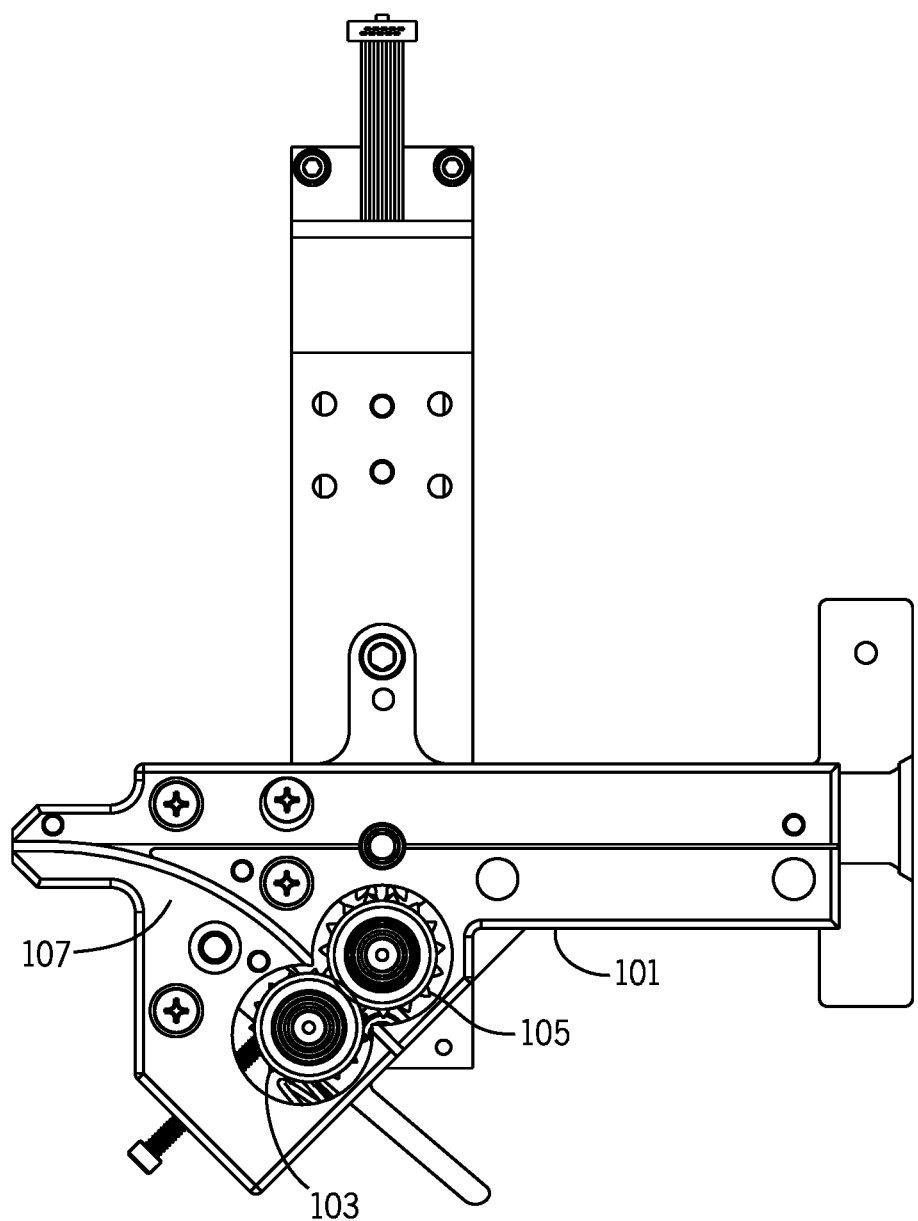
FIG. 8 is a top view of an exemplary cassette attached to a drive module in accordance with an embodiment.
Figure 9:
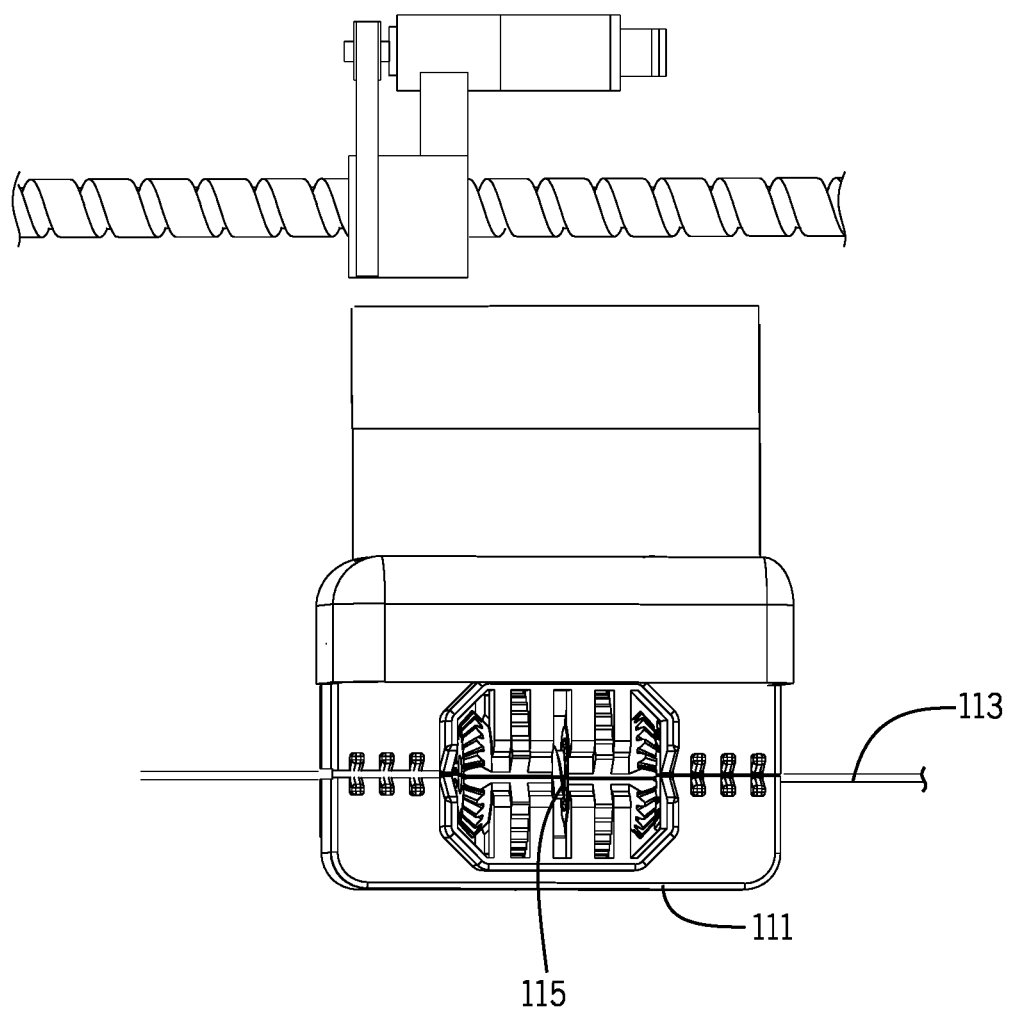
FIG. 9 is a top view of an exemplary cassette attached to a drive module which is connected to a stage in accordance with an embodiment.

FIG. 7 is a perspective view of an exemplary cassette in accordance with an embodiment. In FIG. 7, the cassette 91 includes a housing 93. The housing includes a cradle 95 configured to receive an elongated medical device. A bevel gear 97 is used to interface with a coupler 98 (shown in FIG. 5) of a drive module and to interface with the elongated medical device to rotate the elongated medical device. In other embodiments, a cassette may be configured to provide a linear degree of freedom or a cassette may be configured to provide two or more degrees of freedom. FIG. 8 is a top view of an exemplary cassette attached to a drive module in accordance with an embodiment. In FIG. 8, the cassette 101 includes a pair of tires 103, 105 which can be connected to the coupler 98 (not shown) of a drive module. The pair of tires 103, 105 may be used to provide linear motion to an elongated medical device positioned in a channel 107. An embodiment of a device module including a cassette 101 is described further below with respect to FIGS. 66-69. FIG. 9 is a top view of an exemplary cassette attached to a drive module which is connected to a stage in accordance with an embodiment. In FIG. 9, the cassette 111 is configured to provide two degrees of freedom in addition to the translation of the assembly. For example, cassette 111 may be configured to provide rotation and to pinch and unpinch an elongated medical device 113 positioned in a channel 115. Such as cassette may be mounted to, for example, a drive module with two or more couplers. Embodiments of a device module including a cassette 111 and a drive module with two or more couplers are described further below with respect to FIGS. 43-47. In another embodiment described further below with respect to FIGS. 48 and 49, two individual drive modules, either mechanically or electrically coupled together, can provide two degrees of freedom for the cassette 111.

Figure 10:
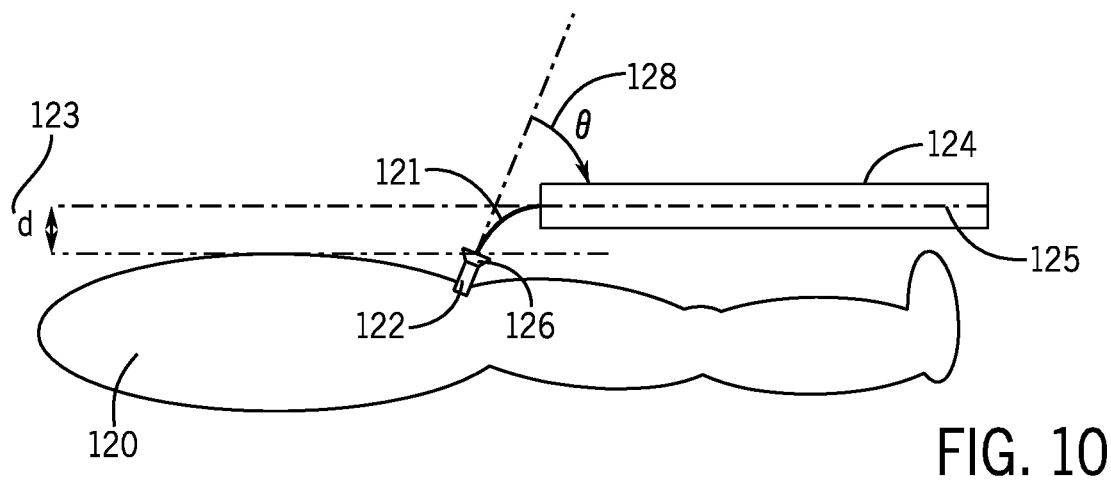
FIG. 10 is a diagram illustrating an elongated medical device axis of manipulation and the introductory point into the patient.

As shown in FIG. 1, one or more EMDs may enter the body of a patient (e.g., a vessel) at an insertion point 16 using, for example, an introducer and introducer sheath. The introducer sheath typically orients at an angle, usually less than 45 degrees, to the axis of the vessel in a patient 120 (shown in FIGS. 10-12). Any height difference between where the EMD enters the body (the introducer sheath's proximal opening 126 shown in FIG. 10) and the longitudinal drive axis of the robotic drive 124 will directly affect the working length for the elongated medical device. The more an elongated medical device needs to compensate for differences in displacement and angle, the less the elongated medical device will be able to enter the body when the robotic drive is at its maximum distal (forward) position. It is beneficial to have a robotic drive that is at the same height and angle as the introducer sheath. FIG. 10 is a diagram illustrating an elongated medical device axis of manipulation and the introductory point into the patient. FIG. 10 shows a height difference (d) 123 between the proximal end 126 of the introducer sheath 122 and the longitudinal device axis and an angular difference (θ) 128 between the introducer sheath 122 and the longitudinal device axis 125 of the robotic drive 124. The elongated medical device 121 is constrained on each axis and creates a curve with tangentially aligned end points. The length of this curve represents a length of the elongated medical device 121 that cannot be driven any further forward by the robotic drive 124 and cannot enter the introducer sheath 122 due to the misalignment. A higher angle (θ) 128 also leads to higher device friction. In general, lower angular misalignment (θ) 128, and linear misalignment d 123 can lead to reduced friction and reduced loss of working length. While FIG. 10 illustrates a simplified example illustrating one linear and one rotational offset, it should be understood that this problem occurs in three dimensions, namely, three linear offsets and three rotational offsets. The thickness of the robotic drive 124 also plays a role in determining the location of the longitudinal device axis 125 relative to the introducer sheath 122.

Figure 11A:
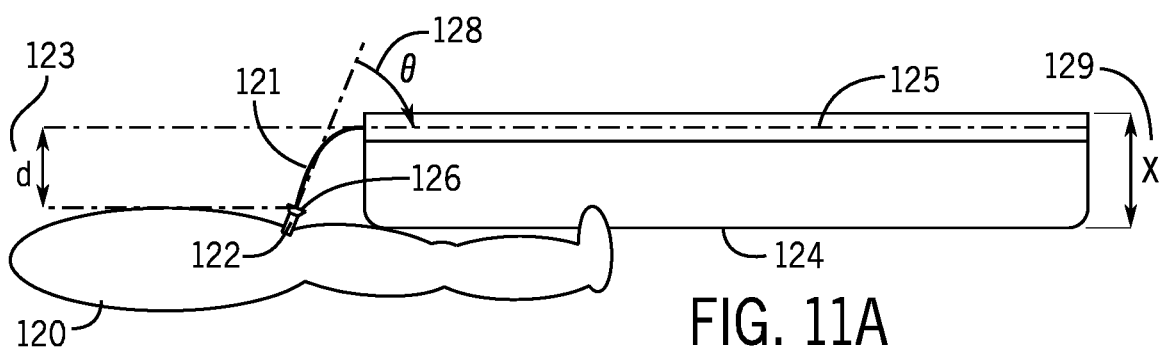
FIGS. 11a and 11b are diagrams illustrating the effect of the thickness of a robotic drive on the loss of working length.
Figure 11B:
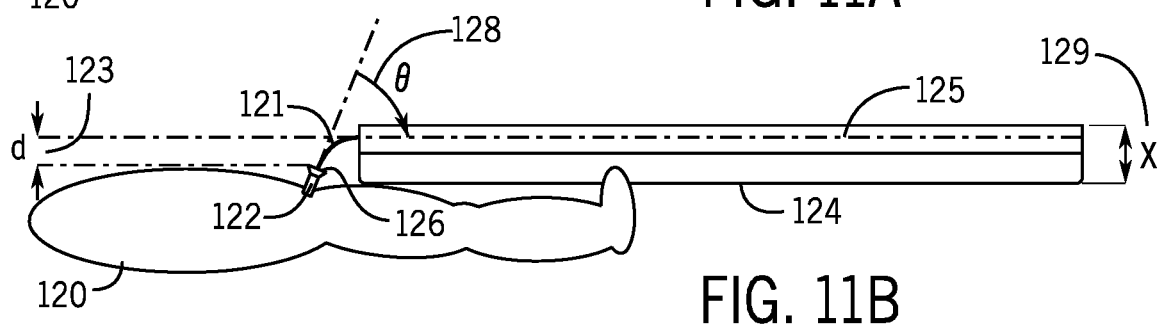
Figure 12:
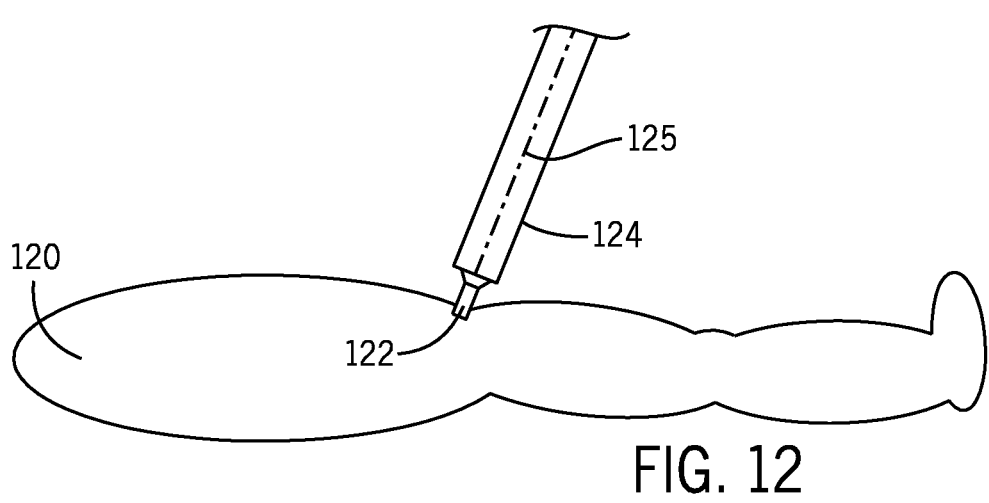
FIG. 12 is a diagram illustrating an exemplary orientation to minimize loss of working length.

FIGS. 11a and 11b are diagrams illustrating the effect of the thickness of a drive module, or robotic drive as a whole, on the loss of working length. FIG. 11a shows the location of the longitudinal device axis 125 of a robotic drive 124 relative to the introducer sheath 122, indicated by d 123, when the robotic drive 124 is thick as shown by the distance (X) 129 between an upper surface and a bottom surface of the robotic drive 124. FIG. 11b shows the location of the longitudinal device axis 125 of a robotic drive 124 relative to the introducer sheath 122, indicated by a shorter d 123, when the robotic drive 124 is shallow as shown by the distance (X) 129 between an upper surface and a bottom surface of the robotic drive 124. Reducing the thickness of the robotic drive 124 to get close to the patient and introducer sheath reduces the distance 123 between introducer sheath axis and device axis and reduces the loss of working length of the elongated medical device. FIG. 12 is a diagram illustrating an exemplary orientation to minimize loss of working length. In FIG. 12, the robotic drive is positioned to align the longitudinal device axis 125 of the robotic drive 124 to that of the introducer sheath 122. This eliminates loss of working length due to angular and linear misalignment of the elongated medical device. However, this position for the robotic drive 124 may not be practical due to the length and size of the robotic drive 124. Orienting a robotic drive at a sharp angle also affects the usability by making it difficult to load and unload elongated medical devices, and adjust and handle the robotic drive.

Figure 13:
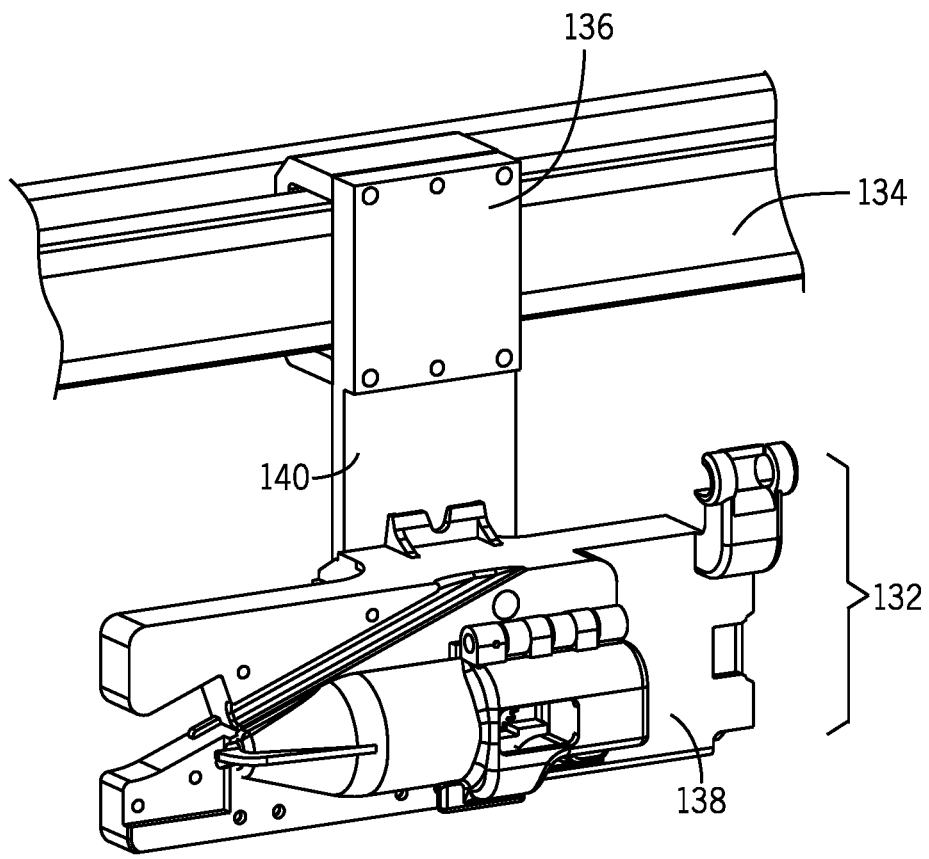
FIG. 13 is a perspective view of a device module with a horizontally mounted cassette in accordance with an embodiment.
Figure 14:
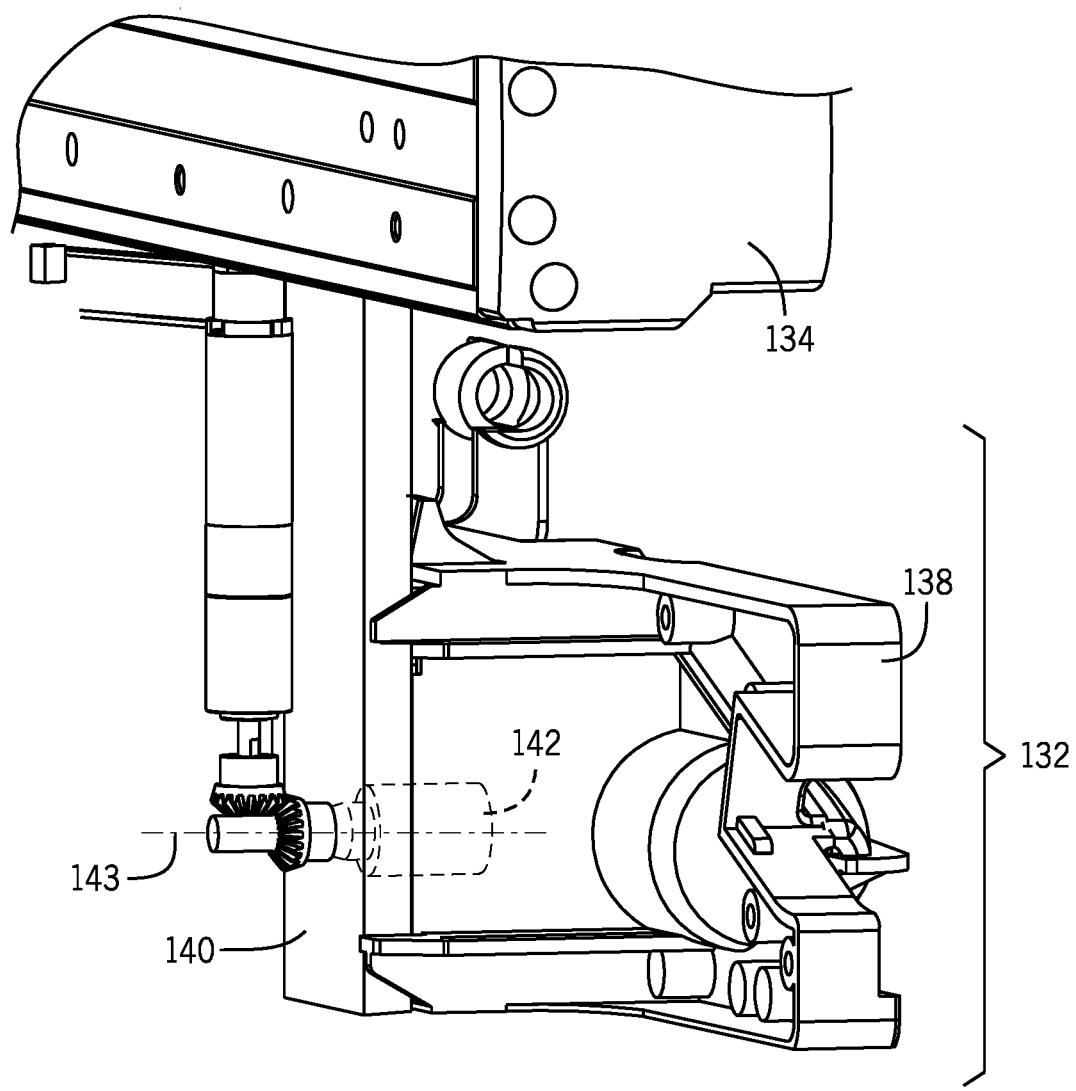
FIG. 14 is a rear perspective view of a device module with a horizontally mounted cassette in accordance with an embodiment.
Figure 15:
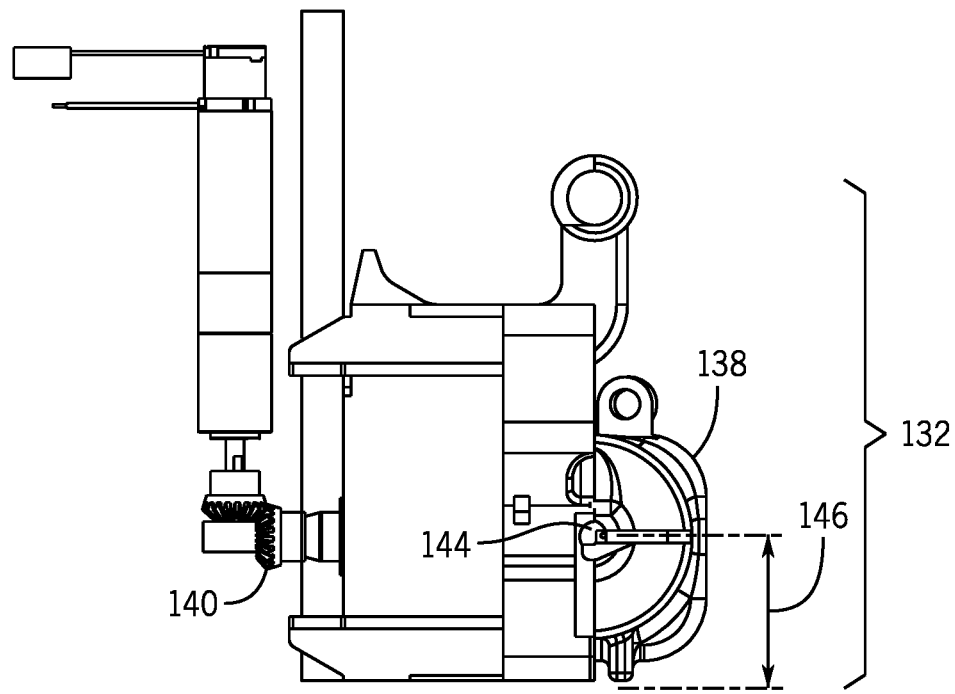
FIG. 15 is a front view of a distal end of a device module with a horizontally mounted cassette in accordance with an embodiment.
Figure 16:
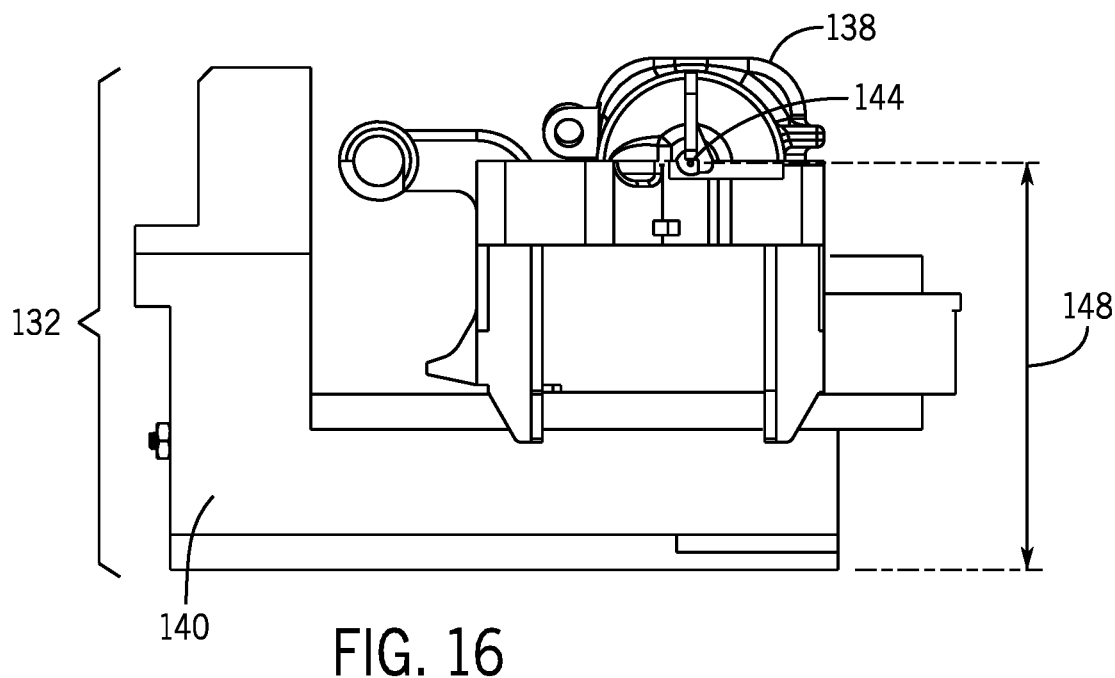
FIG. 16 is a front view of a distal end of a device module with a vertically mounted cassette in accordance with an embodiment.

To reduce the distance between the robotic drive and the patient and the distance between the longitudinal device axis of the robotic drive and the introducer sheath, the cassette of a device module 3 (shown in FIG. 3) may be mounted to the drive module in a horizontal orientation. FIG. 13 is a perspective view of a device module with a horizontally mounted cassette in accordance with an embodiment and FIG. 14 is a rear perspective view of a device module with a horizontally mounted cassette in accordance with an embodiment. In FIGS. 13 and 14, a device module 132 includes a cassette 138 that is horizontally mounted to a drive module 140. The device module 132 is connected to a stage 136 that is moveably mounted to a rail or linear member 134. The drive module 140 includes a coupler 142 that is used to provide a power interface to the cassette 138 to, for example, rotate an elongated medical device (not shown) positioned in the cassette. The coupler 142 rotates about an axis 143. By mounting the cassette 138 horizontally, the drive module 140 that the cassette 138 attaches to located off to the side and no longer positioned between the cassette 138 and the patient. FIG. 15 is a front view of a distal end of a device module with a horizontally mounted cassette in accordance with an embodiment. In FIG. 15, a distance 146 between the device axis of the elongated medical device 144 and the bottom surface of the device module 132 is shown. The horizontal mounting of the cassette 138 eliminates the need for the drive module 140 to be placed under the device axis and between the elongated medical device 144 and the patient. Rather, only a portion of the cassette 138 is positioned between the elongated medical device 138 and the patient. Horizontally mounting the cassette 138 also reduces the distance 146 between the elongated medical device and bottom surface of the device module 132 which allows the robotic drive to get closer to the patient and reduces loss of working length in an elongated medical device. By comparison, FIG. 16 is a front view of a distal end of a device module with a vertically mounted cassette in accordance with an embodiment. In FIG. 16, a device module 132 is shown where the cassette 138 is vertically mounted to a drive module 140. The drive module 140 is under the cassette 138 and increases the distance 148 between the device axis of the elongated medical device 144 and the bottom surface of the device module 132. This can prevent the device axis from being as close to the introducer (not shown) as possible. A drive module 140 positioned under the cassette 138 may also interfere with the patient. In various other embodiment, a cassette may be mounted to the drive module at any angle. In yet another embodiment, the cassette may be mounted vertically on an underside of the drive module to eliminate the need for a drive module between the device axis and the patient.

Figure 17:
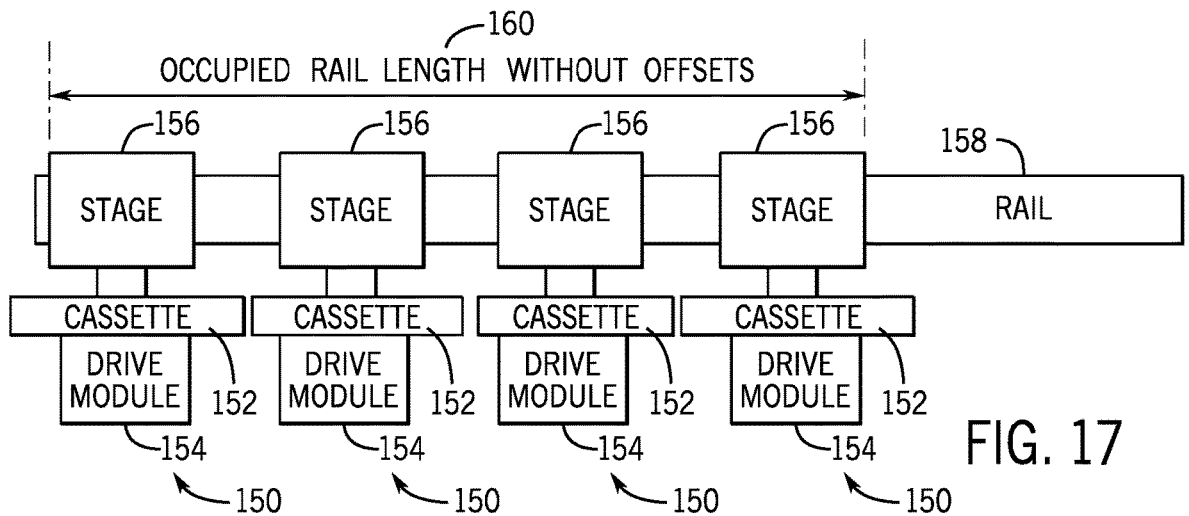
FIG. 17 is a block diagram illustrating an occupied length on a linear member without offsets between device modules and stages in accordance with an embodiment.

In order to reduce the length of the rail or linear member 60 (shown in FIG. 3) of the robotic drive system 24 (shown in FIG. 3), offset brackets 78 (shown in FIG. 3) may be used to create offsets between a stage and a device module to reduce gaps between stages on the linear member when cassettes are brought together. FIG. 17 is a block diagram illustrating an occupied length on a linear member without offsets between device modules and stages in accordance with an embodiment. As mentioned above, in one embodiment a device module may be directly mounted to a stage with no offset between the device module and the stage. In FIG. 17, four device modules 150 are shown and each device module 150 includes a cassette 152 mounted to a drive module 154. Each device module 150 is directly connected to a stage 156 which is coupled to a rail or linear member 158. When the device modules 150 are brought close together along the rail 158, the stages 156 for each device module 150 are also brought closer together. However, as shown in FIG. 17, the length of each cassette 152 of each device module 150 may limit how close each stage 156 may be brought to another stage 156 on the rail. The four stages 156 (plus safety cushions on each side) define an occupied rail length 160 which affects the overall length required for the rail 158. The occupied rail length and the overall length of the rail 158 may be shortened by using offsets and offset brackets as shown in FIGS. 18A-21.

Figure 18A:
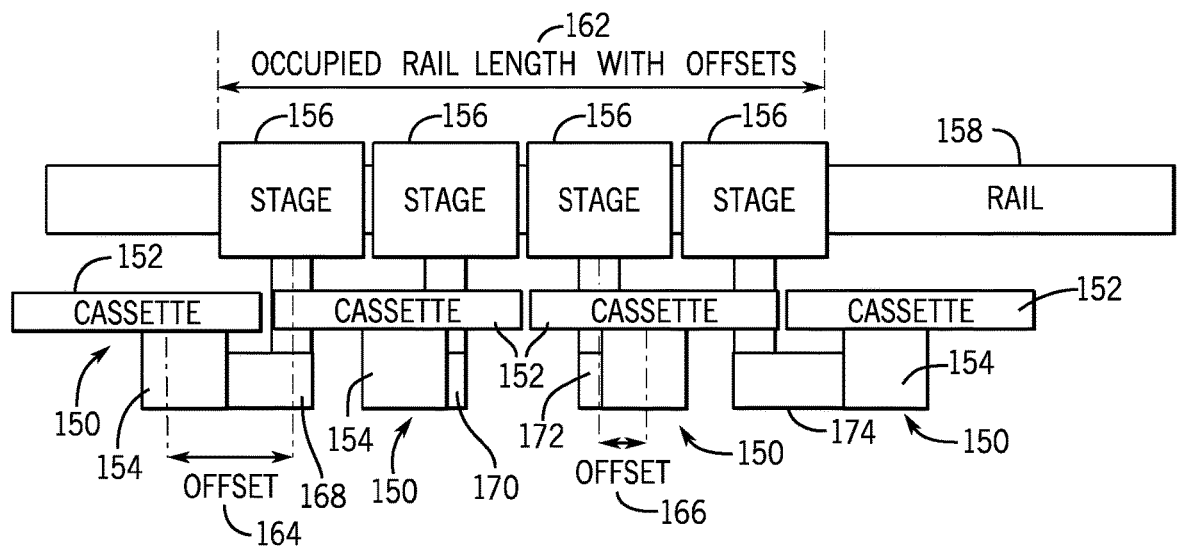
FIG. 18A is a block diagram illustrating occupied length on a linear member with offsets between device modules and stages in accordance with an embodiment.
Figure 18B:
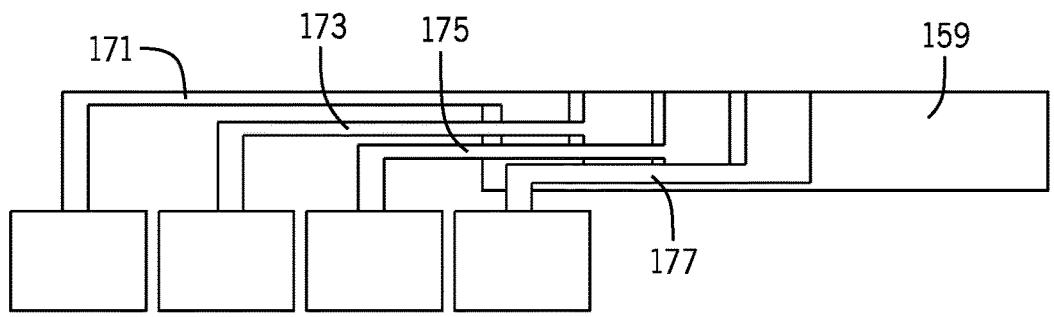
FIG. 18B is a block diagram illustrating an example offset bracket configuration in accordance with an embodiment.
Figure 18C:
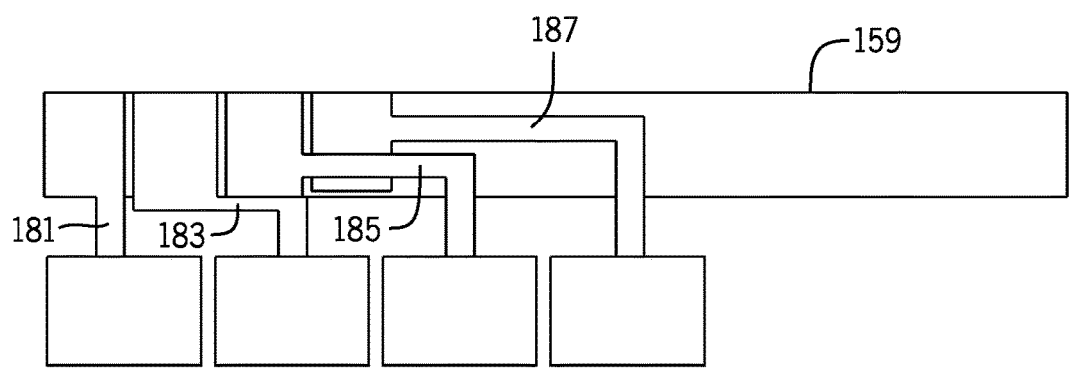
FIG. 18C is a block diagram illustrating an example offset bracket configuration in accordance with an embodiment.
Figure 19:
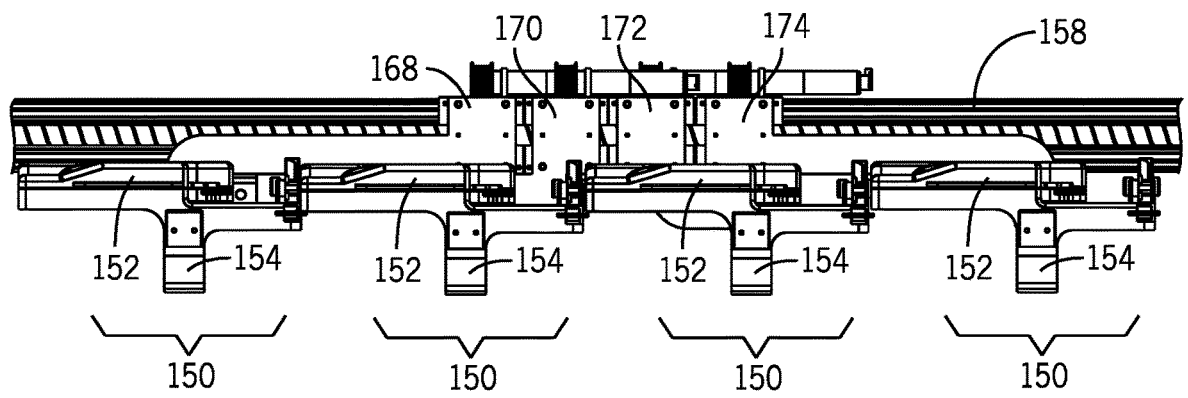
FIG. 19 is a side view of a robotic drive with offset brackets in accordance with an embodiment.
Figure 20:
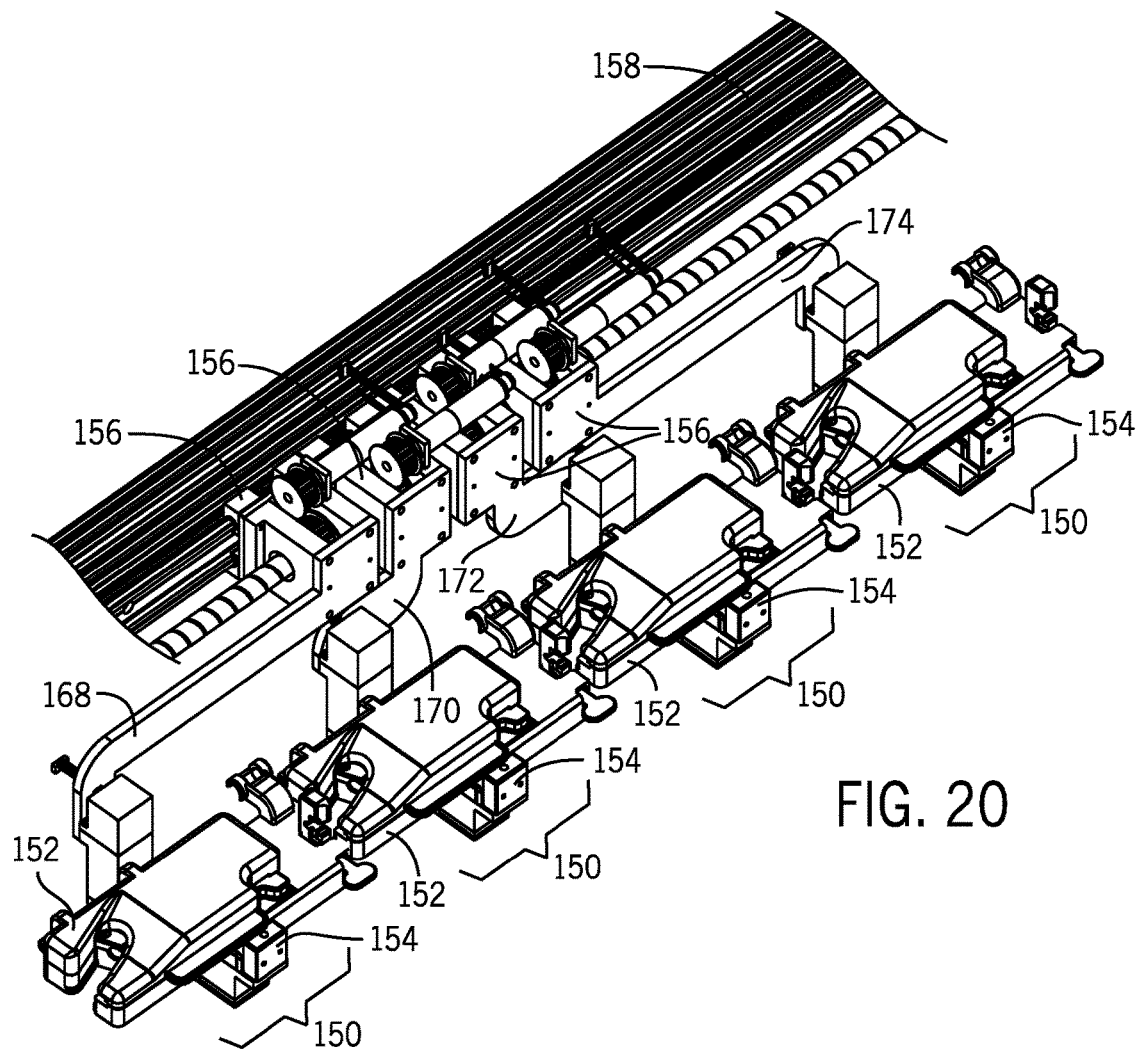
FIG. 20 is an isometric view of a robotic drive with offset brackets in accordance with an embodiment.
Figure 21:
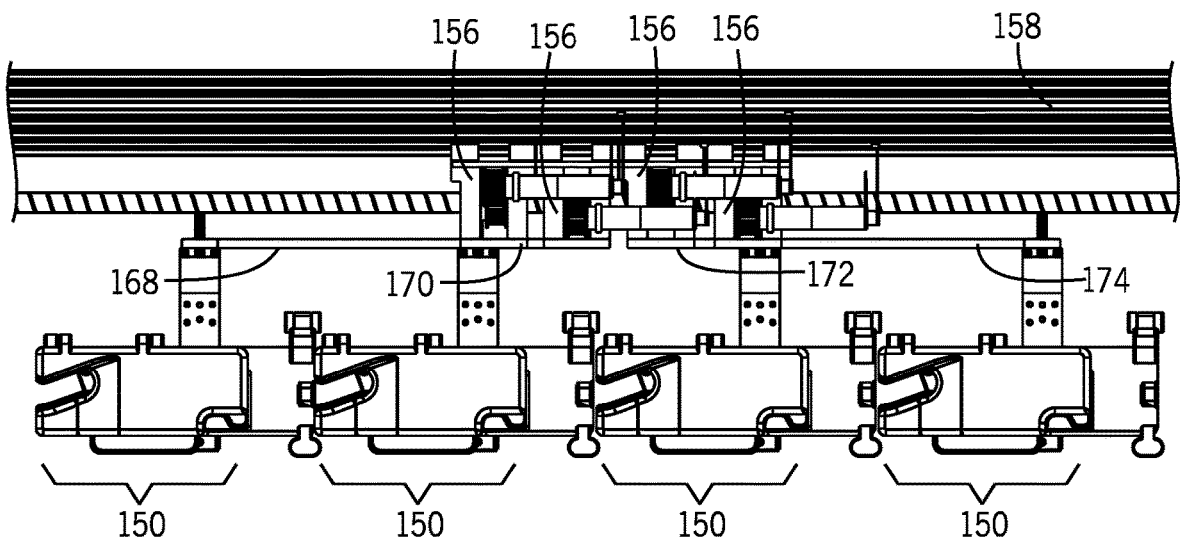
FIG. 21 is a top view of a robotic drive with offset brackets in accordance with an embodiment.

FIG. 18A is a block diagram illustrating occupied length on a linear member with offsets between device modules and stages in accordance with an embodiment. In FIG. 18A, four device modules 150 are shown and each device module 150 includes a cassette 152 mounted to a drive module 154. Each device module 150 is connected to an offset bracket 168, 170, 172, 174 which is used to connect the device module 150 to a stage 156. Each stage is coupled to a rail or linear member 158. When brought close together the four stages 156 define an occupied rail length 162 which, as mentioned, affects the overall length required for the rail 158. Each offset bracket 168, 170, 172, 174 defines an offset distance from the center of the respective stage 156 to which it is attached to a center of the cassette 152 of the device module 150 attached to the stage 156. For example, a first offset bracket 168 defines a first offset 164 between the center of the associated stage 156 and the center of the associated cassette 152. A fourth offset bracket 174 may be configured to define an offset that is the same as the first offset 164 distance or a different offset distance. A third offset bracket 172 defines a second offset 166 between the center of the associated stage 156 and the center of the associated cassette 152. A second offset bracket 170 may be configured to define an offset that is the same as the second offset 166 distance or a different offset. The offsets allows the stages 156 to be brought towards the center of the rail 158 which reduces the overall length of the robotic drive. FIG. 18A shows one embodiment of the configuration of the offset brackets, however, in other embodiments, different offset bracket configurations may be used, for example, as shown in FIGS. 18B and 18C. In FIG. 18B, each offset bracket 171, 173, 175, 177 positioned along a linear member or rail 159 extends away from a distal end of the linear member 159 in a distal direction (i.e., forward facing) towards the patient. This configuration can allow the linear member 159 (and other elements of the robotic drive) to be farther away from an access site in the patient and an imaging system of the catheter procedure system. In FIG. 18C each offset bracket 181, 183, 185, 187 positioned along a linear member 159 extends towards a proximal end of the linear member or rail 159 in a proximal direction (i.e., backward facing) away from the patient. FIG. 19 is a side view of a robotic drive with offsets brackets in accordance with an embodiment. FIG. 20 is an isometric view of a robotic drive with offset brackets in accordance with an embodiment. FIG. 21 is a top view of a robotic drive with offset brackets in accordance with an embodiment. In FIGS. 19-21, offset brackets 168, 170, 172 and 174 are used to compensate for the lengths of the cassettes 152 so as to eliminate dead space between the stages 156. The offsets created by the offset brackets 168, 170, 172 and 174 are used to minimize the length of the rail or linear member 158 by eliminating dead space between the stages 156. In addition, if the length of a stage 156 is greater than the length of the device module 150, the offsets may be used to compensate for differences in length between the stage 156 and device module 150.

Figure 22:
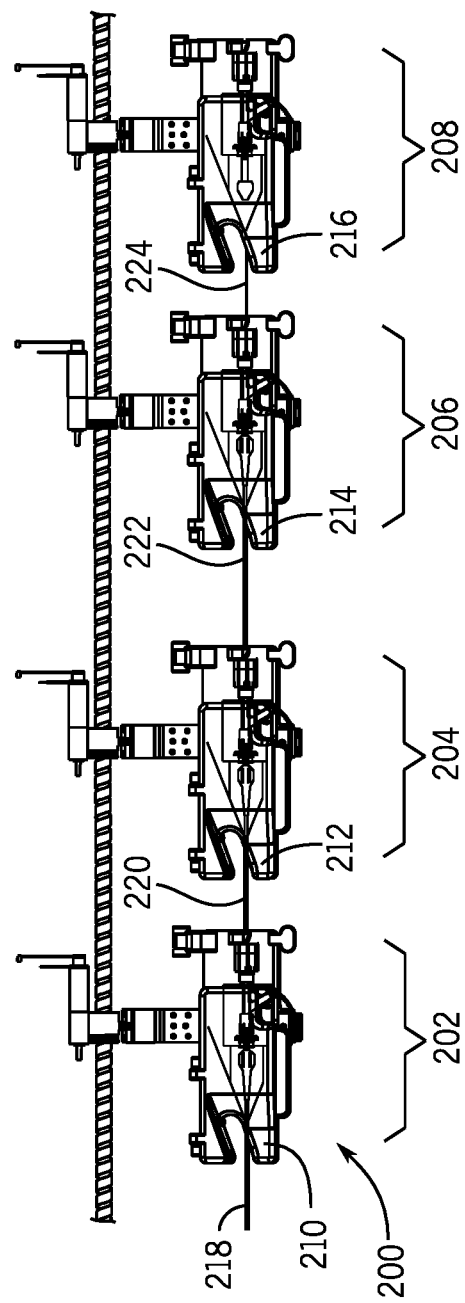
FIG. 22 is a top view of a portion of a robotic drive configured to drive four elongated medical devices in accordance with an embodiment.

FIG. 22 is a top view of a portion of a robotic drive configured to drive four elongated medical devices in accordance with an embodiment. In FIG. 22, the portion of the robotic drive 200 includes four device modules, in particular, a first device module 202 with a first cassette 210, a second device module 204 with a second cassette 212, a third device module 206 with a third cassette 214 and a fourth device module 208 with a fourth cassette 216. The robotic drive 200 is configured to drive four elongated medical devices and accordingly, each cassette 210, 212, 214 and 216 is populated with an elongated medical device. For example, a first elongated medical device 218 may be positioned in the first cassette 210 and may be, for example, a guide catheter that is configured to receive the three proximal elongated medical devices in a lumen of the guide catheter. A second elongated medical device 220 may be positioned in the second cassette 212 and may be, for example, a distal access or a diagnostic catheter that is configured to receive the two proximal elongated medical devices in a lumen of the distal access catheter. A third elongated medical device 222 may be positioned in the third cassette 214 and may be, for example, an over-the-wire balloon catheter or a microcatheter that is configured to receive the most proximal elongated medical device in a lumen of the elongated medical device 222. A fourth elongated medical device 224 may be positioned in the fourth cassette 216 and may be, for example, a guidewire. In order to support different numbers and configurations of elongated medical devices for different procedures, in one embodiment each cassette may be similar and an on-device adapter may be used to interface the elongated medical device to a cassette. For example, different steps of an endovascular procedure may require different numbers of elongated medical devices. A procedure may start with two coaxial catheters (a bi-coaxial catheter or bi-axial configuration) and a guidewire, then exchange to a configuration with three coaxial catheters (a tri-coaxial catheter or tri-axial configuration) and a guidewire, and subsequently back to a bi-axial catheter system and a guidewire. As used herein, the terms tri-axial, bi-axial and mono-axial refer to the number of serially concentric catheters but not including any wire based EMDs. When fewer elongated medical devices are used in a procedure, the device module in which an elongated medical device is positioned may be changed without requiring the removal of a cassette to change positions and unpopulated cassettes do not need to be removed from the robotic drive. Rather, the elongated medical devices and the on-device adapters between the elongated medical device and the cassette may be moved between unpopulated cassettes.

Figure 23:
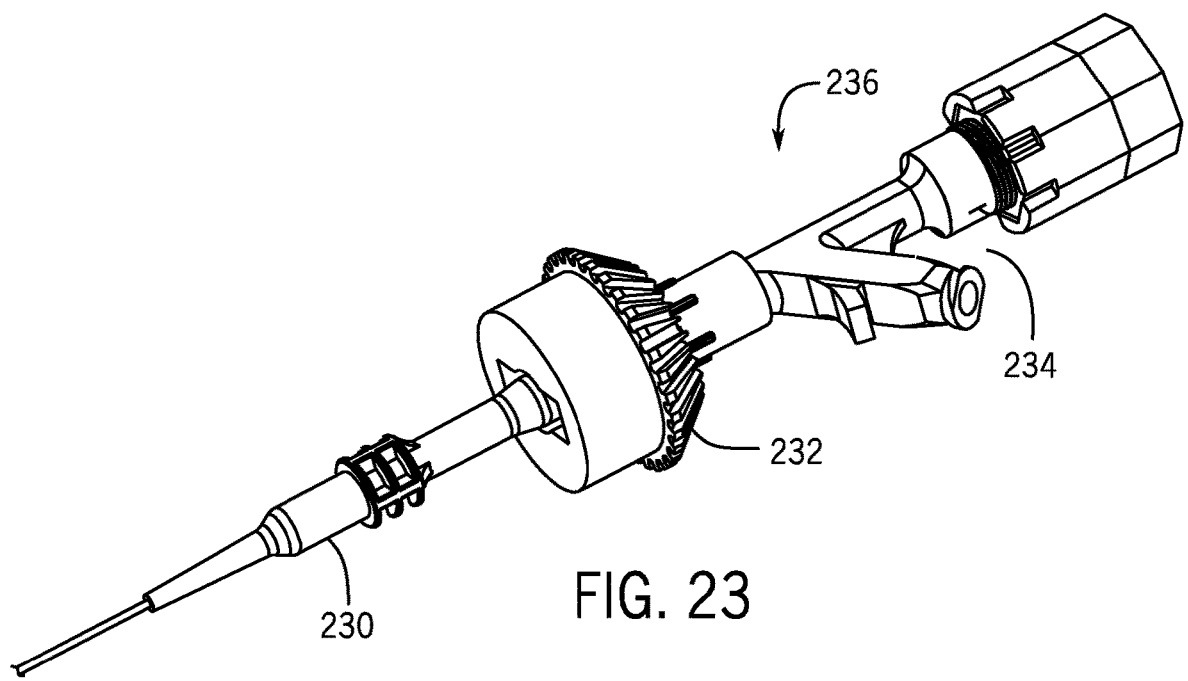
FIG. 23 is a perspective view of a catheter with an on-device adapter in accordance with an embodiment.
Figure 24:
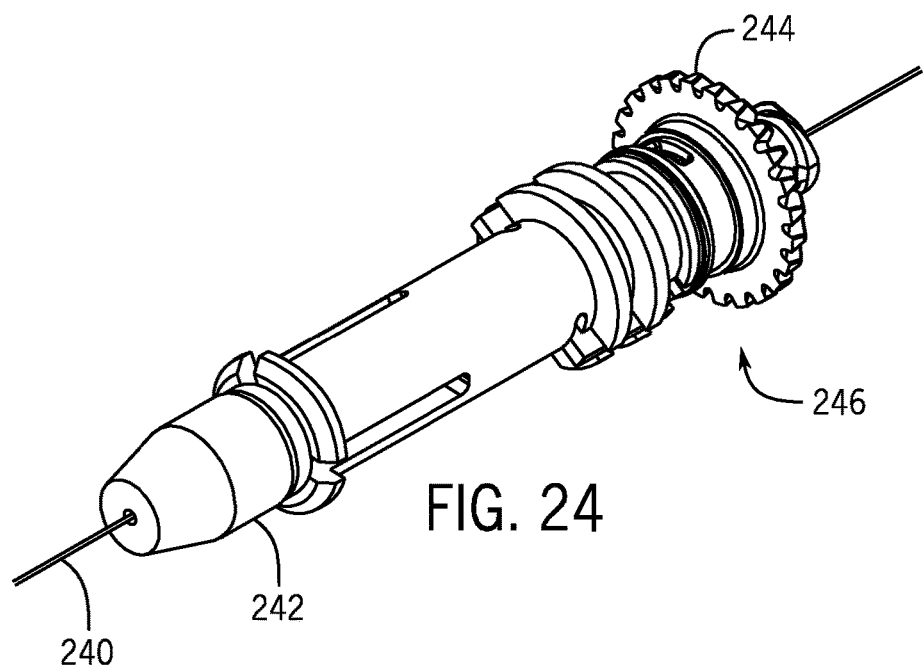
FIG. 24 is a perspective view of a guidewire with an on-device adapter in accordance with an embodiment.

FIG. 23 is a perspective view of a catheter with an on-device adapter in accordance with an embodiment and FIG. 24 is a perspective view of a guidewire with an on-device adapter in accordance with an embodiment. As used herein, an on-device adapter is a sterile apparatus capable of releasably clamping to an EMD to provide a driving interface. In FIG. 23, a catheter 230 includes a hemostasis valve or hub (e.g., a rotating hemostasis valve) 234 on the proximal end 236 of the catheter 230. An on-device adapter 232 is positioned on the catheter 230 distal to the hemostasis value 234 on the proximal end 236 of the catheter. In the embodiment of FIG. 23, the external surface of the on-device adapter is formed as a gear. The gear feature of the on-device adapter 232 is configured to interact with a gear 97 (shown in FIG. 7) of a cassette, for example, cassette 91 shown in FIG. 7. When power is transferred from a device module (not shown) to the gear in the cassette (e.g., via a coupler), the gear in the cassette interacts with the gear 232 on the catheter 230 to rotate the catheter. In another embodiment, rotation of the on-device adapter 232 may be configured to pinch/unpinch the catheter 230. In an embodiment, an internal surface of the on-device adapter 232 is firmly attached to a standard luer section of the elongated medical device (e.g., catheter 230). In another embodiment, the internal surface of the on-device adapter is clamped to a lateral surface it the proximal end of the elongated medical device. In another embodiment, the on-device adapter is attached to a cylindrical section (shaft) of the EMD. In yet another embodiment, the on-device adapter is not directly attached to the EMD, by is attached to the EMD via an interface. The power can transfer from the cassette to the on-device adapter in different ways such as, for example, gears (as mentioned above), or friction surface (e.g., tire and roller), belt, pneumatic, or magnetic/electromagnetic coupling.

Figure 25:
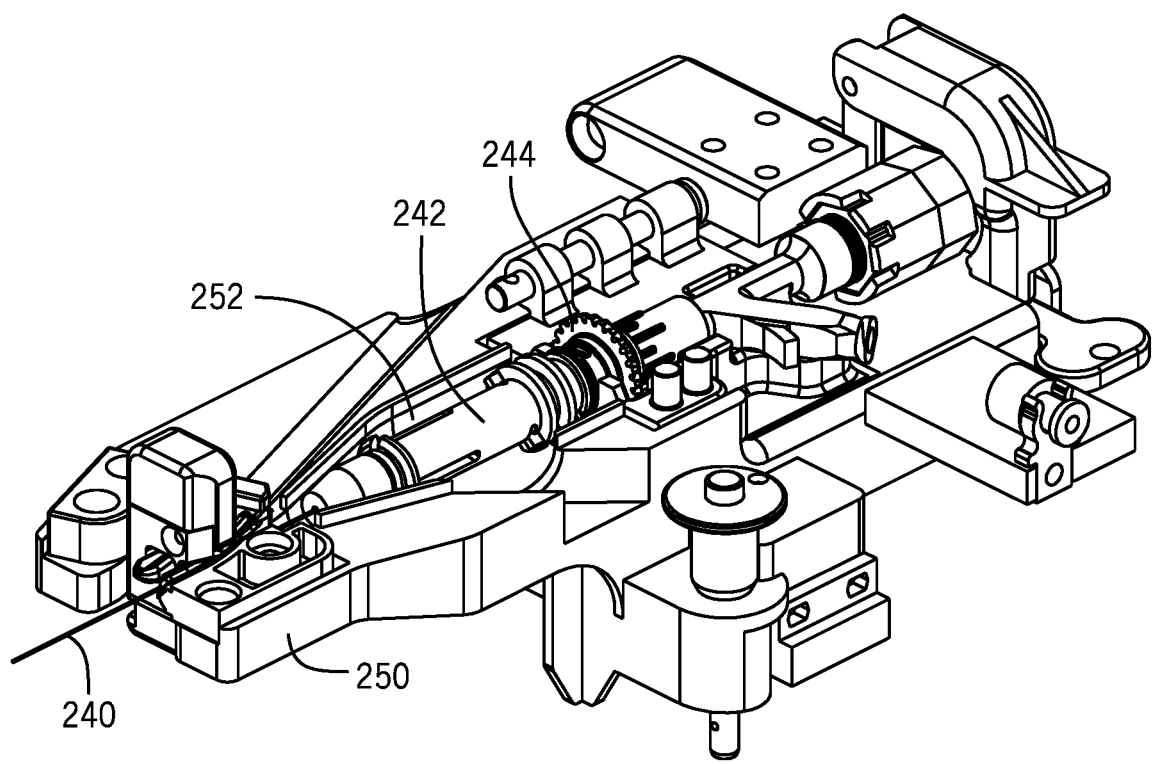
FIG. 25 is a perspective view of a cassette with an installed elongated medical device with an on-device adapter in accordance with an embodiment.

In FIG. 24, a guidewire 240 is shown with an on-device adapter 242. In the embodiment of FIG. 24, the on-device adapter 242 is a collet with a gear 244 on the proximal end 246 of the collet. The collet 242 is configured to grip the guidewire 240. The term collet as used herein is a device to releasably fix a portion of an EMD thereto. In one embodiment the collet includes at least two members that move relative to each other to releasably fix the EMD to at least one of the two members. Fixed means no intentional relative movement of the collet and EMD during operation parameters. The gear 244 is configured to interact with a gear 97 (shown in FIG. 7) of a cassette, for example, cassette 91 shown in FIG. 7. When power is transferred from a device module (not shown) to the gear in the cassette (e.g., via a coupler), the gear in the cassette interacts with the gear 244 on the guidewire 240 to rotate the guidewire 240. In another embodiment, rotation of the on-device adapter 242 via gear 244 may be configured to pinch/unpinch the guidewire 240. The elongated medical device and on-device adapter may be positioned in the cassette as shown in FIG. 25. In FIG. 25, a guide wire 240 and collet 242 are positioned in a cradle 252 of the cassette 250.

Figure 26:
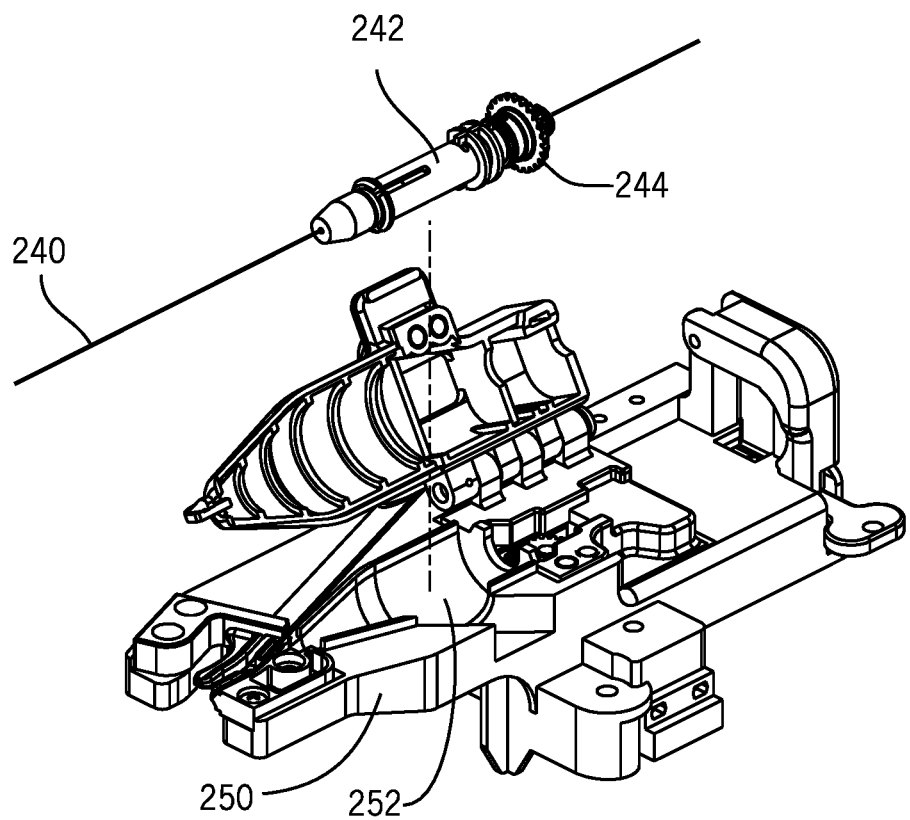
FIG. 26 is a exploded view of a cassette and an elongated medical device with an on-device adapter that is removed from the cassette in accordance with an embodiment.

As mentioned, the elongated medical device and the on-device adapter may be removed from one cassette and moved to another unpopulated cassette. FIG. 26 shows a guide wire 240 and collet 244 with a gear 244 removed from the cassette 250. As mentioned, when the cassettes are similar and an on-device adapter is used to interface an elongated medical device to the cassette, the device and on-device adapter may be moved between unpopulated cassettes enabling the number of devices and configuration of the robotic drive to be changed. For example, the number of devices in the exemplary robotic drive 200 in FIG. 22 may be changed to three devices as shown in FIG. 27. In FIG. 27, the first cassette 210, the second cassette 212 and the third cassette 214 are populated with a first elongated medical device 218 (e.g., a guide catheter), second elongated medical device 220 (e.g., a distal access catheter) and a third elongated medical device 222 (e.g., a guidewire), respectively. The fourth cassette 216 is unpopulated and may remain attached to its drive module in the robotic drive. Accordingly, the more proximal cassettes in the robotic drive may be left unpopulated when fewer elongated medical devices need to be actuated for the procedure. In an example, a user may install all the cassettes in a robotic drive at the beginning of a case and does not need to uninstall the cassettes to move devices. The devices (and corresponding on-device adapters may be moved to and from the different cassettes. This can greatly increase usability and exchange speed. In addition, this can make changing device sizes easier. For example, 0.035 and 0.014 wires normally have different collet sizes for manual cases. For the system described with respect to FIGS. 22-27, different on-device adapters would allow different sized devices to be driven in the same cassettes. For example, a different sized collet may be used that corresponds with the 0.035 or the 0.014 wire allowing each sized device to be changed and used in any of the cassettes.

Figure 28A:
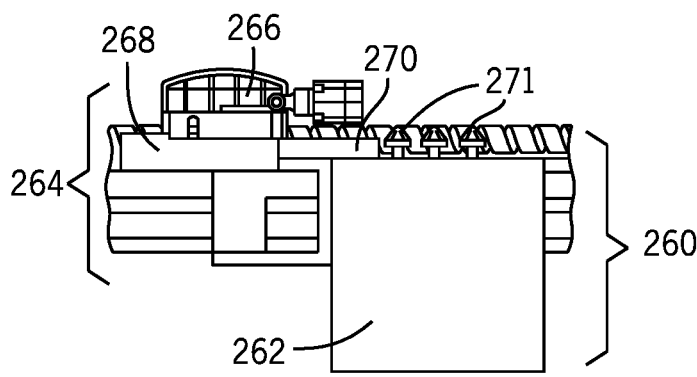
FIG. 28A is a diagram of a first device module mechanically coupled to a second device module to share linear movement of the first device module in accordance with an embodiment.
Figure 28B:
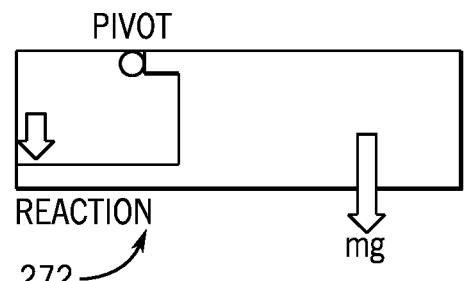
FIG. 28B is a diagram of an exemplary mechanical mount for a device module in accordance with an embodiment.
Figure 29:
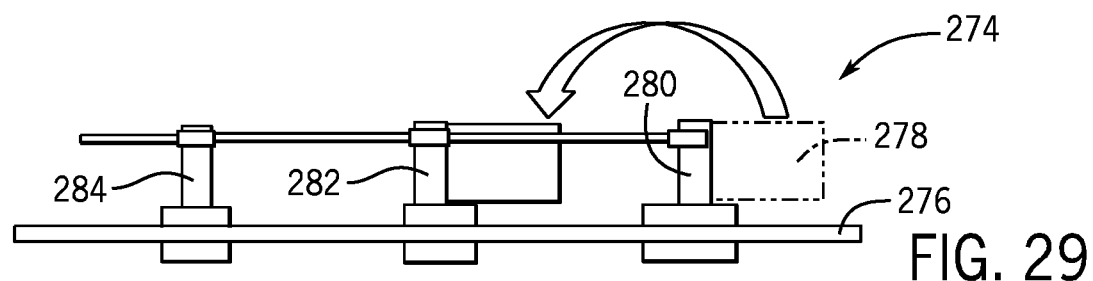
FIG. 29 is a block diagram illustrating changing a position of a device module in a robotic drive where the device module is mechanically coupled to another device module in accordance with an embodiment.

As mentioned above, linear motion of a device module in the robotic drive may be provided by coupling the device module to a stage connected to a rail or linear member and a stage translation motor. The device module may then be translated linearly by using the stage translating motor to actuate the stage to move along the rail. In another embodiment, linear motion for a first device module may be provided by directly mounting the first device module to a second device module in the robotic drive rather than coupling the first device module to the rail. FIG. 28A is a diagram of a first device module mechanically coupled to a second device module to share linear movement of the first device module in accordance with an embodiment. In FIG. 28A, a first device module 260 with a first drive module 262 is shown. A cassette for the first device module 260 is not shown for simplicity, however, the first device module 260 would also include a cassette mounted on the drive module 262. In one embodiment, the first drive module 262 includes multiple couplers 271 to provide multiple degrees of freedom to an elongated medical device positioned in a cassette (not shown) mounted on the first drive module 262. A second device module 264 includes a second drive module 268 and a cassette 266 mounted to the second drive module 268. In an embodiment, the first device module 260 may be mechanically mounted to the second device module 264. In another embodiment, the first device module 260 may also be electrically coupled to the second device module 264. A mount 270 may be used to mechanically couple the first device module 260 to the second device module 264. The mount 270 may be a kinematic mount such as kinematic mount 272 shown in FIG. 28B. The mount may be configured to allow the removal of the first device module 260 so that it may be moved and removably mounted to a different device module in the robotic drive to facilitate different configurations of elongated medical devices. For example, the first device module 260 may be manually repositioned by a user to change the number of catheters driven in front of it in the robotic drive. FIG. 29 is a block diagram illustrating changing a position of a device module in a robotic drive between where the device module is mechanically coupled to another device module in accordance with an embodiment. In FIG. 29, a robotic drive 274 includes a first device module 278 that is mounted to a second device module 280. The second device module 280 is mounted to a rail or linear member 276. The first device module 278 and the second device module may be moved together linearly along the rail 276. The robotic drive 274 also include a third device module 282 and fourth deice module 284 that are each mounted to the rail 276. The first device module 278 may be disconnected from the second device module 280 and moved to a different position by mounting the first device module 278 to the third device module 282. The first device module 278 will then move linearly as the third device module 282 move linearly along the rail 276.

Figure 30:
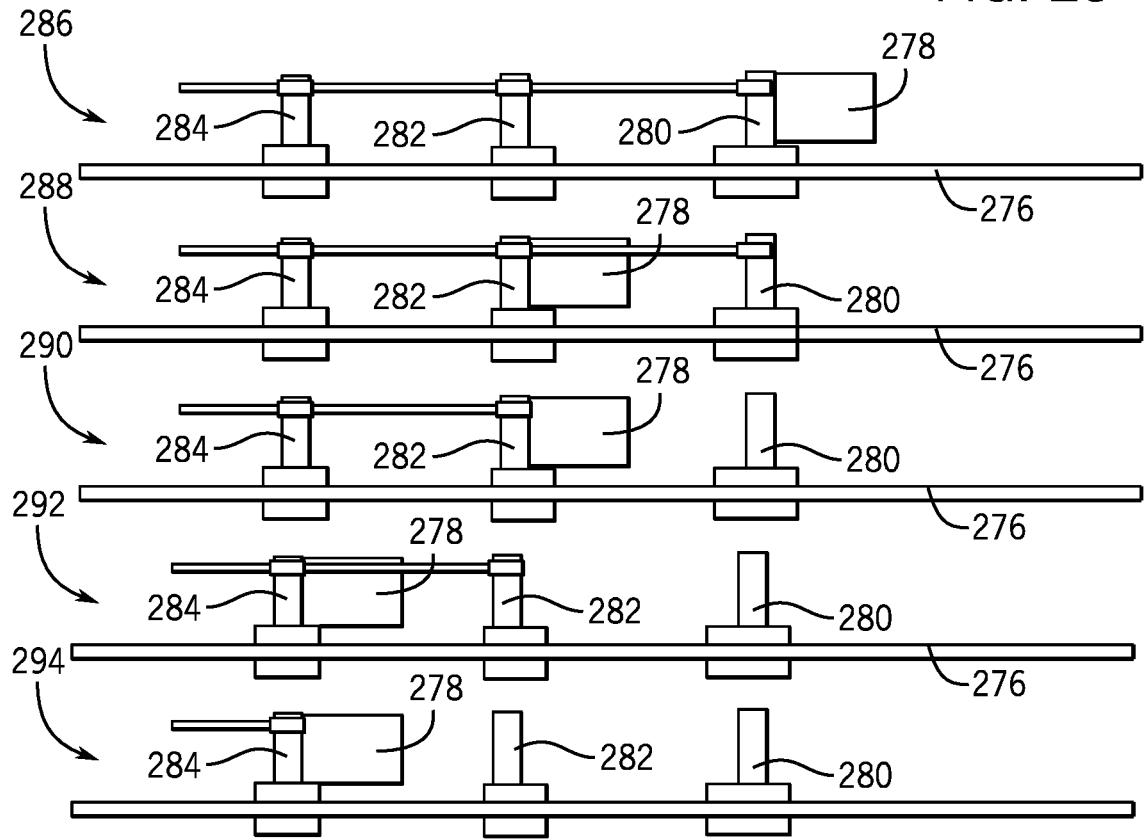
FIG. 30 is a block diagram illustrating different positions for a device module in a robotic drive where the device module is mechanically coupled to another device module in accordance with an embodiment.

FIG. 30 is a block diagram illustrating different positions for a device module in a robotic drive where the device module is mechanically coupled to another device module in accordance with an embodiment. In a first configuration 286, the first device module 278 is mounted to the second device module 280 and each of the four device modules 278, 280, 282 and 284 are populated with an elongated medical device. In a second configuration 288, the first device module 278 is mounted to the third device module 282 and each of the four device modules 278, 280, 282 and 284 are populated with an elongated medical device. In a third configuration 290, the first device module 278 is mounted to the third device module 282 and first 278, third 282 and fourth 284 device modules are populated with an elongated medical device. In the third configuration, the second device module 280 is not populated with an elongated medical device. In a fourth configuration 292, the first device module 278 is mounted to the fourth device module 284 and first 278, third 282 and fourth 284 device modules are populated with an elongated medical device. In the fourth configuration, the second device module 280 is not populated with an elongated medical device. In a fifth configuration 294, the first device module 278 is mounted to the fourth device module 284 and first 278 and fourth 284 device modules are populated with an elongated medical device. In the fifth configuration, the second device module 280 and the third device module 282 are not populated with an elongated medical device.

Figure 31:
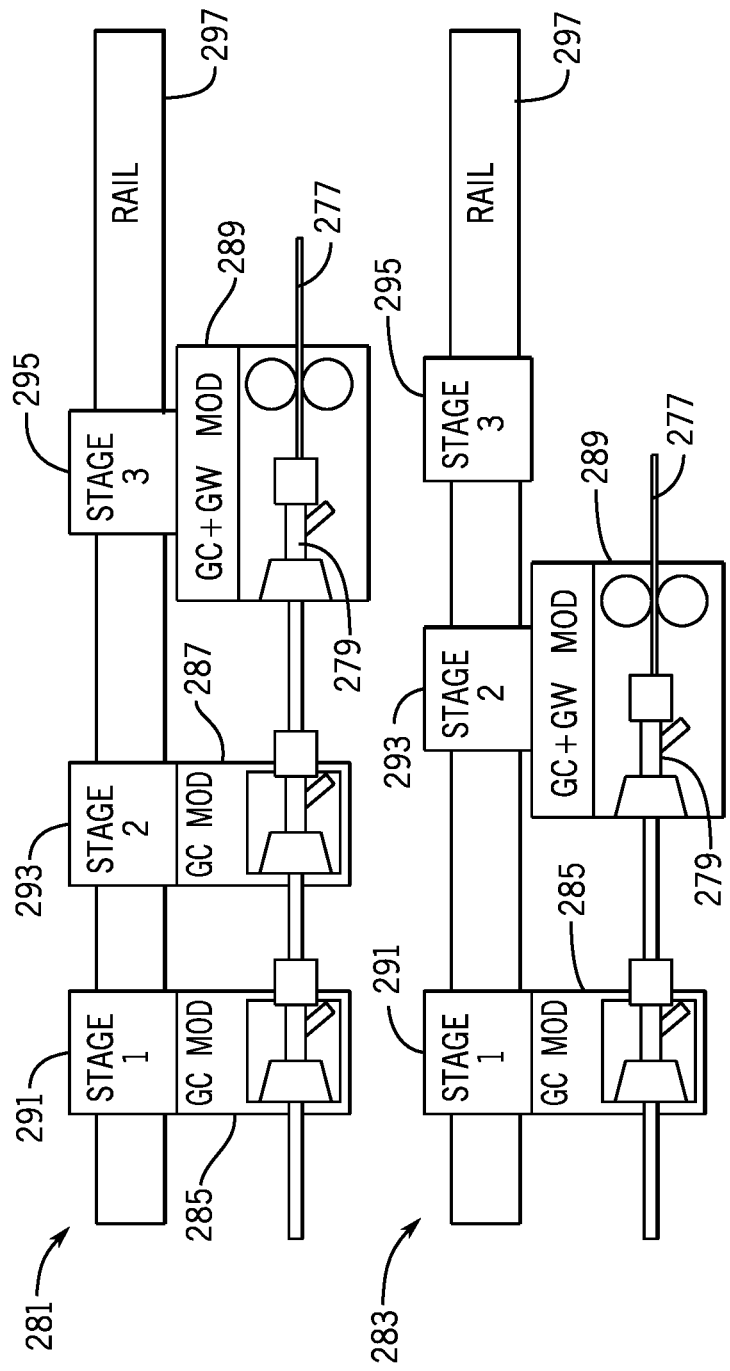
FIG. 31 is a block diagram illustrating changing the position of a device module in a robotic drive where the device module is configured to be populated with more than one elongated medical device in accordance with an embodiment.

In another embodiment, a device module that is configured to be populated with more than one elongated medical device may be movable between stages on a rail or linear member in a robotic drive. FIG. 31 is a block diagram illustrating changing the position of a device module in a robotic drive where the device module is configured to be populated with more than one elongated medical device in accordance with an embodiment. In a first configuration 281, a first device module 285 is coupled to a first stage 291 moveably mounted to a rail or linear member 297. A second device module 287 is coupled to a second stage 293 moveably mounted to the rail 297. A third device module 289 is coupled to a third stage 295 moveably mounted to the rail 297. The first device module 285 and the second device module 287 are each populated with a single elongated medical device, for example, a catheter. The third device module 289 is configured to be populated with two elongated medical devices. In the embodiment of FIG. 31, the third device module 289 is populated with a guidewire 277 and a guide catheter 279. As mentioned, the third device module 289 may be removed from the third stage 295 and moved to a different stage mounted to the rail 297. In the second configuration 283, the second device module 287 has been removed from the second stage 293. In addition, the third device module 289 has been removed from the third stage 295 and coupled to the second stage 293 and is in a position behind the first device module 285. In the second configuration 283, a device module is not coupled to the third stage 295.

Figure 32:
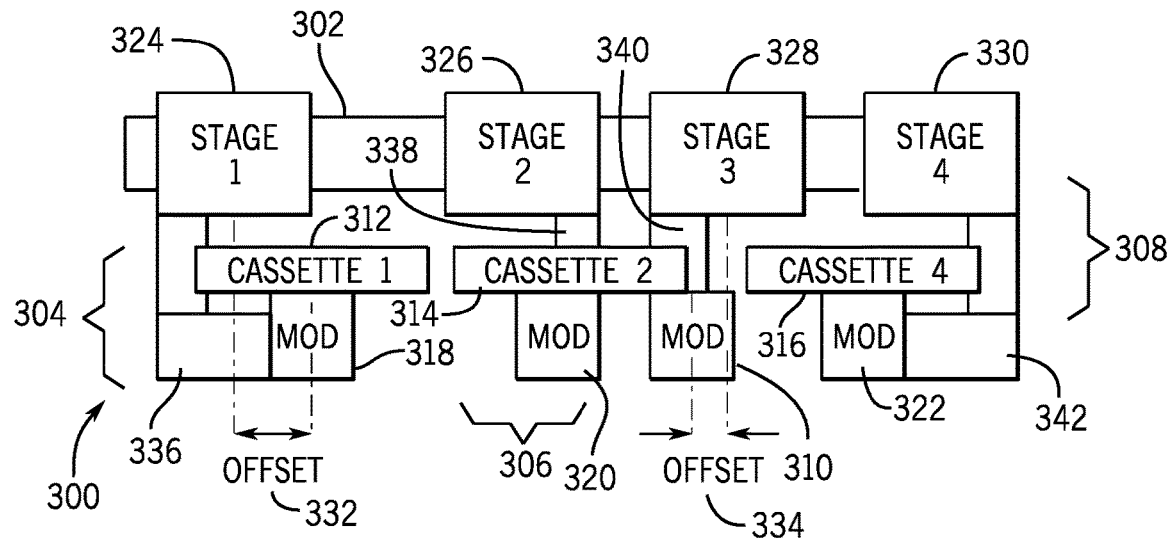
FIG. 32 is a block diagram of a robotic drive including three device modules and a nested unpopulated drive module in accordance with an embodiment.
Figure 33:
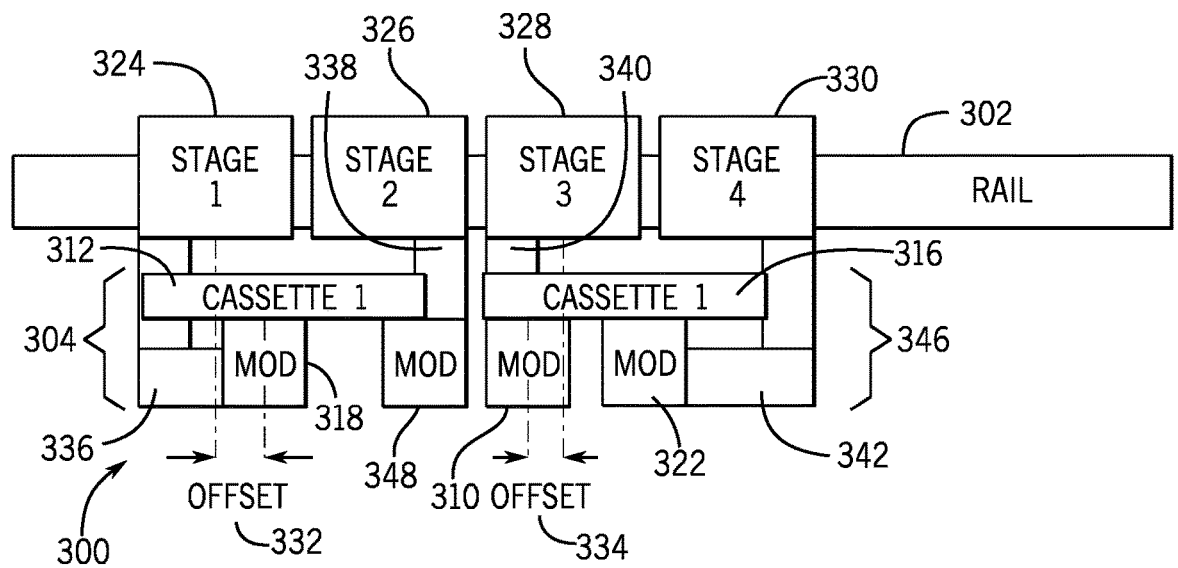
FIG. 33 is a block diagram of a robotic drive including two device modules and two nested unpopulated drive modules in accordance with an embodiment.

In various embodiments of a robotic drive (e.g., robotic drive 24 shown in FIG. 3), a device stack-up for a particular procedure my require that a certain device module (e.g., a device module for a guidewire) be located in a particular position, for example, connected to the most proximal stage on the rail or linear member. However, the device stack-up may not require the use of all of the positions in front of the most proximal stage. In order to facilitate configurations with fewer devices, the robotic drive may be configured to allow the nesting of unpopulated drive modules in an unused volume under a cassette either distal or proximal to the unpopulated drive module. FIG. 32 is a block diagram of a robotic drive including three device modules and a nested unpopulated drive module in accordance with an embodiment. In FIG. 32, the robotic drive 300 includes a rail or linear member 302 and a first device module 304 connected to a first stage 324, a second device module 306 connected to a second stage 326, an unpopulated drive module 310 connected to a third stage 328 and a third device module 308 connected to a fourth stage 330. The first device module 304 includes a cassette 312 mounted to a drive module 318, the second device module 306 includes a cassette 314 mounted to a drive module 320, and the third device module 308 includes a cassette 316 mounted to a drive module 322. The unpopulated drive module 310 is positioned (or nested) in an area of overlap with a proximal end of the cassette 314 of the second device module 306, for example, in an unused volume under the cassette 314. This allows the unpopulated drive module 310 to be skipped in the device stack-up and an elongated medical device populated in the cassette 316 of the third device module 308 to be fed directly to the second device module 306. In addition, the third device module 308 may be moved closer to the second device module 306. In another embodiment, a second drive module may be unpopulated and nested in an area of overlap with a proximal end of a cassette, for example, in the unused volume under the cassette. FIG. 33 is a block diagram of a robotic drive including two device modules and two nested unpopulated drive modules in accordance with an embodiment. In FIG. 33, the cassette from the second device module 306 (shown in FIG. 32) is removed leaving a second unpopulated drive module 348. In this embodiment, the second unpopulated drive module 348 may be positioned in an area of overlap with the proximal end of cassette 312, for example, in an unused volume under the cassette 312 of a first device module 304. The first unpopulated drive module 310 is positioned in area of overlap with the proximal end of cassette 316, for example, in an unused volume under the cassette 316 of a second device module 346. This allows the unpopulated drive modules 310 and 348 to be skipped in the device stack-up and an elongated medical device populated in the cassette 316 of the second device module 308 to be fed directly to the first device module 344. In addition, the second device module 346 may be moved closer to the first device module 344.

Figure 34:
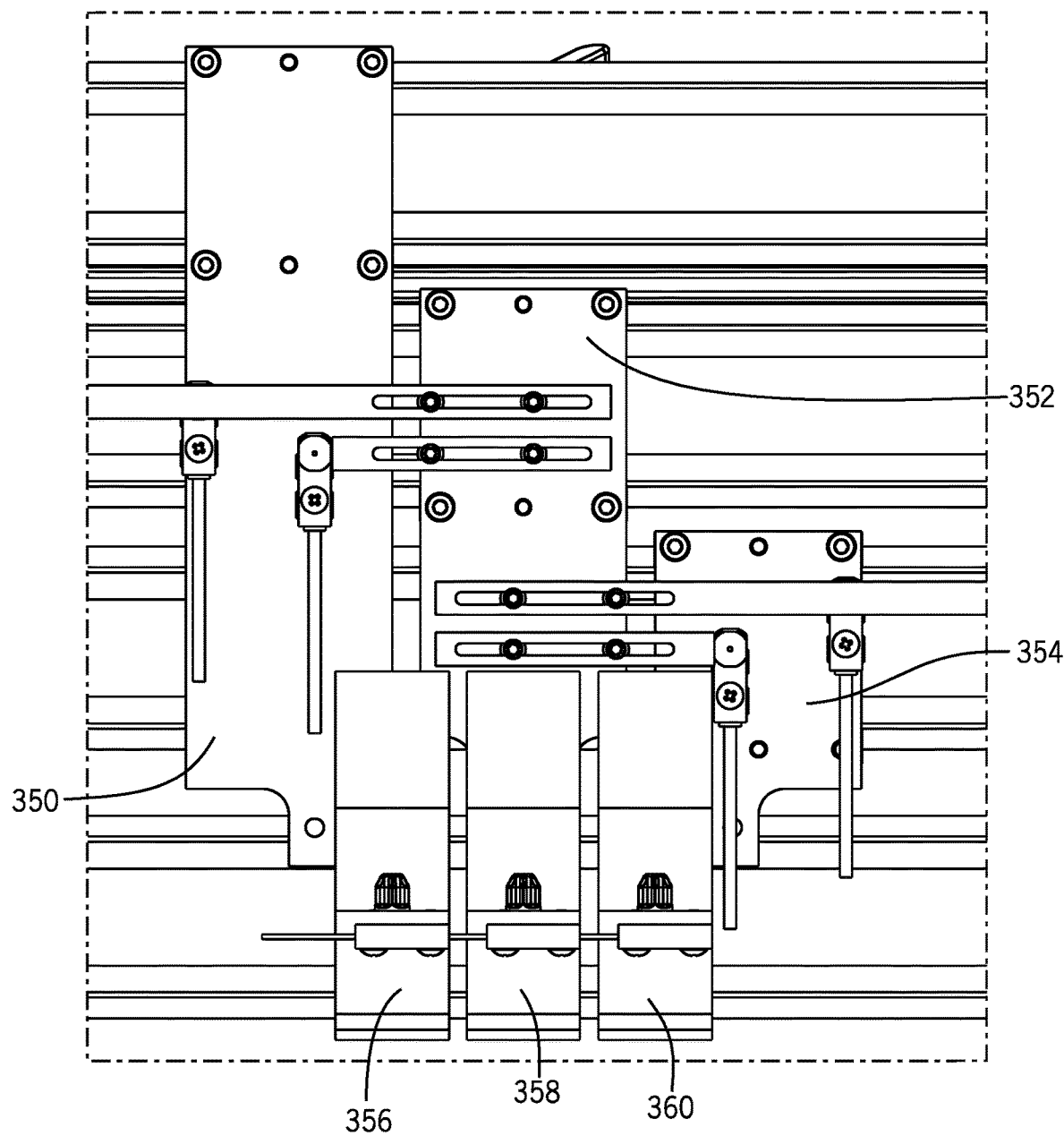
FIG. 34 is a side view of three unpopulated drive modules and offset brackets in accordance with an embodiment.
Figure 35:
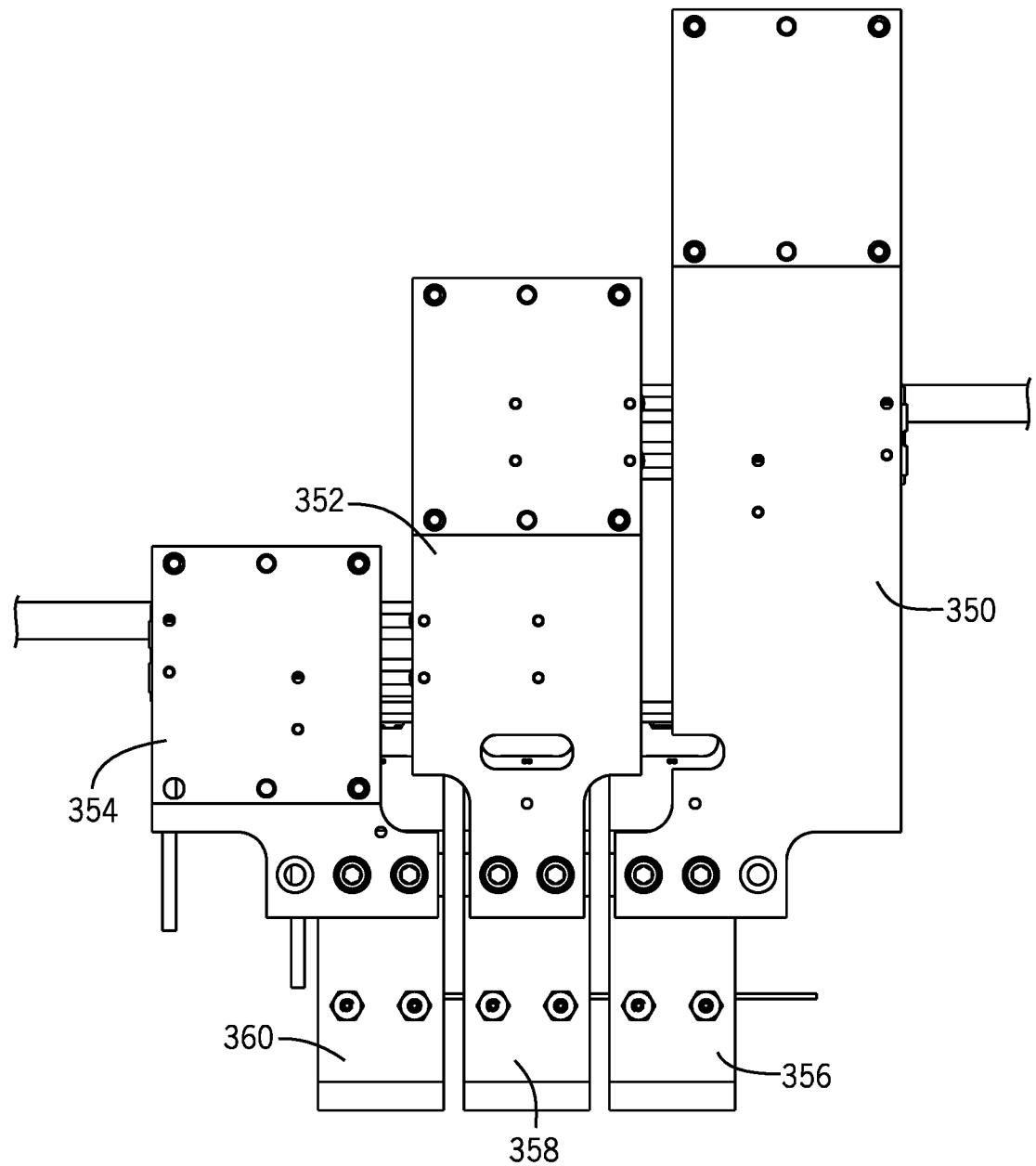
FIG. 35 is a side rear view of three unpopulated drive modules and offset brackets in accordance with an embodiment.

To nest unpopulated drive modules, the length of the drive modules may be minimized and the drive modules should be able to get very close to one another. To facilitate the nesting of unpopulated drive modules between device modules, offset brackets may be used to connect a device module or unpopulated drive module to a stage. The offsets created by the offset brackets allow the drive modules to get close enough to nest properly while the length of the stages to which the drive modules are attached does not need to be changed. Referring to FIGS. 32 and 33, the first device module 304 is connected to a first offset bracket 336 that defines a first offset 332 between the center of the first stage 324 and the center of the drive module 318 of the first device module 304. The third device module 308 or the second device module 346 may also be connected to a similar fourth offset bracket 342 to define the first offset 332. The first unpopulated drive module 310 is connected to a third offset bracket 340 that defines a second offset 334 between the center of the third stage 328 and the center of the unpopulated drive module 310. The second device module 306 or the second unpopulated drive module 348 may be connected to a similar second offset bracket 338 to define the second offset 334. FIG. 34 is a side view of three unpopulated drive modules and offset brackets in accordance with an embodiment and FIG. 35 is a side rear view of three unpopulated drive modules and offset bracket sin accordance with an embodiment. In FIGS. 34 and 35, a first drive module 356 is connected to a first offset bracket 350, a second drive module 358 is connected to a second offset bracket 352 and a third drive module 360 is connected to a third offset bracket 354.

Figure 36:
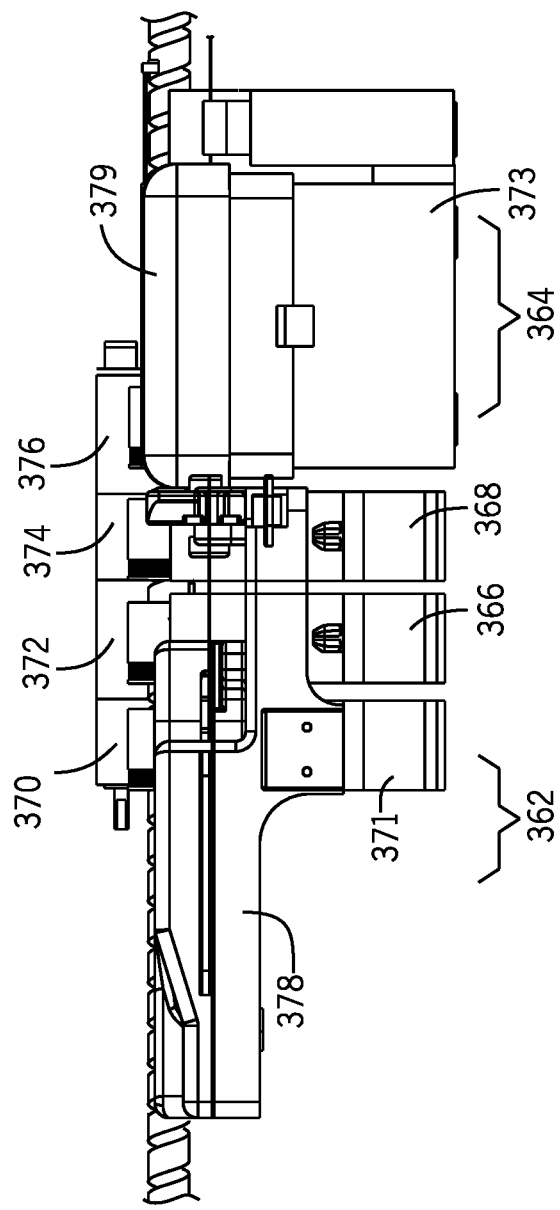
FIG. 36 is a side view of two nested unpopulated drive modules and two device modules in accordance with an embodiment.
Figure 37:
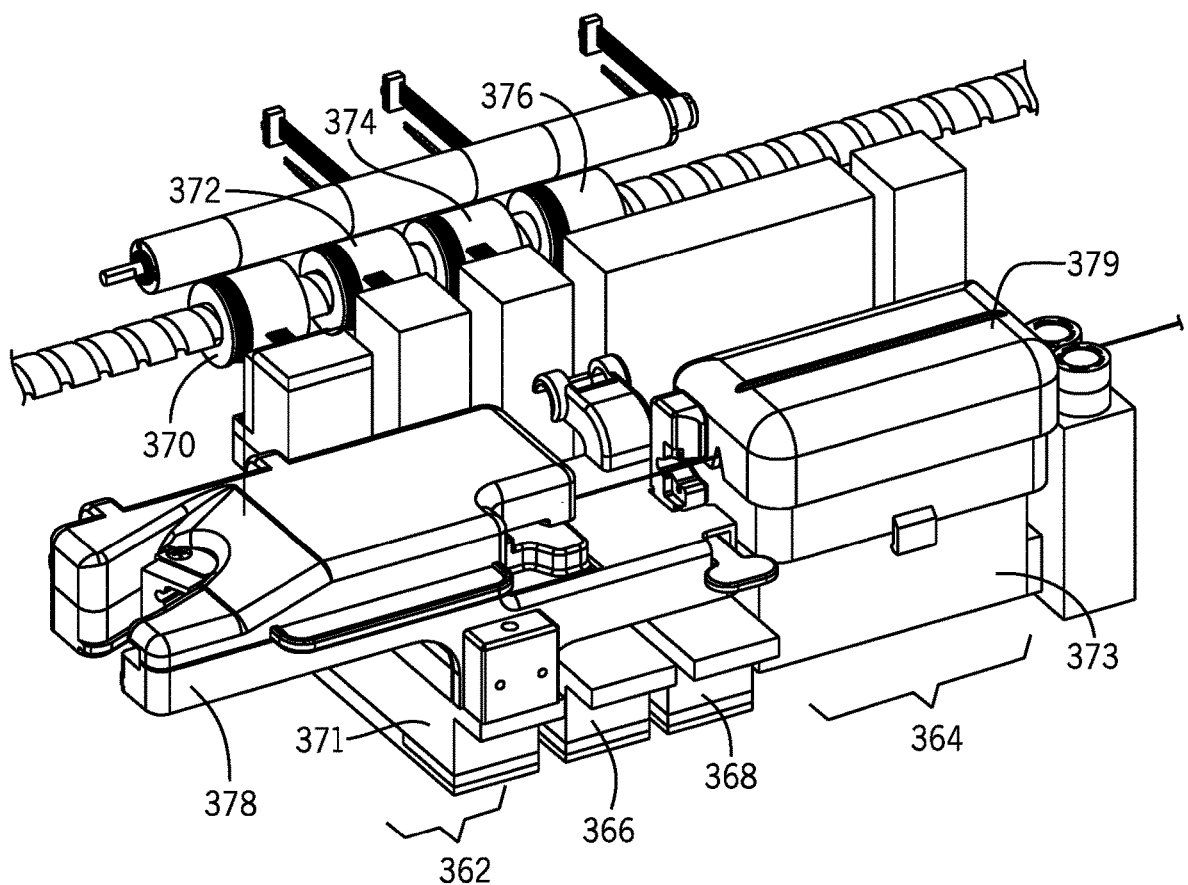
FIG. 37 is an isometric view of a robotic drive with two nested unpopulated drive modules and two device modules in accordance with an embodiment.

FIG. 36 is a side view of two device modules and two nested unpopulated drive modules in accordance with an embodiment and FIG. 37 is an isometric view of a robotic drive with two device modules and two nested unpopulated drive modules in accordance with an embodiment. In FIGS. 36 and 37, a first device module 362 includes a cassette 378 mounted to a drive module 371 and second device module 364 includes a cassette 379 mounted to a drive module 373. The first device module 362 is connected to a first stage 370 and the second device module 364 is connected to a fourth stage 376. A first unpopulated drive module 366 and a second unpopulated drive module 368 are connected to a second stage 372 and a third stage 374, respectively, and are located between the first drive module 362 and the second drive module 364 along the rail or linear member. In the embodiment of FIGS. 36 and 37, the first unpopulated drive module 366 and the second unpopulated drive module 368 are positioned (or nested) in unused volume under the cassette 378 of the first device module 362. To facilitate nesting of unpopulated drive modules, each drive module 366, 368 and 371 has at least one dimension that is smaller or less than at least one dimension of a cassette (e.g., cassette 378) that may be mounted on the drive module. For example, a length of the drive module 366, 368, 371 as measured from a proximal side to a distal side when the device module 366, 368, 371 is coupled to the linear member or rail may be smaller or less than a length of the cassette (e.g., cassette 378) along a longitudinal axis of the cassette. In some embodiments, the size and dimensions of the drive modules 366, 368 and 371 are minimized so that, for example, the drive modules takes up a minimal amount of space along a linear member or rail (e.g., linear member or rail 60 shown in FIG. 3) of the robotic drive when not populated with a cassette. In an embodiment, the unused volume under the cassette 378 is defined by the difference in length between the cassette 378 and the drive module 371 to which the cassette 378 is mounted. As shown in FIGS. 36 and 37, the nested unpopulated drive modules 366 and 368 allow the second device module 364 to be brought close to the first device module 362 and, in an embodiment, may eliminate the need for a device support between the second device module 364 and the first device module 362.

Figure 38:
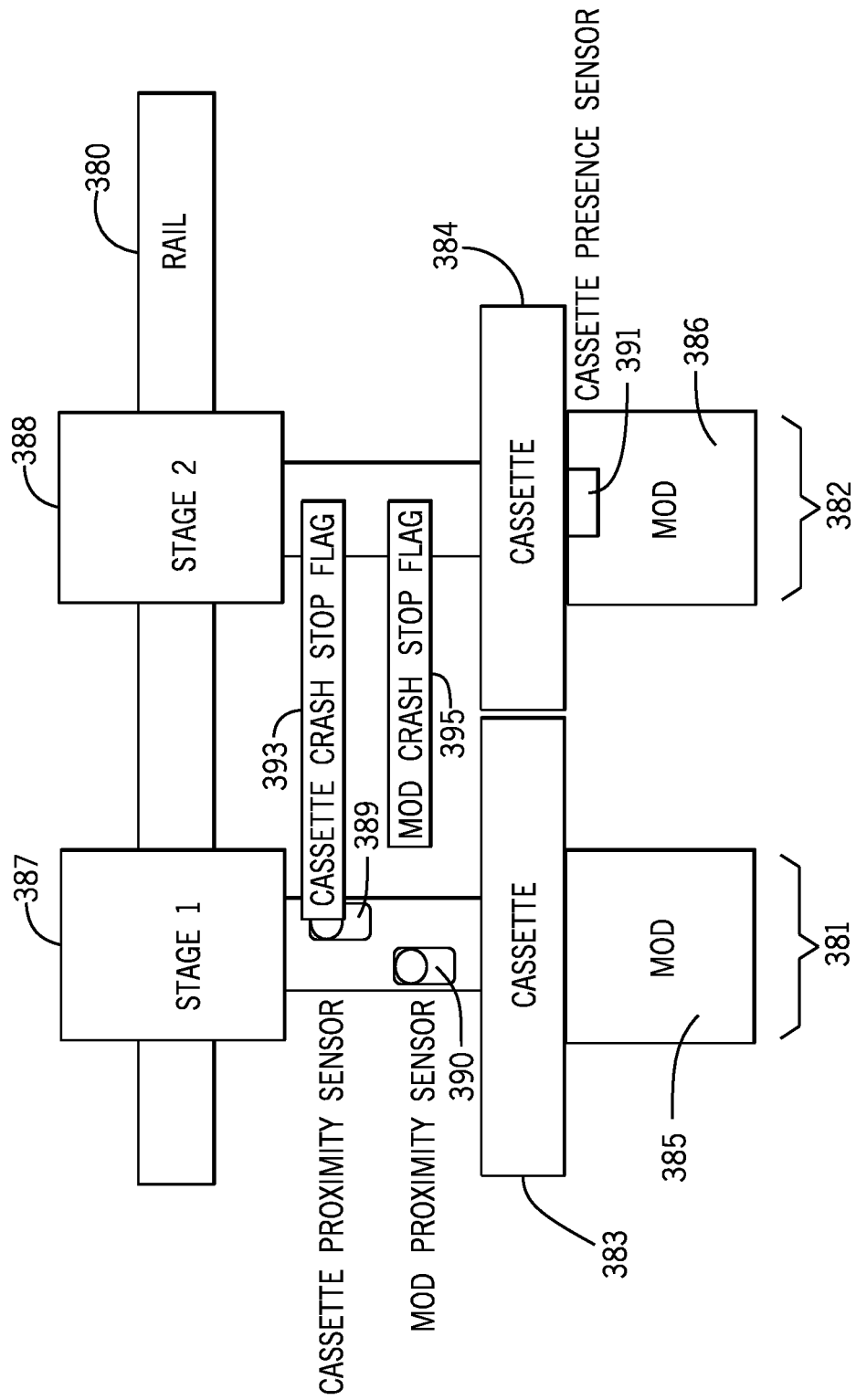
FIG. 38 is a block diagram illustrating a cassette crash prevention apparatus and method in accordance with an embodiment.

The robotic drive may include a crash prevention control system to control how close the cassettes and drive modules can get to one another without making contact. In an embodiment of a robotic drive that includes the ability to nest unpopulated drive modules as described above with respect to FIGS. 32-37, the crash prevention control system may be configured to have a first set of parameters for a drive module with a cassette attached and a second set of parameters for a drive module that does not have a cassette attached (i.e., the drive module is unpopulated). FIG. 38 is a block diagram illustrating a cassette crash prevention apparatus and method in accordance with an embodiment. In FIG. 38, a first device module 381 includes a first cassette 383 mounted to a first drive module 385. The first device module 381 is coupled to a first stage 387 mounted to a rail or linear member 380. The first device module 381 also includes a cassette proximity sensor 389 and a drive module proximity sensor 390. The sensors 389, 390 are shown positioned on the drive module 385. In other embodiments, the sensors 389, 390 may be positioned on a stage, a cassette, etc. A second device module 382 includes a second cassette 384 mounted to a second drive module 386. The second device module 382 is coupled to a second stage 388 that is mounted to the rail 380. A cassette crash stop flag 393 and a module crash stop flag 395 are located in the stage 388. Alternatively, the crash stop flags 393, 395 may be located on the drive module 386. In an embodiment, the crash stop flags 393, 395 are formed from metal and trip the corresponding proximity sensor 389, 390, respectively when moved in front of the proximity sensor. The second device module 382 also includes a cassette presence sensor 391 that may be located, for example, on the second drive module 386. The cassette presence sensor 391 may be, for example, a reed switch sensor with magnets. If the second cassette 384 is present on the second drive module 386, the cassette presence sensor 391 may provide a signal indicating the second cassette 384 is mounted on the second drive module 386. In this instance, the cassette proximity sensor 389 is used to determine if the second cassette 384 is getting too close to the first cassette 383. In one embodiment, when the second cassette 384 is within a threshold distance of the first cassette 383, for example, when the cassette crash stop flag 393 moves in front of the proximity sensor 389, the cassette proximity sensor 389 provides a control signal and an alert may be provided to a user or the movement of the second cassette may be stopped.

Figure 39:
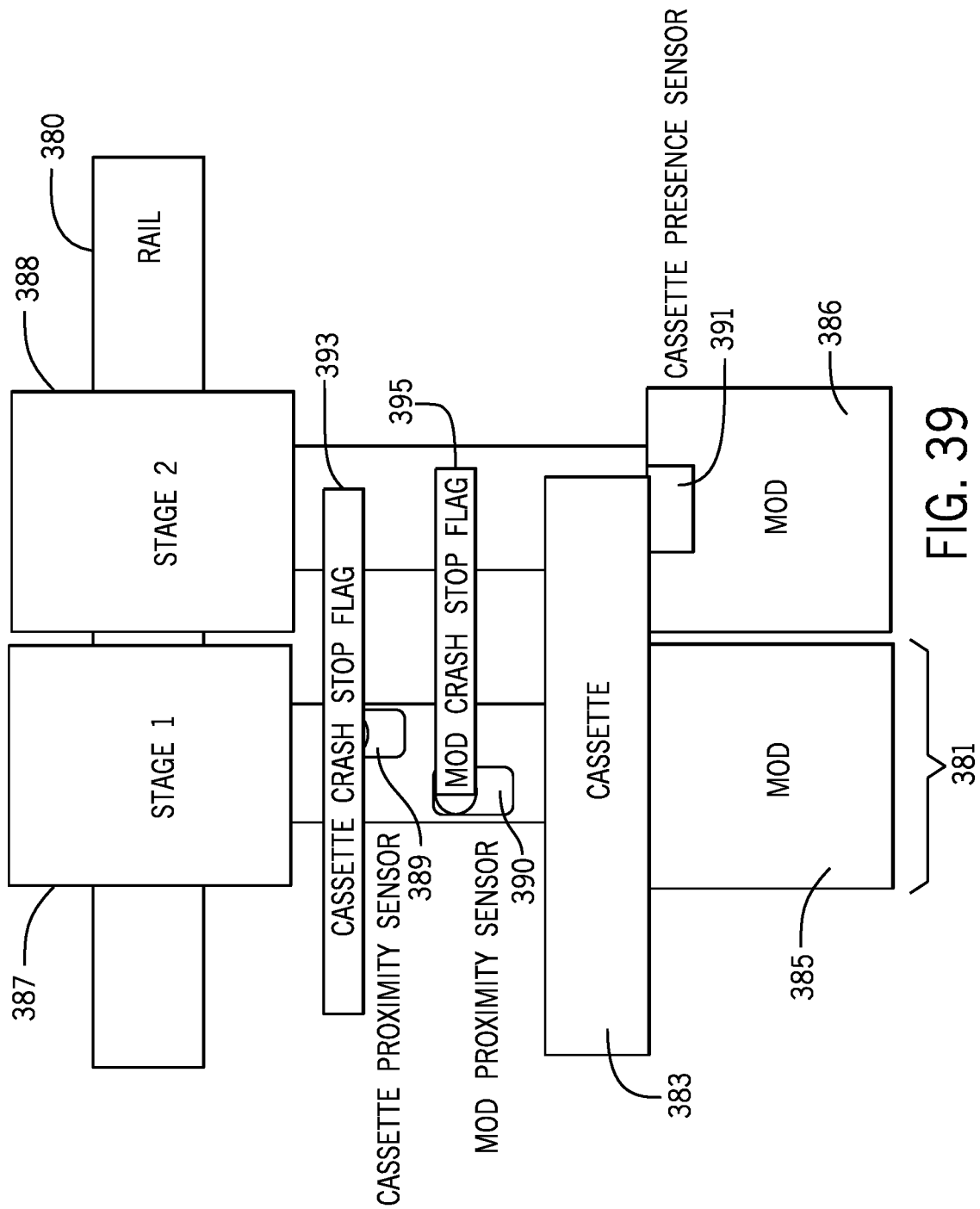
FIG. 39 is a block diagram illustrating an unpopulated drive module crash prevention apparatus and method in accordance with an embodiment.

If the second cassette 384 is not mounted to the second device module 386, then the drive module proximity sensor 390 is used to determine the location of the second drive module 386 relative to the first drive module 385. FIG. 39 is a block diagram illustrating an unpopulated drive module crash prevention apparatus and method in accordance with an embodiment. In FIG. 39, a first device module 381 includes a first cassette 383 mounted to a first drive module 385. The first device module 381 is coupled to a first stage 387 mounted to a rail or linear member 380. The first drive module 381 also includes a cassette proximity sensor 389 and a drive module proximity sensor 390. The sensors 389, 390 are shown positioned on the drive module 385. In other embodiments, the sensors 389, 390 may be positioned on a stage, a cassette, etc. A second drive module 386 is unpopulated with a cassette and is coupled to the second stage 388 that is mounted to the rail 380. A cassette crash stop flag 393 and a module crash stop flag 395 are located in the stage 388. Alternatively, the crash stop flags 393, 3905 may be located on the drive module 386. In an embodiment, the crash stop flags 393, 395 are formed from metal and trip the corresponding proximity sensor 389, 390, respectively when moved in front of the proximity sensor. The second drive module 386 also includes a cassette presence sensor 391. The cassette presence sensor 391 may be, for example, a reed switch sensor with magnets. If a cassette is not present on the second drive module 386, the cassette presence sensor 391 may provide a signal indicating a cassette is not mounted on the second drive module 386. In this instance, the drive module proximity sensor 390 is used to determine if the second drive module 386 is getting too close to the first drive module 385. In one embodiment, when the second drive module 386 is within a threshold distance of the first drive module 385, for example, when the module crash stop flag 395 moves in front of the proximity sensor 390, the drive module proximity sensor 390 provides a control signal and an alert may be provided to a user or the movement of the second drive module may be stopped. In another embodiment, if the robotic drive is configured to allow nesting of drive modules, the control computing system may be configured to couple the linear movement of a nested drive module to the linear motion of the device module having the cassette under which the nested drive module is positioned.

Figure 41:
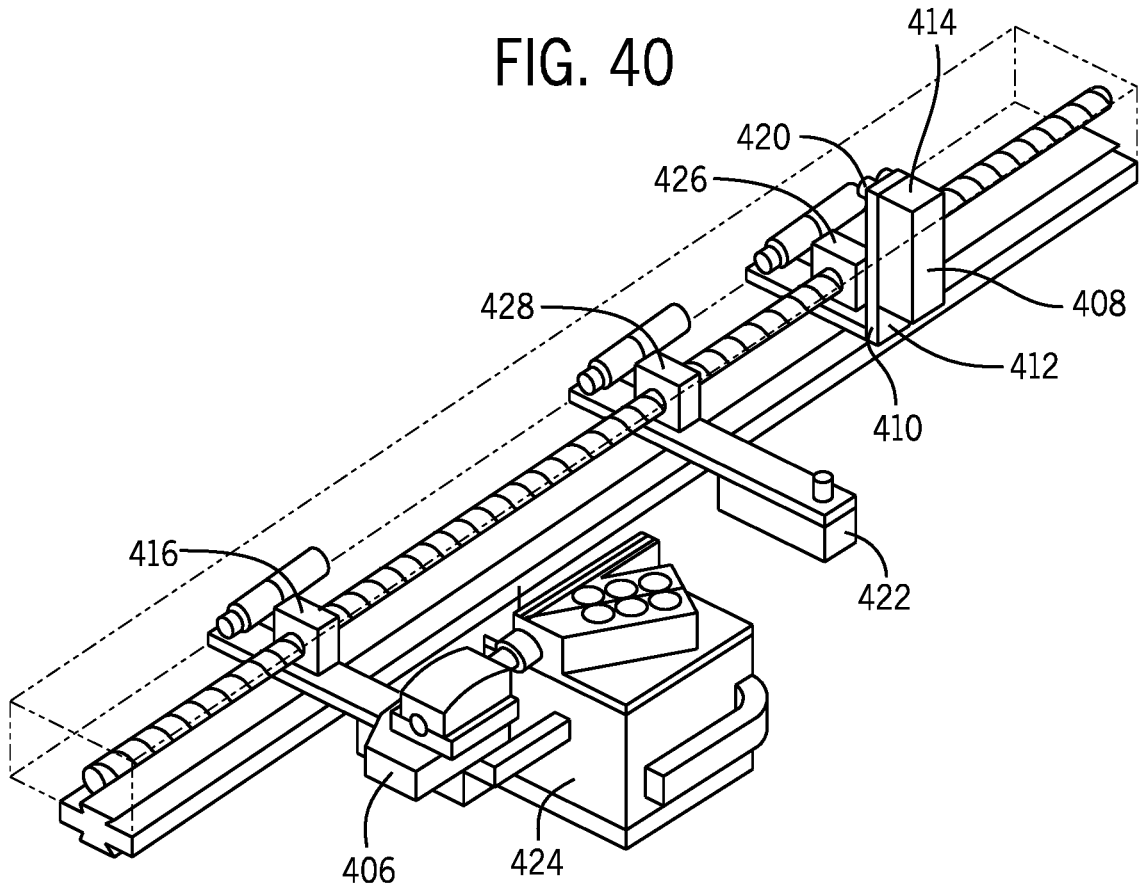
FIG. 41 is a perspective view of the robotic drive of FIG. 40 in accordance with an embodiment.

In another embodiment, a rail or linear member with two slides may be provided to allow certain device modules to be moved past unpopulated drive modules to a different position along the linear member either towards the patient or away from the patient. FIG. 40 is a front view of a robotic drive with a linear member having two slides in accordance with an embodiment and FIG. 41 is a perspective view of the robotic drive of FIG. 40 in accordance with an embodiment. Referring to FIGS. 40 and 41, a rail or linear member 400 has a first slide 402 and a second slide 404 configured to be connected to stages and the corresponding device modules or unpopulated drive modules. While the embodiment in FIGS. 40 and 41 shows a rail with a first slide 402 on an upper surface of the rail and a second slide on the bottom surface of the rail, it should be understood that the slide may be of other opposing surface of the rail. In another embodiment, two separate rails may be used rather than a rail with two slides. A first device module 406 is connected to the first slide 402 of the rail 400 using a stage 416. A second device module 424 is connected to the second slide 404 of the rail 400 using a second stage 418. A first unpopulated drive module 408 is connected to the first slide 402 of the rail 400 using a third stage 426. A second unpopulated drive module 422 is connected to the first slide 402 of the rail 400 using a fourth stage 428. The unpopulated drive modules 408, 422 may be configured to be moved from a vertical to a horizontal position (e.g., "flipped up"). As shown in FIGS. 40 and 41, the first unpopulated drive module 408 includes a pivot 410 located on a first end 412 of the first unpopulated drive module 408. When rotated about the pivot, a second end 414 of the first unpopulated drive module with the coupler 420 moves from a vertical to a horizontal position. In this position, the second drive module 424 may be moved linearly by moving the second stage 418 along the second slide 404 past the "flipped up" drive module 408. For example, the device module 424 on the second slide 404 may be a dedicated guidewire module and the second slide (or rail) allows the robotic drive to be reconfigured by changing the number of, for example, catheter device modules that are in front of the guidewire module.

Figure 42B:
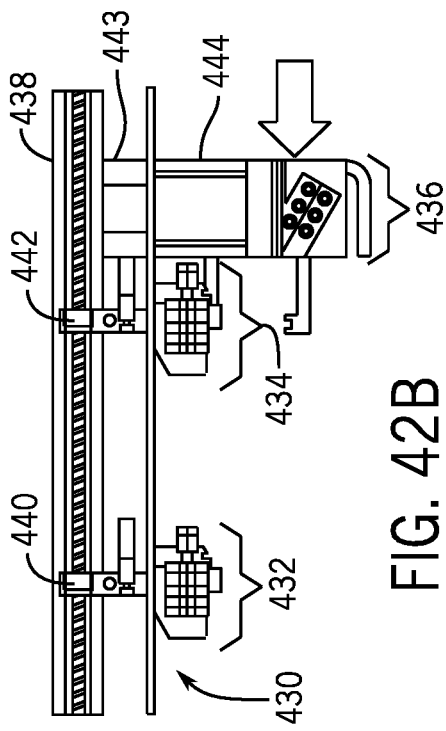
FIGS. 42A-42D illustrate a translating device module that may be repositioned along a linear member in a robotic drive in accordance with an embodiment.
Figure 42A:
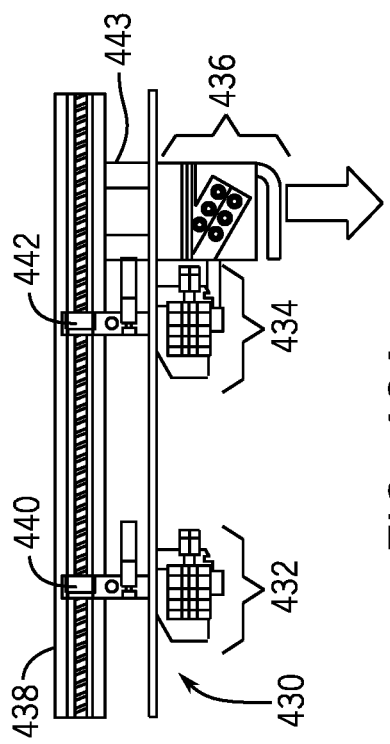
Figure 42D:
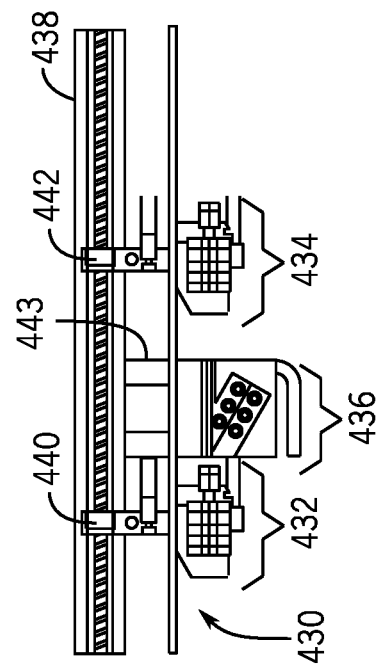
Figure 42C:
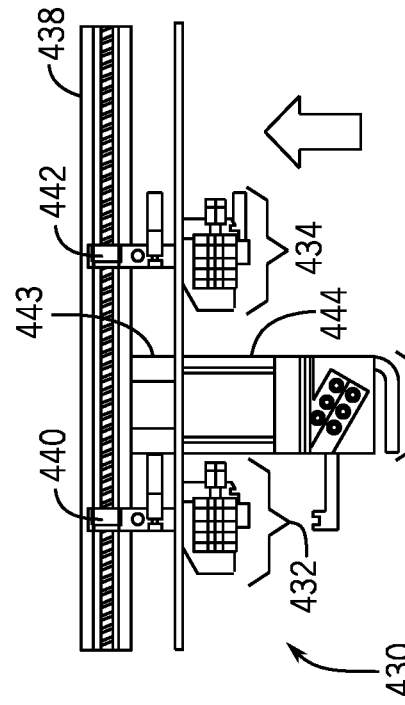

In another embodiment, a device module may be connected to a second slide on a rail or a second rail and be configured to translate in a manner that allows the device module to be moved past another device module or an unpopulated drive module to a different position. FIGS. 42A-42D illustrate a translating device module that may be repositioned along a rail in a robotic drive in accordance with an embodiment. FIG. 42A shows a robotic drive 430 that includes a first device module 432 connected to a first slide (e.g., first slide 402 shown in FIG. 40) of a rail or linear member 438 using a first stage 440, a second device module 434 connected to the first slide of the rail 438 using a second stage 442 and a third device module 436 connected to a second slide (e.g., second slide 404 shown in FIG. 40) of the rail 438 using a third stage 443. The third device module 436 includes an extension member 444 as shown in FIG. 42B that can be pulled out away from the rail 438 so that the device module 436 is able to pass the other device modules 432 and 434 (or alternatively, unpopulated drive modules) on the first slide of the rail 438. The third drive module 436 may then be moved linearly by moving the third stage along the second slide of the rail 438 to a position past the second device module 434 as shown in FIG. 42C. In FIG. 42D, when the third device module 436 is in the desired position, the extension member 444 may be moved back towards the rail 438.

Figure 43:
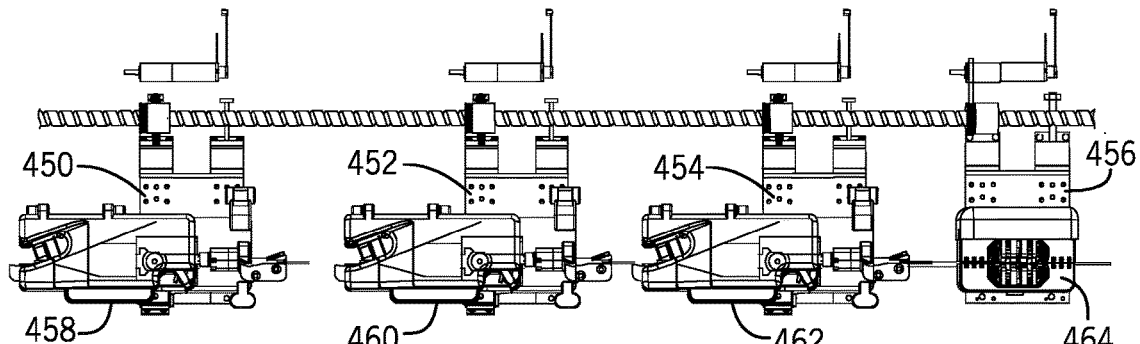
FIG. 43 is a top view of a portion of robotic drive in a tri-axial configuration and including drive modules with more than one coupler in accordance with an embodiment.
Figure 44:
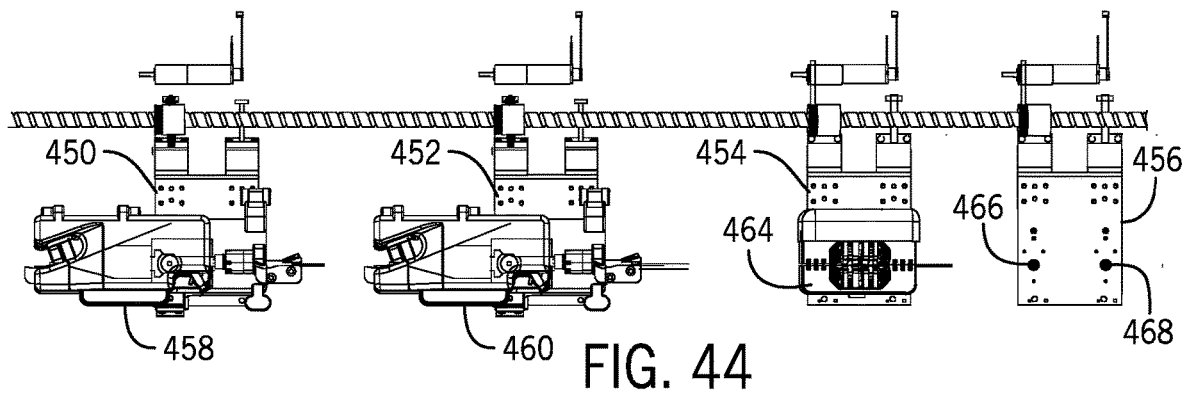
FIG. 44 is a top view of a portion of a robotic drive in a bi-axial configuration and including drive modules with more than one coupler in accordance with an embodiment.
Figure 45:
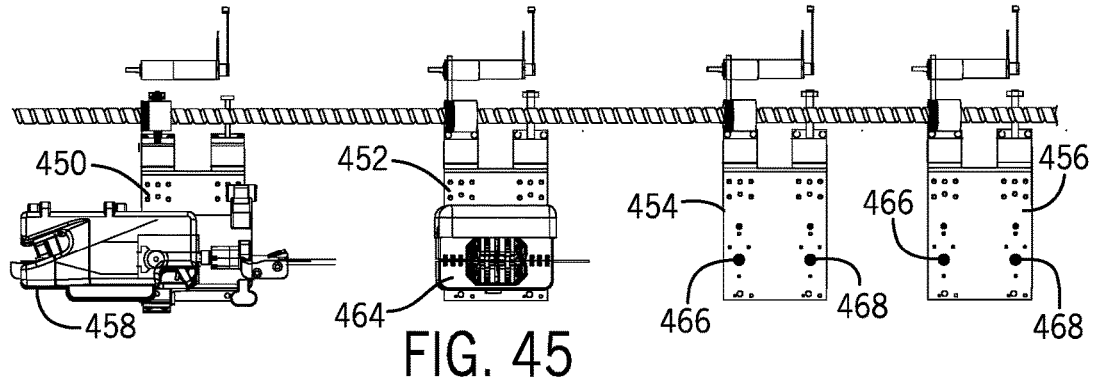
FIG. 45 is a top view of a portion of a robotic drive in a mono-axial configuration and including drive modules with more than one coupler in accordance with an embodiment.

As discussed above, in one embodiment a cassette used in a device module (e.g., cassette 91 shown in FIG. 7) may be configured to provide one degree of freedom (e.g., rotation). Accordingly, a drive module with a single coupler (e.g., drive module 68 shown in FIG. 5) may be used to drive the single degree of freedom of the cassette. In another embodiment, a cassette used in a device module (e.g., cassette 111 shown in FIG. 9) may be configured to provide two or more degrees of freedom (e.g., rotation and pinch/unpinch for a guidewire). Accordingly, a drive module may be configured to include two or more couplers to support cassettes that provide one or more degrees of freedom. In an embodiment, the drive module with two or more couplers includes a separate motor for each coupler. FIG. 43 is a top view of a portion of robotic drive in a tri-axial configuration and including drive modules with more than one coupler in accordance with an embodiment. As mentioned above, as used herein the terms tri-axial, bi-axial and mono-axial refer to the number of serially concentric catheters but not including any wire based EMDs. In FIG. 43, a first drive module 450, a second drive module 452, a third drive module 454, and a fourth drive module 456 are shown. A cassette 458, 460, 462 and 464 is mounted to each drive module 450, 452, 454 and 456, respectively. Cassettes 458, 460, 462 are configured to provide one degree of freedom and the fourth cassette 464 is configured to provide two degrees of freedom. Each of the four drive modules include two couplers as shown in FIGS. 44 and 45. FIG. 44 is a top view of a portion of a robotic drive in a bi-axial configuration and including drive modules with more than one coupler in accordance with an embodiment and FIG. 45 is a top view of a portion of a robotic drive in a mono-axial configuration and including drive modules with more than one coupler in accordance with an embodiment. In FIG. 44, the fourth drive module 456 is unpopulated and in FIG. 45, the third 454 and fourth 456 drive module are unpopulated. In FIG. 44, unpopulated drive module 456 includes a first coupler 466 and a second coupler 468. A separate motor (not shown) may be provided in the drive module 456 to drive each coupler 466, 468. The first coupler 466 and the second coupler 468 are aligned along a device axis (not shown) which enables being put into a grid/matrix. Each drive module 450, 452, 454 and 456 may be used to couple to a cassette with one or two degrees of freedom. For example, in FIG. 44 the second drive module 452 is coupled to a cassette 460 with a single degree of freedom and in FIG. 45, the second drive module 452 is coupled to a cassette with two degrees of freedom. Each drive module 450, 452, 454 and 456 uses a separate stage translation motor to drive linear movement of the respective drive module along a rail or linear member.

Figure 46:
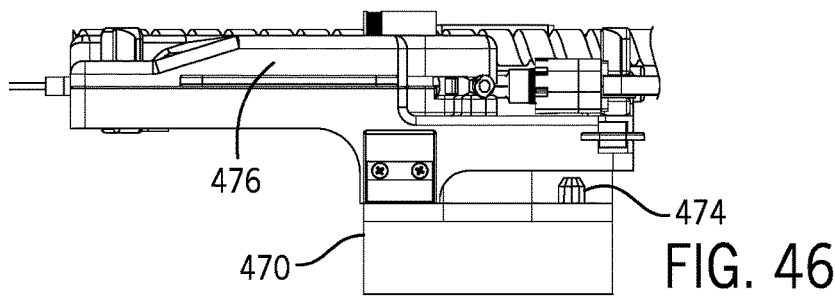
FIG. 46 is a side view of a cassette with one degree of freedom mounted to a drive module with more than one coupler in accordance with an embodiment.
Figure 47:
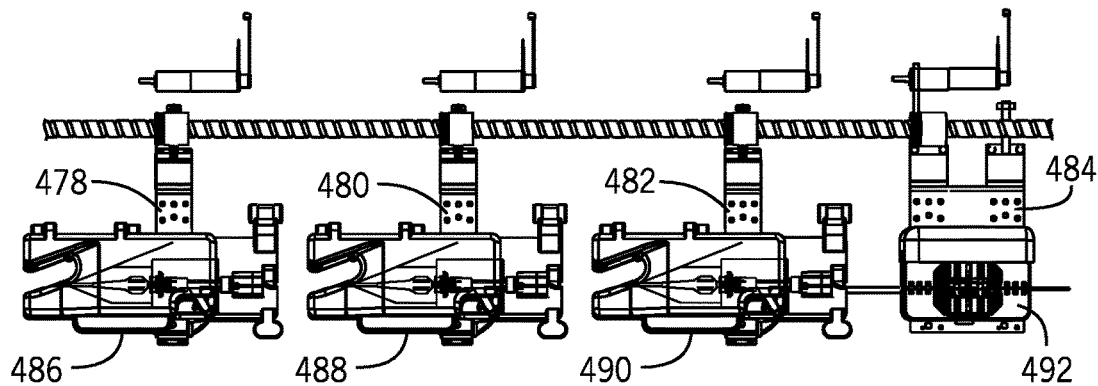
FIG. 47 is a top view of a portion of a robotic drive in a tri-axial configuration and including both drive modules with a single coupler and drive modules with more than one coupler in accordance with an embodiment.

FIG. 46 is a side view of a cassette with one degree of freedom mounted to a drive module with more than one coupler in accordance with an embodiment. In FIG. 46, a cassette 476 with a single degree of freedom mounts to a drive module 470 using a first coupler (not shown) and the second coupler 474 remains unpopulated and does not engage with the cassette 476. In an embodiment, the control computing system of the robotic drive may be configured to automatically lock-out the unused coupler 474. In one example, a sensor may be provided in the drive module 470 that can detect what type of cassette is mounted to the drive module. In another example, a user may enter the type of cassette using, for example, a control station. In another embodiment, a robotic drive may include a combination of drive modules with a single coupler and drive modules with two or more couplers. FIG. 47 is a top view of a portion of a robotic drive in a tri-axial configuration and including both drive modules with a single coupler and drive modules with more than one coupler in accordance with an embodiment. FIG. 47 shows three drive modules 478, 480 and 482 with a single coupler and one drive module 484 with two couplers. Cassettes 486, 488 and 490 with a single degree of freedom are mounted to the drive modules 478, 480 and 482, respectively. A cassette 492 with two degrees of freedom is mounted to the drive module 484 with two couplers. Having a robotic drive system that includes drive modules with two or more couplers provide the ability to reconfigure the robotic drive by only moving cassettes between drive modules.

Figure 48:
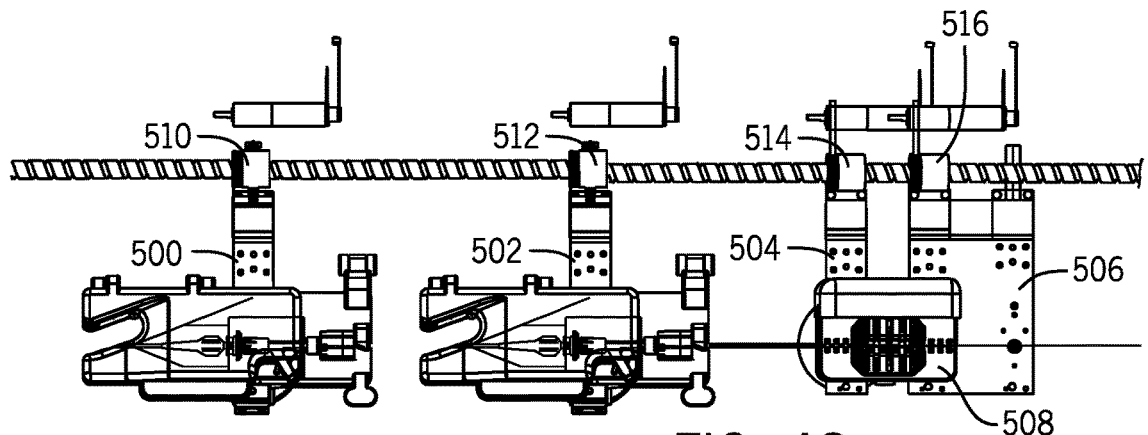
FIG. 48 is a top view of a portion of a robotic drive in a bi-axial configuration and includes a cassette mounted to two drive modules in accordance with an embodiment.
Figure 49:
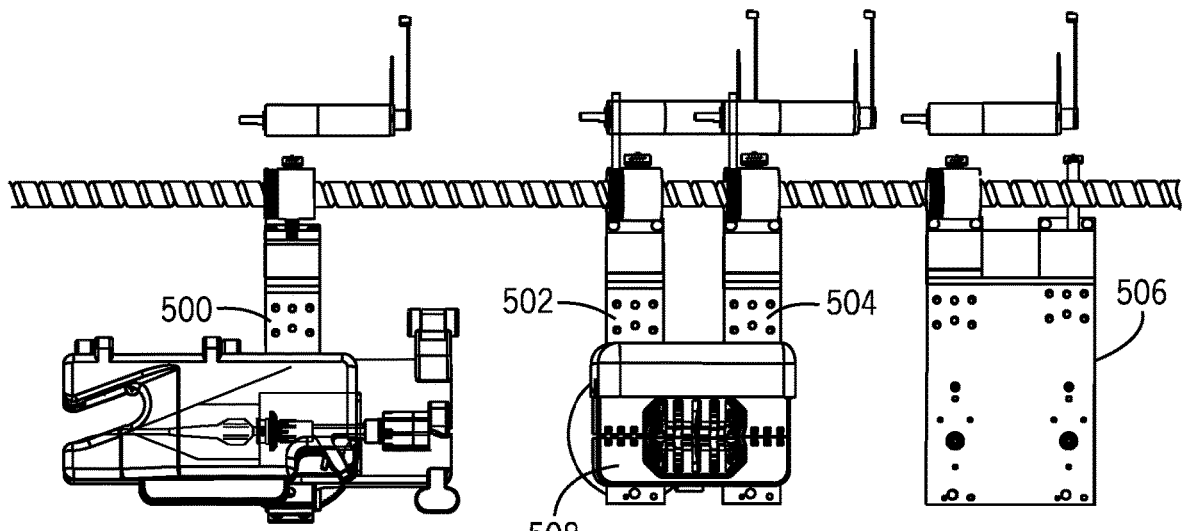
FIG. 49 is a top view of a portion of a robotic drive in mono-axial configuration and includes a cassette mounted to two drive modules in accordance with an embodiment.

In another embodiment, a cassette that is configured to provide two or more degrees of freedom (e.g., rotation and pinch/unpinch for a guidewire) may be mounted on two independently driven drive modules, in other words, the cassette may straddle between two drive modules engaging a coupler on each drive module. Accordingly, two drive modules may be used to manipulate elongated medical device that require more complex degrees of freedom. FIG. 48 is a top view of a portion of a robotic drive in a bi-axial configuration and includes a cassette mounted to two drive modules in accordance with an embodiment and FIG. 49 is a top view of a portion of a robotic drive in mono-axial configuration and includes a cassette mounted to two drive modules in accordance with an embodiment. In FIG. 48, a first drive module 500, a second drive module 502 and a third drive module 504 are provided that each have a single coupler and are connected to a first 510, second 512 and third 514 stage, respectively. A fourth drive module 506 includes two couplers as described above with respect to FIGS. 43-47 and is connected to a fourth stage 516. While the fourth drive module 506 is shown as having two couplers, the fourth drive module could also be a single coupler drive module similar to drive modules 500-504. A cassette 508 that is configured to provide two degrees of freedom is mounted so as to engage both the coupler the third drive module 504 and one of the couplers of the fourth drive module 506. For example, cassette 508 may be configured to provide rotation and to pinch/unpinch the elongated medical device. Linear movement of the elongated medical device is provide by linear movement of the third 504 and fourth 506 drive modules via the third 514 and fourth 516 stages along a rail or linear member. Each coupler can provide power to drive one of the degrees of freedom for the cassette 508. The third drive module 504 and the fourth drive module are positioned a predetermined distance from one another that allows the cassette to be mounted on each drive module 504, 506. The control computing system (not shown) of the robotic drive may be configured to linearly translate the third drive module 504 and the fourth drive module 506 as a unit so that the relative distance between the couplers on each drive module 504, 506 remains the same. For example, the third 504 and fourth 506 drive modules are electronically coupled to effectively form a single drive module. In another embodiment, the cassette may be mounted to two single coupler drive modules. In FIG. 49, the cassette 508 is mounted so as to engage the coupler of the second drive module 502 and the coupler of the third drive module 504. In another embodiment, two independent drive modules may be mechanically coupled together and connect to a single stage so that a single stage translation motor may be used to drive the mechanically coupled pair of drive modules. This may be used, for example, to reduce the number of catheters in front of device module with a cassette that provide two or more degrees of freedom. Straddling drives can also be used for single devices that require relative linear translation. For example, some self-expanding stents or coils may require pulling on a wire or shaft to deploy. Two modules may be utilized where one modules holds onto the body or sheath of the deployment device while the other module handles the deployment wire or shaft.

Figure 50:
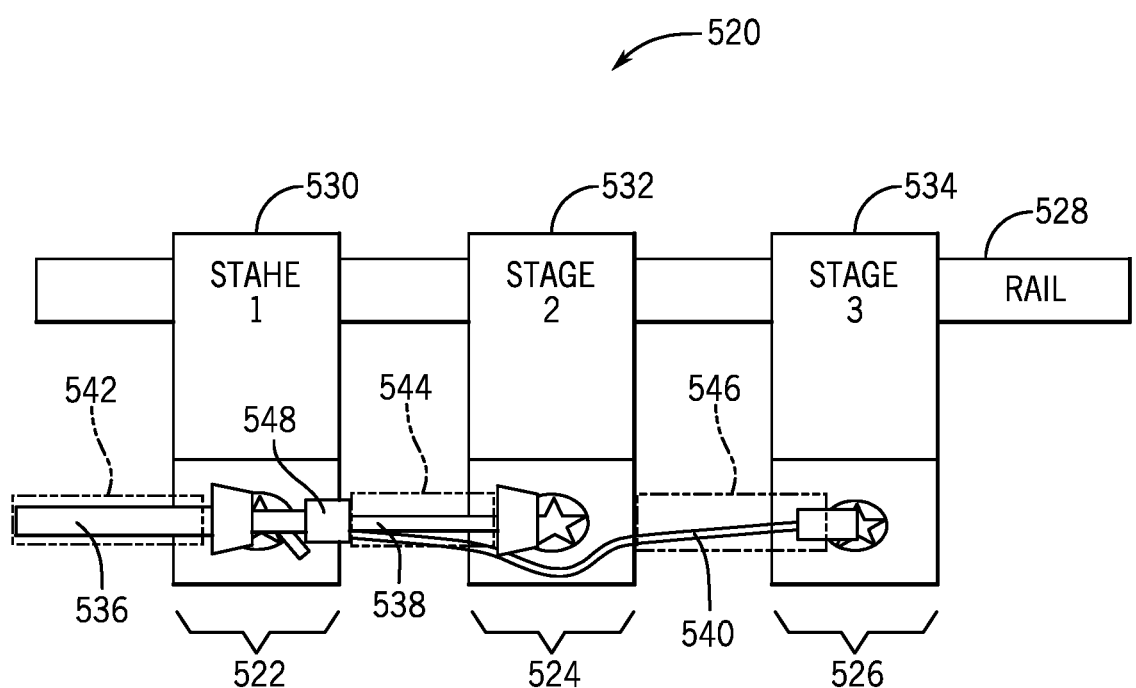
FIG. 50 is a block diagram of a parallel configuration for elongated medical devices in a robotic drive in accordance with an embodiment.
Figure 51:
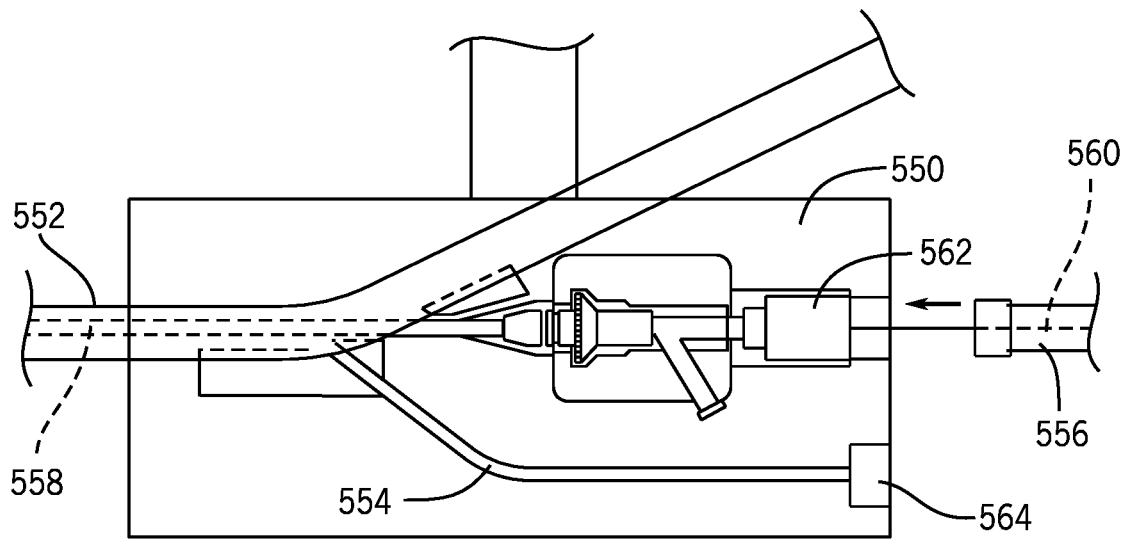
FIG. 51 is a top view of a cassette with a bypass channel and elongated medical devices in a serial configuration in accordance with an embodiment.
Figure 52:
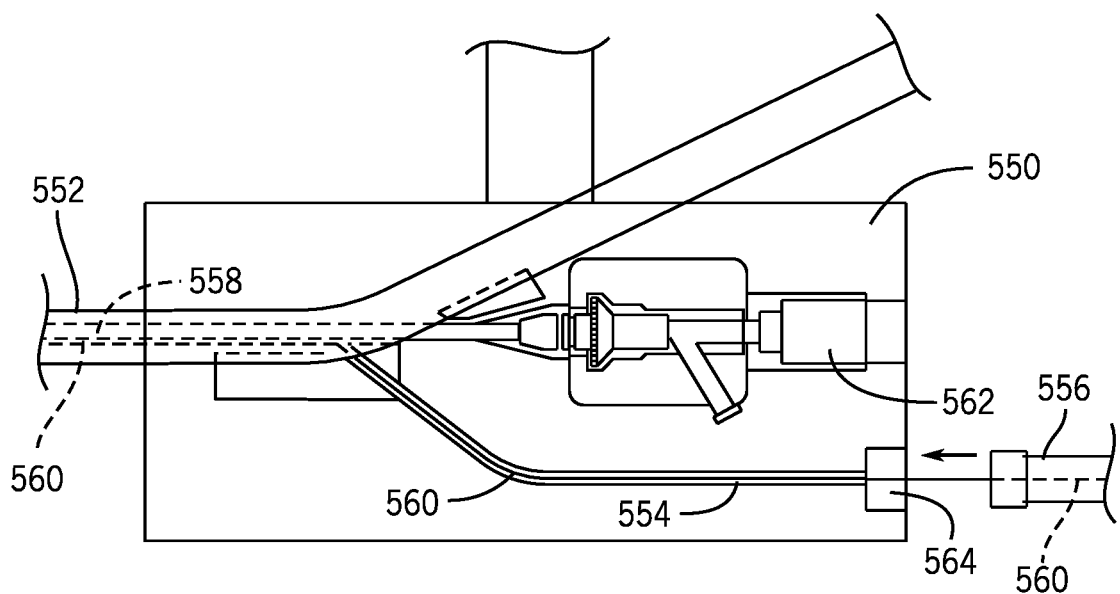
FIG. 52 is a top view of a cassette with a bypass channel and elongated medical devices in a parallel configuration in accordance with an embodiment.

As discussed above, the robotic drive may be reconfigured to provide various serial device configurations. In other embodiments, various apparatus and methods may be used to provide a robotic drive with both serial and parallel device configurations. FIG. 50 is a block diagram of a parallel configuration for elongated medical devices in a robotic drive in accordance with an embodiment. The robotic drive configuration 520 includes a first device module 522, a second device module 524 and a third device module 526 connected to a rail or linear drive module 528 using a first stage 530, a second stage 532 and a third stage 534, respectively. The first device module 522 includes a first elongated medical device (EMD) 536, the second device modules 524 includes a second EMD 538 and the third device module 526 includes a third EMD 540. The first EMD 536 is supported by a first support track 542 and is configured to receive the second 538 and third 540 EMDs in a parallel configuration. The second EMD 538 and the third EMD 540 are supported between the second device module 524 and the first device module 522 using a second support track 544. The third EMD 540 is supported between the third device module 526 and the second device module 524 with a third support track 546. In an embodiment, the first 542, second 544, and third 546 support tracks may be a device support as described further below with respect to FIGS. 79-107. Rather than enter a hub of the second device module 524 and pass through the second EMD 538 in a serial configuration, the third EMD 540 is positioned in a bypass channel (shown in FIGS. 51 and 52) on a cassette of the second device module 524 so as to bypass the hub and enter the second support track 544 parallel to the second EMD 538. The second 538 and third 540 EMDs then enter a hub 548 of the first EMD 536 on the first device module 522. The second 538 and third 540 EMDs may then enter and pass through the first EMD 536 in a parallel configuration. As mentioned, a cassette in the second device module 524 includes a bypass channel to support the third EMD 540 as it bypasses the second EMD 538. FIG. 51 is a top view of a cassette with a bypass channel and elongated medical devices in a serial configuration in accordance with an embodiment and FIG. 52 is a top view of a cassette with a bypass channel and elongated medical devices in a parallel configuration in accordance with an embodiment. Referring to FIGS. 51 and 52, a cassette 550 incudes a bypass channel 554 and a bypass channel connection point 564. The cassette 550 includes a first EMD 558 and a first support track 552. In FIG. 51, a second EMD 560 is shown that is supported by a second support track 556 that connects to a hub 562 so that the second EMD may enter the hub 562 and pass through the first EMD 558 in a serial configuration. In an embodiment, the first 552 and second 556 support tracks may be a device support as described further below with respect to FIGS. 79-107. In FIG. 52, to provide a parallel device configuration, the second support track 556 connects to the connection point 564 so that the second EMD 560 may be positioned in and move along the bypass channel 554. The first support track 552 is configured to receive the second EMD 560 at the distal end of the bypass channel 554 so that the second EMD 560 travels through the second support track 552 parallel to the first EMD 558. In the embodiment shown in FIG. 52, the first EMD 558 is a catheter that is positioned along a central axis of the cassette 550 and the second EMD 560 is a wire-based device (e.g., a guidewire). In another embodiment, the first EMD 558 may be a wire-based device that is positioned along the central axis of the cassette 550 and the second EMD 560 may be a catheter (e.g., a rapid exchange catheter).

Figure 53:
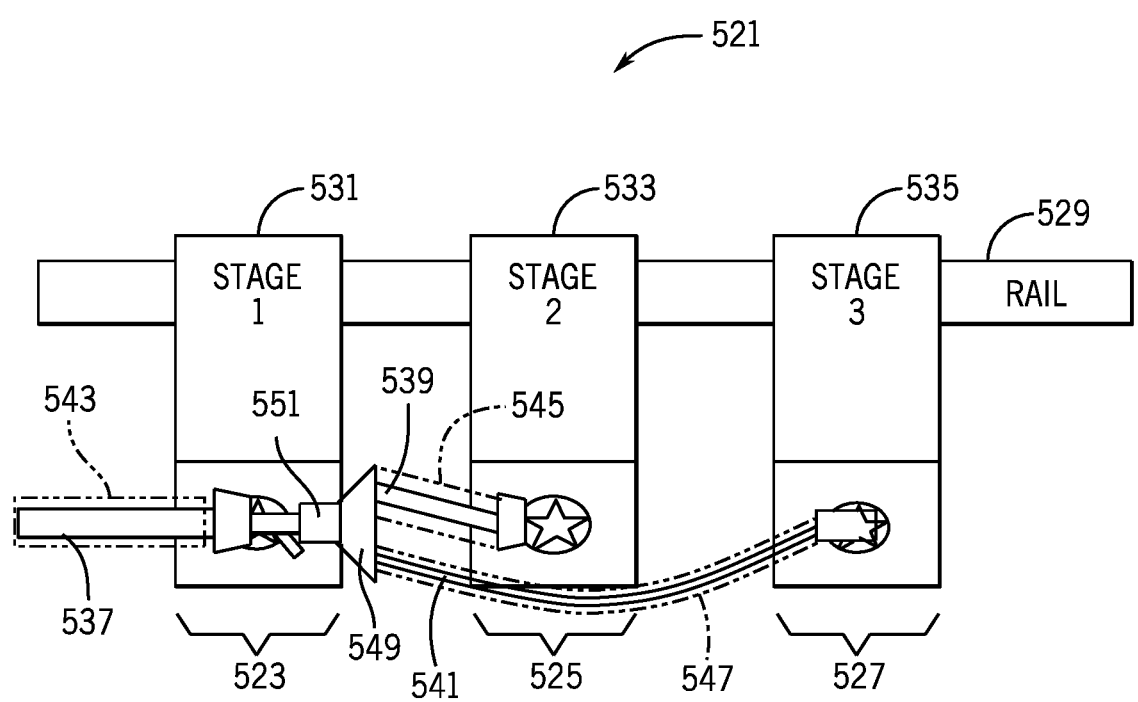
FIG. 53 is a block diagram of a parallel configuration for elongated medical devices in a robotic drive in accordance with an embodiment.
Figure 54:
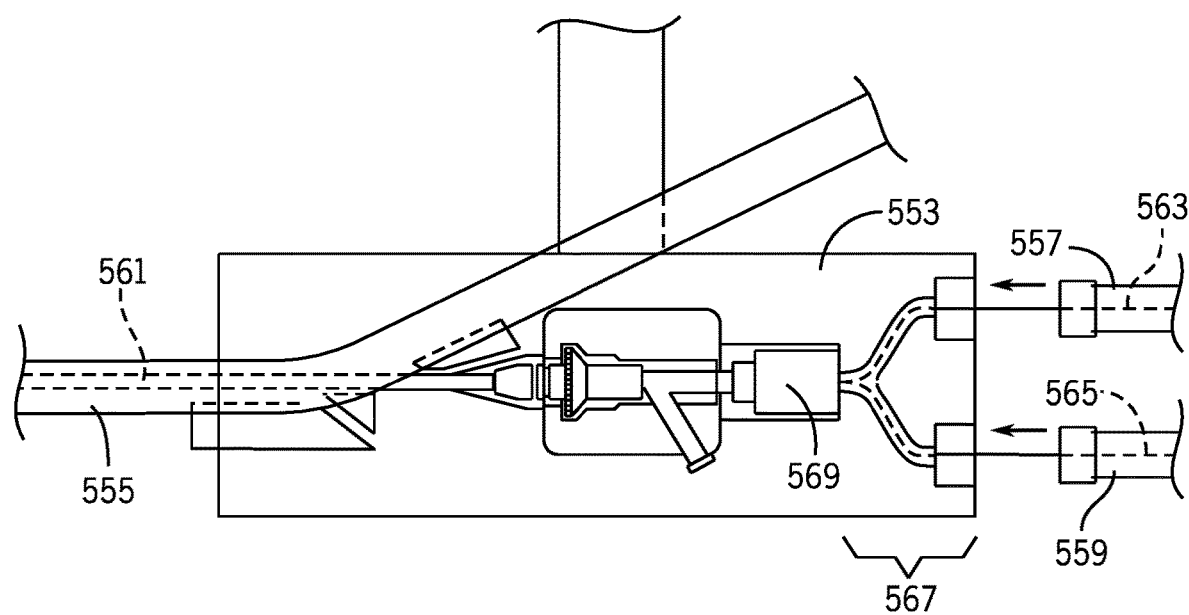
FIG. 54 is a top view of a cassette configured to receive two elongated medical devices in a parallel configuration in accordance with an embodiment.

In another embodiment, a support track may be used to support an elongated medical device as it bypasses a hub to provide a parallel device configuration. FIG. 53 is a block diagram of a parallel configuration for elongated medical devices in a robotic drive in accordance with an embodiment. The robotic drive configuration 521 includes a first device module 523, a second device module 525 and a third device module 527 connected to a rail or linear member 529 using a first stage 531, a second stage 533 and a third stage 535, respectively. The first device module 523 includes a first elongated medical device (EMD) 537, the second device modules 525 includes a second EMD 539 and the third device module 527 includes a third EMD 541. The first EMD 537 is supported by a first support track 543 and is configured to receive the second 539 and third 541 EMDs in a parallel configuration. The second EMD 539 is supported between the second device module 525 and the first device module 523 with a second support track 545. In an embodiment, the first 542 and second 545 support tracks may be a device support as described further below with respect to FIGS. 79-107. The second support track connects to a hub adapter 549 in the first device module 523. The third EMD 541 is supported between the third device module 527 and the first device module 523 using a third support track 547. Rather than enter a hub of the second device module 525 and pass through the second EMD 539 in a serial configuration, the third EMD 541 and the third support track 547 are positioned so as to bypass the hub. The third support track 547 is connected to the hub adapter 549. The second EMD 539 and the third EMD 541 enter the hub adapter 549 and then a hub 551 of the first EMD 537 in a parallel configuration. The second 539 and the third 541 EMDs may then enter and pass through the first EMD 537 in a parallel to one another. The hub adapter 549 is configured to connect to and receive two or more support tracks. FIG. 54 is a top view of a cassette configured to receive two elongated medical devices in a parallel configuration in accordance with an embodiment. A cassette 553 incudes a first EMD 561 and a first support track 555. A second EMD 563 is shown that is supported by a second support track 557 that connects to a hub adapter 567. A third EMD 565 is shown that is supported by a third support track 559 that connects to the hub adapter 567. Accordingly, the hub adapter 567 is configured to connect to the second support track 557 and the third support track 559 so that the second EMD 563 and the third EMD 565 may enter the hub 569 and pass through the first EMD 555 in a parallel configuration.

Figure 55:
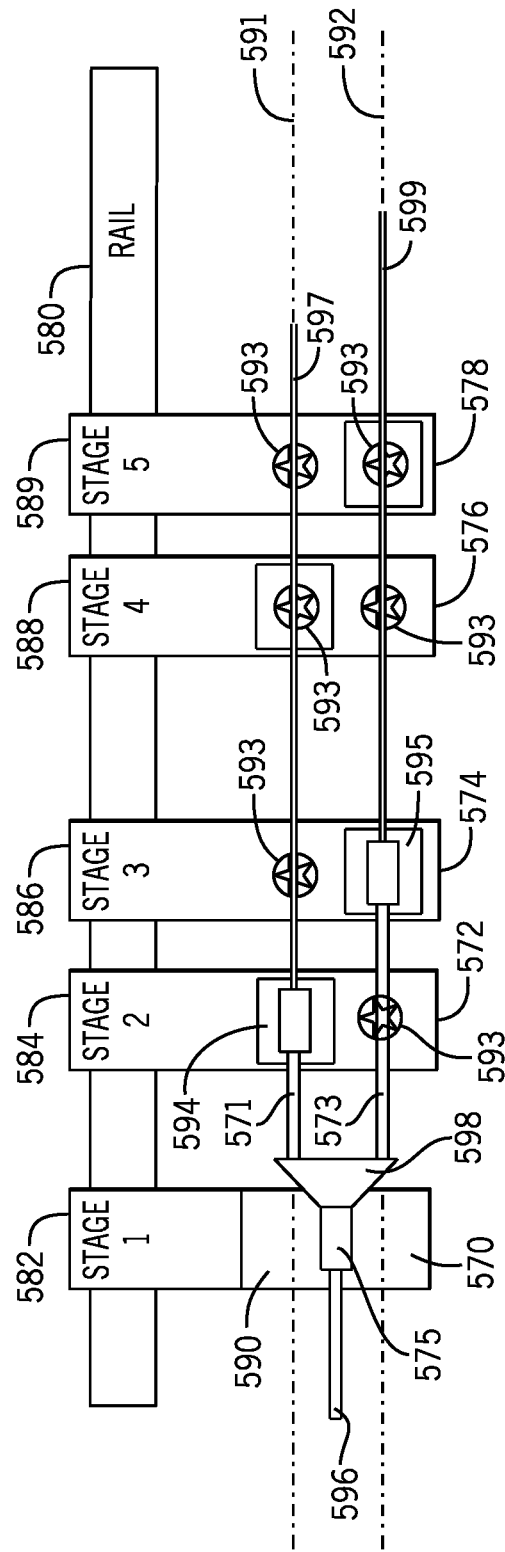
FIG. 55 is a block diagram of a robotic drive configuration with multiple device axes in accordance with an embodiment.

In another embodiment, a parallel device configuration may be facilitated by providing multiple couplers on each drive module so as to provide multiple device axis in the robotic drive. FIG. 55 is a block diagram of a robotic drive configuration with multiple device axes in accordance with an embodiment. A first drive module 570, a second drive module 572, a third drive module 574, a fourth drive module 576 and a fifth drive module 578 are connected to a rail or linear member 580 using a first stage 582, a second stage 584, a third stage 586, a fourth stage 588 and a fifth stage 589, respectively. Each drive module includes two couplers 593. The two couplers 593 on each drive module 570, 572, 574, 576, 578 are positioned parallel to one another such that each coupler defines a device axis. A first device axis 591 is defined by a first coupler on each drive module 570, 572, 574, 576, 587 and a second device axis 592 is defined by a second coupler on each drive module 570, 572, 574, 576, 587. In FIG. 55, the couplers on fourth 576 and fifth 578 drive modules are unpopulated. A first cassette 590 is mounted to the first drive module 570 and includes a first EMD (not shown) supported in a first support track 596. A second cassette 594 is mounted to a coupler 593 on the first device axis 591 and includes a second EMD 597 that is supported by a second support track 571 between the second drive module 572 and the first drive module 570. The second coupler on the second drive module 572 that is on the second device axis 592 is unpopulated. A third cassette 595 is mounted to a coupler 593 on the second device axis 592 and includes a third EMD 599 that is supported by a third support track 573 between the second drive module 572 and the first drive module 570. In an embodiment, the first 596, second 571 and third 573 support tracks may be a device support as described further below with respect to FIGS. 79-107. The second coupler on the third drive module 574 that is on the first device axis 591 is unpopulated. The second support track 571 and the third support track 573 each connect a hub adapter 598 (e.g., a hub adapter as described above with respect to FIG. 54). The second EMD 597 and the third EMD 599 enter the hub adapter 598 and then a hub 575 of the first EMD in a parallel configuration. In other embodiments, additional cassettes and EMDs in the fourth 576 and fifth 578 drive modules may be provided in either a serial or parallel configuration.

Figure 56:
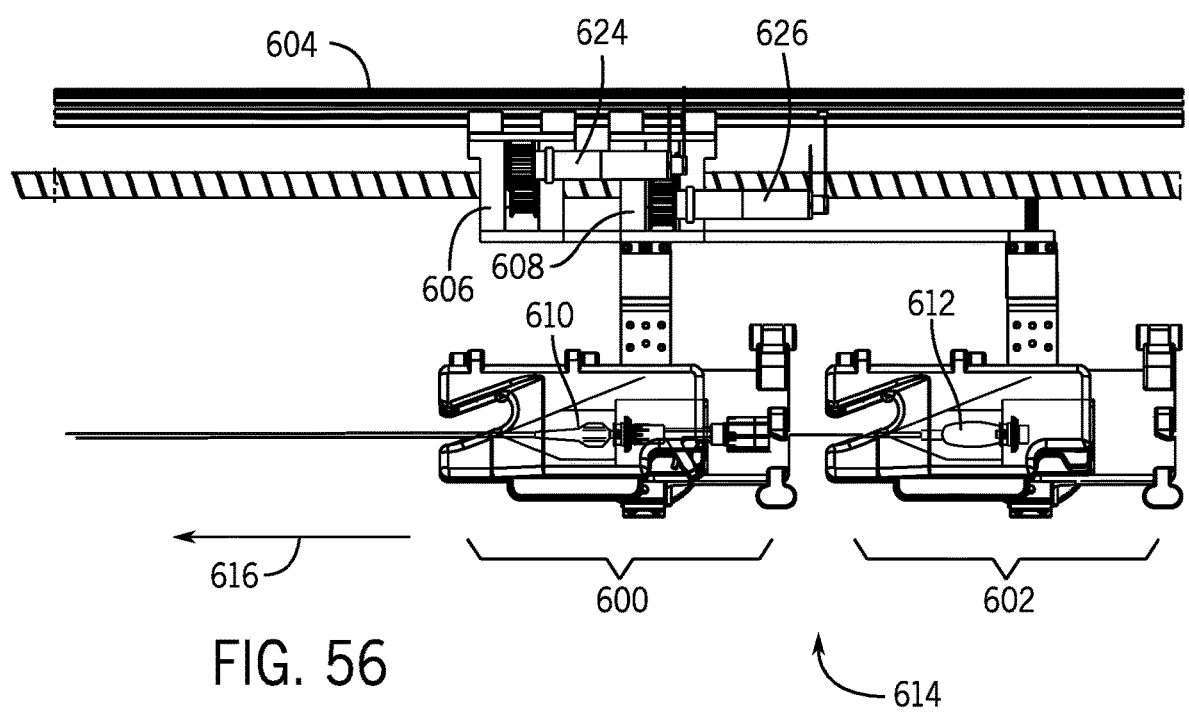
FIG. 56 is a block diagram of an elongated medical device positioned across two device modules in a first position in accordance with an embodiment.
Figure 57:
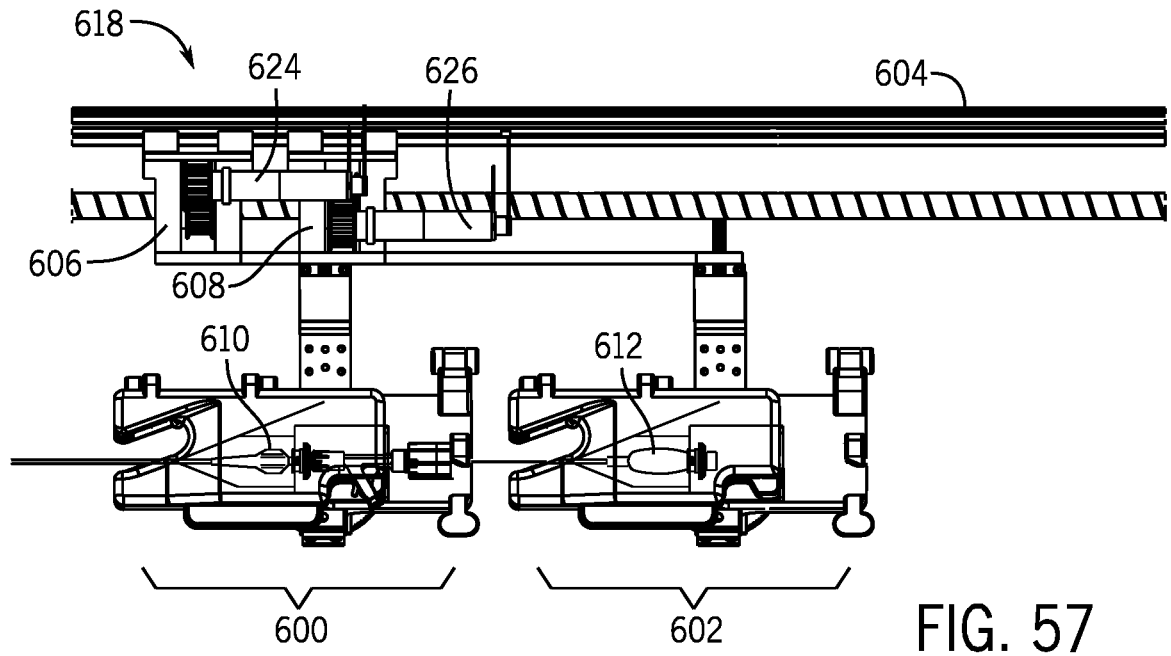
FIG. 57 is a top view of an elongated medical device positioned across two device modules in a second position in accordance with an embodiment.
Figure 58:
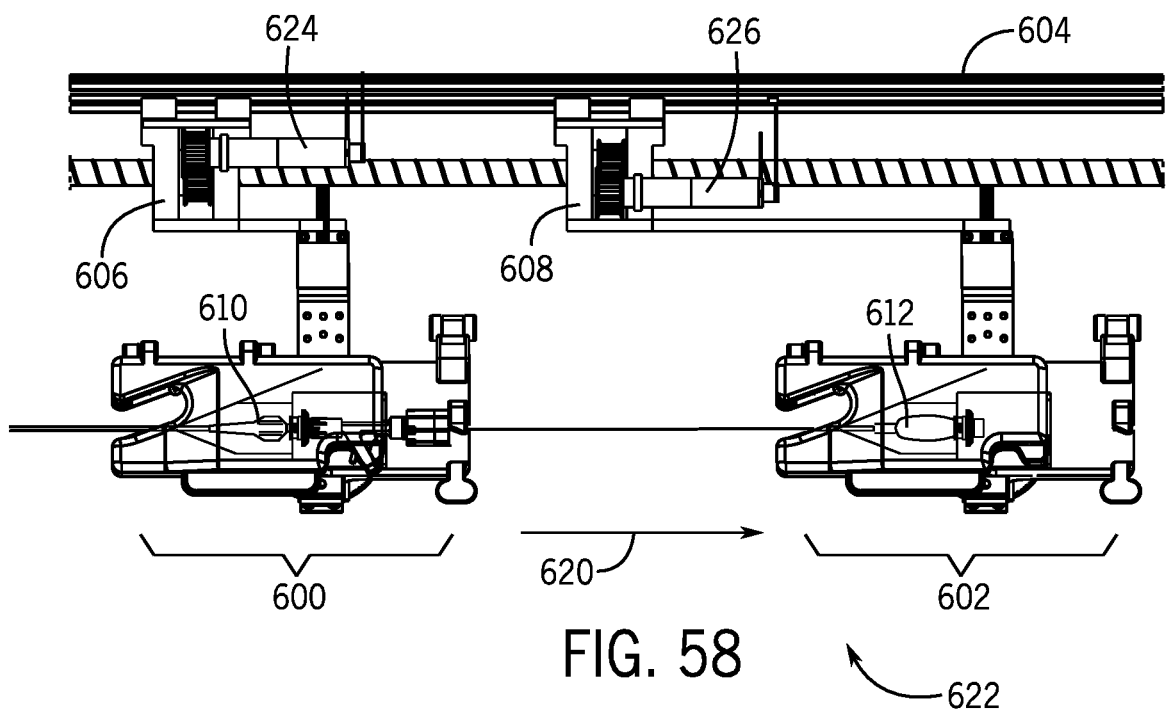
FIG. 58 is a top view of an elongated medical device positioned across two device modules in a third position in accordance with an embodiment.

In another embodiment, an EMD that includes a deployable portion may be positioned across two device modules and the independent linear motion of the device modules used to deploy the EMD. For example, a self-expanding stent or coil may requiring pulling on a wire or a shaft or knob to deploy. FIG. 56 is a top view of an elongated medical device positioned across two device modules in a first position in accordance with an embodiment. A first device module 600 is connected to a rail or linear member 604 using a first stage 606 and a second device module 602 is connected to the rail 604 using a second stage 608. A first linear translation motor 624 is coupled to the first stage 606 and is configured move the first stage 606 and the first device module 600 linearly along the rail 604. A second linear translation motor 626 is coupled to the second stage 608 and is configured move the second stage 608 and the second device module 602 linearly along the rail 604. A linearly deployable EMD includes a first section 610 positioned in the first device module 600 and a second section 612 positioned in the second device module 604. The first section 610 may be for example, a body or sheath of the linearly deployable EMD and the second section 612 may be, for example, a deployment wire and/or a deployment shaft or knob. The linear movement, e.g., indicated by arrow 616, of the first 600 and second 602 device modules may be coupled together so that the two modules move together from a first position 614 (shown in FIG. 57) to a second position 618 (shown in FIG. 58) to linearly translate the deployable EMD. FIG. 57 is a top view of an elongated medical device positioned across two device modules in a second position in accordance with an embodiment. In FIG. 57, the first 600 and second 602 drive modules have been moved together in a distal direction by coupling the linear motion of the first 606 and second 608 stages along the rail or linear member 604. To deploy the linearly deployable EMD, the second stage 608 and the second device module 602 may be moved independently using the second stage translation motor 626. FIG. 58 is a top view of an elongated medical device positioned across two device modules in a third position in accordance with an embodiment. In FIG. 58, the second stage 608 and the second device module 602 have been moved away from the first stage 606 and first device module 600 in a proximal direction as indicated by arrow 620. The second device module 602 with the second section 612 of the EMD is shown in a third position 622. Linear movement of the second device module 602 provides the required linear motion (e.g., pulling) on the second section 612 of the EMD to deploy the device.

Figure 59:
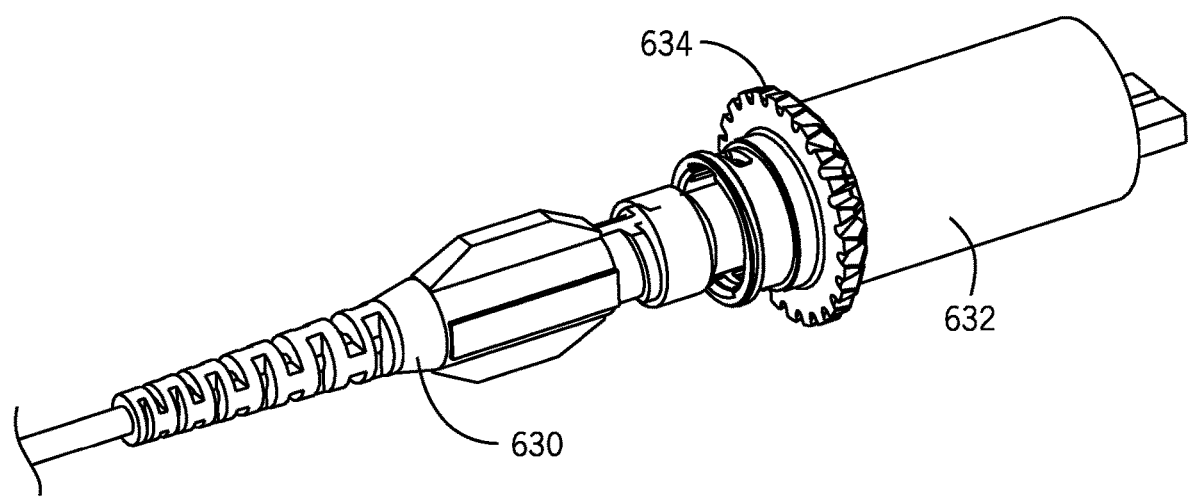
FIG. 59 is a perspective view of an exemplary rotationally deployable elongated medical device with an on-device adapter in accordance with an embodiment.
Figure 60:
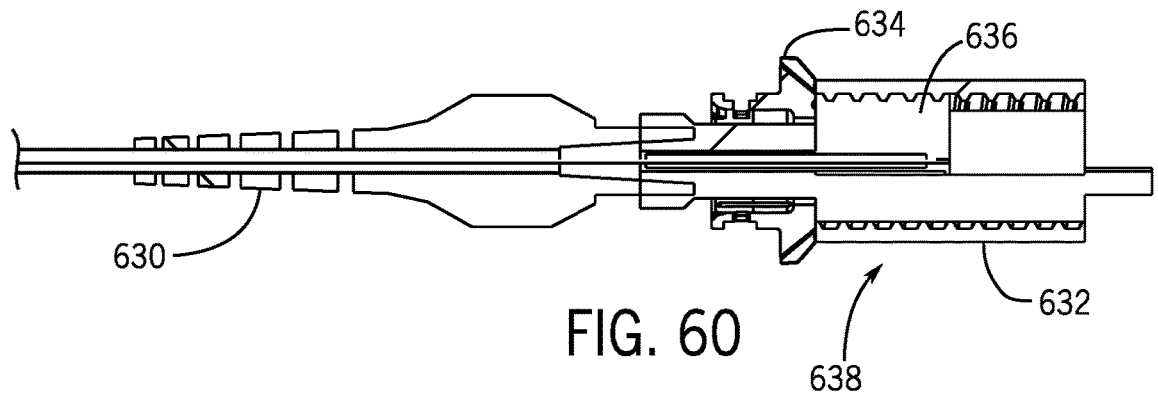
FIG. 60 is cross-sectional view of the rotationally deployable EMD of FIG. 59 in an un-deployed state in accordance with an embodiment.
Figure 61:
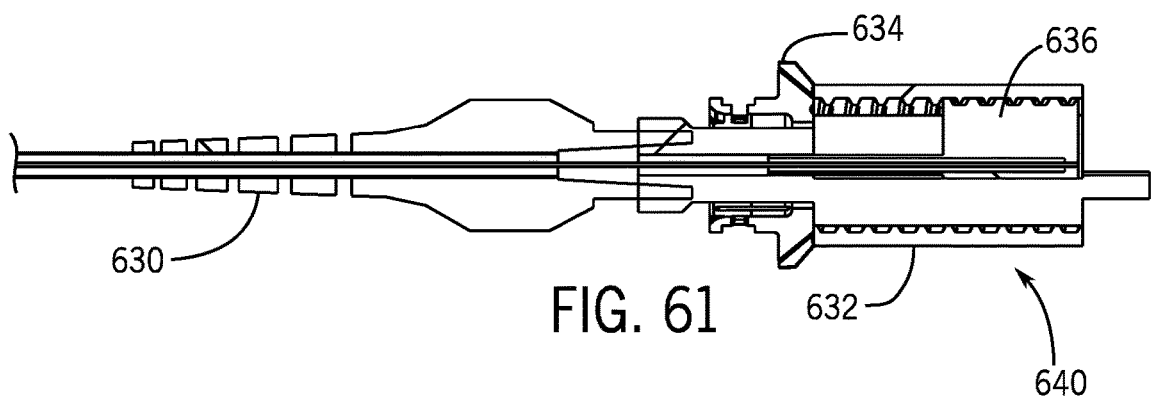
FIG. 61 is cross-sectional view of the rotationally deployable EMD of FIG. 59 in a deployed state in accordance with an embodiment.
Figure 62:
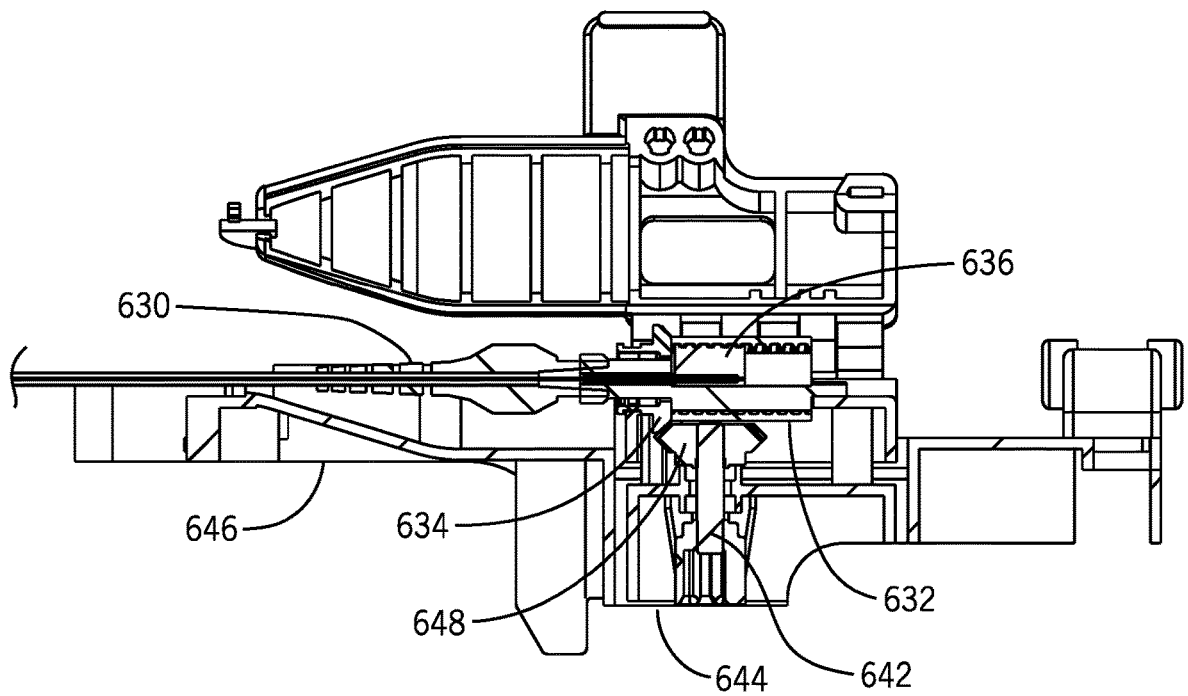
FIG. 62 is a cross-sectional vie of the rotationally deployable EMD of FIG. 59 in a cassette on a drive module in accordance with an embodiment.

In another embodiment, a coupler in a drive module of a device module may be used to deploy a rotationally deployable EMD. For example, a stent system may include a shaft or knob to retract a sheath over a self-expanding stent. A rotating motion may be used to accomplish the unsheathing. FIG. 59 is a perspective view of an exemplary rotationally deployable elongated medical device with an on-device adapter in accordance with an embodiment. A rotationally deployable EMD 630 includes a shaft or knob 632 that may be rotated to deploy, for example, a stent. An on-device adapter 634, for example, a gear, is provided around the shaft to interface with a cassette in a device module of a robotic drive. FIG. 60 is cross-sectional view of the rotationally deployable EMD of FIG. 59 in an un-deployed state in accordance with an embodiment, FIG. 61 is cross-sectional view of the rotationally deployable EMD of FIG. 59 in a deployed state in accordance with an embodiment and FIG. 62 is a cross-sectional vie of the rotationally deployable EMD of FIG. 59 in a cassette on a drive module in accordance with an embodiment. The shaft 632 includes a deployable element 636 that is shown in FIG. 60 in a first position 638 where the device 630 is not deployed. The deployment element 636 may be, for example, a screw mechanism. The on-device adapter 634 may be used to interface with a bevel gear 648 in a cassette 646 as shown in FIG. 62. The bevel gear is coupled to a coupler 642 in a drive module 644 to which the cassette 646 is mounted. Rotation of the coupler 642 rotates the bevel gear 648 which in turn rotates the on-device adapter 634. Rotation of the on-device adapter 634 causes the shaft 632 to rotate which translates the deployment element 636 linearly to a second position 640 as shown in FIG. 61, which causes the deployment (e.g., unsheathing) of the device 630.

Figure 63:
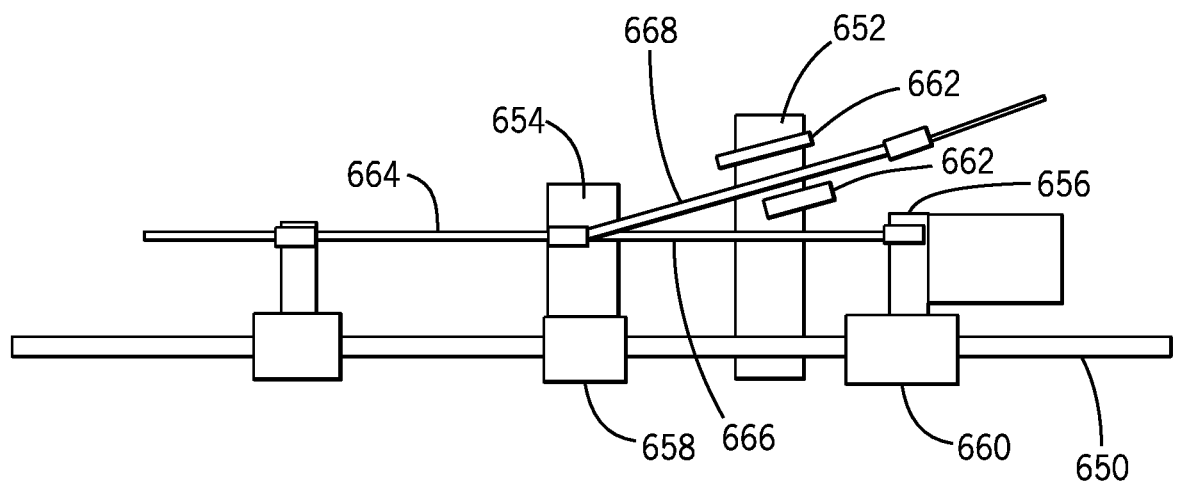
FIG. 63 is a block diagram of a parallel device configuration using a global parking clamp in accordance with an embodiment.
Figure 64:
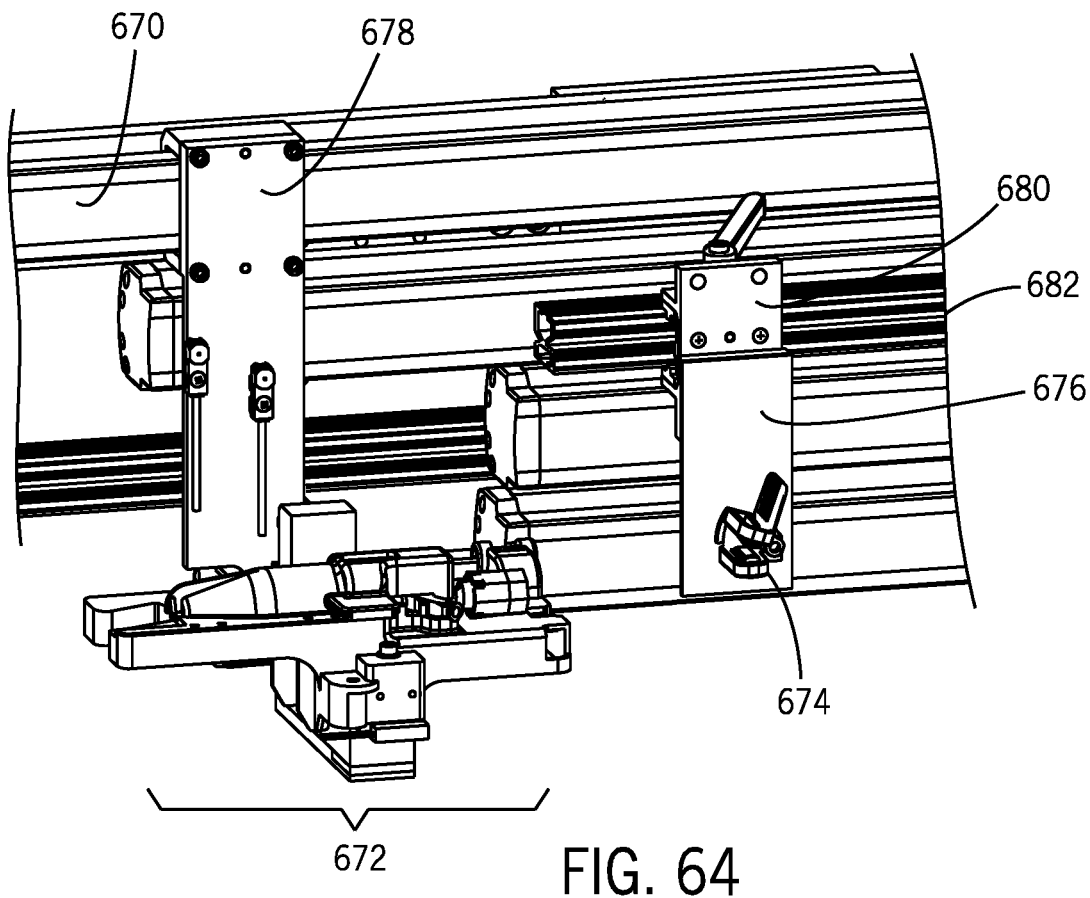
FIG. 64 is a perspective view of a moveable global parking clamp in accordance with an embodiment.

In another embodiment, a parallel device layout may be provided by using a parking clamp that is mounted to a frame of the robotic drive or moveably mounted to the rail or linear member of the robotic drive. FIG. 63 is a block diagram of a parallel device configuration using a global parking clamp in accordance with an embodiment. A global parking clamp 662 is mounted to a frame 652 of the robotic drive which includes a first device module 654 and as second device module 656. The first device module 654 is connected to a rail or linear member 650 using a first stage 658 and the second device module is connected to the rail 650 using a second stage 660. The first device module includes a first EMD 664 that is configured to receive a second EMD 666 that is included in the second device module 656 and a third EMD 668 that is held by the global parking clamp 662. The global parking clamp 662 may be configured, for example, to fix the third EMD 668 relative to a patient (not shown). The clamp 662 allows the other modules 654, 656 to move linearly while holding the clamped third EMD 668 fixed relative to the patient. The second 666 and third 668 EMD enter the first EMD 664 parallel to one another. In another embodiment, the global parking clamp may be movable. FIG. 64 is a perspective view of a moveable global parking clamp in accordance with an embodiment. In FIG. 64, a device module 672 is connected to a first rail or linear member 670 using a first stage 678. A global parking clamp 674 is coupled to a second rail 682 using a mounting bracket 676 connected to a second stage 680 that is mounted to the second rail 682. Accordingly, the global parking clamp 674 may be moved by linearly translating the second stage 680 along the second rail 682 either manually or robotically with a stage translation motor (not shown). As mentioned, the global parking clamp 674 may be used to hold an EMD (not shown) that may be provided in a parallel configuration.

Figure 65:
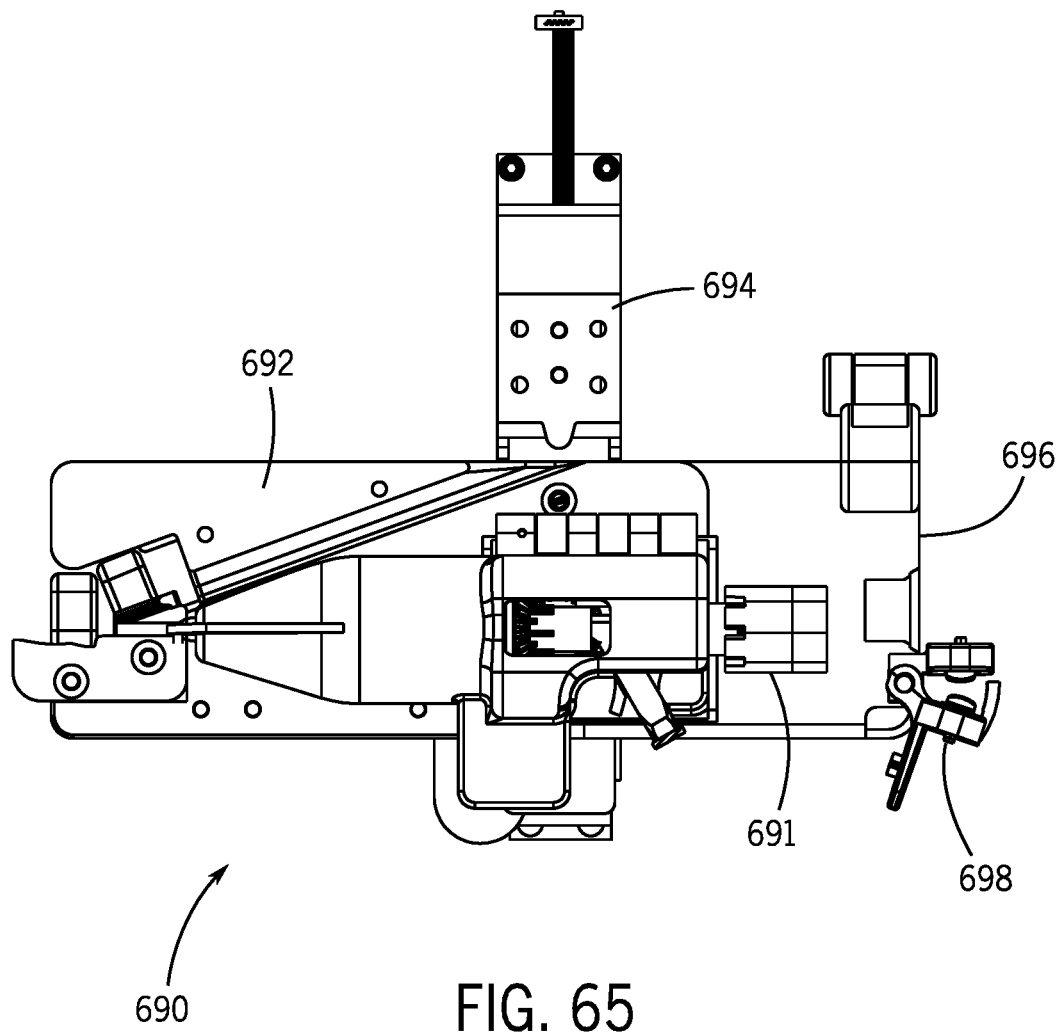
FIG. 65 is top view of a device module including a cassette with a module parking clamp in accordance with embodiment.

A parking clamp may also be provided directly on a cassette to facilitate a parallel device configuration. FIG. 65 is top view of a device module including a cassette with a module parking clamp in accordance with embodiment. In FIG. 65, a device module 690 includes a cassette 692 mounted to a drive module 694. A module parking clamp 698 is mounted to a proximal end 696 of the cassette 692. Accordingly, the parking clamp 698 is fixed relative to an EMD (not shown) that is inserted into the clamp 698 and held by the clamp 698. The EMD held by the clamp 7698 may be positioned so as to enter the hub 691 if the EMD positioned in the cassette parallel to another EMD that is in a serial configuration with hub 691. Linear movement of the device module 690 may be may be used to move the EMD in the clamp 698 when the clamp 698 is active to adjust the position of the clamped EMD. The clamp 698 may be manually or robotically actuated. In one embodiment, the clamp 698 may be used to hold the deployment wire for a self-deploying stent. In another embodiment, the clamp may be used to park a balloon for a balloon assisted coiling.

Figure 66:
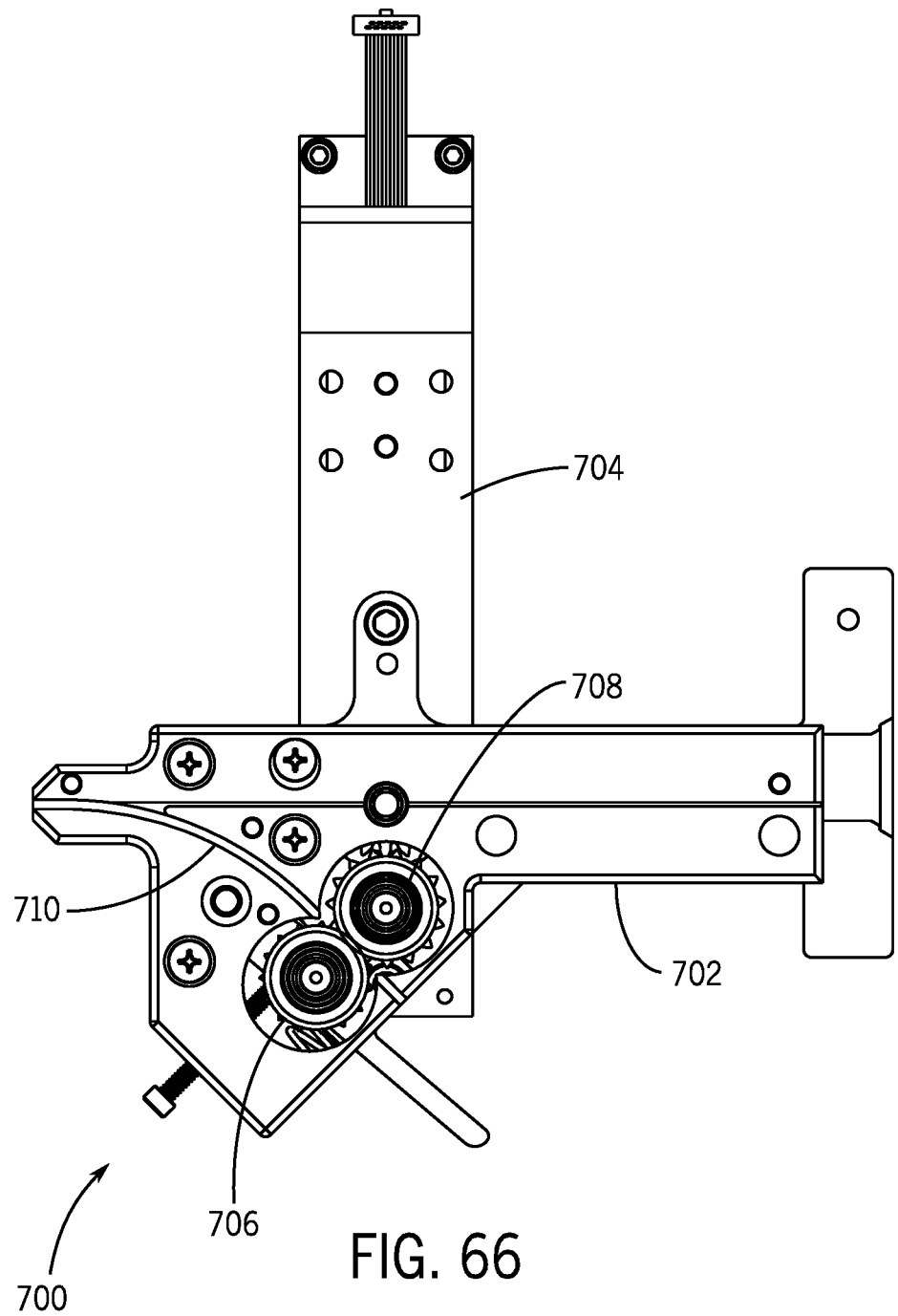
FIG. 66 is a top view of a device module including a cassette with a rapid exchange tire drive in accordance with an embodiment.

In another embodiment, a parallel device configuration may be provided by using a cassette that is configured to provide a linear degree of freedom for a rapid exchange elongated medical device, such as for example, a rapid exchange balloon. FIG. 66 is a top view of a device module including a cassette with a rapid exchange tire drive in accordance with an embodiment. Device module 700 includes a cassette 702 mounted to a drive module 704. In an embodiment, the drive module 704 may include an auxiliary encoder (not shown) that may be used to measure movement of an EMD. The cassette 702 includes a first tire 706 and a second tire 708 on opposite sides of a channel 710. An EMD (not shown) may be positioned in the channel 710. The pair of tires 706,708 may be used to provide linear motion to an EMD positioned in the channel 710. The channel 710 is used to direct the EMD begin driven by the tires 706, 708 into the more distal hub of a distal EMD (not shown) it is being driven into. Tires 706 and 708 may be connected to a coupler (shown in FIGS. 67 and 68) of a drive module 704 to receive power to drive the EMD. Accordingly, the cassette 702 is configured to repurpose a coupler that is normally used for a rotary degree of freedom and use it for a linear degree of freedom with a tire drive formed by the pair of tires 706 and 708.

Figure 67:
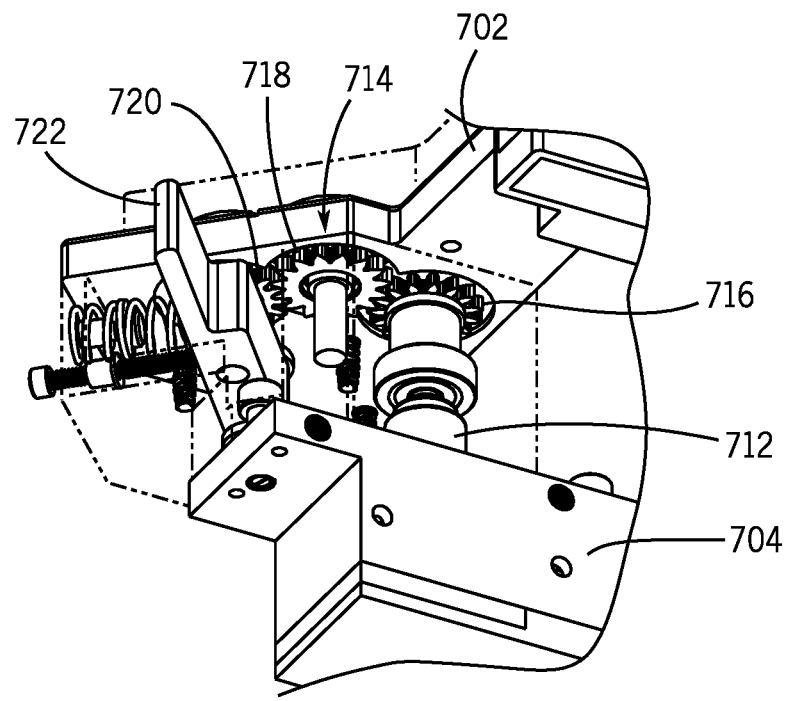
FIG. 67 is a perspective view of a drive mechanism and interface between a drive module and the rapid exchange tire drive in accordance with an embodiment.
Figure 68:
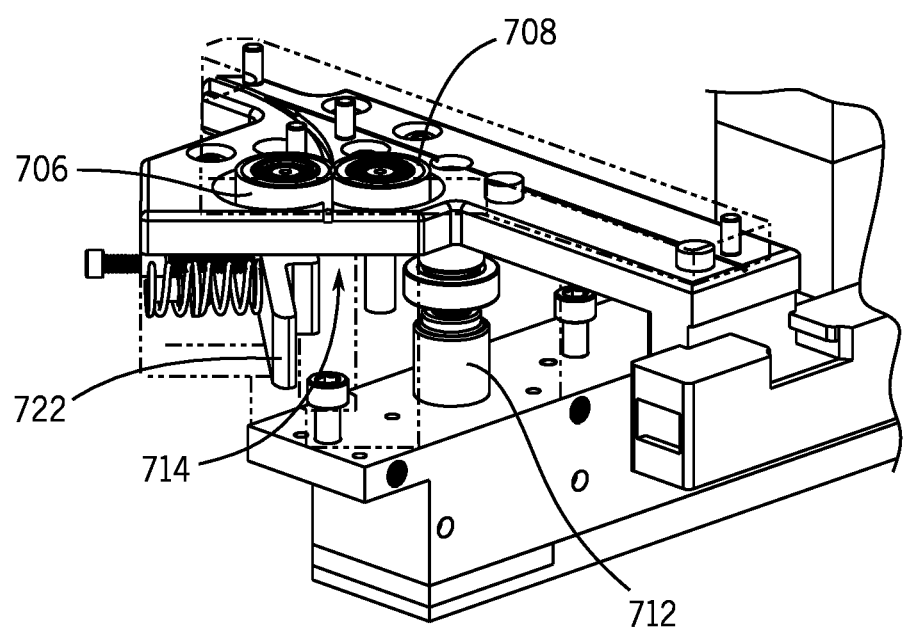
FIG. 68 is a perspective view of an drive mechanism and interface between a drive module and the rapid exchange tire drive in accordance with an embodiment.

FIG. 67 is a perspective view of a drive mechanism and interface between a drive module and the rapid exchange tire drive in accordance with an embodiment and FIG. 68 is a perspective view of a drive mechanism and interface between a drive module and the rapid exchange tire drive in accordance with an embodiment. Referring to FIGS. 67 and 68, the cassette 702 is configured to interface with a coupler 712 (i.e., a rotary power interface) of the drive module 704 and transform the rotary motion into translational motion via a tire drive (e.g., tires 706 and 708 shown in FIGS. 66 and 68). Cassette 702 includes a gear assembly 714 to interface with the coupler 712. When the cassette 702 is mounted to the drive module 704, the coupler 712 is coupled to a first gear 716 of the gear assembly 714 in the bottom surface of the cassette 702. The first gear is in contact with a second gear 718 which is used to rotate the second tire 708 and the second gear is on contact with a third gear 720 which is used to rotate the first tire 706. The first 706 and second 708 tires are positioned on the cassette 702 offset from the rotational axis of the coupler 712, allowing the tires 706, 708 to be away from the central device longitudinal axis. The gear assembly 714 also includes a manual unpinch arm 722 that may be used to unclamp the tires 706 and 708 to facilitate loading and unloading of an EMD. The manual unpinch arm 722 is used to separate the tires 706,708 to all an EMD to be unloaded from the drive. When the unpinch lever 722 is not actuated, it may also clamp the EMD at a certain force between the tires 706, 708 via a spring (not shown). In an embodiment, the force can be adjusted to increase or decrease the clamped driving force. For example, the adjustment mechanism may be a screw that changes the compressed length of the spring. Rotation of the coupler 712 causes rotation of the first gear 716 which in turn rotates the second gear 718 which in turn causes rotation of the third gear 720. Accordingly, the first tire 706 and the second tire 708 may be rotated so as to cause linear motion of an EMD in the channel 710 (shown in FIG. 66). In an embodiment, the EMD positioned in the channel 710 and driven by tires 706 and 708 is a rapid exchange EMD such as, for example, a rapid exchange catheter or a rapid exchange balloon. In an embodiment, the drive module 704 may include a sensor to detect when a rapid exchange cassette 702 is mounted to the drive module.

Figure 69:
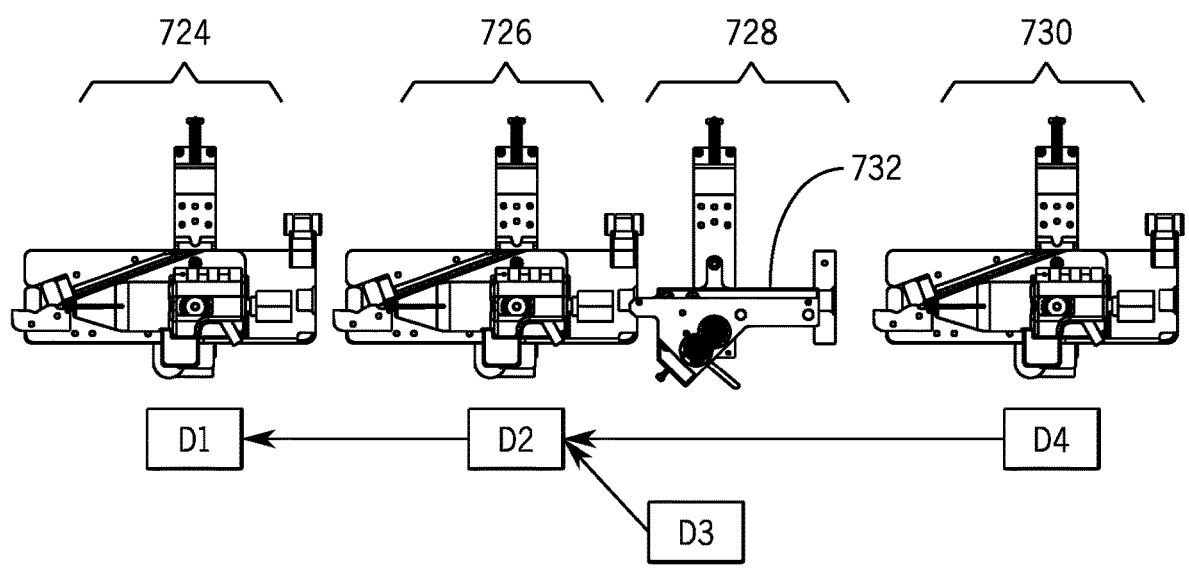
FIG. 69 is an exemplary robotic drive device module configuration including a rapid exchange tire drive in accordance with an embodiment.

FIG. 69 is an exemplary robotic drive device module configuration including a rapid exchange tire drive in accordance with an embodiment. The configuration shown in FIG. 69 includes a first drive module 724, a second device module 726, a third device module 728 and a fourth device module 730. The third device module 728 includes a rapid exchange cassette 732 (for example, cassette 702 described above with respect to FIG. 66) to provide an EMD in parallel in addition to the EMDS that may be provided in a serial in the first 724, second 726 and fourth 730 device modules. The third device module 728 with rapid exchange cassette 732 (including the tire drive) may be positioned directly behind second device module 726 and, therefore, directly behind a y-connector on the second drive module 726. Accordingly, the tire drive will not interfere with the more proximal EMDs. In addition, the configuration may allow for reducing more proximal EMDs loss of working length by allowing the more proximal EMDs to get closer to the more distal hub. The ability to position the third device module 728 directly behind the second device module 726 may eliminate the need for a support track (or device support) between the second 726 and third 728 device modules. The second 726 and third 728 device modules may be coupled mechanically or electronically so that they move together linearly. In other embodiments, a rapid exchange cassette 732 may be provided in a different position in the order of device modules in a robotic drive, for example, the rapid exchange cassette may be utilized on the second device module 726 and a non-rapid exchange cassette in the third device module 728. In this example, the fourth device module 730 may remain unpopulated. The rapid exchange cassette 732 may also be removed from the robotic drive if not needed for a particular case. The ability to utilize a tire drive (i.e., shaft driving) for linear translation of an EMD that requires only the linear degree of freedom rather than hub driving the single degree of freedom EMD may have several advantages such as full manipulation over the entire EMD range once inside a Y-connector, faster traverse speeds with no resets (continuous motion), and eliminating the need for device support tracks.

Figure 70:
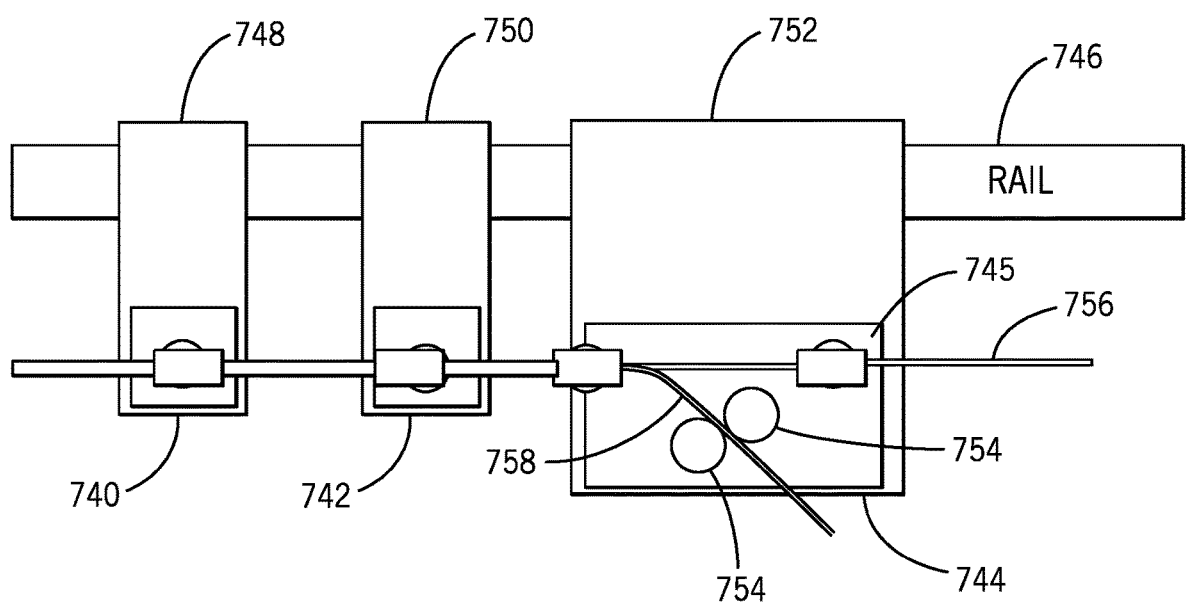
FIG. 70 is a block diagram of a robotic drive configuration including a dedicated guidewire and rapid exchange catheter device module in accordance with an embodiment.

FIG. 70 is a block diagram of a robotic drive configuration including a dedicated guidewire and rapid exchange catheter device module in accordance with an embodiment. The configuration in FIG. 70 includes a first device module 740 and a second device module 742 coupled to a rail or linear member 746 using a first stage 748 and a second stage 750, respectively. In addition, the most proximal device module 744 is a dedicated guidewire and rapid exchange catheter device module. The guidewire and rapid exchange catheter device module 744 is coupled to the rail 746 using a third stage 752. The guidewire and rapid exchange catheter device module 744 incudes a cassette 745 that is configured to provide linear translation to a rapid exchange catheter 758 using, for example, tires 754 and to provide rotation and linear translation for a guidewire 756. The guidewire 756 and rapid exchange catheter 758 move in parallel through an EMD distal to the guidewire and rapid exchange catheter deice module 744. In FIG. 70, the first device module 740 and the second device modules 742 may include catheters configured to receive the guidewire 756 and rapid exchange catheter 758. Accordingly, in this configuration multiple catheters may be provided in front (i.e., distal to) the guidewire and rapid exchange catheter drive.

Figure 71:
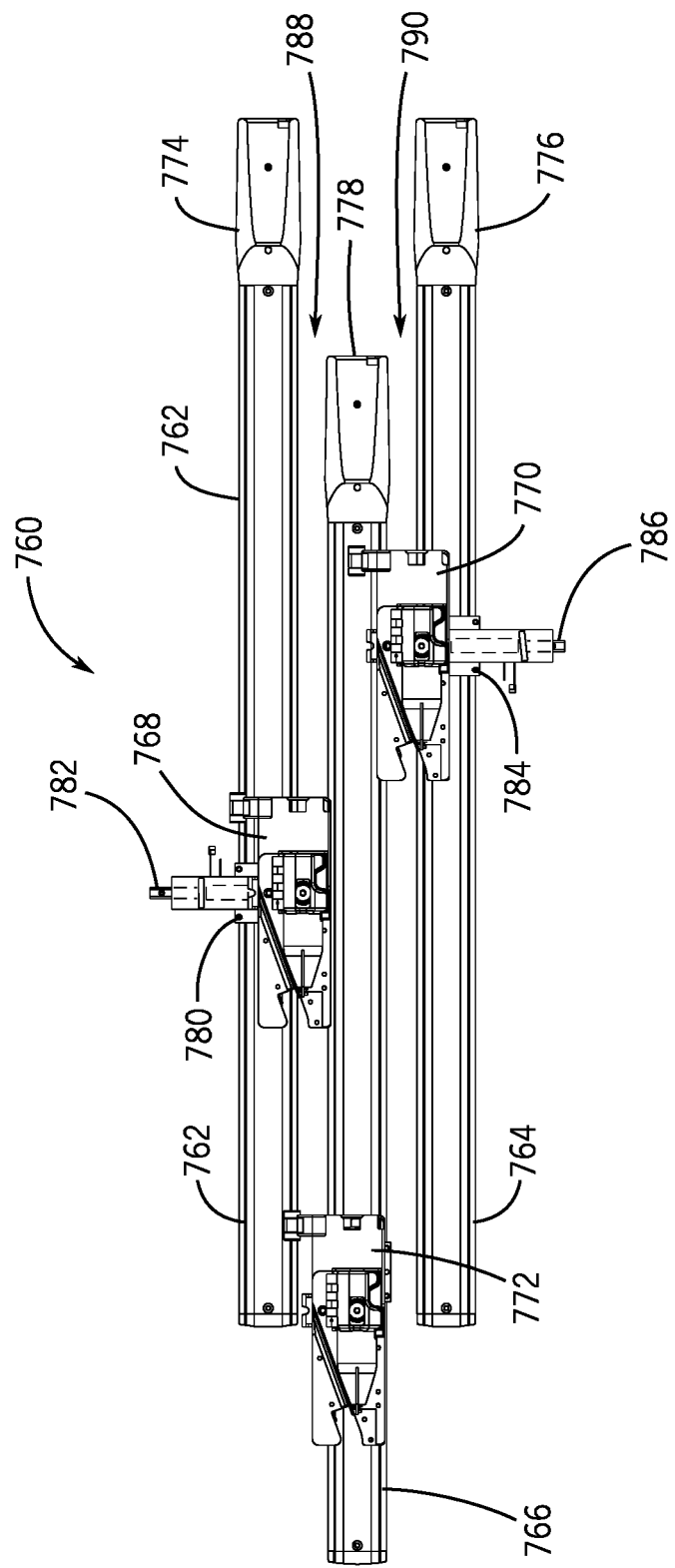
FIG. 71 is a top view of a robotic drive with multiple parallel linear members in accordance with embodiment.

In another embodiment, a robotic drive may include multiple parallel rails or linear members that enable device modules to move past one another and that is designed to facilitate reconfiguring the device modules between serial and parallel configurations. FIG. 71 is a top view of a robotic drive with multiple parallel rails in accordance with embodiment. The robotic drive 760 includes a first rail or linear member 762, a second rail or linear member 764 and a third rail or linear member 766 that are positioned parallel to one another. A first device module 768 is coupled to the first rail 762 using a first stage 780. A first stage translation motor 774 is used to drive the first stage 780 linearly along the first rail 762. A second device module 770 is coupled to the second rail 764 using a second stage 784. A second stage translation motor 776 is used to drive the second stage 784 linearly along the second rail 764. A third device module 772 is coupled to the third rail 766 using a third stage 785 (shown in FIGS. 75 and 77). A third stage translation motor 778 is used to drive the third stage 785 linearly along the third rail 766. A first position offset slide 782 is mounted to the first stage 780 and may be used to adjust the position of the first device module 768 relative to the first 762, second 764 and third 766 rails. A second position offset slide 786 is mounted to the second stage 784 and may be used to adjust the position of the second device module 770 relative to the first 762, second 764 and third rails. A third position offset slide (not shown) may also be mounted to the third stage 785 (shown in FIGS. 75 and 77) for adjusting the position of the third device module 772. When each device module 768, 770 and 772 are in a position where they are aligned over the respective rail 762, 764, 766 to which they are attached, each device module 768, 770 772 may be moved linearly and may move past one another along their respective rails. In addition, the position of the first device module 768, second device module 770 and third device module 772 may be adjusted so that the various device modules are aligned in a serial or parallel configuration for driving EMDs (EMDs not shown). In FIG. 71, the first device module 768 has been moved along the first position offset slide 782 to a position over a first gap 788 between the first 762 and third 766 rails. The second device module 770 has been moved along the second position offset slide 786 to a position over a second gap 790 between the second 764 and third 766 rails. A device module may be moved along a position offset slide either manually or robotically.

Figure 72:
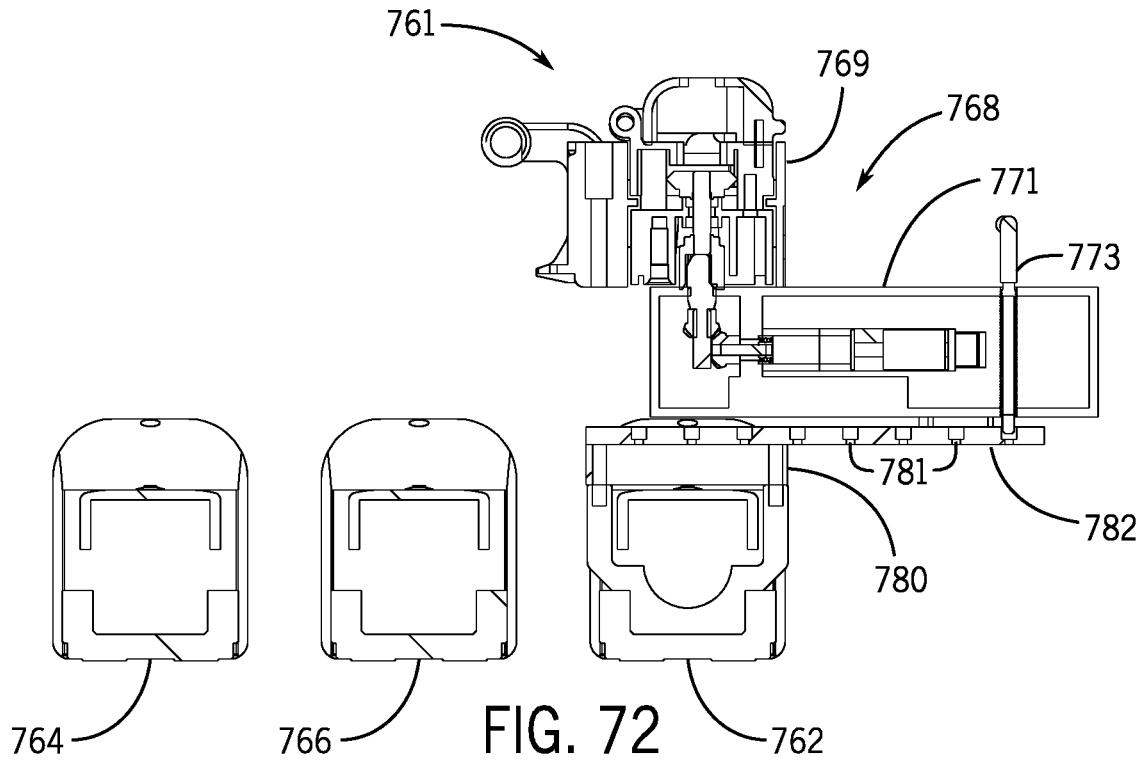
FIG. 72 is a sectioned view of a device module with a position offset slide and the device module in a first position in accordance with an embodiment.
Figure 73:
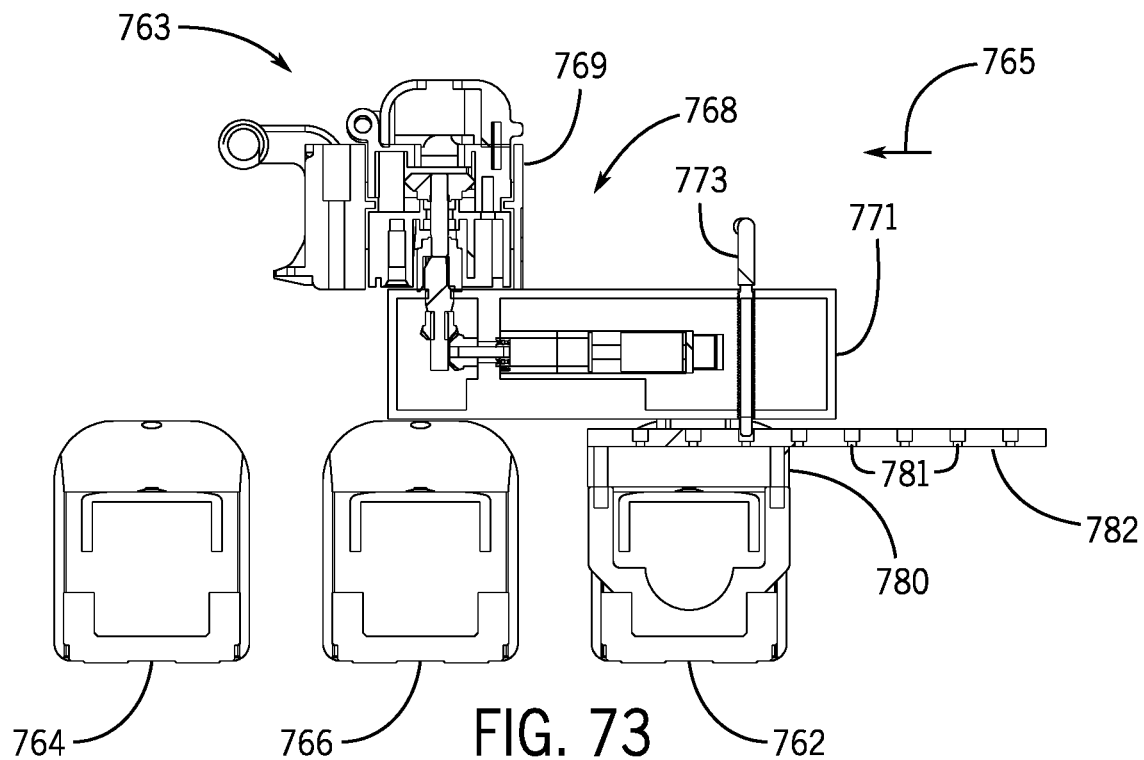
FIG. 73 is a sectioned view of a device module with a position offset slide and the device module in a second position in accordance with an embodiment.

FIG. 72 is a sectioned view of a device module with a position offset slide and the device module in a first position in accordance with an embodiment and FIG. 73 is a sectioned view of a device module with a position offset slide and the device module in a second position in accordance with an embodiment. The first device module 768 includes a cassette 769 mounted to a drive module 771. The drive module 771 is mounted to the first position offset slide 782 which is mounted to the first stage 780 which is connected to the first rail 762. The first device module 768 is shown in a first position 761 where the first device module 768 is positioned over the first rail 762. The first device module 768 may be moved along the first position offset slide 782 from the first position to a second position 763 shown in FIG. 73. The first device module 768 is moved in a direction (indicated by arrow 765) towards the third rail 766. In the second position 763, the first device module 768 is in a position over the third rail 766. In an embodiment, the drive module may include a sprung plunger 773 and the sprung plunger 773 may be used to lock the position of the device module 768 along the first position offset slide 782. For example, the sprung plunger 773 may be positioned in one of the holes 781 in the first position offset slide 782 to secure it in place so as to prevent the device module 768 from moving from, for example, the second position 763. In other embodiments, the first device module 768 may be moved along the first position offset slide 782 until it is in a position over the second rail 764. The positions of the other device modules may also be adjusted to provide different configurations as discussed below.

Figure 74:
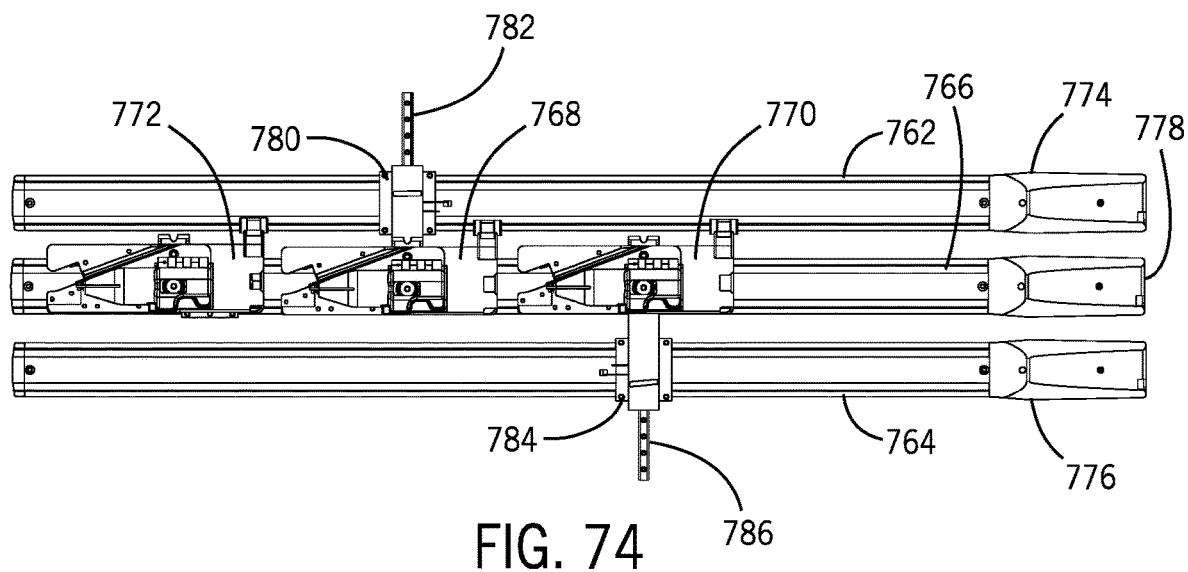
FIG. 74 is a top view of device modules in an exemplary serial configuration in a multiple linear member robotic drive in accordance with an embodiment.
Figure 75:
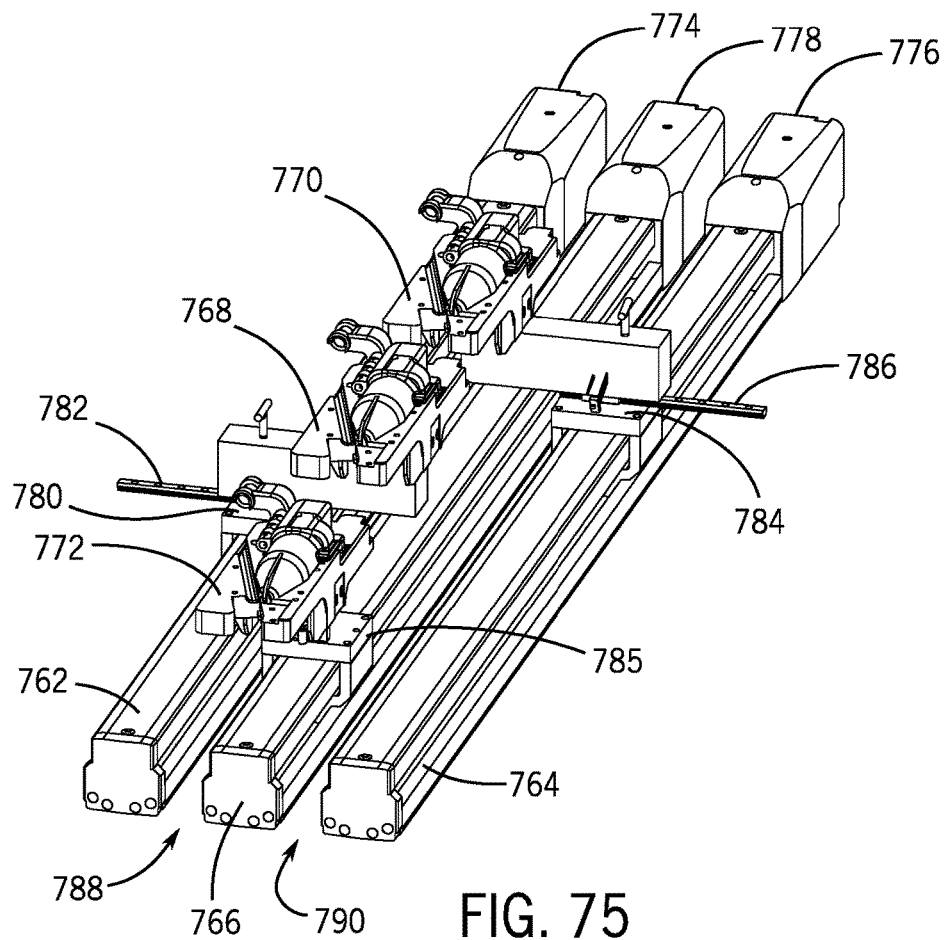
FIG. 75 is a perspective view of device modules in an exemplary serial configuration in a multiple linear member robotic drive in accordance with an embodiment.

FIG. 74 is a top view of device modules in an exemplary serial configuration in a multiple rail robotic drive in accordance with an embodiment. The first 768, second 770 and third 772 device modules are in a serial configuration with each device module positioned over the third rail 766. The first device module 768 is positioned along the first rail 762 and along the first position offset slide 782 so that it is located behind the third device module 772. The second device module 770 is positioned along the second rail 764 and along the second position offset slide 786 so that it is located behind the first device module 768. In the serial configuration of FIG. 74, the device axis of each device module 768, 770 and 772 are aligned. FIG. 75 is a perspective view of device modules in an exemplary serial configuration in a multiple rail robotic drive in accordance with an embodiment. In FIG. 75, the first 768, second 770 and third 770 device modules are in a serial configuration with each device module positioned over a gap 788 between the first 762 and third 766 rails. The first device module 768 is positioned along the first rail 762 and along the first position offset slide 782 so that it is located behind the third device module 772. The second device module 772 is positioned along the second rail 764 and along the second position offset slide 786 so that it is located behind the first device module 768. In the serial configuration of FIG. 75, the device axis of each device module 768, 770 and 772 are aligned.

Figure 76:
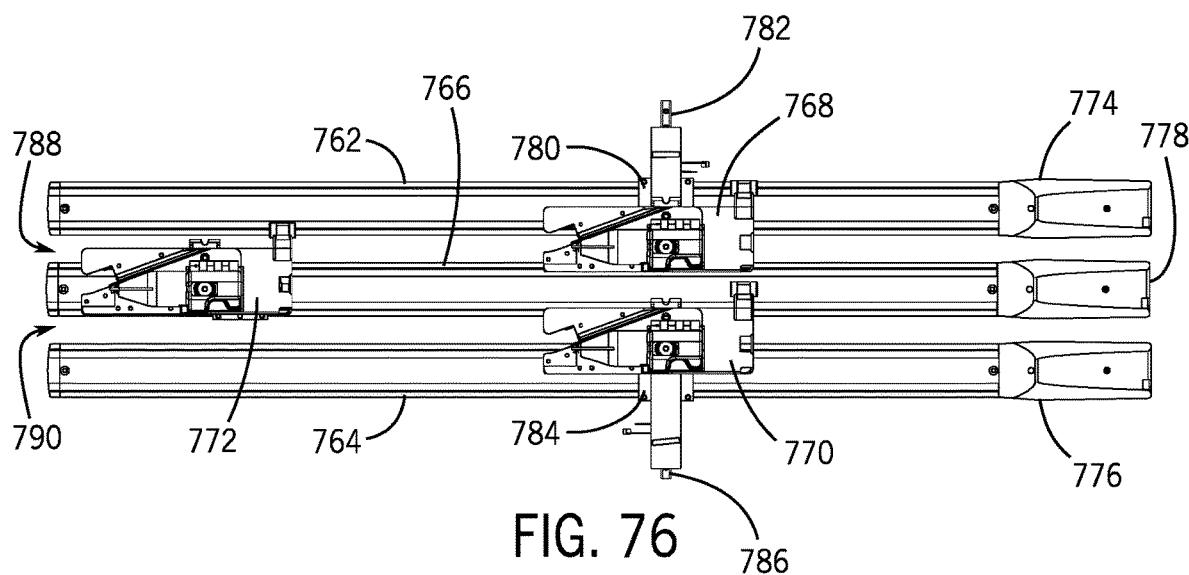
FIG. 76 is a top view of device modules in an exemplary parallel configuration in a multiple linear member robotic drive in accordance with an embodiment.
Figure 77:
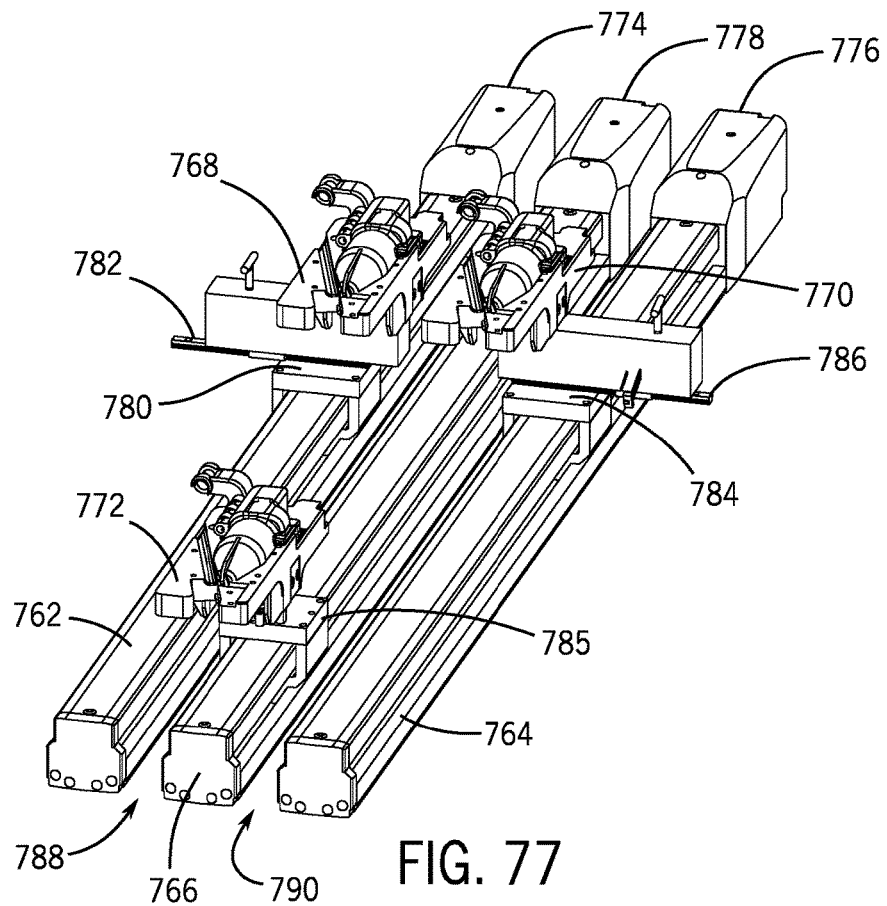
FIG. 77 is a perspective view of device modules in an exemplary parallel configuration in a multiple linear member robotic drive in accordance with an embodiment.

FIG. 76 is a top view of device modules in an exemplary parallel configuration in a multiple rail robotic drive in accordance with an embodiment. The first 768 and second 770 device modules are in a parallel configuration. The first device module 768 is positioned over a gap 788 between the first 762 and third 766 rails and the second device module 770 is positioned over a gap 790 between the second 764 and third 766 rails. The third device module 772 is positioned over the third rail 766 and is located along the third rail 766 at a position in front of the first 768 and second 770 device modules. The first device module 768 is positioned along the first rail 762 and along the first position offset slide 782 so that it is located behind the third device module 772 and over the gap 788. The second device module 770 is positioned along the second rail 764 and along the second position offset slide 786 so that it is located behind the first device module 768 and over gap 790. In configuration of FIG. 76, the EMD (not shown) in the first device module 768 and the EMD (not shown) in the second device module 770 would enter the hub of the third device module 772 in parallel. FIG. 77 is a perspective view of device modules in an exemplary parallel configuration in a multiple rail robotic drive in accordance with an embodiment. The first 768 and second 770 device modules are in a parallel configuration. The first device module 768 positioned over the first rail 762 and the second device module 770 positioned over the third rail 766. The third device module 772 is positioned over the gap 788 between the first 762 and third 766 rails and is located along the third rail 766 at a position in front of the first 768 and second 770 device modules. The first device module 768 is positioned along the first rail 762 and along the first position offset slide 782 so that it is located behind the third device module 772 and over the first rail 762. The second device module 770 is positioned along the second rail 764 and along the second position offset slide 786 so that it is located behind the first device module 768 and over the third rail 766. In configuration of FIG. 77, the EMD (not shown) in the first device module 768 and the EMD (not shown) in the second device module 770 would enter the hub of the third device module 772 in parallel.

Figure 78A:
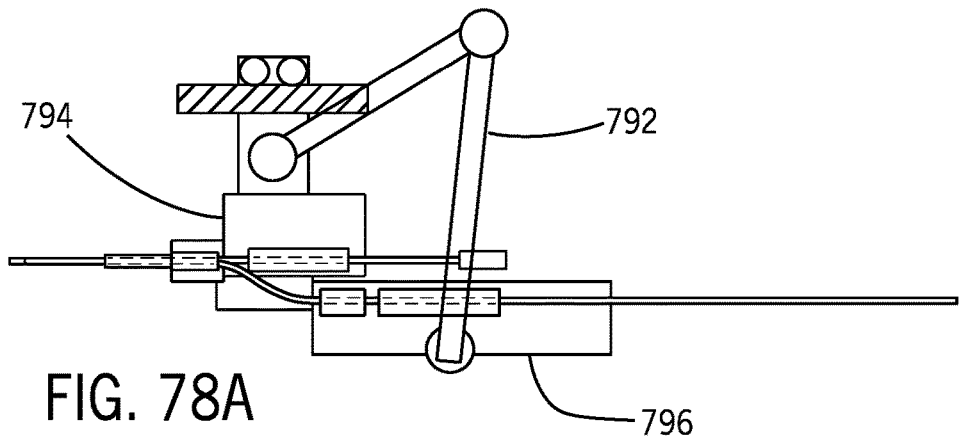
FIGS. 78A-C illustrate reconfiguring device module positions using a positioning system in accordance with an embodiment.
Figure 78B:
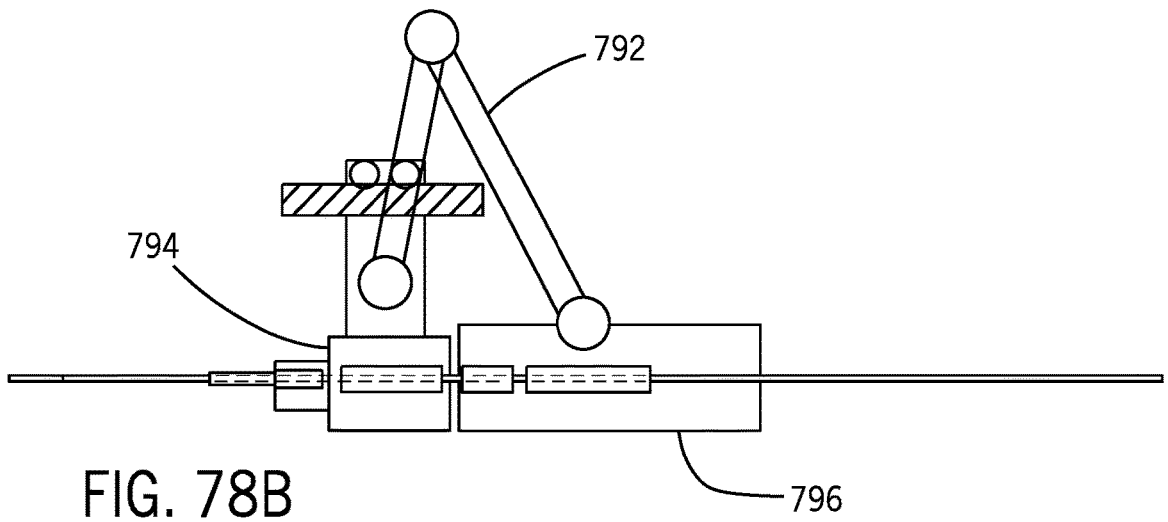
Figure 78C:
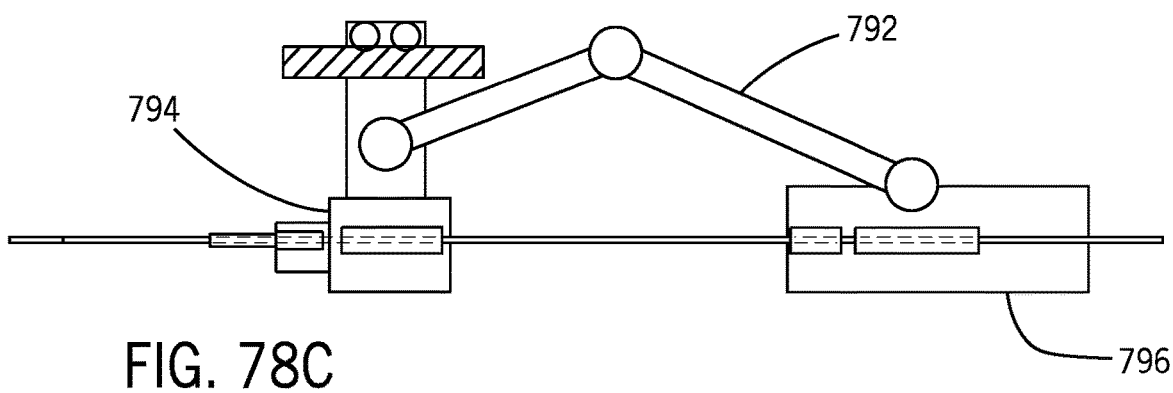

In another embodiment, the position of device modules may be performed using a positioning system such as, for example, a robotic arm. FIGS. 78A-C illustrate reconfiguring device module positions using a positioning system in accordance with an embodiment. In FIG. 78A, a first device module 794 is in a fixed position. A positioning system, 792, for example, a robotic arm, is connected to a second device module 796 and is operated to move and hold the second device module 796 in a parallel configuration. The robotic arm 792 may be used to move the second device module 796 to a serial configuration as shown in FIG. 78B. In FIG. 78C, the robotic arm 792 may further be used to linearly translate the second device module 796. In other embodiment, two or more robotic arms may be provided that are each connected to a device module and used to move and reconfigure the position of the respective drive module with respect to the other drive modules. In this embodiment, the device modules are not attached to a rail or linear member and are instead acting as the arm's end effector. For a serial configuration, the arms align the device modules to follow a line or other trajectory, which could include a curved path that avoids patient interference. For a parallel configuration, the arms align selected modules in a parallel configuration, allowing the proximal hubs to pass one another.

As mentioned above with respect to FIG. 3, the robotic drive 24 may include a device support 79a-d between each device module 32a-d and between the most distal device module 32a and the device support connection 72. Each device support 79a-d is configured to prevent elongated medical devices from buckling as they are advanced outside of a patient and prior to being advanced into a more distal EMD. In an embodiment, each device support 79a-d may be a flexible tube with a lengthwise slit and is used in conjunction with a splitter on a cassette. Each device support 79a-d is fixed or constrained at both ends so that the device support may be kept in tension so that the flexible tube is limited in the amount of displacement it can buckle under a compressive load. Buckling the EMD limits the amount of force that can be applied and can permanently damage the elongated medical device. The compressive load can be caused by several factors, which may include friction between the EMD and device support, friction between the device support and a cassette (e.g., a splitter in the cassette (discussed below with respect to FIGS. 102-104)), etc. Maintaining the device support under tension may eliminate the need for extra column strength and allow for smaller, more flexible device supports. In one embodiment where the device support is a flexible tube, tension may be provided by fixing a front (or distal) and rear (or proximal) point (or location) of the flexible tube. The device supports 79a-d shown in FIG. 3 are one embodiment of a device support with fixed front (or distal) and rear (or proximal) points (or locations). In another embodiment, the device support may be an accordion or spring type support that provides appropriate tension. Each of these different embodiments of a device support are discussed further below.

Figure 79:
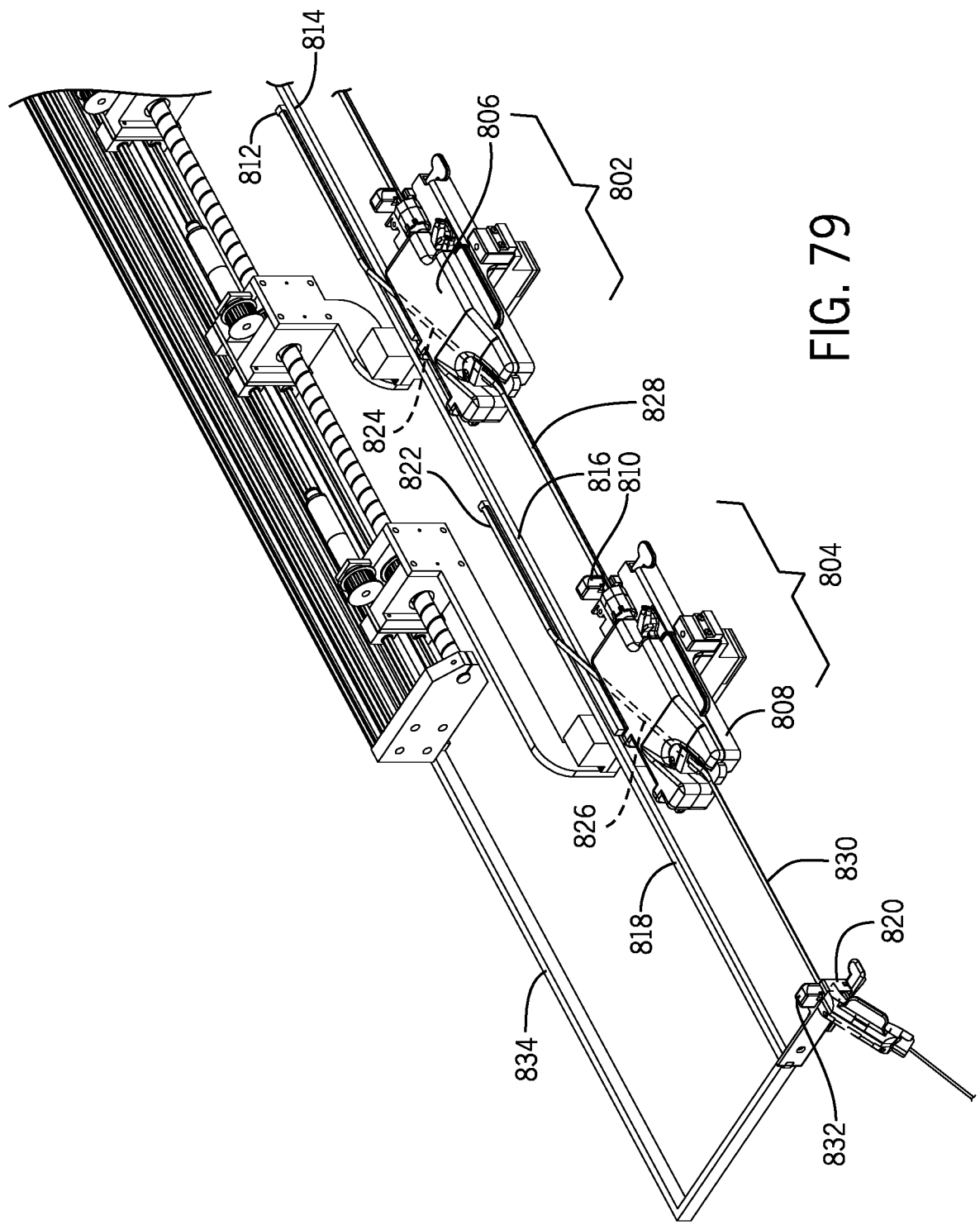
FIG. 79 is a perspective view of device supports with fixed front (or distal) and rear (or proximal) points to provide tension in accordance with an embodiment.

FIG. 79 is a perspective view of device supports with fixed front (or distal) and rear (or proximal) points to provide appropriate tension in accordance with an embodiment. FIG. 79 illustrates the device support embodiment shown in FIG. 3. In FIG. 79, a first device module 802 includes a first cassette 806 that has a first device support 828, e.g., a flexible tube, positioned in a channel 824 of the cassette 802. The first cassette 806 and the first device support 828 are moveable relative to one another. In FIG. 79, the first device support 828 extends out from the distal end of the first cassette 806 and a first end of the first device support 828 connects to a proximal end of a second device module 804 at a first front (or distal) fixed point 810. The second device module 804 is located distal to the first device module 802. The second device module 804 includes a second cassette 808 and a support arm 816 that extends from the second device module 804 in a proximal direction towards the first cassette 806. A second end of the first device support 828 extends out from the proximal end of the first cassette 806 and connects to a first rear (or proximal) fixed point 812 on a proximal end of the support arm 816 of the second device module. The first device support 828 is held in place by fixed first front 810 and first rear 812 points. The first front and rear fixed points 810 and 812 are kept a constant distance from one another. The first front and rear fixed points 810 and 812 may be rigid or may have some elasticity to account for manufacturing and assembly tolerance. The first device module 802 also includes a support arm 814 that may be used to provide a rear (or proximal) fixed point for a device support for a cassette (not shown) located proximal to the first cassette 806.

The second device module 804 is the most distal module and closest to the patient (not shown). The second cassette 808 of the second device module 804 includes a second device support 830, e.g., a flexible tube, positioned in a channel 826 of the second cassette 808. The second cassette 808 and the second device support 830 are moveable relative to one another. Since there is no device module or cassette in front of the second device module 804, a distal support connection 832 mounted to a distal support arm 834 is used to provide a second front (or distal) fixed point 820 for the distal end of the second device support 830. The distal support connection 832 and distal support arm 834 are described further below with regard to FIGS. 108-116. A second end of the second device support 828 extends out from the proximal end of the second cassette 808 and connects to a second rear (or proximal) fixed point 822 on a proximal end of the support arm 818 connected to the distal support arm 834. The second device support 830 is held in tension by fixed second front 820 and rear 822 points. The second front and rear fixed points 820 and 822 are kept a constant distance from one another. The second front and rear fixed points 820 and 822 may be rigid or may have some elasticity to account for manufacturing and assembly tolerance.

Figure 80:
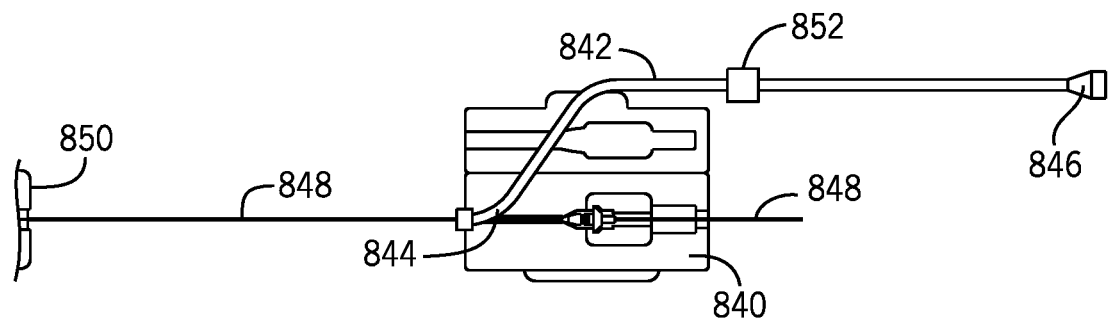
FIG. 80 is a diagram showing a top view of a cassette with a device support in a withdrawn position to facilitate exchange of an elongated medical device in accordance with an embodiment.
Figure 81:
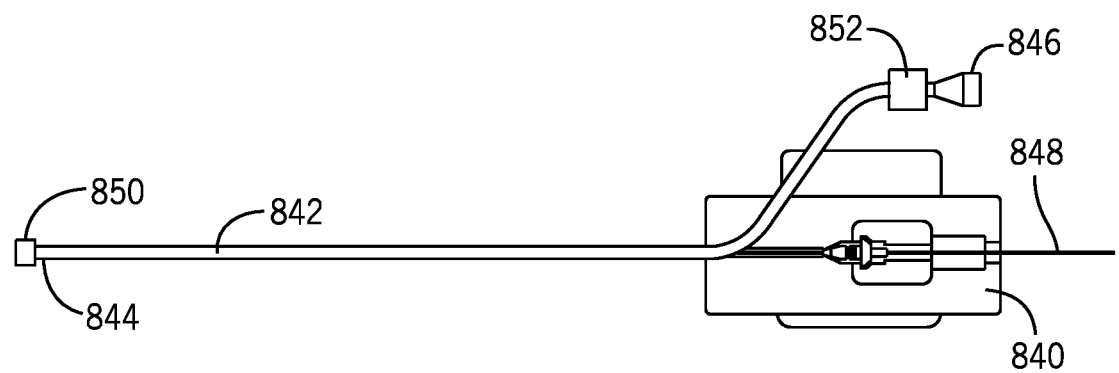
FIG. 81 is a diagram showing a top view of a cassette with a device support in an extended position constrained at two ends in accordance with an embodiment.

In one embodiment, the distal end of the first device support 828 connected to the first front fixed point 810 and the distal end of the second device support 830 connected to the second front fixed point 820 may be detached or disconnected, as discussed further below, to facilitate loading and unloading of EMDs before, during and after a procedure. FIG. 80 is a diagram showing a top view of a cassette with a device support in a withdrawn position to facilitate exchange of an elongated medical device in accordance with an embodiment. In FIG. 80, a device support 842 of a cassette 840 has been detached from a front (or distal) fixed point 850 and is in a retracted position which exposes an EMD 848 to facilitate loading and unloading of the EMD. As discussed above, the front fixed point 850 is located on a device module distal to the cassette 840. The device support 842 is shown over the cassette 840 cover in FIG. 80 for clarity. A first (or distal) end 844 of the device support 842 is located at the distal end of the cassette 840. A second (or proximal) end 846 of the device support 842 has moved past a rear (or proximal) fixed point 852. As discussed above, the rear fixed point 852 is located on a support arm of, for example, a cassette, drive module or stage, distal to the cassette 840. Additionally, the fixed rear point 852 may be attached to the frame of the robotic drive. FIG. 81 is a diagram showing a top view of a cassette with a device support in an extended position constrained at two ends in accordance with an embodiment. When the device support 842 is pulled over the EMD 848, the first end 844 is attached to the front fixed point 850 and the second end 846 is constrained by the rear fixed point 852. As discussed above, the front fixed point 850 and the rear fixed point 852 are fixed relative to a device module the distal end of the EMD 848 is entering. The device support 842 is shown over the cassette 840 cover in FIG. 81 for clarity.

Figure 82:
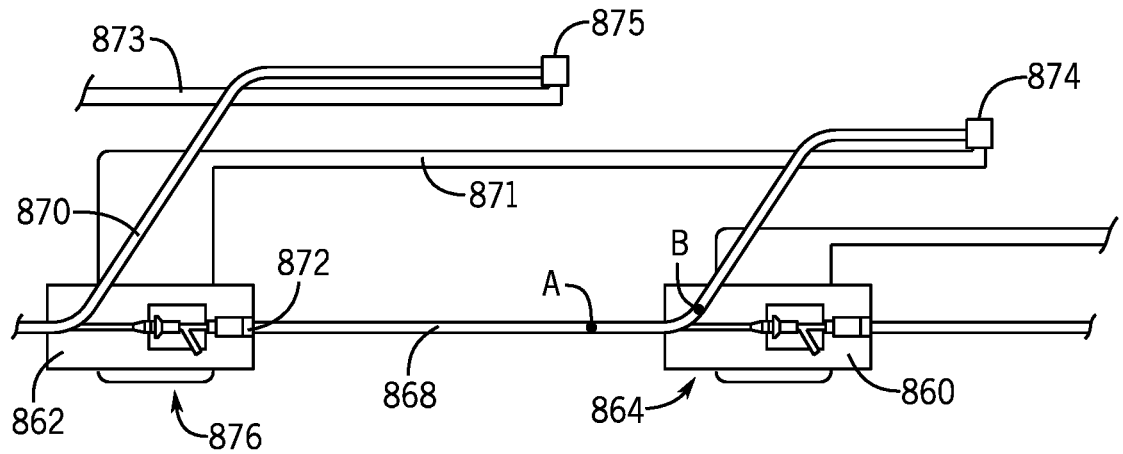
FIG. 82 is a top view of two device modules with device supports in accordance with an embodiment.
Figure 83:
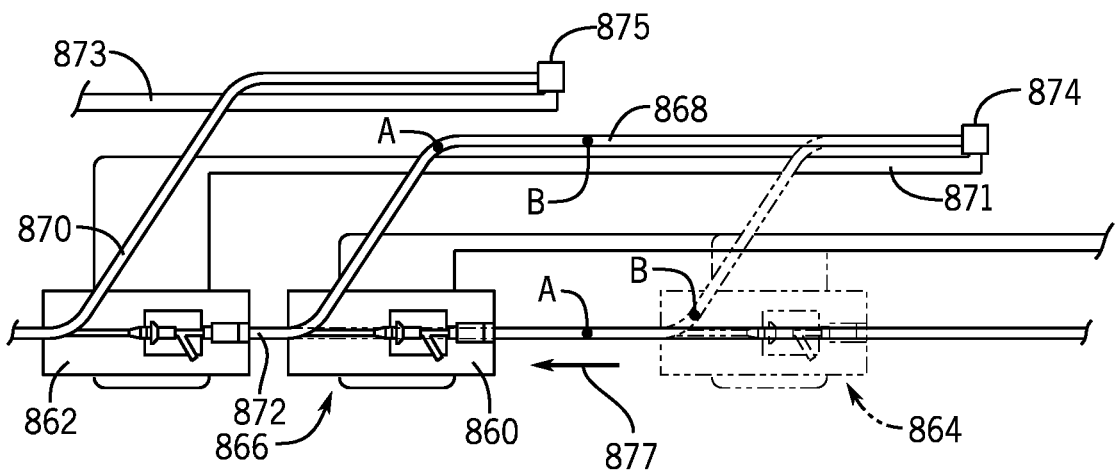
FIG. 83 is a top view illustrating forward translation of a device module linearly relative to a device support in accordance with an embodiment.

Constraining (fixing) each device support on both ends allows for relative motion between all of the device modules in a robotic drive. FIG. 82 is a top view of two device modules with device supports in accordance with an embodiment. A first device module 860 has a first device support 868 constrained at a first front (or distal) fixed point 872 at the proximal end of a second device module 862 and at a first rear (or proximal) fixed point 874 located on a proximal end of a support arm 871 of the second device module 862. The second device module 862 has a second device support 870 that is constrained at a second front (or distal) fixed point (not shown) and a second rear (or proximal) fixed point 875 located in the proximal end of a support arm 873 of a device module (not shown) distal to the second device module 862. The first device module 860 may be translated forward from a first position 864. The second device module 862 is at a first position 876. FIG. 83 is a top view illustrating forward translation of a device module linearly relative to a device support in accordance with an embodiment. When the first device module 860 moves forward towards the patient (as indicated by arrow 877) from the first position 864 to a second position 866, the first rear (or proximal) fixed point 874 takes the load developed as a cassette of the first device module 860 (and the device module) moves along the first device support 868 (e.g., friction between the cassette and the first device support 868). Accordingly, the first device support 868 will not buckle between the distal end of the cassette on the first device module 860 and the proximal end or rear of a cassette on the second device module 862. As the first device module 860 advances distally toward the second device module 862 (which is stationary at its first position 876 in this example) it moves relative to the first device support 868 as illustrated by reference points A and B located along the length of the first device support 868. When the first device module 860 is at the first position 864, reference point A and reference point B on the located proximate to the distal end of the first device module 860. As the first device module 860 advances along the first device support 868, the first device support 868 remains stationary because the second device module 862 to which it is coupled via the first distal fixed point 872 and the first proximal fixed point 874 is also stationary. When the first deice module 860 is located at the second position 866, reference point A and reference point B are located off axis and proximal to the first device module 860. The first device module 860 may also be translated backwards from the second position 866 to the first position 864.

Figure 84:
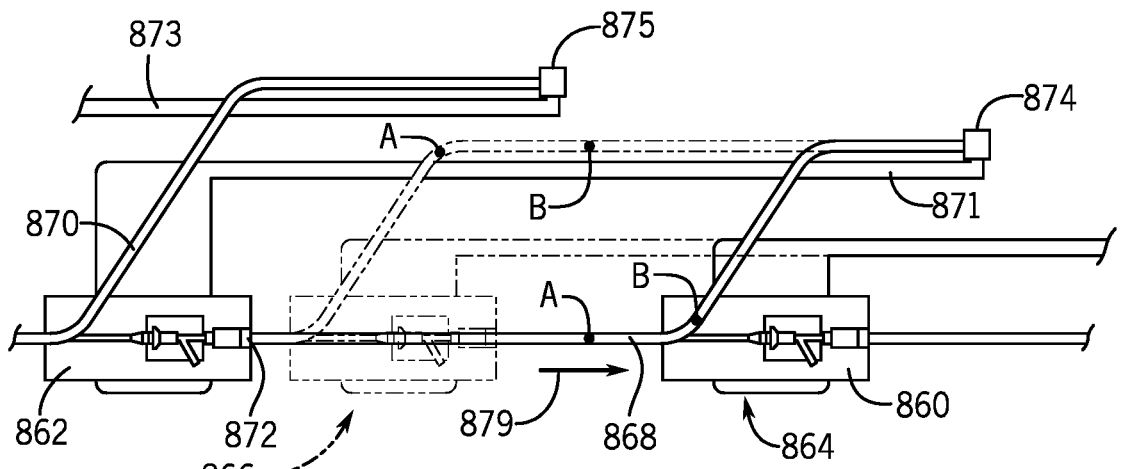
FIG. 84 is a top view illustrating reverse translation of a device module linearly relative to a device support in accordance with an embodiment.

FIG. 84 is a top view illustrating reverse translation of a device module linearly relative to a device support in accordance with an embodiment. When the first device module 860 moves backwards (retracts) away from the patient (as indicated by arrow 879) from the second position 866 to the first position 864, the first front (or distal) fixed point 872 takes the load developed as a cassette of the first device module 860 (and the device module) moves along the first device support 868 (e.g., friction between the cassette and the first device support 868). Accordingly, the first device support 868 will not buckle between the cassette on the first device module 860 and the first rear fixed point 874. As the first device module 860 moves proximally away from the second device module 862 (which is stationary at its first position 876 in this example) it moves relative to the first device support 868 as illustrated by reference points A and B located along the length of the first device support 868. When the first device module 860 is at the second position 866, reference point A and reference point B are located off axis and proximal to the first device module 860. As the first device module 860 moves proximally (retracts) along the first device support 868, the first device support 868 remains stationary because the second device module 862 to which it is coupled via the first distal fixed point 872 and the first proximal fixed point 874 is also stationary. When the first device module 860 is at the first position 864, reference point A and reference point B are the located proximate to the distal end of the first device module 860.

Figure 85:
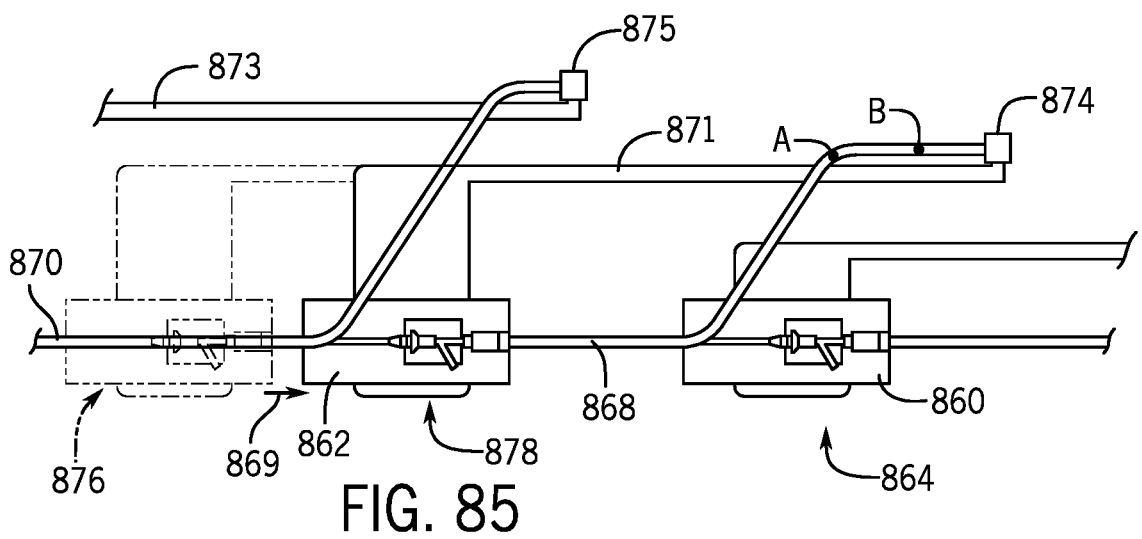
FIG. 85 is a top view illustrating reverse translation of a device support linearly relative to a device module in accordance with an embodiment.

FIG. 85 is a top view illustrating reverse translation of a device support linearly relative to a device module in accordance with an embodiment. When the second device module 862 moves backwards away from the patient (as indicated by arrow 869) from a first position 876 to a second position 878, the second front (or distal) fixed point (not shown) distal to the second device module 862 takes the load developed as a cassette of the second device module 862 (and the device module) moves along the second device support 870 (e.g., friction between the cassette and the second device support 870). Accordingly, the second device support 870 will not buckle between the cassette on the second device module 162 and the second rear fixed point 875. Since the device supports 868 and 870 are each being supported between two known points, the length of each device support does not need to change. As the second device module 862 moves proximally towards the first device module 860 (which is stationary at its first position 864 in this example) the second device module 862 moves relative to the second device support 870. In addition, the first device support 868 (coupled to the second device module 862 via first distal 872 and first proximal 874 fixed points) moves relative to the first device module 860 as illustrated by reference points A and B located along the length of the first device support 868. When the second device module 862 is at the first position 876, reference point A and reference point B are located proximate to the distal end of the first device module 860 as shown in FIG. 82. As the second device module 862 moves proximally (retracts) along the second device support 870, the second device support 870 remains stationary because it is coupled to a more distal device module (not shown) which is stationary in this example. However, the first device support 868 moves proximally with the second device module 862 to which it is coupled via the first distal fixed point 872 and the first proximal fixed point 874. At the second position 878 of the second device module 862, reference point A and reference point B are located proximate to the distal end of the first device module 860.

FIG. 86 shows a simplified top view of four device modules and four device supports for a robotic drive in accordance with an embodiment. A first device module 902 incudes a first device support 904 with one end connected to a support arm 918 and one end connected to a distal support point. A second device module 906 includes a second device support 908 with one end connected to a support arm 920 and one end connected to the first device module 902. A third device module 910 includes a third device support 912 with one end connected to a first front (or distal) fixed point 926 on the second device module 906 and another end connected to a first rear (or proximal) fixed point 928 on a support arm 922. A fourth device module 914 includes a fourth device support 916 with one end connected to a second front (or distal) fixed point 930 on the third device module 910 and another end connected to a second rear (or proximal) fixed point 932 on a support arm 924. In various embodiments, the support arms 918, 920, 922 and 924 may be connected to the drive module or the cassette of a device module. In another embodiment, the support arms 918, 920, 922 and 924 may be foldable, telescoping or use other methods to shorten the length of the support arm when not in operation. FIG. 87 shows a simplified top view illustrating movement of a device module relative to a device support in accordance with an embodiment. The third device module 910 starts at a first position 934 (shown with dotted lines) and moves to a second position 936 (as indicated by arrow 946). As the third device module 910 moves forward (toward a patient), it moves along the third device support 912 that is fixed to second device module 906 at the first front (or distal) fixed point 926 and is fixed to the support arm 922 extending from the second device module 906 at a first rear (or proximal) fixed point 928. As the third device module translates, the portion of the device support 912 moving through the third device module 910 changes, while the first front 926 and rear 928 fixed points do not move. The length of a first section 942 of the device support 912 spanning between the second device module 906 and the third device module 910 decreases while the length a second section 944 of the device support 912 spanning between the third device module 910 and the rear fixed point 928 increases. This allows the third device module 910 (and the associated EMDs) to remain fully supported between the span between the third device module 910 and the second device module 906 during linear motion. Another relative motion occurring during the movement of the third device module 910 between the first position 934 and the second position 936 involves the fourth device support 916 of the fourth device module 914 and the second front (or distal) 930 and second rear (or proximal) 932 fixed points for the fourth device support 916. The fourth device support 916 is fixed to the third device module 910 at the second front fixed point 930 and is fixed to the support arm 924 extending from the third device module 910 at a second rear fixed point 932. Because the third device module 910 is moving, the second front 930 and rear 932 fixed points are moving as well. A first section 938 of the fourth device support 916 slides through the fourth device module 914, increasing in length in the span between the fourth device module 914 and the third device module 910 while a second section 940 of the fourth device support 916 decreases in length in the span between the fourth device module 914 and the rear fixed point 932.

Figure 88:
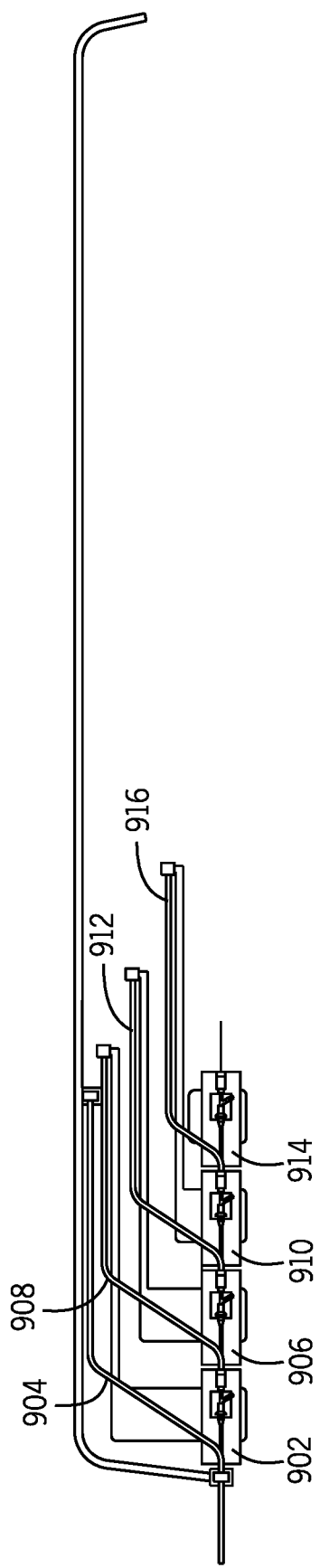
FIG. 88 shows a simplified top view illustrating the four device modules of FIG. 86 in a forward position relative to their respective device support in accordance with an embodiment.
Figure 89:
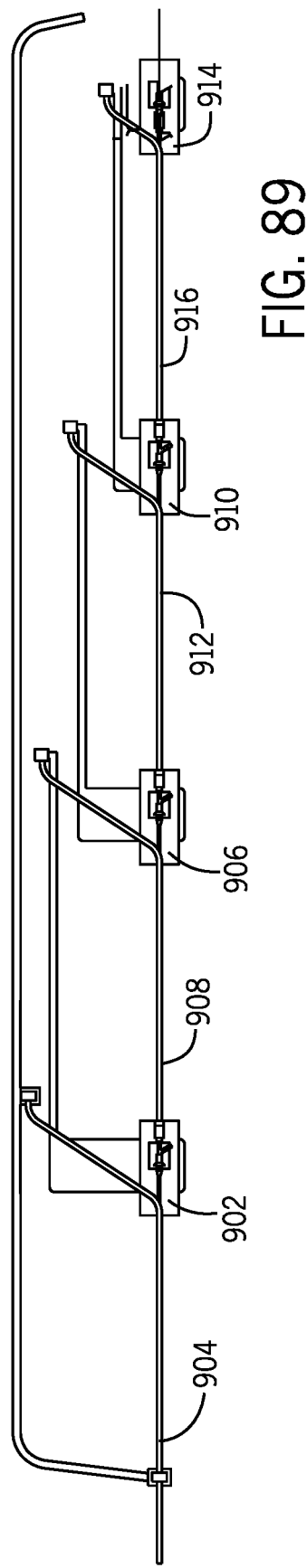
FIG. 89 shows a simplified top view illustrating the four device modules of FIG. 86 in a withdrawn position relative to their respective device support in accordance with an embodiment.

FIG. 88 shows a simplified top view illustrating the four device modules of FIG. 86 in a forward position relative to their respective device support in accordance with an embodiment. In FIG. 88, the first device module 902, the second device module 906, the third device module 910 and the fourth device module 914 are each shown in the maximum forward position along their respective device support 904, 908, 912 and 916. FIG. 89 shows a simplified top view illustrating the four device modules of FIG. 86 in a withdrawn position relative to their respective device support in accordance with an embodiment. In FIG. 89, the first device module 902, the second device module 906, the third device module 910 and the fourth device module 914 are shown in a maximum extended (rear) position along their respective device support 904, 908, 912 and 916. In an embodiment, the device support length is determined by the straight length of the device support and the S-shaped spline that takes the device support off the longitudinal device axis of a device module and directs it towards the support arm longitudinal axis. In one embodiment, each device support 904, 908, 912 and 914 may include compliance to pretention the device support to help with slack when transitioning between forward and reversed directions.

Figure 90:
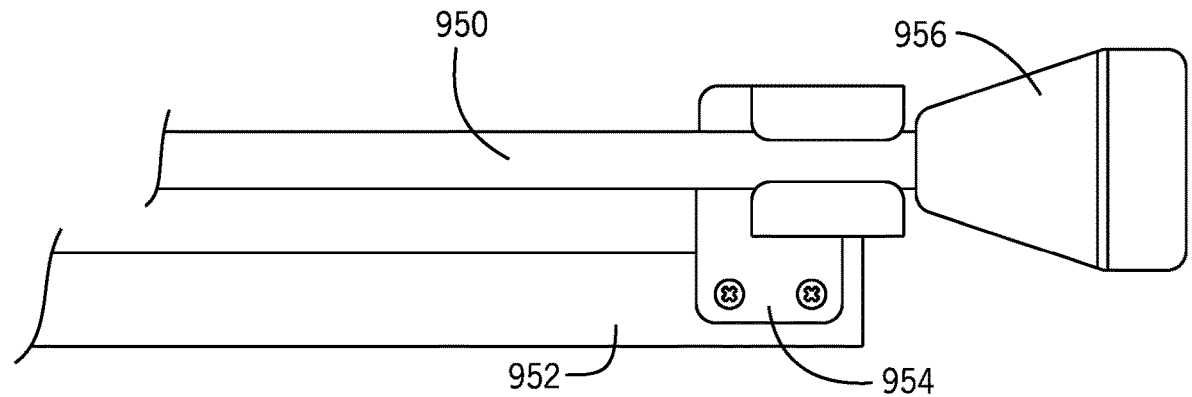
FIG. 90 is a side view of a proximal end of a device support that is extended and a rear constraint for a rear fixed point to which the device support is connected in accordance with an embodiment.
Figure 91:
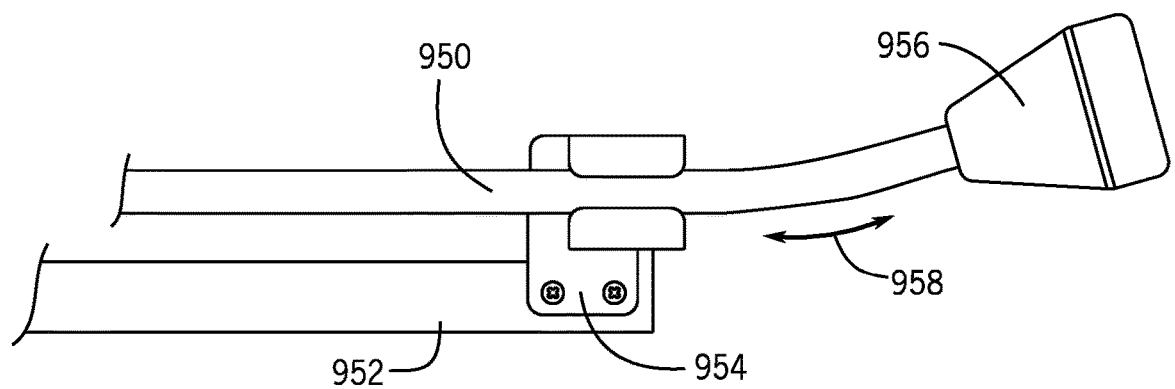
FIG. 91 is a side view of a proximal end of a device support that is partially retracted and a rear constraint for a rear fixed point to which the device support is connected in accordance with an embodiment.

As discussed above, each device support is constrained at a rear (or proximal) fixed point that is connected to a support arm extending from a device module in front (e.g., distal to) the device module associate with the device support. In an embodiment, the rear fixed point includes a rear constraint that may be configured to only react tensile forces. FIG. 90 is a side view of a proximal end of a device support that is extended and a rear constraint for a rear (or proximal) fixed point to which the device support is connected in accordance with an embodiment and FIG. 91 is a side view of a proximal end of a device support that is partially retracted and a rear constraint for a rear (or proximal) fixed point to which the device support is connected in accordance with an embodiment. A proximal end 952 of a support arm includes a retaining clip 954 which holds the proximal end of the device support 950. A hard stop 956 is positioned on the end of the device support and is configured to hold the device support in tension when the device support moves forward and allowing the device support to be retracted for device loading (as described above with respect to FIGS. 80 and 81). Forward motion and retraction of the device support 950 is indicated with arrow 958. An operator may pull back on the device support 950 without removing it from the retaining clip 954. The rear constraint formed from the retaining clip 954 and the hard stop 956 only reacts tensile forces. The device support will not buckle because the retaining clip 954 cannot react compressive forces.

Figure 94:
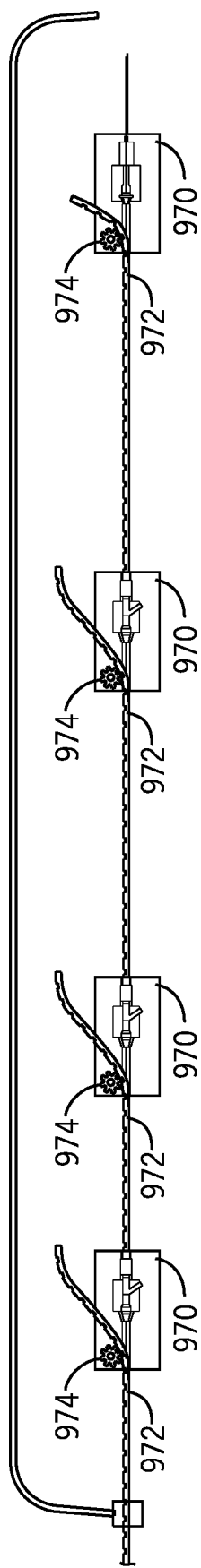
FIG. 94 shows a simplified top view of device modules with drive device supports in accordance with an embodiment.
Figure 95:
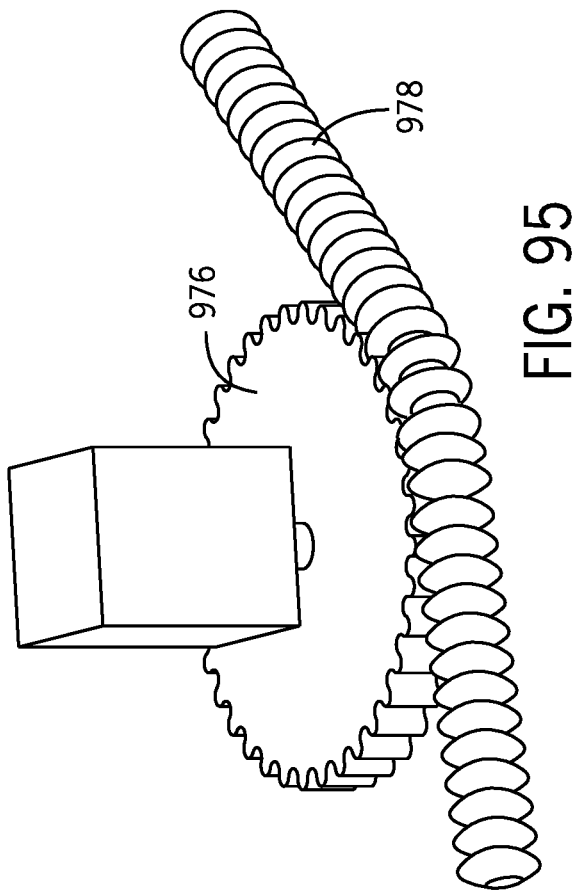
FIG. 95 shows an exemplary geared tensioner in accordance with an embodiment.

In another embodiment, the tension on the device support provided by front (or distal) fixed point that connects the device support to a more distal device module and a rear (or proximal) fixed point created by storing the proximal end of the device support on a reel or spool at each cassette. In this embodiment, support arms would not be required to provide the fixed point on the proximal end of the device support. FIG. 92 shows a simplified top view of device modules with device supports stored on a reel in accordance with an embodiment and FIG. 93 shows an exemplary spooled tensioner in accordance with an embodiment. In FIG. 92, each device module 960 includes a reel or spool 962 on which the device support may be wound. An exemplary spooled tensioner is shown in FIG. 93 that includes a spool 962 on which the flexible tube of the device support 964 is wound. The proximal end of the device support is fixed to the spool 962. The distal or "free" end of the device support may be pulled out by an operator or robotically actuated by the robotic drive and attached to a front fixed point on a distal cassette. A torque may be applied to the spool to apply tension to the device support 964. The torque could be applied by a solely mechanical apparatus such as a constant torque spring or a rack and pinion. In another embodiment, the torque may be applied by, for example, a motor (not shown) which is controlled by the control computing system 34 (show in FIG. 2). FIG. 94 shows a simplified top view of device modules with driven device supports in accordance with an embodiment and FIG. 95 shows an exemplary geared tensioner in accordance with an embodiment. In FIG. 94, each device module 970 includes a drive mechanism 974 which interacts with or engage a device support 972 to provide tension on the device support and allow the device support 972 to move forward and backwards. The drive mechanism may be, for example, a wheel or gear. In one embodiment, the drive mechanism 974 may engage the device support via friction on the walls of the flexible tube of the device support 972. In another embodiment, the device support may have radial holes along a side which are then engaged by a pin-drive gear, also called a tractor feed. In another embodiment, the device support is a ribbed or convoluted tube and the drive mechanism is a toothed gear that engages and tensions the ribbed or convoluted tube. An exemplary geared tensioner 976 is shown in FIG. 95 that engages a convoluted flexible tube 978.

Figure 96:
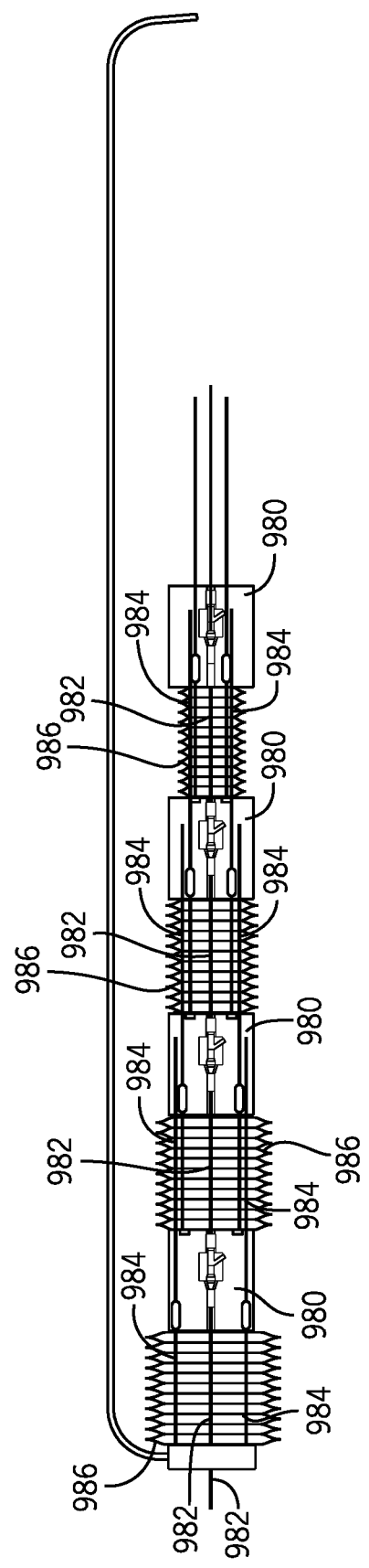
FIG. 96 shows a simplified top view of device modules with device supports formed with accordions or springs in accordance with an embodiment.
Figure 97:
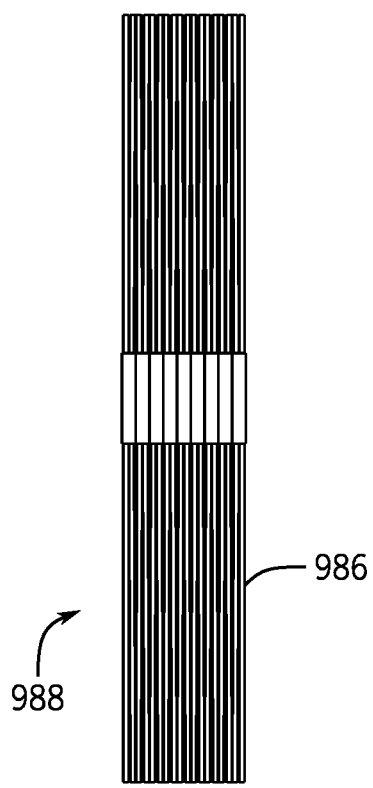
FIG. 97 illustrates a compressed accordion/spring in accordance with an embodiment.
Figure 98:
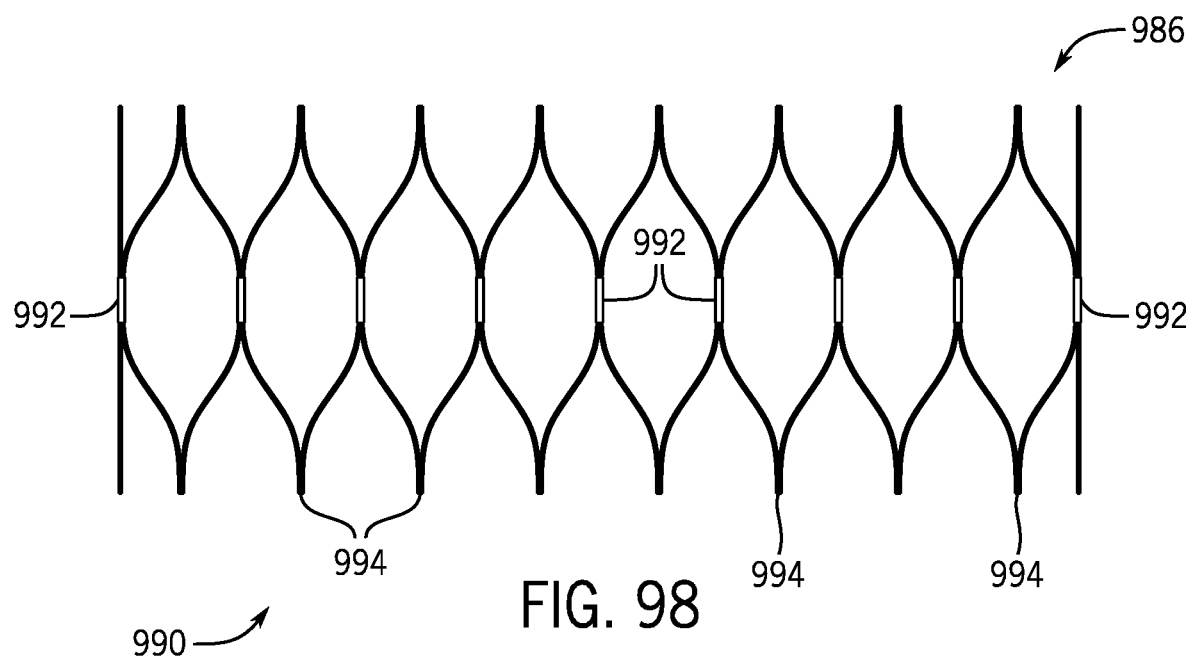
FIG. 98 illustrates a stretched accordion/spring in accordance with an embodiment.

In another embodiment, the device support may be an accordion or spring. FIG. 96 shows a simplified top view of device modules with device supports formed with accordions or springs in accordance with an embodiment. In FIG. 96, a device support between the device modules 980 is formed from an accordion element 986 and two linear guides 984 which are positioned in parallel to one another on opposite sides of the accordion element 986. An EMD 982 is positioned through openings 992 (shown in FIG. 98) in each segment 994 (shown in FIG. 98) of the accordion element 986. The accordion based device support is always in tension. In one embodiment, the accordion device support has compliance built in such that is capable of handling the relative translational motion between two device modules 980. Even though the accordion member acts as a tensile spring and typically stays in tension, it may still deflect from the device axis when axial load is applied. The linear guides (or guiding rails) 984 shown in FIG. 96 constrain the accordion so it is limited in deflection away from the device axis. In one embodiment, the linear guides 984 of a first device module mount to the proximal end of the more distal second device module and the other end of the linear guides 984 are free to slide through the accordion and the first device module. An embodiment where four accordions exist to support four device modules can have the accordion linear guides offset so that the linear guides for not interfere with one another when the device module are close. FIG. 97 illustrates a compressed state 988 of the accordion element 986. The linear guides are not shown in FIG. 97 for clarity. FIG. 98 illustrates a stretched state 990 of the accordion element 986. The linear guides are not shown for clarity. The accordion element 986 includes multiple segments 994 that each include an opening 992 through which an EMD may be positioned. The number of segments 994 and the lengths of the segments 994 may be optimized so that the unsupported distance between discrete segments 994 is such that an EMD will not buckle at maximum loads experienced during a procedure. The accordion device support has multiple flexures which auto-balance to give equal spacing regardless of the overall tension so that no single gap across the length of a segment 994 becomes large enough for buckling. In other words, the gaps across each segment 994 length want to be the same across all segments 994. This helps minimize the unsupported distance an EMD needs to travel, which allows the accordion element 996 to reach higher loads before buckling.

Figure 99A:
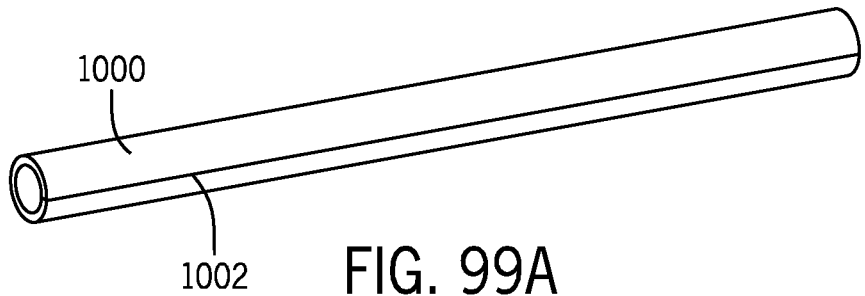
FIG. 99A-C are perspective views of exemplary slit shapes for a device support flexible tube in accordance with an embodiment.
Figure 99B:
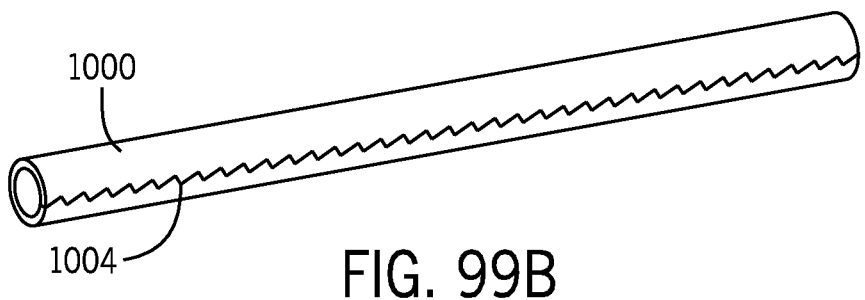
Figure 99C:
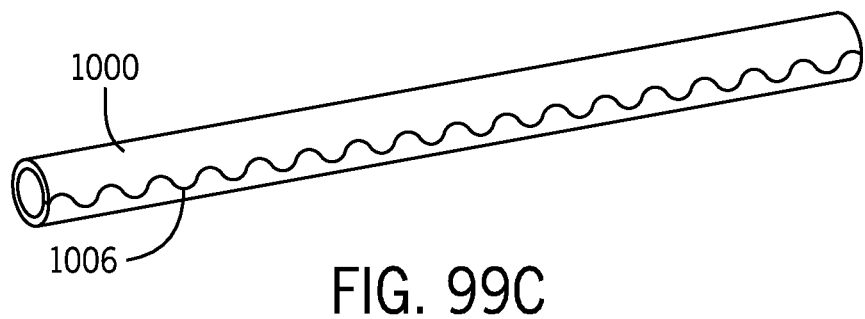

The profile of a device support formed from a flexible tube should support being opened and closed, for example, to allow EMDs to be loaded into the device support. When the slit at the distal end of the device support flexible tube is forced apart (e.g., using a splitter as discussed further below), the device support may be advanced to encapsulate the EMD and when, closed, the EMD is adequately supported and retained so as to not pop out and buckle. FIGS. 99A-C are perspective views of exemplary slit shapes for a device support flexible tube in accordance with an embodiment. In FIG. 99A, a device support flexible tube 1000 is shown with a straight slit 1002 lengthwise along the tube. In another example, a device support flexible tube 1000 may have a serrated shaped slit 1004 lengthwise along the tube as shown in FIG. 99B. In yet another examples, a device support flexible tube 1000 may have a wave shaped slit 1006, similar to a sine wave, lengthwise along the tube as shown in FIG. 99C. The slit of the device support 1000 may be opened by a wedge or splitter (shown in FIG. 102-104 and discussed further below) that is positioned close to an entry point for an EMD to the device support. The wedge or splitter spreads the opening wide enough to clear the EMD. The elasticity of the flexible tube causes the slit to recover and close on the other side of the EMD, encapsulating and retaining the EMD. The serrated shape and shape similar to a sine may be used so that the material in the area of the slit overlaps so as to improve EMD retention in the device support.

The EMDs utilized in a robotic drive for an interventional procedure may vary in size, for example, the various EMDs that may be used may vary from 9FR to 2FR or even a 0.010" guidewire. For example, in a multi-axial robotic drive configured for an endovascular therapy procedure to treat acute ischemic stroke, it can be expected that the first EMD in the device stack-up is between 6 and 9 FR. The second and third EMDs in the device stack-up may be between 2.5 to 6 FR. The fourth EMD may be a wire-based EMD with a diameter between 0.010 to 0.038". In order to properly support and retain EMDs with different sizes, different device supports may be provided for each EMD where the device support for each EMD is designed to work with the corresponding size of EMD. For example, by minimizing the diametrical clearance between the EMD and the device support tube, any device buckling inside the tube will store less energy and have less linear motion hysteresis. In an embodiment, the device support of each cassette may be designed to be modular so that the correctly sized device support may be added to a cassette based on the EMD being supported by the cassette. In addition, a splitter and device support connector (both discussed further below with respect to FIGS. 102-107) that are designed to work with a specific size of EMD may also be modular and switched based on the specific size of EMD being supported by a cassette. In another embodiment, different versions of a cassette may be provided for each subset of device sizes, where the cassette has an appropriately sized device support pre-installed. The appropriate cassette design for the specific size or range of sizes of an EMD may be mounted to a drive of the robotic drive and removed when a different design is needed for a different size of EMD or a different size range. For example, a cassette may be designed to support a range of sizes of the wire-based EMD which can vary between 0.010" and 0.038".

Figure 100:
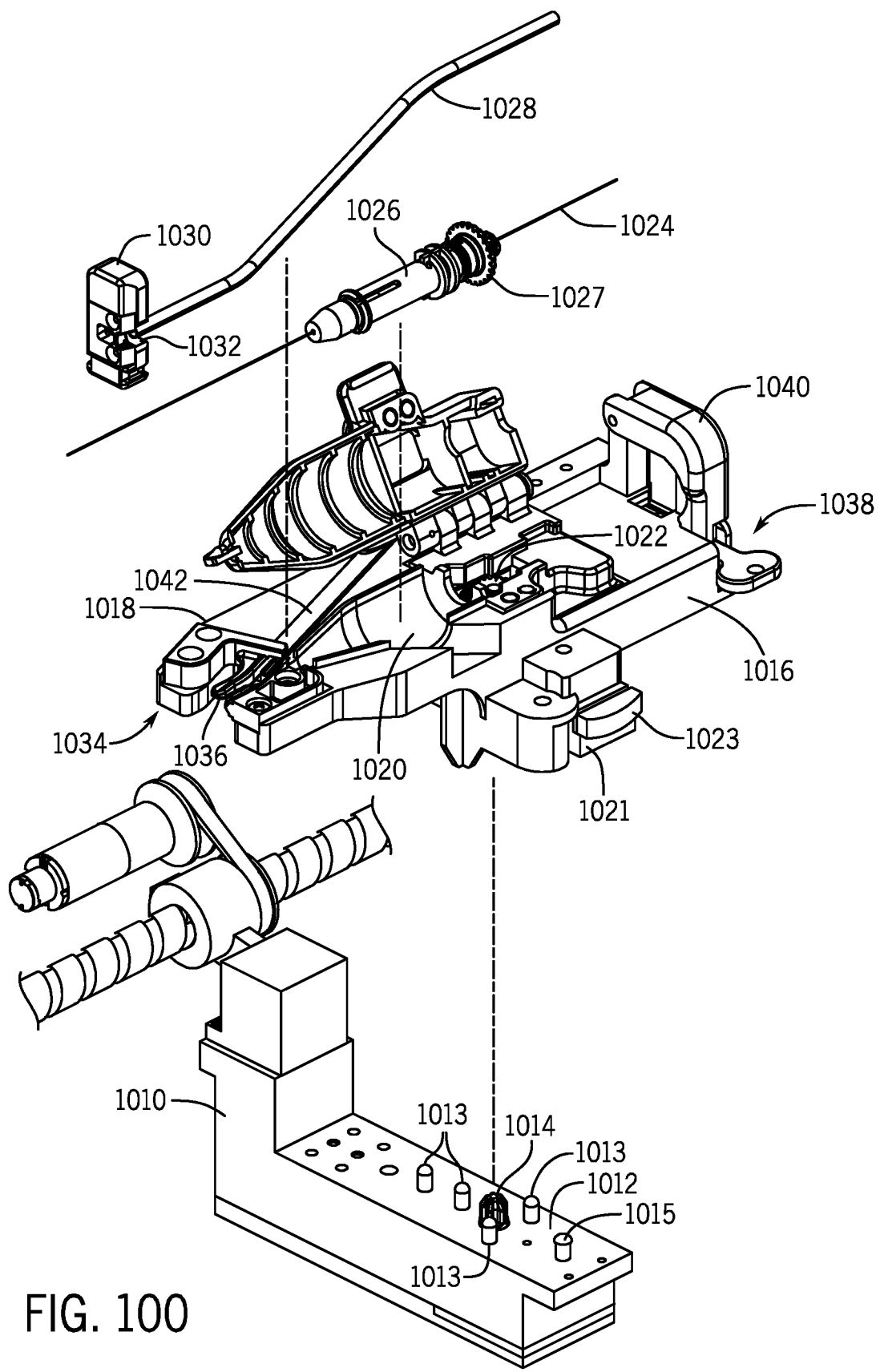
FIG. 100 is an exploded view of a device module and an elongated medical device in accordance with an embodiment.

As discussed above with respect to FIG. 3, a device module 32 of a robotic drive 24 includes a drive module 68 and a cassette 66 mounted on and releasably coupled to the drive module 68. FIG. 100 is an exploded view of a device module and an elongated medical device in accordance with an embodiment. A drive module 1010 includes a mounting surface 1012 and a coupler 1014. A motor and a drive belt (not shown) may be housed in the drive module 1010 and connected to the coupler 1014. The motor and belt are used to control a rotational position of the coupler 1014. Drive module 1010 may include an encoder (not shown) for device position feedback. The drive module 1010 shown in FIG. 100 has one coupler 1014, however, it should be understood that the drive module 1010 may have more than one coupler 1014 and more than one motor. (for example, one motor for each coupler or one motor driving multiple couplers) The rotation of the coupler 1014 may be used to provide another degree of freedom for an EMD positioned in a cassette 1016 that may be mounted on the mounting surface 1012 so as to interface with the coupler 1014. For example, the coupler 1014 may be used to rotate an EMD 1024 when the EMD is positioned in the cassette 1016. If the drive module 1010 has two or more couplers 1014, each coupler may be used to provide a degree of freedom for an EMD.

As mentioned, a cassette 1016 may be positioned on the mounting surface 1012 of the drive module 1010 and used to interface with an EMD 1024 positioned in the cassette 1016. As mentioned above, the drive module 1010 may be configured to have at least one dimension that is smaller or less than at least one dimension of a cassette 1016 as shown in FIG. 100. For example, a length of the drive module 1010 as measured from a proximal side to a distal side when the device module 1010 is coupled to a linear member or rail may be smaller or less than a length of the cassette 1016 along a longitudinal axis of the cassette. In some embodiments, the size and dimensions of the drive module 1010 are minimized so that, for example, the drive module 1010 takes up a minimal amount of space along a linear member or rail (e.g., linear member or rail 60 shown in FIG. 2) of the robotic drive when not populated with a cassette 1016. The cassette 1016 includes a housing 1018. In an embodiment, the cassette housing 1018 may be releasably attached to the drive module 1010. The drive module 1010 may also include one or more additional elements 1013 on the mounting surface 1012 such as, for example, positioning pins, alignment pins, etc. to interact with elements on a cassette 1016 (e.g., connection points, slots, channels, etc.) to enable a releasable attachment of the cassette 1016 to the drive module 1010. In one embodiment, cassette housing 1018 is releasably connected to the drive module 1010 using a quick release mechanism 1021. In one embodiment, the quick release mechanism 1021 includes a spring-biased member in cassette housing 1018 that is actuate by a latch release 1023 that releasably engages with a quick release locking pin 1015 secured to the drive module 1010.

Figure 101A:
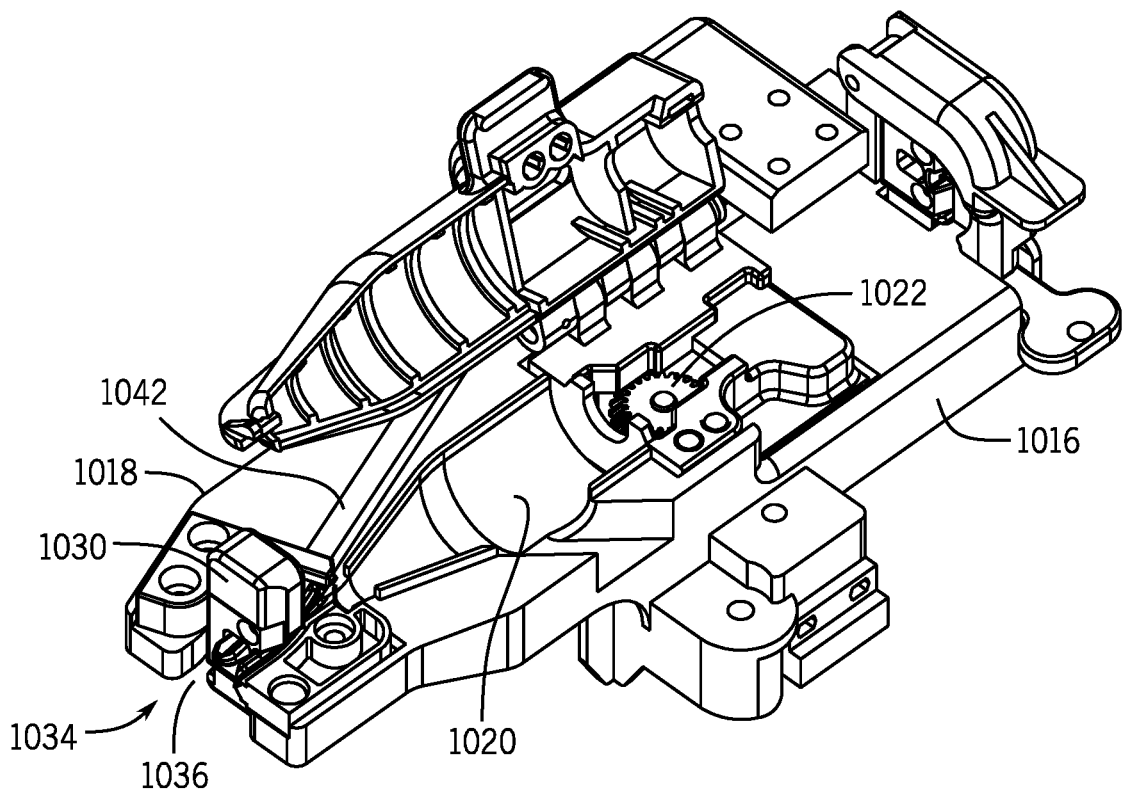
FIG. 101A is a perspective view of a cassette with a device support installed and in a retracted position in accordance with an embodiment.
Figure 101B:
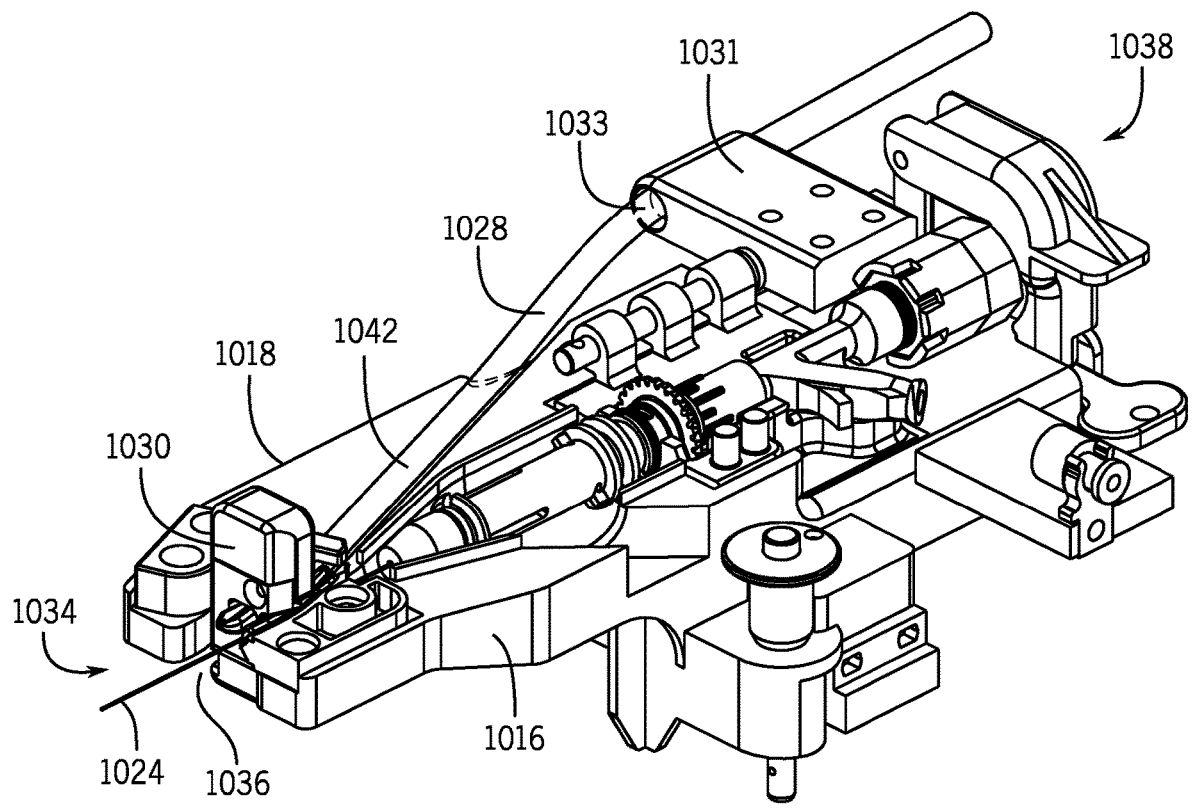
FIG. 101B is a perspective view of a cassette with a device support installed in accordance with an embodiment.

The cassette housing 1018 includes a cradle 1020 configured to receive the EMD 1024. A bevel gear 1022 is used to interface with the coupler 1014 of the drive module 1010 and to interface with the EMD 1024 to rotate the EMD 1024. In one embodiment, EMD 1024 is provided with an on-device adapter 1026 (discussed above with respect to FIGS. 23-25) to interface the EMD 1024 to the cassette 1016, for example, an interface to bevel gear 1022. In the example shown in FIG. 100, the EMD is a guidewire and the on-device adapter 1026 is a collet with a gear 1027. When power is transferred from the device module 1010 to the gear 1022 in the cassette 1016 (e.g., via the coupler 1014), the gear 1022 in the cassette interacts with the gear 1027 on the collet to rotate the guidewire 1024. A device support 1028 is positioned in the cassette in a channel 1042 which may be covered by the housing 1018. As discussed above, the device support 1028 and the cassette 1016 are configured to move relative to one another. The device support 1028 includes a connector 1030 which is used to connect to a device module (e.g., to a cassette, to other elements of the device module, or to elements positioned in the device module) distal (or in front of) the cassette 1016 in a robotic drive. Connector 1030 includes a recess 1032. In a withdrawn or retracted position, the connector 1030 is positioned in a recess 1036 in the housing 1018 on a distal end 1034 of the cassette 1016. As discussed above, the connector 1030 and device support 1028 may be pulled outward from the cassette 1016 so the connector may be attached to a more distal cassette in the robotic drive. A forward constraint 1040 is provided on a proximal end 1038 of the cassette 1016 and is used to connect to a connector of a device support on another cassette proximal to (or behind) the cassette 1016 in a robotic drive. FIG. 101A is a perspective view of a cassette with a device support installed and in a retracted position in accordance with an embodiment. In the retraced position, the connector 1030 is positioned in the recess 1036 in the housing 1018 at the distal end 1034 of the cassette 1016. FIG. 101B is a perspective view of a cassette with a device support installed and in a retracted position in accordance with an embodiment. The device support 1028 is positioned in a channel 1042 of the cassette. The cassette 1016 incudes a proximal support member 1031 positioned on the proximal end 1038 of the cassette 1016. The proximal support member 1031 includes an opening and is configured to provide support to the device support 1028. Device support 1028 is positioned in and passes through the opening 1033. The opening 1033 is sized so that the device support can move through the opening 1033 as the device support 1028 is advanced and retracted.

Figure 102:
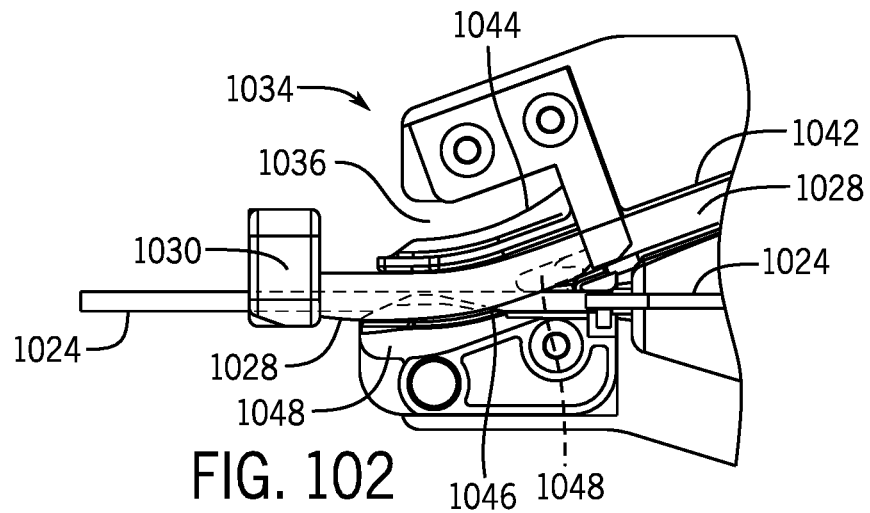
FIG. 102 is a top view of a device support and connector extended from a cassette ahead of an EMD entry point in accordance with an embodiment.
Figure 103:
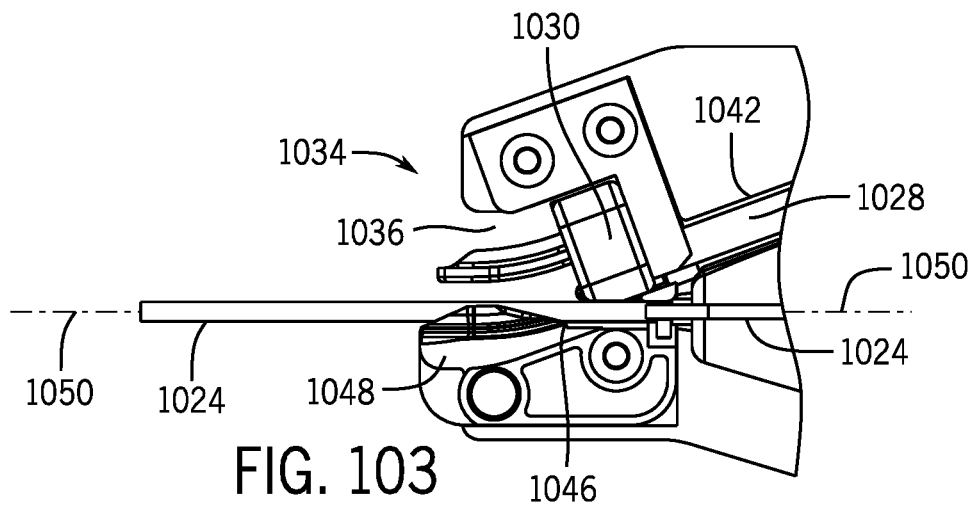
FIG. 103 is a top view of a device support and connector withdrawn behind an EMD entry point in accordance with an embodiment.
Figure 104:
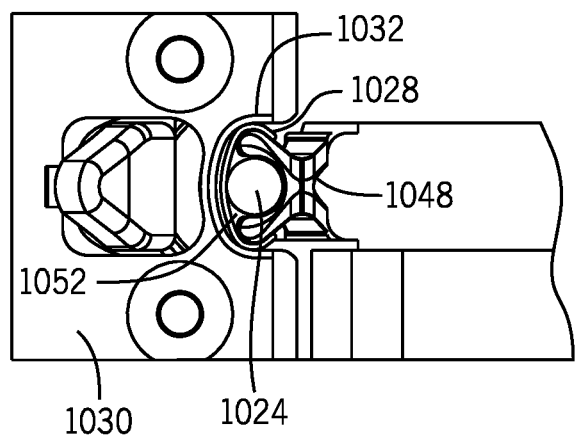
FIG. 104 is an end view of a splitter holding open a device support in accordance with an embodiment.
Figure 105:
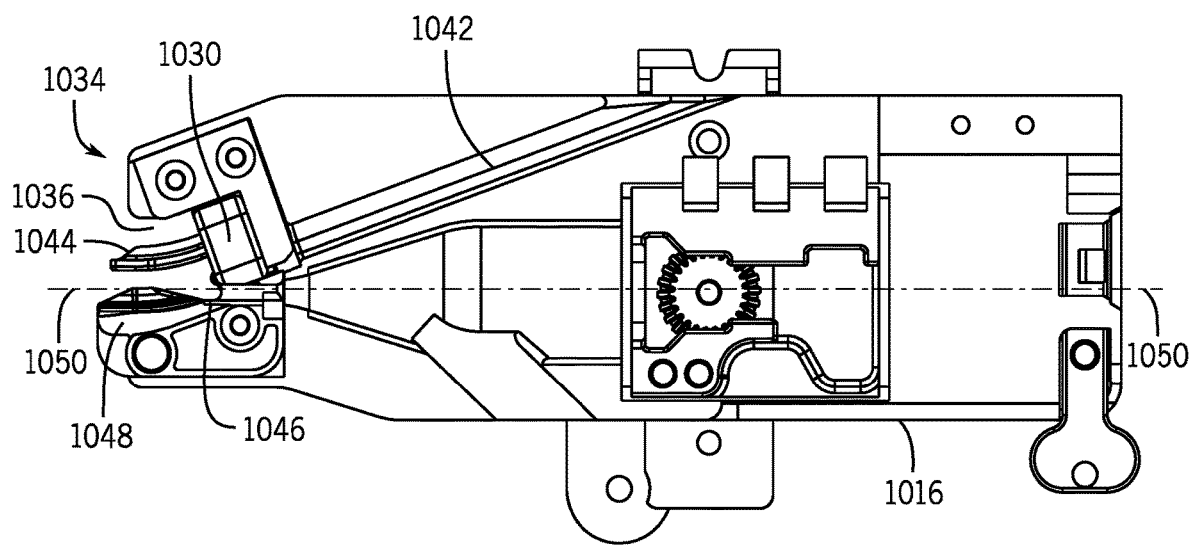
FIG. 105 is a top view of cassette with a device support connector withdrawn and off of a device axis to facilitate loading of an EMD in accordance with an embodiment.

FIG. 102 is a top view of a device support and connector extended from a cassette ahead of an EMD entry point in accordance with an embodiment. A device support 1028 and connector 1030 are extended out from the recess in the distal end 1034 of the cassette housing. A guide 1044 and a splitter 1048 are positioned in the recess 1036 on opposite sides of the path of the device support 1028 as it is moved into and out of the recess 1036 and channel 1042. In the extended position, the device support encapsulates an EMD 1024. The EMD enters the device support 1028 at an EMD entry point 1046 which is located between a proximal section and a distal section of the splitter 1048. The proximal and distal sections of the splitter are shown with dotted lines. As mentioned above, the device support 1028 includes a lengthwise slit so the distal end of the device support may be forced apart (e.g., by using a splitter as described below) and closed to allow the device support to encapsulate an EMD as the device support is advanced. The connector 1030 holds open an end of the device support tube allowing it to pass over the splitter 1048 as shown in FIG. 104. Referring to FIGS. 102 and 104, the splitter 1048 holds the slit in the device support 1028 open as the EMD 1024 is encapsulated by the device support 1028 as the connector 1030 and device support 1028 pass over the splitter 1048 and EMD entry point 1046. The end of the device support tube 1028 is positioned in a recess 1032 of the connector. Using the splitter 1048 to hold open the device support 1028 on both sides of EMD entry point 1046 reduces or eliminates friction forces on the EMD 1024. For example, this prevents the walls of the device support 1028 tube from rubbing the EMD 1024 which can cause damage to the EMD 1024 at the entry point and would introduce noise to a load sensing system (not shown) which may be used to read the force or torque the EMD is subjected to. The EMD 1024 passes through a cavity 1052 in the center of the splitter 1048. The connector 1030 and the splitter 1048 are designed so that the device support 1028 is held open as it passes over a gap between the proximal and distal section of the splitter 1048. Splitter 1048 is also designed such that the unsupported length of the EMD 1024 at any point is not such that it can catastrophically buckle. Guide 1044 is configured to guide the device support 1028 over the gap and retain the device support 1028 on the splitter 1048. As mentioned above, the splitter 1048 may be designed for specific EMD and device support size ranges. FIG. 103 is a top view of a device support and connector withdrawn behind an EMD entry point in accordance with an embodiment and FIG. 105 is a top view of cassette with a device support connector withdrawn and off of a device axis to facilitate loading of an EMD in accordance with an embodiment. To facilitate loading of an EMD 1024 in a cassette 1016 (shown in FIG. 100), the device support 1028 and connector 1030 are retracted into the recess 1036 before an EMD 1024 is loaded. As shown in FIGS. 103 and 105, the connector 1030 may be retracted onto the splitter 1048 and guide 1044 and behind (or proximal to) the EMD entry point 1046. In addition, the retracted (or withdrawn) position of the connector 1030 is off of a longitudinal EMD axis 1050. This allows for EMD placement into cassette 1016, for example, loading a side loading EMD. Retracting the connector 1030 behind the EMD entry point also reduces the unsupported EMD length and reduces working length loss.

Figure 106:
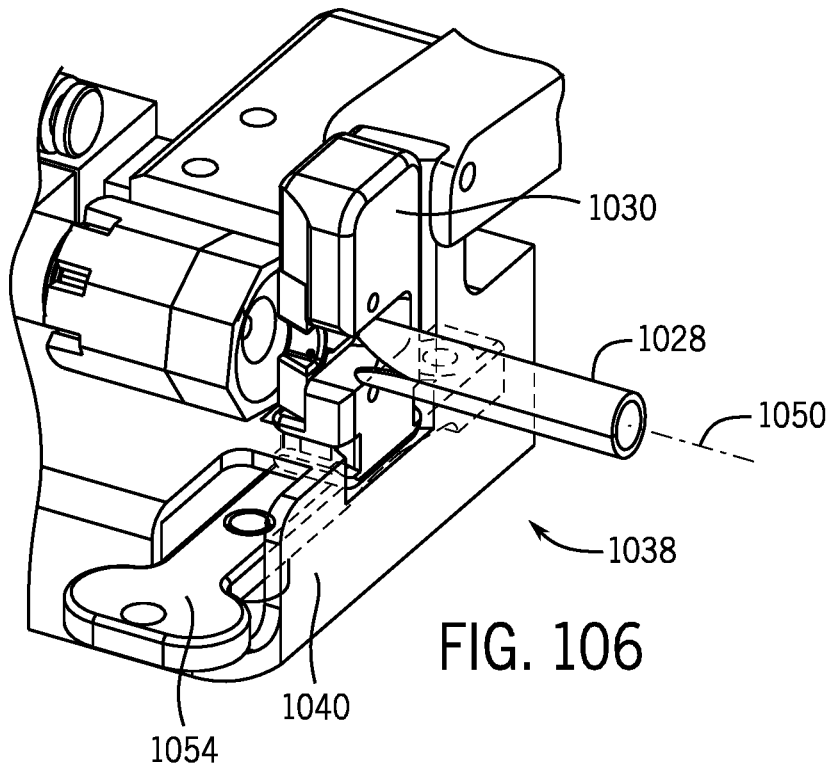
FIG. 106 is a perspective view of a forward constraint and a connector in accordance with an embodiment.
Figure 107:
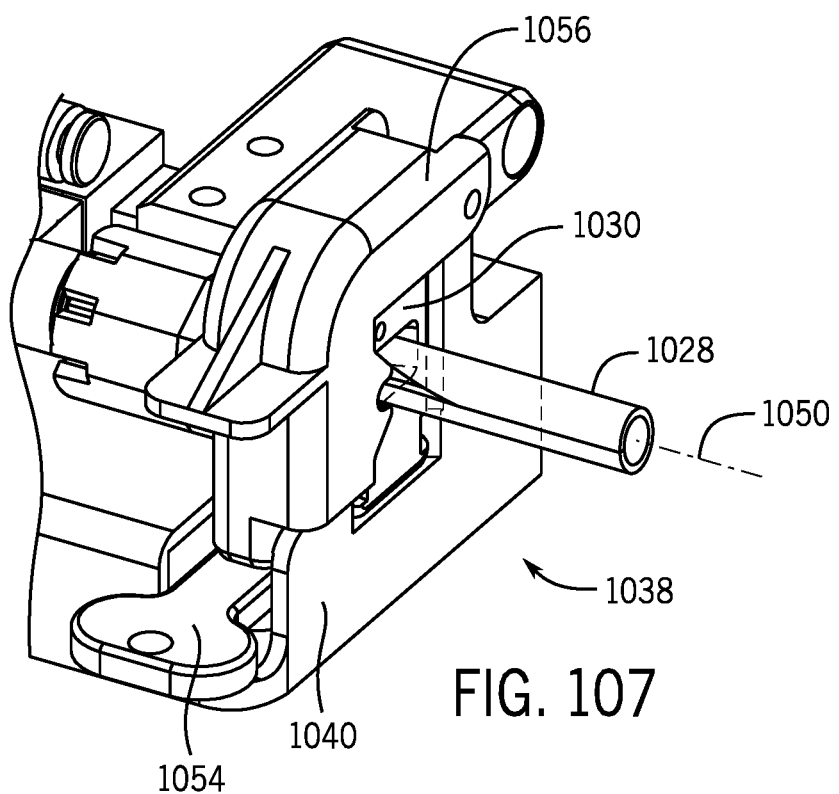
FIG. 107 is a perspective view of a forward constraint with a lid in accordance with an embodiment.

As discussed above with respect, the connector 1030 and device support 1028 may be pulled outward from the cassette 1016 so the connector may be attached to a more distal device module (e.g., a cassette of the device module) in the robotic drive. In an embodiment, a forward constraint 1040 (shown in FIG. 100) may be provided on a proximal end 1038 of a first cassette and is used to connect to a connecter of a device support on a second cassette proximal to (or behind) the first cassette in the robotic drive. FIG. 106 is a perspective view of a forward constraint and a connector in accordance with an embodiment. Forward constraint 1040 includes a latching mechanism 1054, for example, a spring latch. A connector 1030 of a device support 1028 from a proximal cassette (not shown) is attached to the spring latch 1052. In one embodiment, the connector 1030 connects to the latching mechanism 1054 by pushing the connector 1030 into the foreword constraint 1040. In an embodiment, the latching mechanism 1054 may require no secondary motion other than axial translation to engage the latching mechanism 1054, but may require one or more additional movements to disengage the latching mechanism 1054 and remove the connector from the forward constraint 1040. For example, there may be buttons, levers or knobs which may need to be released before the connector 1039 becomes disengaged. The connector 1030 may be manually disengaged or disengaged using a control computing system 34 (shown in FIG. 2). The connector 1030 attaches to the forward constraint 1040 approximately along the longitudinal EMD axis 1050 of an EMD (not shown) contained in the device support 1028. This prevents shearing of the EMD by moving perpendicular to the lathing mechanism 1054. In another embodiment, a secondary latch or tightening mechanism may be provide to further secure the connector 1030 and reduce play. FIG. 107 is a perspective view of a forward constraint with a lid in accordance with an embodiment. In FIG. 107, a lid 1056 is connected to the forward constraint 1040, for example using a pivot. The lid 1056 may be closed over the connector 1030 and latched to further constrain the connector 1030 in the forward constraint 1040.

Figure 108:
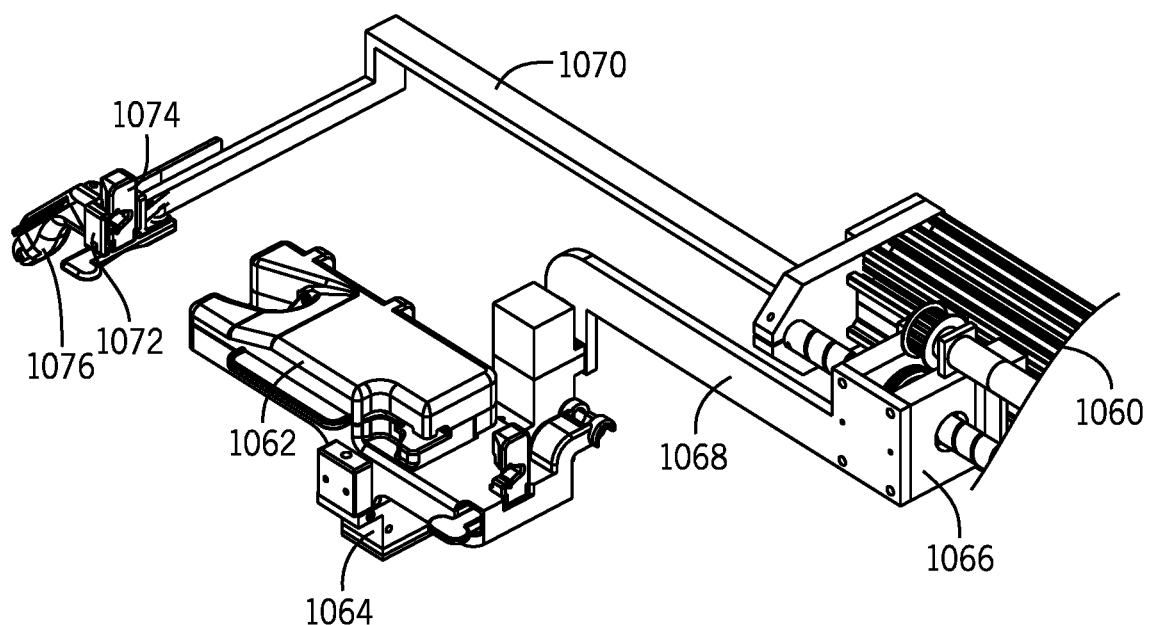
FIG. 108 is a perspective view of a distal support arm and distal support connection in accordance with an embodiment.
Figure 109:
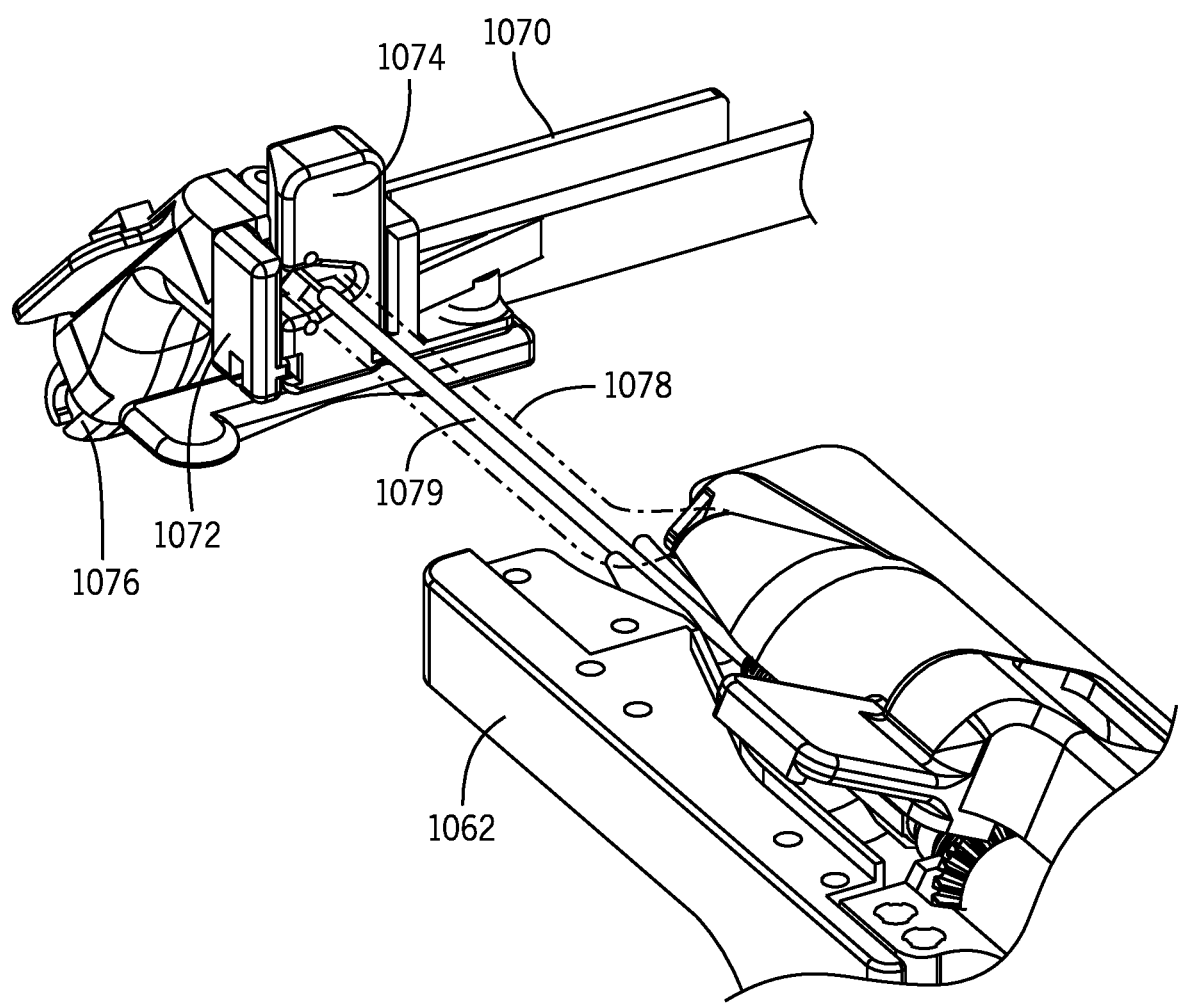
FIG. 109 is a perspective view of a distal support connection coupled to a device support and connector in accordance with an embodiment.
Figure 110:
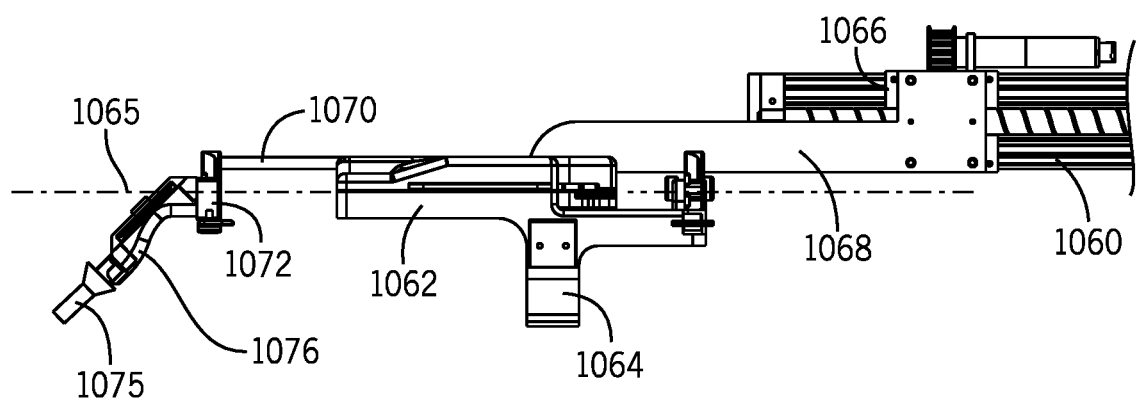
FIG. 110 is a side view of a distal support arm, distal support connection and an introducer interface support in accordance with an embodiment.

As discussed above with respect to FIG. 3, a distal support connection mounted to a distal support arm may be used to provide a front (or distal) fixed point to support the distal end of the device support in the cassette of the most distal device module in the robotic drive, i.e., the device module closest to the patient. FIG. 108 is a perspective view of a distal support arm and distal support connection in accordance with an embodiment. A cassette 1062 is mounted to a drive module 1064 which is connected to a stage 1066 using an offset bracket 1068. The stage 1066 is moveably mounted to a rail or linear member 1060 and may be moved linearly along the rail 1060. A distal support arm 1070 may be attached to a frame of the robotic drive, for example, a frame of the rail 1060. In one embodiment, the distal support arm 1070 may be rigidly attached to the frame. In another embodiment, the distal support arm 1070 may be attached to a patient table or the patient. The distal support arm 1070 extends away from the robotic drive and is connected to a device support connection 1072 to provide a distal fixed point for the device support. In one embodiment, the distal support arm 1070 may also be used to provide a distal define for the cassette 1062 and drive module 1064. A distal define is used to define the most distal aspect of the most distal device (e.g., cassette 1062 and drive module 1064) of the robotic drive. In another embodiment, the distal define may be provided using a separate distal define arm (not shown) that may be coupled to, for example, the frame of the robotic drive. The distal support connection 1072 may also be coupled to an introducer sheath hub. An introducer interface support 1076 may be connected to the device support connection 1072. A connector 1074, for example, a connector on a distal end of a device support as described above with respect to FIGS. 102-105 may be attached to the device support connection 1072 to provide a distal fixed point and support for the distal end of the device support. A device support is not shown in FIG. 108, but would be positioned in the cassette 1062 as shown in FIG. 109. FIG. 109 is a perspective view of a distal support connection coupled to a device support and connector in accordance with an embodiment. A device support 1078 is shown as a dotted line encapsulating an EMD 1079 and extending between the cassette 1062 and the device support connection 1072. The connector 1074 is attached to the device support connection 1072. The device support connection 1072 may be, for example, a forward constraint such as described above with respect to FIGS. 106 and 107. The device support connection 1072 is mounted to a distal support arm 1070 and may be connected to an introducer interface support 1076. FIG. 110 is a side view of a distal support arm, distal support connection and an introducer interface support in accordance with an embodiment. The introducer interface support 1076 is configured to support an EMD 1079 (shown in FIG. 109) between the device support 1078 (shown in FIG. 109) and an introducer sheath 1075 connected to a distal end of the introducer interface support 1076 as discussed further below. The introducer interface support 1076 ensures that the EMD 1079 does not buckle or prolapse between the distal end of the device support 1078 and the hub of an introducer sheath 1075. In an embodiment, the introducer interface support 1076 may also be used to redirect an EMD from a position that is axially aligned with the robotic drive device axis 1065 to a position that is axially aligned with the introducer sheath 1075 or other supporting member.

The introducer sheath 1075 is inserted at an access point (e.g., the femoral artery) into a patient's vasculature that will lead the EMD to the target location in the patient (e.g., a lesion). The introducer sheath 1075 should be held in place so that it does not come out of the patient. In one embodiment, the distal support arm 1070 and the device support connection 1072 may be used to fix the position of the introducer sheath 1075 and may react forces on the introducer sheath 1075 created from the friction between the introducer sheath 1075 and the EMD moving inside of the introducer sheath 1075. In another embodiment the introducer sheath 1075 may be support by a separate structure than the distal support arm 1070 and device support connection 1072, for example, the introducer sheath may be attached to the patient or a patient table using known methods.

Figure 111:
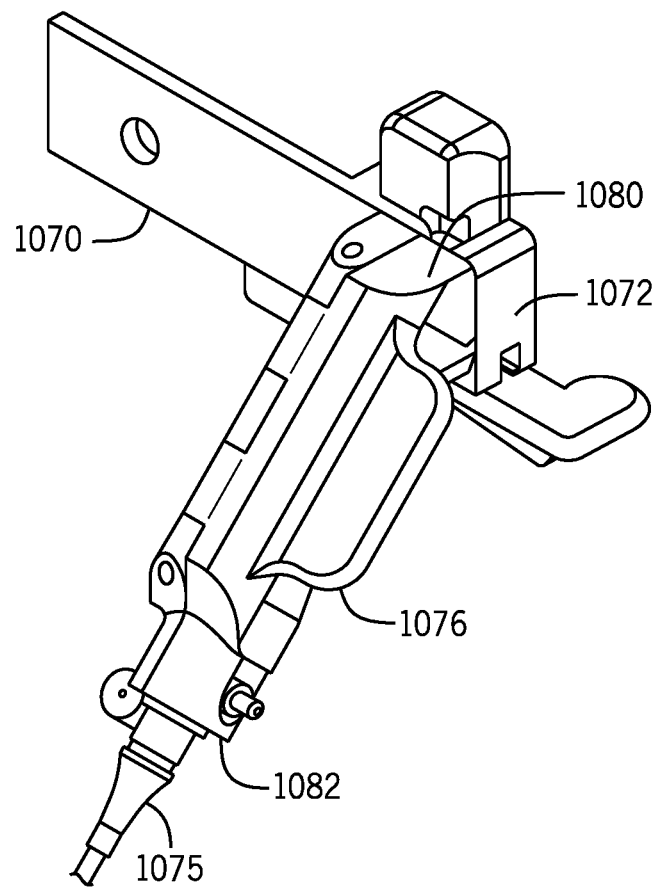
FIG. 111 is a perspective view of an introducer interface support connected to an introducer sheath in accordance with an embodiment.

FIG. 111 is a perspective view of an introducer interface support connected to an introducer sheath in accordance with an embodiment. The introducer interface support 1076 is connected at its proximal end 1080 to a device support connection 1072 that is connected to a distal support arm 1070. An introducer sheath 1075 is connected to a distal end 1082 of the introducer interface support 1076. The introducer interface support 1076 may be configured to receive the introducer sheath 1075 with a side port (not shown). The side port and its tubing (not shown) can allow for administration of medicine, contrast or saline injection or drawing blood samples. An EMD (not shown) enters the body of a patient through the introducer sheath 1075 which is inserted into a vessel (typically an artery). In one embodiment, the introducer interface support 1076 opens to allow the EMD to be placed in the introducer interface support 1076. In another embodiment, an EMD may be inserted axially into the introducer interface support 1076. In another embodiment, the EMD and introducer interface support 1076 may be frictionally fit so that the introducer interface support 1076 does not need to open or have the EMD inserted axially. As mentioned, the introducer interface support 1076 provides support to the EMD in the distance between the connector 1072 and the introducer sheath 1075. The introducer interface support 1076 may be rigid (as shown in FIG. 111) or flexible. For example, the introducer interface support 1076 may be made of flexible material or the introducer interface support 1076 may have a joint near the device support connection 1072 which allows for a limited range of motion of the distal end 1082 (where the introducer sheath 1075 is held) to account for perturbation of the robotic drive or movement of the patient.

Figure 112:
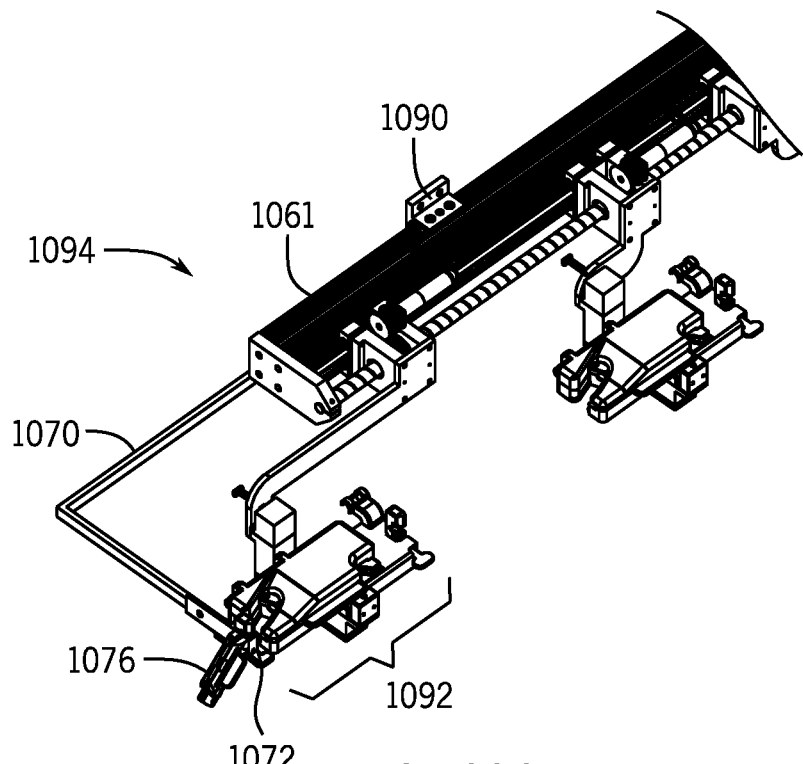
FIG. 112 is a perspective view of a movable distal support arm in a first position in accordance with an embodiment.
Figure 113:
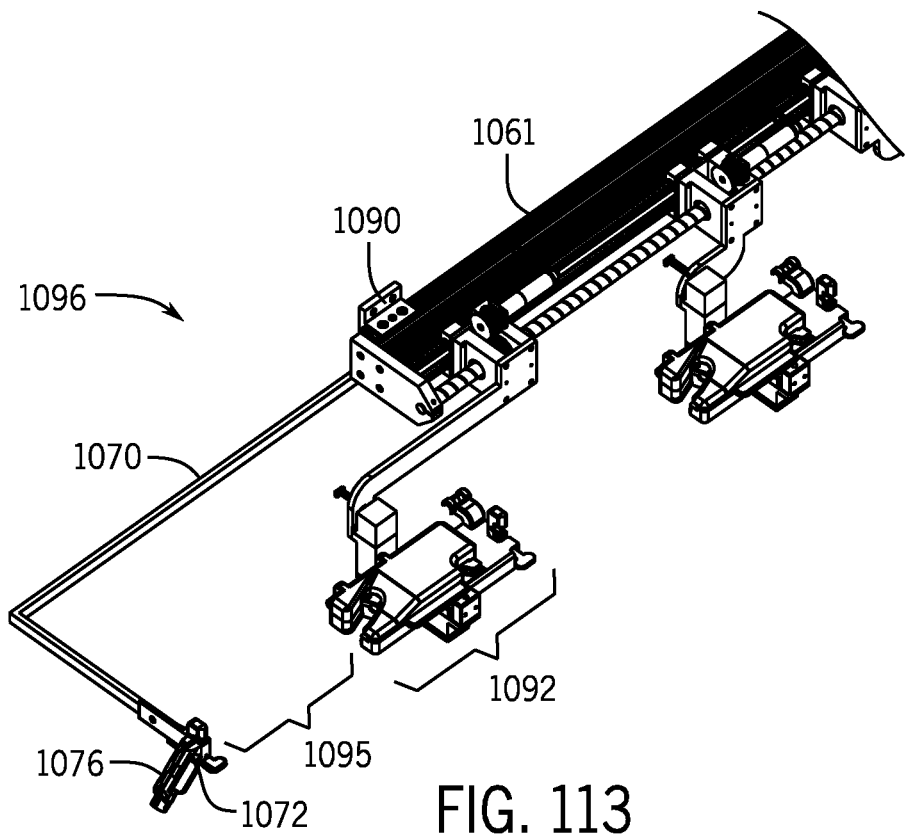
FIG. 113 is a perspective view of a moveable distal support arm in a second position in accordance with an embodiment.

In another embodiment, the distal support arm 1070 may be movably connected to the robotic drive. A moveable distal support arm 1070 may have one or more degrees of freedom to account for excess exposed EMD length that may not need to be actuated. For example, with shorter patients and/or less tortuously, more of the first guide catheter may be exposed because it will never need to enter the patient. If the distal support arm (and therefore the device support connection 1072) can move forward, it can account for the excess length of the guide catheter that does not need to be actuated. This may also help reduce the overall length of the rail or linear member 1061 (and rail 1060 shown in FIGS. 108 and 110). FIG. 112 is a perspective view of a movable distal support arm in a first position in accordance with an embodiment. A distal support arm 1070 may be moveable connected to a rail 1061 using a stage 1090. In FIG. 112, the distal support arm 1070 is in a first position 1094 where the distal support connection 1072 is located proximate to the distal end of a device module 1092. The stage 1090 may be manually or robotically moved along the rail 1061 to change the position of the distal support arm 1070. FIG. 113 is a perspective view of a moveable distal support arm in a second position in accordance with an embodiment. In FIG. 113, the stage 1090 and the distal support arm 1070 have been moved linearly to a second more distal position 1096 from the device module 1092. Accordingly, the device support connection 1072 and the device module 1092 are separated by a distance 1095. In the embodiment shown in FIGS. 112 and 113, the distal support arm 1070 has one degree of freedom. In another embodiment, the distal support arm 1070 may be an articulating or driven arm with multiple degrees of freedom.

Figure 114:
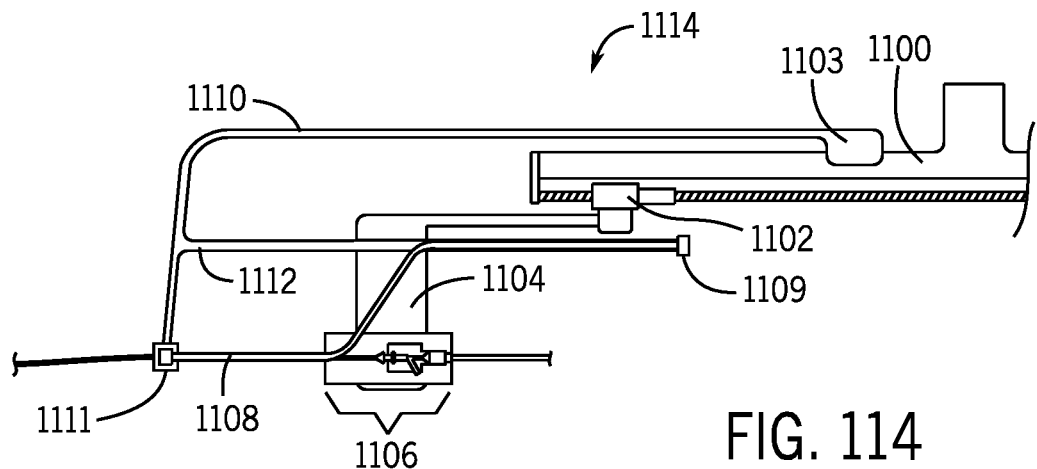
FIG. 114 is a top view of a moveable distal support arm and movable support arm in a first position in accordance with an embodiment.

As discussed above, each end of the device support may be connected to fixed points (front (or distal) and rear (or proximal)) to provide appropriate tension to the device support between device modules or between most distal device module and a device support connection to prevent an EMD from buckling. The device support connection 1072 described above provides a front (or distal) fixed point for the device support of the most distal cassette in the robotic drive. The device support of the most distal cassette may be provided with a rear (or proximal) fixed point using a support arm (e.g., support arm 77 shown in FIG. 3) that is connected to the distal support arm 1070. For a moveable distal support arm, the support arm will also be moveable. FIG. 114 is a top view of a moveable distal support arm and movable support arm in a first position in accordance with an embodiment. In FIG. 114, a distal support arm 1110 is in a first position 1114. A device module 1106 is connected to a rail or linear member 1100 using a first stage 1102. A device support 1108 is positioned in the device module 1106 (e.g., in a cassette of the device module) and a distal end of the device support 1108 is connected to a device connection point 1111 (front (or distal) fixed point) connected to the distal support arm 1110. A proximal end of the device support 1108 is connected to a proximal end of a support arm 1112 at a rear (or proximal) fixed point 1109. A second stage 1103 is connected to the rail 1100 (or a different rail (not shown) in the system) and may be manually or robotically moved along the rail 1100 to change the position of the distal support arm 1110 and the support arm 1112. FIG. 115 is a top view of a moveable distal define arm and movable support arm in a second position in accordance with an embodiment. In FIG. 115, the second stage 1103, the distal support arm 1110 and the support arm 1112 have been moved linearly to a second more distal position 1116 from the device module 1106. The support arm 1112 moves with the device support connection 1111 so there is always the same length of the device support 1108 between the device support connection 1111 and the rear fixed point 1109. FIG. 116 is a top view illustrating movement of a distal support arm and a support arm from the second position to the first position in accordance with an embodiment. In FIG. 116, the device support connection 1111, the support arm 1112, the distal support arm 1110 and the second stage 1103 start at the second position 1116 (indicated by dotted lines). The second stage 403 may be actuated to move linearly along the rail 1100 to the first position 1114 as indicated by arrow 1118. The first position of the device support connection, the support arm, the distal support arm, the rear fixed point, and the second stage are indicated by the reference numbers 1111', 1112', 1110', 1109', and 1103', respectively.

Using a catheter-based procedure system with a robotic drive to perform a procedure can involve loading and unloading devices into and out of the system and exchanging devices. For loading/unloading a device, the device being loaded/unloaded is inside the next distal EMD with a more proximal device (e.g., a microwire) that has an indwelling portion. A device exchange involves having a more proximal device (e.g., a microwire) with an indwelling portion and the device that is being unloaded needs to be removed from the proximal device without disturbing the location of the indwelling. The speed, safety and efficiency of exchanges may be impacted by various factors including the experience level of the user or operator, the time-critical nature of the type of procedure (e.g., an endovascular treatment of acute ischemic stroke) and the robotics of the system may apply additional constraints, steps or challenges. Each of these factors can increase the time for an exchange for a robotic procedure when compared to a manual procedure. The methods, apparatus and processes described below may be used to make exchanges faster, safer, and more consistent.

Full driving an EMD is defined as initially actuating the EMD from a starting position with the distal tip of the EMD slightly inserted into a more distal EMD so that the EMD does not protrude distally out of the more distal EMD and advancing the EMD as far as is needed which may be up to its entire working length. The length required for a robotic drive that is configured to hub drive an EMD and is capable of fully driving an over-the-wire EMD, the actuating length would be the length of all the EMDs that may be used added end to end. The actuating length may also take into account the lengths of the hubs of the device, the lengths of the hemostasis valve y-connectors and gear adapter, and the distance between device modules For example, for a robotic drive configured for endovascular treatment of acute ischemic stroke that includes a guide catheter (e.g., with a length of 95 cm), an aspiration catheter (e.g., with a length of 135 cm), a microcatheter (e.g., with a length of 165 cm) and a microwire (e.g., with a length of 180-200 cm), the robotic drive actuating distance would need to be almost 7 meters long. To reduce the length, a manual loading procedure may be used that allows a bedside operator, with at least minimal experience, to load and unload an EMD without risking vascular damage to the patient.

FIG. 117 is a block diagram illustrating loading or unloading an EMD in a robotic drive with a safe loading distance in accordance with an embodiment. For loading an EMD, an operator takes second EMD 1126 (or in other embodiments more than one EMD) and inserts the second EMD 1126 into a hub of a more distal first EMD 1124. For example the first EMD 1124 may be a guide catheter and the second EMD 1126 may be a distal access catheter. The robotic drive (e.g., a control computing system) may be configured to automatically position a second device module 1122 (coupled to a rail or linear member 1132) at a distance from a first device module 1120 (coupled to the rail 1132), herein referred to as a loading offset 1130. The loading offset is selected so that when the operator places the second (proximal) EMD 1126 into the second device module 1122, the second EMD 1126 will not exit a distal end 1134 of the more distal first EMD 1124. Therefore, the second EMD 1126 will not be exposed to the vasculature. In order for the second (proximal) device module 1122 to be positioned properly, a relative distance from the first (more distal) device module 1120 must be known. The loading offset 1130 may be based on a desired gap 1128 (e.g., 5 cm) between the distal end 1134 of the first EMD 1124 and a distal end 1136 of the second EMD 1126 when the second EMD 1126 is being loaded, the length of the first (distal) EMD 1124 and the length of the second (proximal) EMD 1126. In another embodiment, various parameters of the robotic drive may also affect the loading offset 1130, such as, for example, hub length and geared adapter length. In various embodiments, the loading offset 1130 may be defined by the difference in EMD lengths (min distal device module EMD length, max loading EMD length), different use cases, input by an operator based on the length of EMDs used or may be determined by the catheter-based procedure system by scanning EMDs opened during the case. The catheter-based procedure system (e.g., a control computing system) may automatically drive the second device module 1122 (e.g., along the rail 1132 of the robotic drive) to the correct position along the rail 1132 with the correct loading offset 1130, for example, in response to a user input provide by the operator. In another embodiment, the second device module 1122 may be jogged by an operator to the correct position along the rail 1132 with the correct loading offset 1130. In yet another embodiment, the second device module 1122 may be manually back driven by an operator to the correct position along the rail 1132 with the correct loading offset 1130. To unload an EMD when they are inside a patient's body, the robotic drive or the physician may drive the second device module 1122 to the position along the rail 1132 the loading offset 1130 distance from the first device module 1120. This ensures that a bedside operator is not manipulating EMDs that ae directly surrounded by the patient's vasculature. While one loading offset 1130 is described with respect to FIG. 117, in other embodiments more than one loading offset may be used where each loading offset provides a zone for safe loading or unloading of an EMD.

When calculating the loading offset 1130, various additional factors may be used. The factors that are used in the calculation may be based on the desired workflow of the catheter-based procedure system. The additional factors may include where the device modules with the EMDs that are being exchanged are currently positioned along a rail, the current stack of devices in the robotic drive and the stack of devices that are to be loaded into the robotic drive. Another factor is if a device module is far enough proximal and additional cassettes are being added distal (e.g., going from a biaxial configuration to a triaxial configuration), the device module may need to be moved distally to allow the additional cassettes to be added to the robotic drive.

One example of why the EMD length is important to know is when a physician is trying to reach a distal clot. The typical stack of EMDs for distal aspiration would be a Guide Catheter (95 cm), Aspiration Catheter (135 cm), Microcatheter (165 cm), and Guidewire (300 cm). If the 165 cm Microcatheter cannot reach the clot because it is "hubbed out" behind the aspiration catheter and Guide Catheter (the devices are at the max forward position), the physician may remove the Aspiration Catheter and insert the Micro Catheter directly into the Guide Catheter. By doing this, the physician can increase the amount of Micro Catheter inserted into the body because they have eliminated the length of the hub of the aspiration catheter and the hemostasis valve on the back of the aspiration catheter. The impact of this change is realized when loading the microcatheter behind the guide catheter. What used to be a 135 cm Aspiration Catheter being loaded behind a 95 cm Guide Catheter is now a 165 cm Micro Catheter being loaded behind a 95 cm Guide Catheter. If the same loading position was used, the Micro Catheter tip would be 30 cm forward, well into the vasculature of the patient. By knowing the length of the EMD being loaded and the length of the EMD it is begin loaded into and using the methods described herein for determining and implementing a safe loading offset, the catheter-based procedure system/robotic drive may ensure that a safe loading distance for all use cases.

Various methods may be used by the catheter-based procedure system/robotic drive to determine the length of the EMDs in a device module. For example, the catheter-based procedure system/robotic drive may determine the EMD lengths for each device module by electrical or optical identification (RFID, Barcode, QR, etc.), the operator manually entering the EMD length data or having a range of designated EMD lengths and choosing the combination of lengths that would result in the device module being driven as far back as possible (worst or the worst, i.e., safest conditions). To enable the use of a safe loading offset, the robotic drive may be configured to detect when a device module is unpopulated (no EMD loaded in the cassette) and move the unpopulated device module out of the way of a device module that needs to reach the loading offset. During use, device modules may interfere with the planned paths of other device modules, so the ability to avoid crash states is important. In another embodiment, if the user is jogging a device module backwards to get it to the loading position, and it runs into another device module, instead of going into a "crashed" state where both device modules are deactivated, the command for the device module being jogged would also be sent to the device module obstructing its path so as to move both device modules in the same direction.

There are multiple methods for inserting an EMD while limiting the EMDs travel forward. In one example, the EMD hub may be dropped into the device module it is being loaded into and the operator ensures the EMD hub is fixed (i.e., the EMD cannot move forward when device is being inserted). The EMD, or set of EMDs, are then inserted into a more distal EMD. When the inserted EMD approaches the loading offset distance, it will become taut, no longer being able to be inserted any further into the patient. In another example, the EMD to be loaded may be axially inserted through the cassette it is being loaded into. The cassette acts as a hard stop, not allowing the EMD hub to be inserted further into the patient. In another example, a mechanical clip may be attached to the EMD shaft to act as a hard stop when being inserted into the more distal EMD Hub.

In an embodiment, the robotic drive (e.g., a control computing system of the robotic drive) may be configured to correctly position an on-device adapter on a wire-based device to allow for a designated amount of throw. In another embodiment, the robotic drive (e.g., a control computing system of the robotic drive) may be configured to generate and provide an alert (e.g., a visual or audible alert) to indicate if the current positions of the device modules along a rail in the robotic drive would not allow all EMDs to be loaded based on, for example, the lengths of the EMDs. In another embodiment, the robotic drive (e.g., a control computing system of the robotic drive) may be configured to provide a notification (e.g., on a display) of where (i.e., what position along the rail) to drive one or more device modules. For example, a user may then command the robotic drive (e.g., using a control station) to drive the one or more device modules based on the position information provided by the robotic drive. In this embodiment, the robotic drive may also be configured to provide a notification (e.g., on a display) when the device modules are in a safe location.

In a manual neuro procedure, technicians will often prepare a multitude of EMDs on a separate sterile table behind the catheter-procedure system table. These EMDs will often be loaded into one another, then loaded into an EMD already inserted into the patient. For example, a distal access catheter, a micro catheter, and a 0.014 guidewire may be assembled together, then the set of prepared EMDs are all be loaded into a guide catheter once access to the carotid artery is gained. The robotic drive, for example, robotic drive 24 shown in FIG. 3, may be configured so that a prepared (or preassembled) "sub-assembly" (or set) of EMDs may be side loaded into two or more of the device modules of robotic drive. In an embodiment, the prepared set of EMDs is loaded into two or more of the device modules at substantially the same time. In another embodiment, each EMD in the preassembled set of EMDs may be loaded into the device modules consecutively. FIG. 118 is a top view of device modules of a robotic drive in a loading position in accordance with an embodiment. A first device module 1140 is in the most distal device module position and has a first device support 1148 that is extended and encapsulates a first EMD 1156 that is supported by the first device module 1140. A second device module 1142, a third device module 1144 and a fourth device module 1146 are positioned proximal to the first device module 1140. The second 1142, third 1144 and fourth 1146 device modules have a second device support 1150, a third device support 1152 and a fourth deice support 1154, respectively. Each of the second 1150, third 1152 and fourth 1154 device supports are pulled to their most proximal position and a cassette cover of a cassette (not shown) loaded onto each device module 1142, 1144 and 146 is opened to facilitate loading of an EMD into the respective device module. In one embodiment, the robotic drive may include sprung members to aid in usability when opening cassette covers and retracting device supports to enable loading. In another embodiment, the robotic drive may include actuated members to aid in usability when opening cassette covers and retracting device supports to enable loading. In this embodiment, the robotic drive may be configured to robotically control the actuating members.

FIG. 119 is a top view of the device modules of FIG. 118 in a loading position and a set of prepared EMDs in accordance with an embodiment. A sub-assembly or set of EMDs 1164 is prepared (or preassembled) that includes a second EMD 1158, a third EMD 1160 and a fourth EMD 1162. The tip of the second EMD 1158 is inserted into a y-connector installed on the first device module 1140. With the cassette cover open and the device supports 1150, 1152, 1154 retracted to their most proximal position, the set of EMDs 1164 may be loaded into their respective device module all at once as indicated by arrows 1166. Namely, the second EMD 1158, third EMD 1160 and fourth EMD 1162 may be loaded at the same time into the second device module 1142, third device module 1144 and fourth device module 1146, respectively. FIG. 120 shows the each EMD 1158, 1160, 1162 in the sub-assembly of prepared EMDs 1164 loaded into their respective device module.

In an embodiment, an on-device adapter (discussed above with respect to FIGS. 23-25) may be added to one or more of the EMDs in the subassembly of EMDs (or device stack) at a prep table which allows the EMDS to be exchanged into the system without the need of adding or removing specialized cassettes. In addition, the design described with respect to FIGS. 118-120 enables a multitude of coaxial devices to be loaded into the robotic drive. This design also may help with safety as an operator may convert a robotic procedure to a manual procedure by removing all the EMDs and continuing a case without large cassettes or device support mechanisms still attached to the EMDs. Only smaller devices such as the on-device adapters (e.g., a gear adapter or collet) would remain attached to the EMDS. Being able to remove an entire device stack (e.g., a prepared sub-assembly of EMDS) out of the cassettes of the device modules and the side loading/unloading design helps enable conversion to a manual procedure from a robotic procedure.

As discussed above, various embodiments utilize an on-device adapter that is positioned on the shaft of an EMD (e.g., a wire-based EMD). The position of an on-device adapter on one or more EMDs can be important for the loading/unloading or exchange of an EMD using a safe offset as described above with respect to FIG. 117 and the loading of a preassembled set of EMDs as described above with respect to FIGS. 118-120. For example, if the on-device adapter is positioned too far proximal on the EMD, the distal tip will extend out of the catheter tip when loading/unloading or attempting an exchange using a safe loading offset which can cause vascular damage. If the on-device adapter is placed too far distal on the EMD, the EMD may not have enough forward throw to extend past the distal tip of the, for example, catheter within which the EMD is positioned. Setting the on-device adapter at a known position along the EMD helps enable safe and effective workflows.

In various embodiment, a gapping tool may be used to enable setting the on-device adapter at a specific location on an EMD. The gapping tool is configured to have the correct offset designating the amount of throw the on-device adapter should have when being loaded into the robotic drive. The gapping tool may be used both on a separate sterile table behind the catheter-procedure system table when the EMD is being prepared or when the EMD is being loaded into the robotic system. In one embodiment, the gapping tool may be configured to position the on-device adapter based on the alignment of the distal tip of the EMD and the distal tip of the catheter in which the EMD is positioned. FIG. 121 is a schematic diagram of an elongated medical device, a gapping tool and an on-device adapter in accordance with an embodiment. In FIG. 121, a gapping tool 1170 is positioned next to and along an EMD 1174 (e.g., a wire-based EMD) between a y-connector (or hub) 1182 of a catheter 1176 and an on-device adapter 1172. The gapping tool 1170 is configured to define a distance 1184 which is based on a desired offset between the y-connector 1182 and the on-device adapter 1182 that provide the amount of throw the on-device adapter should have when being loaded into the robotic drive. First, the distal tip 1178 of the EMD 1173 is substantially aligned with the distal tip 1180 of the catheter 1176 as shown in FIG. 121. When the distal tip 1178 of the EMD 1174 and the distal tip 1180 of the catheter 1176 are aligned the gapping tool may be positioned next to the EMD 1174 to indicate the proper position or offset of the on-device adapter on the EMD 1174 from the y-connector 1182 of the catheter 1176 (i.e., the device into which the EMD 1174 is being actuated). In an embodiment, the gapping tool 1170 may be adjustable so that the distance 1184 (or gap) may be adjusted based on parameters of the catheter-based procedure system, for example, parameters of the robotic drive.

In another embodiment, the gapping tool may be configured to position or align an on-device adapter based on the lengths of the EMDs and other devices (e.g., a length of a y-connector). FIG. 122 is a schematic diagram of an elongated medical device, a gapping tool and an on-device adapter in accordance with an embodiment. In this embodiment, the positon of an on-device adapter from either end (the proximal end or the distal end) of the EMD 1192 (e.g., a wire-based EMD) may be calculated based on the length of the catheter (not shown) into which the EMD is being position, the length of the EMD 1192 and other parameters such as, for example, the length of a y-connector of the catheter). In FIG. 122, the gapping tool 1190 is shown positioned next to and along the EMD 1192 and used to position the on-device adapter 1194 from a proximal end 1196 of the EMD 1192. Gapping tool 1190 is configured to be adjustable to change the desired offset for the on-device, for example, based on parameters of the catheter-based procedure system such as parameters of the robotic drive. For example, gapping tool 1190 may include a scale 1198 and a slide 1197 that may be moved to adjust the distance (or gap) 1195 defined by the gapping tool 1180. Because the gapping tool 1190 is configured to position or align an on-device adapter based on known lengths of the EMDs, gapping tool 1190 may be used to position the on-device adapter 1194 on the EMD 1192 before the EMD is positioned in a catheter in the vasculature. In another embodiment, the gapping tool may be configured to resemble a custom tape measure. FIG. 123 is a diagram of an example gapping tool in accordance with an embodiment. Gapping tool 1200 includes a scale 1202. The scale 1202 may be shifted to account for the desire throw, length of the hub and y-connector, etc. In an embodiment, the scale 1202 may be read in cm of catheter length. In FIG. 123, the gapping tool 1200 is shown positioned net to an EMD 1204 with an on-device adapter 1206. In another embodiment, the tape measure form of the gapping tool may be configured in a spiral shape as shown in FIG. 124. The spiral shape of the gapping tool 12010 with scales 1212 may improve usability of the gapping tool 1210. The gapping tool 1210 may be unwound when needed to be positioned along the EMD to position an on-device adapter on the EMD.

Computer-executable instructions for robotic interventional procedures according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

A control computing system as described herein may include a processor having a processing circuit. The processor may include a central purpose processor, application specific processors (ASICs), circuits containing one or more processing components, groups of distributed processing components, groups of distributed computers configured for processing, etc. configured to provide the functionality of module or subsystem components discussed herein. Memory units (e.g., memory device, storage device, etc.) are devices for storing data and/or computer code for completing and/or facilitating the various processes described in the present disclosure. Memory units may include volatile memory and/or non-volatile memory. Memory units may include database components, object code components, script components, and/or any other type of information structure for supporting the various activities described in the present disclosure. According to an exemplary embodiment, any distributed and/or local memory device of the past, present, or future may be utilized with the systems and methods of this disclosure. According to an exemplary embodiment, memory units are communicably connected to one or more associated processing circuit. This connection may be via a circuit or any other wired, wireless, or network connection and includes computer code for executing one or more processes described herein. A single memory unit may include a variety of individual memory devices, chips, disks, and/or other storage structures or systems. Module or subsystem components may be computer code (e.g., object code, program code, compiled code, script code, executable code, or any combination thereof) for conducting each module's respective functions.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A robotic drive system for driving one or more elongated medical devices, the robotic drive system comprising:
    a linear member; and
    at least four device modules coupled to the linear member, wherein each device module is independently controllable to move linearly along the linear member;
    wherein
        the at least four device modules are configured to be switched between a first configuration where each device module is populated with a corresponding elongated medical device and a second configuration where a subset of the at least four device modules is populated with a corresponding elongated medical device, and
        the first configuration is a triaxial configuration.

2. The robotic drive system according to claim 1, wherein each device module comprises:
    a drive module; and
    a cassette mounted on the drive module; and
    wherein the drive module has at least one dimension that is smaller than at least one dimension of the cassette.

3. The robotic drive system according to claim 1, wherein the second configuration is a biaxial configuration.

4. The robotic drive system according to claim 1, wherein the second configuration includes a catheter or a wire-based elongated medical device.

5. A robotic drive system for driving one or more elongated medical devices, the robotic drive system comprising:
    a linear member; and
    at least four device modules coupled to the linear member, wherein each device module is independently controllable to move linearly along the linear member;
    wherein
        the at least four device modules are configured to be switched between a first configuration where each device module is populated with a corresponding elongated medical device and a second configuration where a subset of the at least four device modules is populated with a corresponding elongated medical device, and
        the first configuration includes at least one of the at least four device modules configured to drive a proximal region of the corresponding elongated medical device along a first longitudinal axis and the second configuration includes at least one of the at least four device modules configured to drive a proximal portion of the corresponding elongated medical device along a second longitudinal axis, which is different from the first longitudinal axis.

6. The robotic drive system according to claim 5, wherein the linear member comprises three or more linear members arranged in parallel, and wherein one of the at least four device modules is moveably coupled to one of the three or more linear members.

7. The robotic drive system according to claim 5, wherein, in the first configuration, the corresponding elongated medical device driven by the at least one of the at least four device modules is an over the wire elongated medical device.

8. The robotic drive system according to claim 5, wherein, in the second configuration, the corresponding elongated medical device driven by the at least one of the at least four device modules is a rapid exchange elongated medical device.

9. The robotic drive system of claim 1, wherein
each device module is configured to manipulate an elongated medical device,
the second configuration is a biaxial configuration,
in the triaxial configuration, the elongated medical device manipulated by three of the at least four device modules is a catheter and the elongated medical device manipulated by a fourth device module of the at least four device modules is a wire-based device, and
in the biaxial configuration, the elongated medical device manipulated by two of the at least four device modules is a catheter, the elongated medical device manipulated by a third device module of the at least four device modules is a wire-based device and a fourth device module of the at least four device modules is unpopulated.

10. The robotic drive system according to claim 9, further comprising:
at least one elongated medical device; and
at least one on-device adapter coupled to the at least one elongated medical device, the at least one on-device adapter configured to interface with one or more of the at least four device modules.

11. The robotic drive system according to claim 9, wherein each device module comprises:
a drive module; and
a cassette mounted on the drive module; and
wherein the cassette of each device module is configured to interface with the drive module of any of the at least four device modules using a common coupling interface, wherein the robotic drive system is reconfigurable by moving at least one cassette from a first drive module to a second drive module.

12. A robotic drive system for driving one or more elongated medical devices, the robotic drive system comprising:
a linear member; and
at least four device modules coupled to the linear member, wherein each device module is independently controllable to move linearly along the linear member; wherein
the at least four device modules are configured to be switched between a first configuration where each device module is populated with a corresponding elongated medical device and a second configuration where a subset of the at least four device modules is populated with a corresponding elongated medical device,
a first device module, among the east four device modules, is coupled to the linear member and configured to manipulate a first elongated medical device,
a second device module, among the at least four device modules, is coupled to the linear member at a position distal to the first device module and configured to manipulate a second elongated medical device, and
the robotic drive system includes a device support having a section moveably positioned in the first device module and having a first end and a second end, wherein the device support is configured to provide a channel to contain and support the first elongated medical device in a distance between the first device module and the second device module, and wherein the first end and the second end of the device support are coupled to the second device module.

13. The robotic drive system according to claim 12, wherein the device support is a flexible tube having a lengthwise slit.

14. The robotic drive system according to claim 12, wherein the first device module comprises:
a drive module; and
a cassette mounted on the drive module, the cassette including a channel configured to receive the section of the device support.

15. The robotic drive system according to claim 14, wherein the device support and the cassette are configured to move relative to one another.

16. The robotic drive system according to claim 15, wherein the cassette is configured to move along the device support.

17. The robotic drive system according to claim 15, wherein the device support is configured to move through the channel of the cassette.

18. The robotic drive system according to claim 12, wherein the device support has a length supported in tension from the first end and the second end.

19. The robotic drive system according to claim 12, wherein the second device module comprises:
a drive module having an arm extending in a proximal direction away from the second device module, wherein the second end of the device support is coupled to the arm; and
a cassette mounted on the drive module, wherein the first end of the device support is coupled to a proximal end of the cassette.

20. The robotic drive system of claim 1, wherein
a first device module, among the at least four device modules, is configured to manipulate a first elongated medical device,
a distal support arm has a device support connection located distal to the first device module, and
a device support is moveably positioned in the first device module and has a first end, a second end and a length supported in tension from the first end and the second end, the device support configured to provide a channel to contain and support the first elongated medical device in a distance between the first device module and the device support connection, wherein the first end and the second end of the device support are coupled to the distal support arm.

21. The robotic drive system according to claim 20, wherein the device support is a flexible tube having a lengthwise slit.

22. The robotic drive system according to claim 20, wherein the first device module comprises:
a drive module; and
a cassette mounted on the drive module, the cassette including a channel configured to receive a section of the device support.

23. The robotic drive system according to claim 22, wherein the device support and the cassette are configured to move relative to one another.

24. The robotic drive system according to claim 23, wherein the cassette is configured to move along the device support.

25. The robotic drive system according to claim 20, wherein the device support has a length supported in tension from the first end and the second end.

26. The robotic drive system according to claim 20, further comprising:
an introducer interface support coupled to the device support connection; and an introducer sheath coupled to the introducer interface support.

27. The robotic drive system according to claim 20, further comprising:
an arm coupled to the distal support arm and extending in a proximal direction away from the device support connection, wherein the second end of the device support is coupled to the arm.

28. The robotic drive system of claim 1, wherein
a first device module, among the at least four device modules, includes a first drive module coupled to the linear member and a cassette mounted to the first drive module, the cassette having a proximal end,
a second device module, among the at least four device modules, includes a second drive module coupled to the linear member at a position proximal to the first drive module, and
the second drive module is configured to be positioned in an area of overlap with the proximal end of the cassette mounted to the first drive module.

29. The robotic drive system according to claim 28, wherein the second drive module has at least one dimension that is smaller than at least one dimension of the cassette.

30. The robotic drive system according to claim 28, wherein the area of overlap is a volume under the proximal end of the cassette.

31. The robotic drive system according to claim 28, further comprising:
a first stage coupled to the linear member and the first drive module; and
a first offset bracket connected between the first drive module and the first stage to couple the first drive module to the first stage.

32. The robotic drive system according to claim 31, further comprising:
a second stage coupled to the linear member and the second drive module; and
a second offset bracket connected between the second drive module and the second stage to couple the second drive module to the second stage.

33. The robotic drive system according to claim 28, further comprising:
a third drive module coupled to the linear member at a position proximal to the first drive module and the second drive module, wherein the third drive module is configured to be positioned in the area of overlap with the proximal end of the cassette mounted to the first drive module.

34. The robotic drive system according to claim 28, further comprising:
at least one sensor positioned on the first drive module and configured to detect when the second drive module is within a threshold distance of the first drive module.

35. The robotic drive system of claim 1, further comprising:
a deployable elongated medical device having a first section and a second section, wherein the first section is positioned on a first of the at least four device modules and the second section is positioned on a second of the at least four device modules; and
wherein an independent linear motion of the second of the at least four device modules along a rail actuates the second section of the deployable elongated medical device.

36. The robotic drive system according to claim 35, wherein the first section of the deployable elongated medical device is a sheath.

37. The robotic drive system according to claim 35, wherein the second section of the deployable elongated medical device is a deployment wire or a deployment shaft.

38. The robotic drive system of claim 1, wherein
the at least four device modules are configured to allow a prepared subassembly of a plurality of elongated medical devices to be side-loaded into the at least four device modules, wherein each of the at least four device modules is configured to receive one of the plurality of elongated medical devices.

39. The robotic drive system according to claim 38, wherein the at least four device modules are configured to receive a respective elongated medical device in the prepared subassembly at substantially the same time.

40. The robotic drive system according to claim 38, wherein the at least four device modules are configured to receive a respective elongated medical device in the prepared subassembly consecutively.

41. The robotic drive system according to claim 38, wherein the plurality of elongated medical devices includes at least one catheter.

42. The robotic drive system according to claim 38, wherein the plurality of elongated medical devices includes at least one wire-based device.

43. The robotic drive system according to claim 38, wherein the prepared subassembly comprises:
at least one on-device adapter positioned on at least one of the plurality of elongated medical devices.

44. A robotic drive system for driving one or more elongated medical devices, the robotic drive system comprising:
a linear member; and
at least four device modules coupled to the linear member, wherein each device module is independently controllable to move linearly along the linear member; wherein
the at least four device modules are configured to be switched between a first configuration where each device module is populated with a corresponding elongated medical device and a second configuration where a subset of the at least four device modules is populated with a corresponding elongated medical device,
the linear member has a length,
a first device module, among the at least four device modules, is configured to manipulate a first elongated medical device, and the first device module has a first center point,
a second device module, among the at least four device modules, is configured to manipulate a second elongated medical device, and the second device module has a second center point, and
the robotic drive system further includes
a first stage coupled to the linear member, the first stage having a third center point,
a first offset bracket connected between the first device module and the first stage to couple the first device module to the first stage, the first offset bracket defining a first offset distance between the first center point of the first device module and the third center point of the first stage,
a second stage coupled to the linear member, the second stage having a fourth center point, and
a second offset bracket connected between the second device module and the second stage to couple the second device module to the second stage, the second offset bracket defining a second offset distance between the second center point of the second device module and the fourth center point of the second stage, wherein a first range of linear motion of the first device module along the linear member and a second range of linear motion of the second device module along the linear member overlap, and wherein the first range of linear motion of the first device module extends beyond the length of the linear member in a distal direction.

45. The robotic drive system according to claim 44, wherein the first device module and the second device module are successive device modules along the linear member.

46. The robotic drive system according to claim 44, wherein the first device module and the second device module are separated by at least one additional device module coupled to the linear member.

47. A robotic drive system for driving one or more elongated medical devices, the robotic drive system comprising:
   a linear member; and
   at least four device modules coupled to the linear member,
      wherein each device module is independently controllable to move linearly along the linear member; wherein
      the at least four device modules are configured to be switched between a first configuration where each device module is populated with a corresponding elongated medical device and a second configuration where a subset of the at least four device modules is populated with a corresponding elongated medical device,
      the linear member has a length,
      a first device module, among the at least four device modules, is configured to manipulate a first elongated medical device and has a first center point,
      a second device module, among the at least four device modules, is configured to manipulate a second elongated medical device, and has a second center point, and
      the robotic drive system further includes
         a first stage coupled to the linear member, the first stage having a third center point,
         a first offset bracket connected between the first device module and the first stage to couple the first device module to the first stage, the first offset bracket defining a first offset distance between the first center point of the first device module and the third center point of the first stage,
         a second stage coupled to the linear member, the second stage having a fourth center point,
         a second offset bracket connected between the second device module and the second stage to couple the second device module to the second stage, the second offset bracket defining a second offset distance between the second center point of the second device module and the fourth center point of the second stage, and
      wherein the first offset distance and the second offset distance are configured to minimize the length of the linear member.

48. The robotic drive system according to claim 47, wherein the first device module comprises:
   a first drive module;
   a first cassette mounted on the first drive module; and
   wherein the first drive module has at least one dimension that is smaller than at least one dimension of the first cassette.

49. The robotic drive system according to claim 47, wherein the second device module comprises:
   a second drive module;
   a second cassette mounted on the second drive module; and
   wherein the second drive module has at least one dimension that is smaller than at least one dimension of the second cassette.

50. The robotic drive system according to claim 48, wherein
   the second device module includes
      a second drive module, and
      a second cassette mounted on the second drive module, and
   the robotic drive system includes at least one sensor positioned on the first drive module and configured to detect when the second drive module is within a threshold distance of the first drive module.

51. The robotic drive system according to claim 2, wherein the cassette is configured to be mounted in a horizontal orientation.

52. A robotic drive system for driving one or more elongated medical devices, the robotic drive system comprising:
   a robotic drive;
   at least four device modules coupled to the robotic drive and configured to move past one another;
   each device module comprising a drive module;
   wherein each device module is configured to receive a corresponding cassette mounted in a horizontal orientation and configured to receive and drive an elongated medical device; and
   wherein the at least four device modules are configured to being switched between
      a first configuration where each device module is populated with an elongated medical device, and
      a second configuration where a subset of the at least four device modules is populated with an elongated medical device.

53. The robotic drive system according to claim 52, further comprising:
   at least one linear member.

54. The robotic drive system according to claim 53, wherein the at least one linear member comprises multiple linear members, wherein at least one of the at least four device modules is coupled to one of the multiple linear members, wherein the multiple linear members are configured to enable the at least four device modules to move past one another.

55. A robotic drive system for driving one or more elongated medical devices, the robotic drive system comprising:
   a linear member; and
   at least four device modules coupled to the linear member,
      wherein each device module is independently controllable; wherein
      the at least four device modules are configured to be switched between a first configuration where each device module is populated with a corresponding elongated medical device and a second configuration where a subset of the at least four device modules is populated with a corresponding elongated medical device, and the first configuration includes at least one of the at least four device modules configured to drive a proximal region of the corresponding elongated medical device along a first longitudinal axis and the second configuration includes at least one of the at least four device modules configured to drive a proximal portion of the corresponding elongated medical device along a second longitudinal axis, which is different from the first longitudinal axis.

\* \* \* \* \*